(12) United States Patent
Blangy

(10) Patent No.: US 9,091,678 B2
(45) Date of Patent: Jul. 28, 2015

(54) METHOD FOR IDENTIFYING COMPOUNDS USEFUL FOR TREATING AND/OR PREVENTING DISEASE-ASSOCIATED BONE LOSS

(75) Inventor: Anne Blangy, Montpellier (FR)

(73) Assignee: CENTRE NATIONAL DE LA RECHERCHE SCIENTIFIQUE (CNRS), Paris (FR)

(*) Notice: Subject to any disclaimer, the term of this patent is extended or adjusted under 35 U.S.C. 154(b) by 321 days.

(21) Appl. No.: 13/059,446

(22) PCT Filed: Aug. 18, 2009

(86) PCT No.: PCT/EP2009/060691
§ 371 (c)(1),
(2), (4) Date: May 9, 2011

(87) PCT Pub. No.: WO2010/020647
PCT Pub. Date: Feb. 25, 2010

(65) Prior Publication Data
US 2011/0212974 A1    Sep. 1, 2011

(30) Foreign Application Priority Data

Aug. 18, 2008    (EP) ................................ 08290783

(51) Int. Cl.
| | | |
|---|---|---|
| G01N 33/53 | (2006.01) | |
| G01N 33/50 | (2006.01) | |
| A61K 31/18 | (2006.01) | |
| A61K 31/341 | (2006.01) | |
| A61K 31/381 | (2006.01) | |
| A61K 31/415 | (2006.01) | |
| A61K 31/4152 | (2006.01) | |
| A61K 31/4178 | (2006.01) | |
| A61K 31/433 | (2006.01) | |
| A61K 31/495 | (2006.01) | |
| A61K 31/517 | (2006.01) | |
| A61K 31/519 | (2006.01) | |

(52) U.S. Cl.
CPC ............ *G01N 33/5008* (2013.01); *A61K 31/18* (2013.01); *A61K 31/341* (2013.01); *A61K 31/381* (2013.01); *A61K 31/415* (2013.01); *A61K 31/4152* (2013.01); *A61K 31/4178* (2013.01); *A61K 31/433* (2013.01); *A61K 31/495* (2013.01); *A61K 31/517* (2013.01); *A61K 31/519* (2013.01); *G01N 2333/4703* (2013.01); *G01N 2500/10* (2013.01); *G01N 2800/10* (2013.01)

(58) Field of Classification Search
None
See application file for complete search history.

(56) References Cited

U.S. PATENT DOCUMENTS

2011/0237907 A1    9/2011    Kirsch et al.

FOREIGN PATENT DOCUMENTS

WO    WO 2005/064007 A2    7/2005

OTHER PUBLICATIONS

Vives et al., "The Rac1 Exchange Factor Dock5 is Essential for Bone Resorption by Osteoclasts," J Bone Min Res, May 2011, vol. 26 No. 5, pp. 1099-1110.
International Search Report issued in application No. PCT/EP2009/060691 on Mar. 31, 2010.
Abassi et al., "Tyrosine 221 in Crk regulates adhesion-dependent membrane localization of Crk and Rac and activation of Rac signaling," EMBO J, 2002, pp. 4571-4582, vol. 21, No. 17.
Battini et al., "A human cell-surface receptor for xenotropic and polytropic murine leukemia viruses: Possible role in G protein-coupled signal transduction," Proc. Natl. Acad. Sci. USA, Feb. 1999, pp. 1385-1390, vol. 96.
Blair et al., "The Mechanism of Osteoclast Acidification," Biology and Physiology of the Osteoclast, Chapter 13, 1992, pp. 259-287.
Blangy et al., "Identification of TRIO-GEFD1 chemical inhibitors using the yeast exchange assay," Biol. Cell, 2006, pp. 511-522, vol. 98.
Brazier et al., "Expression Profile of RhoGTPases and RhoGEFs During RANKL-Stimulated Osteoclastogenesis: Identification of Essential Genes in Osteoclasts," J Bone Min Res, 2006, pp. 1387-1398, vol. 21, No. 9.
Bulk et al., "Adjuvant Therapy with Small Hairpin RNA Interference Prevents Non-Small Cell Lung Cancer Metastasis Development in Mice," Cancer Res, Mar. 2008, pp. 1896-1904, vol. 68, No. 6.
Carano et al., "Bisphosphonates Directly Inhibit the Bone Resorption Activity of Isolated Avian Osteoclasts In Virto," J. Clin. Invest., Feb. 1990, pp. 456-461, vol. 85.
Coelho et al., "Interferon-α and -β differentially regulate osteoclastogenesis: Role of differential induction of chemokine CXCL11 expression," PNAS, Aug. 2005, pp. 11917-11922, vol. 102, No. 33.
Côté et al., "GEF what? Dock180 and related proteins help Rac to polarize cells in new ways," Trends in Cell Biology, 2007, pp. 383-393, vol. 17, No. 8.
Côté et al., "Identification of an evolutionarily conserved superfamily of DOCK180-related proteins with guanine nucleotide exchange activity," J Cell Science, 2002, pp. 4901-4913, vol. 115.

(Continued)

*Primary Examiner* — Michael Pak
(74) *Attorney, Agent, or Firm* — Foley & Lardner LLP

(57) ABSTRACT

The present invention concerns a method for identifying a compound which inhibits the activation of RAC GTPase by DOCK5 protein comprising the steps of (i) coexpressing the DOCK5 and the RAC proteins in a cell, wherein said DOCK5 protein induces the conversion of inactive RAC, which inactive RAC is bound to GDP, to active RAC, which active RAC is bound to GTP, (ii) contacting or not said cell with said compound, (iii) determining the conversion of inactive RAC to active RAC in the presence or absence of said compound, and (iv) selecting the compound inhibiting the conversion of inactive RAC to active RAC. Said compound is useful for treating disease-associated bone loss.

9 Claims, 8 Drawing Sheets

(56) References Cited

OTHER PUBLICATIONS

Database UniProt [Online] Jul. 1, 2008 (XP-002499980), 3 pages.
Database UniProt [Online] Jul. 1, 2008 (XP-002499981), 3 pages.
Database UniProt [Online] Nov. 1, 1997 (XP-002499983), 14 pages.
Database UniProt [Online] Aug. 31, 2004 (XP-002499982), 22 pages.
De Toledo et al., "The yeast exchange assay, a new complementary method to screen for Dbl-like protein specificity: identification of a novel RhoA exchange factor." FEBS Letters, 2000, pp. 287-292, vol. 480.
Edgar R.C., "MUSCLE: multiple sequence alignment with high accuracy and high throughput," Nucleic Acids Research, 2004, pp. 1792-1797, vol. 32, No. 5.
Fukuda et al., "Regulation of Osteoclast Apoptosis and Motility by Small GTPase Binding Protein Rac1," J Bone Min Res, 2005, pp. 2245-2253, vol. 20, No. 12.
Girotra et al., "The use of parathyroid hormone in the treatment of osteoporosis," Rev Endocr Metab Disord, 2006, pp. 113-121, vol. 7.
Gumienny et al., "CED-12/ELMO, a Novel Member of the CrkII/Dock180/Rac Pathway, Is Required for Pagocytosis and Cell Migration," Cell, Oct. 2001, pp. 27-41, vol. 107.
Ha et al., "Proteomic profile of osteoclast membrane proteins: Identification of Na*/H* exchanger domain containing 2 and its role in osteoclast fusion," Proteomics, 2008, pp. 2625-2639, vol. 8.
Lassaux et al., "Residues in the Murine Leukemia Virus Capsid That Differentially Govern Resistance to Mouse Fv1 and Human Ref1 Restrictions," J Virology, May 2005, pp. 6560-6564, vol. 79, No. 10.
Needleman et al., "A General Method Applicable to the Search for Similarities in the Amino Acid Sequence of Two Proteins," J. Mol. Biol., 1970, pp. 443-453, vol. 48.
Omi et al., "Mutation of Dock5, a member of the guanine exchange factor Dock180 superfamily, in the rupture of lens cataract mouse," Experimental Eye Research, 2008, pp. 828-834, vol. 86.
Parrini et al., "Pak1 Kinase Homodimers Are Autoinhibited in trans and Dissociated upon Activation by Cdc42 and Rac1," Molecular Cell, Jan. 2002, pp. 73-83, vol. 9.
Pearson et al., "Improved tools for biological sequence comparison," Proc. Natl. Acad. Sci. USA, Apr. 1988, pp. 2444-2448, vol. 85.
Razzouk et al., "Rac-GTPase, osteoclast cytoskeleton and bone resorption," EJCB, Apr. 1999, pp. 249-255, vol. 78.
Schlesinger et al., "Bisphosphonates," Biology and Physiology of the Osteoclast, Chapter 18, 1992, pp. 397-417.
Väänanen et al., "Evidence for the Presence of a Proton Pump of the Vacuolar H*-ATPase Type in the Ruffled Borders of Osteoclasts," J Cell Biol, Sep. 1990, pp. 1305-1311, vol. 111.

A

B

C

A

B

Figure 8A
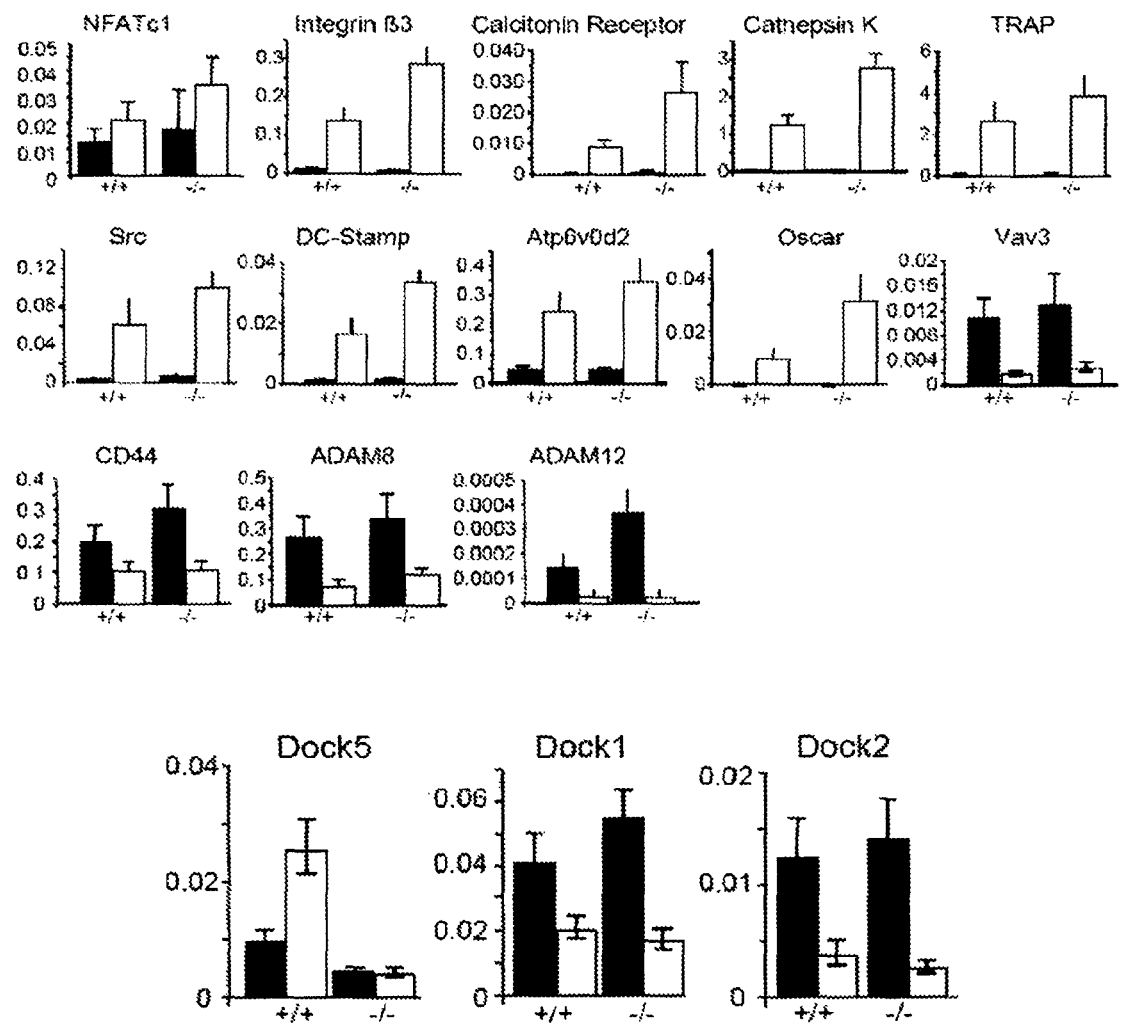
Figure 8B
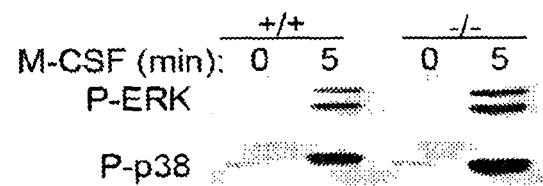
Figure 8C

SEQUENCE LISTING

<160> NUMBER OF SEQ ID NOS: 10

<210> SEQ ID NO 1
<211> LENGTH: 1868
<212> TYPE: PRT
<213> ORGANISM: Mus musculus

<400> SEQUENCE: 1

```
Met Ala Arg Trp Ile Pro Thr Lys Arg Gln Lys Tyr Gly Val Ala Ile
1               5                   10                  15

Tyr Asn Tyr Asn Ala Ser Gln Asp Val Glu Leu Ser Leu Gln Ile Gly
            20                  25                  30

Asp Thr Val His Ile Leu Glu Met Tyr Glu Gly Trp Tyr Arg Gly Tyr
        35                  40                  45

Ala Leu Gln Asn Arg Ser Lys Lys Gly Ile Phe Pro Glu Thr Tyr Ile
    50                  55                  60

His Leu Lys Glu Ala Thr Val Glu Asp Gly Gln His Glu Thr Val
65                  70                  75                  80

Ile Pro Gly Glu Leu Pro Leu Val Gln Glu Leu Thr Asn Thr Leu Arg
                85                  90                  95

Glu Trp Ala Val Ile Trp Arg Lys Leu Tyr Val Asn Asn Lys Val Thr
            100                 105                 110

Leu Phe Arg Gln Leu Gln Gln Met Thr Tyr Ser Leu Ile Glu Trp Arg
        115                 120                 125

Ser Gln Ile Leu Ser Gly Thr Leu Pro Lys Asp Glu Leu Ala Glu Leu
    130                 135                 140

Lys Lys Lys Val Thr Ala Lys Ile Asp His Gly Asn Arg Met Leu Gly
145                 150                 155                 160
```

-continued

```
Leu Asp Leu Val Val Arg Asp Asp Asn Gly Asn Ile Leu Asp Pro Asp
            165                 170                 175
Glu Thr Ser Thr Val Ala Leu Phe Arg Ala His Glu Val Ala Ser Lys
        180                 185                 190
Arg Ile Glu Glu Lys Ile Gln Glu Lys Ser Ile Leu Gln Asn Leu
    195                 200                 205
Asp Leu Arg Gly Gln Ala Ile Phe Ser Thr Val His Thr Tyr Gly Leu
    210                 215                 220
Tyr Val Asn Phe Lys Asn Phe Val Cys Asn Ile Gly Glu Asp Ala Glu
225                 230                 235                 240
Leu Phe Ile Ala Leu Tyr Asp Pro Asp Gln Ser Thr Phe Ile Ser Glu
                245                 250                 255
Asn Tyr Leu Ile Arg Trp Gly Ser Asn Gly Met Pro Lys Glu Ile Glu
            260                 265                 270
Lys Leu Asn Asn Leu Gln Ala Val Phe Thr Asp Leu Ser Ser Thr Asp
        275                 280                 285
Leu Ile Arg Pro Arg Ile Ser Leu Val Cys Gln Ile Val Arg Val Gly
    290                 295                 300
Arg Met Glu Leu Lys Glu Gly Lys Lys His Thr Cys Gly Leu Arg Arg
305                 310                 315                 320
Pro Phe Gly Val Ala Val Met Asp Ile Ser Asp Ile Val His Gly Lys
                325                 330                 335
Val Asp Asp Glu Glu Lys Gln His Phe Ile Pro Phe Gln Gln Ile Ala
            340                 345                 350
Met Glu Thr Tyr Ile Arg Gln Arg Gln Leu Ile Met Ser Pro Leu Ile
        355                 360                 365
Thr Ser His Val Ile Gly Glu Asn Glu Pro Leu Thr Ser Val Leu Asn
    370                 375                 380
Lys Val Ile Ala Ala Lys Glu Val Asn His Lys Gly Gln Gly Leu Trp
385                 390                 395                 400
Val Ser Leu Lys Leu Leu Pro Gly Asp Leu Thr Gln Val Gln Lys Asn
                405                 410                 415
Phe Ser His Leu Val Asp Arg Ser Thr Ala Ile Ala Arg Lys Met Gly
            420                 425                 430
Phe Pro Glu Ile Ile Leu Pro Gly Asp Val Arg Asn Asp Ile Tyr Val
        435                 440                 445
Thr Leu Ile His Gly Glu Phe Asp Lys Gly Lys Lys Lys Thr Pro Lys
    450                 455                 460
Asn Val Glu Val Thr Met Ser Val Phe Asp Glu Glu Gly Asn Leu Leu
465                 470                 475                 480
Glu Lys Ala Ile His Pro Gly Ala Gly Tyr Glu Gly Val Ser Glu Tyr
                485                 490                 495
Lys Ser Val Val Tyr Gln Val Lys Gln Pro Cys Trp Tyr Glu Thr
            500                 505                 510
Val Lys Val Phe Ile Ala Ile Glu Glu Val Thr Arg Cys His Ile Arg
        515                 520                 525
Phe Thr Phe Arg His Arg Ser Ser Gln Glu Ser Arg Asp Lys Ser Glu
    530                 535                 540
Arg Ala Phe Gly Val Ala Phe Val Lys Leu Met Asn Ala Asp Gly Thr
545                 550                 555                 560
Thr Leu Gln Asp Gly Arg His Asp Leu Val Val Tyr Lys Gly Asp Asn
                565                 570                 575
Lys Lys Met Glu Asp Ala Lys Tyr Tyr Leu Thr Leu Pro Gly Thr Lys
```

-continued

```
            580                 585                 590
Ala Glu Leu Glu Glu Lys Glu Leu Gln Ala Ser Lys Asn Pro Ser Val
            595                 600                 605

Phe Thr Pro Ser Lys Asp Ser Thr Lys Asp Ser Phe Gln Ile Ala Thr
            610                 615                 620

Leu Ile Cys Ser Thr Lys Leu Thr Gln Asn Val Asp Leu Leu Gly Leu
625                 630                 635                 640

Leu Asn Trp Arg Ser Asn Ser Gln Asn Ile Lys His Asn Leu Lys Lys
                    645                 650                 655

Leu Met Glu Val Asp Gly Gly Glu Ile Val Lys Phe Leu Gln Asp Thr
                    660                 665                 670

Leu Asp Ala Leu Phe Asn Ile Met Met Glu Met Ser Asp Asn Glu Thr
                    675                 680                 685

Tyr Asp Phe Leu Val Phe Asp Ala Leu Val Phe Ile Ile Ser Leu Ile
                    690                 695                 700

Gly Asp Ile Lys Phe Gln His Phe Asn Pro Val Leu Glu Thr Tyr Ile
705                 710                 715                 720

Tyr Lys His Phe Ser Ala Thr Leu Ala His Val Lys Leu Ser Lys Val
                    725                 730                 735

Leu Asn Phe Tyr Val Ala Asn Ala Glu Asp Pro Ser Lys Thr Glu Leu
                    740                 745                 750

Leu Phe Ala Ala Leu Lys Ala Leu Lys Tyr Leu Phe Arg Phe Ile Ile
                    755                 760                 765

Gln Ser Arg Val Leu Tyr Leu Arg Phe Tyr Gly Gln Ser Glu Asp Gly
                    770                 775                 780

Asp Glu Phe Asn Asp Ser Ile Arg Gln Leu Phe Leu Ala Phe Asn Thr
785                 790                 795                 800

Leu Met Asp Arg Pro Leu Glu Glu Ala Val Lys Ile Lys Gly Ala Ala
                    805                 810                 815

Leu Lys Tyr Leu Pro Ser Ile Ile Asn Asp Val Lys Leu Val Phe Asp
                    820                 825                 830

Pro Met Glu Leu Ser Val Leu Phe Cys Lys Phe Ile Gln Ser Ile Pro
                    835                 840                 845

Asp Asn Gln Leu Val Arg Gln Lys Leu Asn Cys Met Thr Lys Ile Val
                    850                 855                 860

Glu Ser Ser Leu Phe Gln Gln Ala Glu Cys Arg Glu Val Leu Leu Pro
865                 870                 875                 880

Leu Leu Thr Asp Gln Leu Ser Gly Gln Leu Asp Asp His Ser Thr Lys
                    885                 890                 895

Pro Asp His Glu Ala Ser Ser Gln Leu Leu Ser Asn Ile Leu Glu Val
                    900                 905                 910

Leu Asp Arg Thr Asp Val Gly Pro Thr Ser Ala His Val Gln Leu Ile
                    915                 920                 925

Met Glu Arg Leu Leu Arg Arg Ile Asn Arg Thr Val Ile Gly Met Ser
                    930                 935                 940

Arg Gln Ser Pro His Ile Gly Ser Phe Val Ala Cys Met Ile Ala Val
945                 950                 955                 960

Leu Arg Gln Met Glu Asp Ser His Tyr Ser His Tyr Ile Ser Thr Phe
                    965                 970                 975

Lys Thr Arg Gln Asp Ile Ile Asp Phe Leu Met Glu Thr Phe Ile Met
                    980                 985                 990

Phe Lys Asp Leu Ile Gly Lys Asn  Val Tyr Ala Lys Asp  Trp Met Val
                    995                 1000                1005
```

-continued

```
Met Asn Met Thr Gln Asn Arg Val Phe Leu Arg Ala Ile Asn Gln
    1010            1015                1020

Phe Ala Glu Val Leu Thr Lys Ser Phe Met Asp Gln Ala Ser Phe
    1025            1030                1035

Glu Leu Gln Leu Trp Asn Asn Tyr Phe His Leu Ala Val Ala Phe
    1040            1045                1050

Leu Thr His Glu Ser Leu Gln Leu Glu Thr Phe Ser Glu Ala Lys
    1055            1060                1065

Arg Asn Lys Ile Val Lys Lys Tyr Gly Asp Met Arg Lys Glu Ile
    1070            1075                1080

Gly Phe Arg Ile Arg Asp Met Trp Tyr Asn Leu Gly Pro His Lys
    1085            1090                1095

Ile Lys Phe Ile Pro Ser Met Val Gly Pro Ile Leu Glu Val Thr
    1100            1105                1110

Leu Thr Pro Glu Val Glu Leu Arg Lys Ala Thr Ile Pro Ile Phe
    1115            1120                1125

Phe Asp Met Met Gln Cys Glu Phe Asn Leu Ser Gly Asn Gly Asn
    1130            1135                1140

Phe His Met Phe Glu Asn Glu Leu Ile Thr Lys Leu Asp Gln Glu
    1145            1150                1155

Val Glu Gly Gly Arg Gly Asp Glu Gln Tyr Lys Val Leu Leu Glu
    1160            1165                1170

Lys Leu Leu Leu Glu His Cys Arg Lys His Lys Tyr Leu Ala Asn
    1175            1180                1185

Ser Gly Glu Ala Phe Ala Phe Leu Val Ser Ser Leu Leu Glu Asn
    1190            1195                1200

Leu Leu Asp Tyr Arg Thr Ile Ile Ile His Asp Glu Ser Lys Glu
    1205            1210                1215

Asn Arg Met Ser Cys Thr Val Asn Val Leu Asn Phe Tyr Lys Asp
    1220            1225                1230

Lys Lys Arg Glu Asp Ile Tyr Ile Arg Tyr Leu Tyr Lys Leu Arg
    1235            1240                1245

Asp Leu His Arg Asp Cys Glu Asn Tyr Thr Glu Ala Ala Tyr Thr
    1250            1255                1260

Leu Leu Leu His Ala Glu Leu Leu Gln Trp Ser Asp Lys Pro Cys
    1265            1270                1275

Val Pro His Leu Leu Gln Arg Asp Ser Tyr Tyr Val Tyr Thr Gln
    1280            1285                1290

Gln Glu Leu Lys Glu Lys Leu Tyr Gln Glu Ile Ile Ser Tyr Phe
    1295            1300                1305

Asp Lys Gly Lys Met Trp Glu Lys Ala Ile Lys Leu Ser Lys Glu
    1310            1315                1320

Leu Ala Glu Thr Tyr Glu Ser Lys Val Phe Asp Tyr Glu Gly Leu
    1325            1330                1335

Gly Ser Leu Leu Lys Lys Arg Ala Leu Phe Tyr Glu Asn Ile Ile
    1340            1345                1350

Lys Ala Met Arg Pro Gln Pro Glu Tyr Phe Ala Val Gly Tyr Tyr
    1355            1360                1365

Gly Gln Gly Phe Pro Ser Phe Leu Arg Asn Lys Ile Phe Ile Tyr
    1370            1375                1380

Arg Gly Lys Glu Tyr Glu Arg Arg Glu Asp Phe Ser Leu Arg Leu
    1385            1390                1395
```

```
Leu Thr Gln Phe Pro Asn Ala Glu Lys Met Thr Ser Thr Thr Pro
    1400                1405                1410

Pro Gly Glu Asp Ile Lys Ser Ser Pro Lys Gln Tyr Leu Gln Cys
    1415                1420                1425

Phe Thr Val Lys Pro Val Met Ser Leu Pro Pro Ser Tyr Lys Asp
    1430                1435                1440

Lys Pro Val Pro Glu Gln Ile Leu Asn Tyr Tyr Arg Ala Asn Glu
    1445                1450                1455

Val Gln Gln Phe Ser Tyr Ser Arg Pro Phe Arg Lys Gly Glu Lys
    1460                1465                1470

Asp Pro Glu Asn Glu Phe Ala Thr Met Trp Ile Glu Arg Thr Thr
    1475                1480                1485

Tyr Arg Thr Ala Tyr Thr Phe Pro Gly Ile Leu Lys Trp Phe Glu
    1490                1495                1500

Ala Lys Glu Ile Ser Val Glu Glu Ile Ser Pro Leu Glu Asn Ala
    1505                1510                1515

Ile Glu Thr Met Glu Leu Thr Asn Glu Arg Val Ser Asn Cys Val
    1520                1525                1530

Gln Gln His Ala Trp Asp His Ser Leu Ser Val His Pro Leu Ser
    1535                1540                1545

Met Leu Leu Ser Gly Ile Val Asp Pro Ala Val Met Gly Gly Phe
    1550                1555                1560

Ser Asn Tyr Glu Lys Ala Phe Phe Thr Glu Lys Tyr Leu Gln Glu
    1565                1570                1575

His Pro Glu Asp Gln Glu Lys Val Glu Leu Leu Lys Arg Leu Ile
    1580                1585                1590

Ala Leu Gln Ile Pro Leu Leu Thr Glu Gly Ile Arg Ile His Gly
    1595                1600                1605

Glu Lys Leu Thr Glu Gln Leu Lys Pro Leu His Ala Arg Leu Ser
    1610                1615                1620

Ser Cys Phe Arg Glu Leu Lys Glu Lys Val Glu Lys Leu Tyr Gly
    1625                1630                1635

Val Ile Thr Leu Pro Pro Ser Met Thr Glu Arg Lys Pro Ser Arg
    1640                1645                1650

Ala Gly Ser Met Val Leu Pro Tyr Ile Leu Ser Ser Thr Leu Arg
    1655                1660                1665

Arg Leu Ser Val Thr Ser Val Ala Ser Ser Val Ile Ser Thr Ser
    1670                1675                1680

Ser Asn Ser Ser Asp Asn Ala Ser Ser Arg Pro Gly Ser Asp Gly
    1685                1690                1695

Ser Ile Leu Glu Pro Leu Phe Glu Arg Arg Ala Ser Ser Gly Ala
    1700                1705                1710

Arg Val Glu Asp Leu Pro Pro Lys Glu Asp Ser Glu Asn Arg Ile
    1715                1720                1725

Ser Lys Phe Lys Arg Lys Asp Trp Asn Leu Ser Lys Ser Gln Val
    1730                1735                1740

Ile Ala Glu Lys Ala Pro Glu Pro Asp Val Met Ser Pro Gly Lys
    1745                1750                1755

Lys Thr Gln Arg Pro Lys Ser Leu Gln Leu Val Asp Ser Arg Leu
    1760                1765                1770

Thr Pro Phe His Ser Pro Ser Pro Leu Gln Ser Thr Ala Leu Ser
    1775                1780                1785

Pro Pro Pro Leu Thr Pro Lys Ala Thr Arg Thr Leu Ser Ser Pro
```

```
                1790                1795                1800

Ser Leu Gln Thr Asp Gly Leu Thr Ala Ser Val Pro Pro Pro Pro
    1805                1810                1815

Pro Pro Lys Ser Lys Pro Tyr Glu Ser Ser Gln Arg Asn Ser Ala
    1820                1825                1830

Glu Ile Ala Pro Pro Leu Pro Val Arg Arg Asp Ser Lys Ala Pro
    1835                1840                1845

Pro Pro Pro Pro Pro Lys Ala Arg Lys Ser Gly Ile Leu Ser Ser
    1850                1855                1860

Glu Pro Gly Ser Gln
    1865

<210> SEQ ID NO 2
<211> LENGTH: 192
<212> TYPE: PRT
<213> ORGANISM: Artificial Sequence
<220> FEATURE:
<223> OTHER INFORMATION: Modified homo sapiens RAC protein

<400> SEQUENCE: 2

Met Gln Ala Ile Lys Cys Val Val Val Gly Asp Gly Ala Val Gly Lys
1               5                   10                  15

Thr Cys Leu Leu Ile Ser Tyr Thr Thr Asn Ala Phe Pro Gly Glu Tyr
            20                  25                  30

Ile Pro Thr Val Phe Asp Asn Tyr Ser Ala Asn Val Met Val Asp Gly
        35                  40                  45

Lys Pro Val Asn Leu Gly Leu Trp Asp Thr Ala Gly Gln Glu Asp Tyr
    50                  55                  60

Asp Arg Leu Arg Pro Leu Ser Tyr Pro Gln Thr Asp Val Phe Leu Ile
65                  70                  75                  80

Cys Phe Ser Leu Val Ser Pro Ala Ser Phe Glu Asn Val Arg Ala Lys
                85                  90                  95

Trp Tyr Pro Glu Val Arg His His Cys Pro Asn Thr Pro Ile Ile Leu
            100                 105                 110

Val Gly Thr Lys Leu Asp Leu Arg Asp Asp Lys Asp Thr Ile Glu Lys
        115                 120                 125

Leu Lys Glu Lys Lys Leu Thr Pro Ile Thr Tyr Pro Gln Gly Leu Ala
    130                 135                 140

Met Ala Lys Glu Ile Gly Ala Val Lys Tyr Leu Glu Cys Ser Ala Leu
145                 150                 155                 160

Thr Gln Arg Gly Leu Lys Thr Val Phe Asp Glu Ala Ile Arg Ala Val
                165                 170                 175

Leu Cys Pro Pro Pro Val Lys Lys Arg Lys Arg Lys Ser Leu Leu Leu
            180                 185                 190

<210> SEQ ID NO 3
<211> LENGTH: 553
<212> TYPE: PRT
<213> ORGANISM: Homo sapiens

<400> SEQUENCE: 3

Met Ser Asn Asn Gly Leu Asp Ile Gln Asp Lys Pro Pro Ala Pro Pro
1               5                   10                  15

Met Arg Asn Thr Ser Thr Met Ile Gly Ala Gly Ser Lys Asp Ala Gly
            20                  25                  30

Thr Leu Asn His Gly Ser Lys Pro Leu Pro Pro Asn Pro Glu Glu Lys
        35                  40                  45
```

```
Lys Lys Lys Asp Arg Phe Tyr Arg Ser Ile Leu Pro Gly Asp Lys Thr
 50                  55                  60

Asn Lys Lys Glu Lys Glu Arg Pro Glu Ile Ser Leu Pro Ser Asp
 65              70                  75                  80

Phe Glu His Thr Ile His Val Gly Phe Asp Ala Val Thr Gly Glu Phe
                 85                  90                  95

Thr Gly Met Pro Glu Gln Trp Ala Arg Leu Leu Gln Thr Ser Asn Ile
                100                 105                 110

Thr Lys Ser Glu Gln Lys Lys Asn Pro Gln Ala Val Leu Asp Val Leu
            115                 120                 125

Glu Phe Tyr Asn Ser Lys Lys Thr Ser Asn Ser Gln Lys Tyr Met Ser
    130                 135                 140

Phe Thr Asp Lys Ser Ala Glu Asp Tyr Asn Ser Ser Asn Ala Leu Asn
145                 150                 155                 160

Val Lys Ala Val Ser Glu Thr Pro Ala Val Pro Pro Val Ser Glu Asp
                165                 170                 175

Glu Asp Asp Asp Asp Asp Ala Thr Pro Pro Val Ile Ala Pro
                180                 185                 190

Arg Pro Glu His Thr Lys Ser Val Tyr Thr Arg Ser Val Ile Glu Pro
        195                 200                 205

Leu Pro Val Thr Pro Thr Arg Asp Val Ala Thr Ser Pro Ile Ser Pro
    210                 215                 220

Thr Glu Asn Asn Thr Thr Pro Pro Asp Ala Leu Thr Arg Asn Thr Glu
225                 230                 235                 240

Lys Gln Lys Lys Lys Pro Lys Met Ser Asp Glu Ile Leu Glu Lys
                245                 250                 255

Leu Arg Ser Ile Val Ser Val Gly Asp Pro Lys Lys Tyr Thr Arg
                260                 265                 270

Phe Glu Lys Ile Gly Gln Gly Ala Ser Gly Thr Val Tyr Thr Ala Met
    275                 280                 285

Asp Val Ala Thr Gly Gln Glu Val Ala Ile Lys Gln Met Asn Leu Gln
    290                 295                 300

Gln Gln Pro Lys Lys Glu Leu Ile Ile Asn Glu Ile Leu Val Met Arg
305                 310                 315                 320

Glu Asn Lys Asn Pro Asn Ile Val Asn Tyr Leu Asp Ser Tyr Leu Val
                325                 330                 335

Gly Asp Glu Leu Trp Val Val Met Glu Tyr Leu Ala Gly Gly Ser Leu
                340                 345                 350

Thr Asp Val Val Thr Glu Thr Cys Met Asp Glu Gly Gln Ile Ala Ala
            355                 360                 365

Val Cys Arg Glu Cys Leu Gln Ala Leu Glu Phe Leu His Ser Asn Gln
    370                 375                 380

Val Ile His Arg Asp Ile Lys Ser Asp Asn Ile Leu Leu Gly Met Asp
385                 390                 395                 400

Gly Ser Val Lys Leu Thr Asp Phe Gly Phe Cys Ala Gln Ile Thr Pro
                405                 410                 415

Glu Gln Ser Lys Arg Ser Thr Met Val Gly Thr Pro Tyr Trp Met Ala
            420                 425                 430

Pro Glu Val Val Thr Arg Lys Ala Tyr Gly Pro Lys Val Asp Ile Trp
        435                 440                 445

Ser Leu Gly Ile Met Ala Ile Glu Met Ile Glu Gly Glu Pro Pro Tyr
    450                 455                 460
```

```
Leu Asn Glu Asn Pro Leu Arg Ala Leu Tyr Leu Ile Ala Thr Asn Gly
465                 470                 475                 480

Thr Pro Glu Leu Gln Asn Pro Glu Lys Leu Ser Ala Ile Phe Arg Asp
            485                 490                 495

Phe Leu Asn Arg Cys Leu Glu Met Asp Val Glu Lys Arg Gly Ser Ala
            500                 505                 510

Lys Glu Leu Leu Gln Val Arg Lys Leu Arg Phe Gln Val Phe Ser Asn
            515                 520                 525

Phe Ser Met Ile Ala Ala Ser Ile Pro Glu Asp Cys Gln Ala Pro Leu
            530                 535                 540

Gln Pro His Ser Thr Asp Cys Cys Ser
545                 550
```

<210> SEQ ID NO 4
<211> LENGTH: 1870
<212> TYPE: PRT
<213> ORGANISM: Homo sapiens

<400> SEQUENCE: 4

```
Met Ala Arg Trp Ile Pro Thr Lys Arg Gln Lys Tyr Gly Val Ala Ile
1               5                   10                  15

Tyr Asn Tyr Asn Ala Ser Gln Asp Val Glu Leu Ser Leu Gln Ile Gly
                20                  25                  30

Asp Thr Val His Ile Leu Glu Met Tyr Glu Gly Trp Tyr Arg Gly Tyr
            35                  40                  45

Thr Leu Gln Asn Lys Ser Lys Lys Gly Ile Phe Pro Glu Thr Tyr Ile
        50                  55                  60

His Leu Lys Glu Ala Thr Val Glu Asp Leu Gly Gln His Glu Thr Val
65                  70                  75                  80

Ile Pro Gly Glu Leu Pro Leu Val Gln Glu Leu Thr Ser Thr Leu Arg
                85                  90                  95

Glu Trp Ala Val Ile Trp Arg Lys Leu Tyr Val Asn Asn Lys Leu Thr
            100                 105                 110

Leu Phe Arg Gln Leu Gln Gln Met Thr Tyr Ser Leu Ile Glu Trp Arg
        115                 120                 125

Ser Gln Ile Leu Ser Gly Thr Leu Pro Lys Asp Glu Leu Ala Glu Leu
    130                 135                 140

Lys Lys Lys Val Thr Ala Lys Ile Asp His Gly Asn Arg Met Leu Gly
145                 150                 155                 160

Leu Asp Leu Val Val Arg Asp Asp Asn Gly Asn Ile Leu Asp Pro Asp
                165                 170                 175

Glu Thr Ser Thr Ile Ala Leu Phe Lys Ala His Glu Val Ala Ser Lys
            180                 185                 190

Arg Ile Glu Glu Lys Ile Gln Glu Lys Ser Ile Leu Gln Asn Leu
        195                 200                 205

Asp Leu Arg Gly Gln Ser Ile Phe Ser Thr Ile His Thr Tyr Gly Leu
    210                 215                 220

Tyr Val Asn Phe Lys Asn Phe Val Cys Asn Ile Gly Glu Asp Ala Glu
225                 230                 235                 240

Leu Phe Met Ala Leu Tyr Asp Pro Asp Gln Ser Thr Phe Ile Ser Glu
                245                 250                 255

Asn Tyr Leu Ile Arg Trp Gly Ser Asn Gly Met Pro Lys Glu Ile Glu
            260                 265                 270

Lys Leu Asn Asn Leu Gln Ala Val Phe Thr Asp Leu Ser Ser Met Asp
        275                 280                 285
```

-continued

```
Leu Ile Arg Pro Arg Val Ser Leu Val Cys Gln Ile Val Arg Val Gly
290                 295                 300

His Met Glu Leu Lys Glu Gly Lys Lys His Thr Cys Gly Leu Arg Arg
305                 310                 315                 320

Pro Phe Gly Val Ala Val Met Asp Ile Thr Asp Ile Ile His Gly Lys
                325                 330                 335

Val Asp Asp Glu Glu Lys Gln His Phe Ile Pro Phe Gln Gln Ile Ala
                340                 345                 350

Met Glu Thr Tyr Ile Arg Gln Arg Gln Leu Ile Met Ser Pro Leu Ile
                355                 360                 365

Thr Ser His Val Ile Gly Glu Asn Glu Pro Leu Thr Ser Val Leu Asn
370                 375                 380

Lys Val Ile Ala Ala Lys Glu Val Asn His Lys Gly Gln Gly Leu Trp
385                 390                 395                 400

Val Ser Leu Lys Leu Leu Pro Gly Asp Leu Thr Gln Val Gln Lys Asn
                405                 410                 415

Phe Ser His Leu Val Asp Arg Ser Thr Ala Ile Ala Arg Lys Met Gly
                420                 425                 430

Phe Pro Glu Ile Ile Leu Pro Gly Asp Val Arg Asn Asp Ile Tyr Val
                435                 440                 445

Thr Leu Ile His Gly Glu Phe Asp Lys Gly Lys Lys Lys Thr Pro Lys
450                 455                 460

Asn Val Glu Val Thr Met Ser Val His Asp Glu Gly Lys Leu Leu
465                 470                 475                 480

Glu Lys Ala Ile His Pro Gly Ala Gly Tyr Gly Ile Ser Glu Tyr
                485                 490                 495

Lys Ser Val Val Tyr Tyr Gln Val Lys Gln Pro Cys Trp Tyr Glu Thr
                500                 505                 510

Val Lys Val Ser Ile Ala Ile Glu Glu Val Thr Arg Cys His Ile Arg
                515                 520                 525

Phe Thr Phe Arg His Arg Ser Ser Gln Glu Thr Arg Asp Lys Ser Glu
530                 535                 540

Arg Ala Phe Gly Val Ala Phe Val Lys Leu Met Asn Pro Asp Gly Thr
545                 550                 555                 560

Thr Leu Gln Asp Gly Arg His Asp Leu Val Val Tyr Lys Gly Asp Asn
                565                 570                 575

Lys Lys Met Glu Asp Ala Lys Phe Tyr Leu Thr Leu Pro Gly Thr Lys
                580                 585                 590

Met Glu Met Glu Glu Lys Glu Leu Gln Ala Ser Lys Asn Leu Val Thr
                595                 600                 605

Phe Thr Pro Ser Lys Asp Ser Thr Lys Asp Ser Phe Gln Ile Ala Thr
610                 615                 620

Leu Ile Cys Ser Thr Lys Leu Thr Gln Asn Val Asp Leu Leu Gly Leu
625                 630                 635                 640

Leu Asn Trp Arg Ser Asn Ser Gln Asn Ile Lys His Asn Leu Lys Lys
                645                 650                 655

Leu Met Glu Val Asp Gly Gly Glu Ile Val Lys Phe Leu Gln Asp Thr
                660                 665                 670

Leu Asp Ala Leu Phe Asn Ile Met Met Glu Met Ser Asp Ser Glu Thr
                675                 680                 685

Tyr Asp Phe Leu Val Phe Asp Ala Leu Val Phe Ile Ile Ser Leu Ile
690                 695                 700
```

```
Gly Asp Ile Lys Phe Gln His Phe Asn Pro Val Leu Glu Thr Tyr Ile
705                 710                 715                 720

Tyr Lys His Phe Ser Ala Thr Leu Ala Tyr Val Lys Leu Ser Lys Val
            725                 730                 735

Leu Asn Phe Tyr Val Ala Asn Ala Asp Asp Ser Ser Lys Thr Glu Leu
                740                 745                 750

Leu Phe Ala Ala Leu Lys Ala Leu Lys Tyr Leu Phe Arg Phe Ile Ile
            755                 760                 765

Gln Ser Arg Val Leu Tyr Leu Arg Phe Tyr Gly Gln Ser Lys Asp Gly
770                 775                 780

Asp Glu Phe Asn Asn Ser Ile Arg Gln Leu Phe Leu Ala Phe Asn Met
785                 790                 795                 800

Leu Met Asp Arg Pro Leu Glu Glu Ala Val Lys Ile Lys Gly Ala Ala
                805                 810                 815

Leu Lys Tyr Leu Pro Ser Ile Ile Asn Asp Val Lys Leu Val Phe Asp
            820                 825                 830

Pro Val Glu Leu Ser Val Leu Phe Cys Lys Phe Ile Gln Ser Ile Pro
                835                 840                 845

Asp Asn Gln Leu Val Arg Gln Lys Leu Asn Cys Met Thr Lys Ile Val
850                 855                 860

Glu Ser Thr Leu Phe Arg Gln Ser Glu Cys Arg Glu Val Leu Leu Pro
865                 870                 875                 880

Leu Leu Thr Asp Gln Leu Ser Gly Gln Leu Asp Asp Asn Ser Asn Lys
                885                 890                 895

Pro Asp His Glu Ala Ser Ser Gln Leu Leu Ser Asn Ile Leu Glu Val
                900                 905                 910

Leu Asp Arg Lys Asp Val Gly Ala Thr Ala Val His Ile Gln Leu Ile
            915                 920                 925

Met Glu Arg Leu Leu Arg Arg Ile Asn Arg Thr Val Ile Gly Met Asn
930                 935                 940

Arg Gln Ser Pro His Ile Gly Ser Phe Val Ala Cys Met Ile Ala Leu
945                 950                 955                 960

Leu Gln Gln Met Asp Asp Ser His Tyr Ser His Tyr Ile Ser Thr Phe
                965                 970                 975

Lys Thr Arg Gln Asp Ile Ile Asp Phe Leu Met Glu Thr Phe Ile Met
                980                 985                 990

Phe Lys Asp Leu Ile Gly Lys Asn Val Tyr Ala Lys Asp Trp Met Val
                995                 1000                1005

Met Asn Met Thr Gln Asn Arg Val Phe Leu Arg Ala Ile Asn Gln
1010                1015                1020

Phe Ala Glu Val Leu Thr Arg Phe Phe Met Asp Gln Ala Ser Phe
1025                1030                1035

Glu Leu Gln Leu Trp Asn Asn Tyr Phe His Leu Ala Val Ala Phe
1040                1045                1050

Leu Thr His Glu Ser Leu Gln Leu Glu Thr Phe Ser Gln Ala Lys
1055                1060                1065

Arg Asn Lys Ile Val Lys Lys Tyr Gly Asp Met Arg Lys Glu Ile
1070                1075                1080

Gly Phe Arg Ile Arg Asp Met Trp Tyr Asn Leu Gly Pro His Lys
1085                1090                1095

Ile Lys Phe Ile Pro Ser Met Val Gly Pro Ile Leu Glu Val Thr
1100                1105                1110

Leu Thr Pro Glu Val Glu Leu Arg Lys Ala Thr Ile Pro Ile Phe
```

```
                    1115                1120                1125

Phe Asp Met Met Gln Cys Glu Phe Asn Phe Ser Gly Asn Gly Asn
            1130                1135                1140

Phe His Met Phe Glu Asn Glu Leu Ile Thr Lys Leu Asp Gln Glu
            1145                1150                1155

Val Glu Gly Gly Arg Gly Asp Glu Gln Tyr Lys Val Leu Leu Glu
            1160                1165                1170

Lys Leu Leu Leu Glu His Cys Arg Lys His Lys Tyr Leu Ser Ser
            1175                1180                1185

Ser Gly Glu Val Phe Ala Leu Leu Val Ser Ser Leu Leu Glu Asn
            1190                1195                1200

Leu Leu Asp Tyr Arg Thr Ile Ile Met Gln Asp Glu Ser Lys Glu
            1205                1210                1215

Asn Arg Met Ser Cys Thr Val Asn Val Leu Asn Phe Tyr Lys Glu
            1220                1225                1230

Lys Lys Arg Glu Asp Ile Tyr Ile Arg Tyr Leu Tyr Lys Leu Arg
            1235                1240                1245

Asp Leu His Arg Asp Cys Glu Asn Tyr Thr Glu Ala Ala Tyr Thr
            1250                1255                1260

Leu Leu Leu His Ala Glu Leu Leu Gln Trp Ser Asp Lys Pro Cys
            1265                1270                1275

Val Pro His Leu Leu Gln Arg Asp Ser Tyr Tyr Val Tyr Thr Gln
            1280                1285                1290

Gln Glu Leu Lys Glu Lys Leu Tyr Gln Glu Ile Ile Ser Tyr Phe
            1295                1300                1305

Asp Lys Gly Lys Met Trp Glu Lys Ala Ile Lys Leu Ser Lys Glu
            1310                1315                1320

Leu Ala Glu Thr Tyr Glu Ser Lys Val Phe Asp Tyr Glu Gly Leu
            1325                1330                1335

Gly Asn Leu Leu Lys Lys Arg Ala Ser Phe Tyr Glu Asn Ile Ile
            1340                1345                1350

Lys Ala Met Arg Pro Gln Pro Glu Tyr Phe Ala Val Gly Tyr Tyr
            1355                1360                1365

Gly Gln Gly Phe Pro Ser Phe Leu Arg Asn Lys Ile Phe Ile Tyr
            1370                1375                1380

Arg Gly Lys Glu Tyr Glu Arg Arg Glu Asp Phe Ser Leu Arg Leu
            1385                1390                1395

Leu Thr Gln Phe Pro Asn Ala Glu Lys Met Thr Ser Thr Thr Pro
            1400                1405                1410

Pro Gly Glu Asp Ile Lys Ser Ser Pro Lys Gln Tyr Met Gln Cys
            1415                1420                1425

Phe Thr Val Lys Pro Val Met Ser Leu Pro Pro Ser Tyr Lys Asp
            1430                1435                1440

Lys Pro Val Pro Glu Gln Ile Leu Asn Tyr Tyr Arg Ala Asn Glu
            1445                1450                1455

Val Gln Gln Phe Arg Tyr Ser Arg Pro Phe Arg Lys Gly Glu Lys
            1460                1465                1470

Asp Pro Asp Asn Glu Phe Ala Thr Met Trp Ile Glu Arg Thr Thr
            1475                1480                1485

Tyr Thr Thr Ala Tyr Thr Phe Pro Gly Ile Leu Lys Trp Phe Glu
            1490                1495                1500

Val Lys Gln Ile Ser Thr Glu Glu Ile Ser Pro Leu Glu Asn Ala
            1505                1510                1515
```

Ile Glu Thr Met Glu Leu Thr Asn Glu Arg Ile Ser Asn Cys Val
1520                1525                1530

Gln Gln His Ala Trp Asp Arg Ser Leu Ser Val His Pro Leu Ser
1535                1540                1545

Met Leu Leu Ser Gly Ile Val Asp Pro Ala Val Met Gly Gly Phe
1550                1555                1560

Ser Asn Tyr Glu Lys Ala Phe Phe Thr Glu Lys Tyr Leu Gln Glu
1565                1570                1575

His Pro Glu Asp Gln Glu Lys Val Glu Leu Leu Lys Arg Leu Ile
1580                1585                1590

Ala Leu Gln Met Pro Leu Leu Thr Glu Gly Ile Arg Ile His Gly
1595                1600                1605

Glu Lys Leu Thr Glu Gln Leu Lys Pro Leu His Glu Arg Leu Ser
1610                1615                1620

Ser Cys Phe Arg Glu Leu Lys Glu Lys Val Glu Lys His Tyr Gly
1625                1630                1635

Val Ile Thr Leu Pro Pro Asn Leu Thr Glu Arg Lys Gln Ser Arg
1640                1645                1650

Thr Gly Ser Ile Val Leu Pro Tyr Ile Met Ser Ser Thr Leu Arg
1655                1660                1665

Arg Leu Ser Ile Thr Ser Val Thr Ser Ser Val Val Ser Thr Ser
1670                1675                1680

Ser Asn Ser Ser Asp Asn Ala Pro Ser Arg Pro Gly Ser Asp Gly
1685                1690                1695

Ser Ile Leu Glu Pro Leu Leu Glu Arg Arg Ala Ser Ser Gly Ala
1700                1705                1710

Arg Val Glu Asp Leu Ser Leu Arg Glu Glu Asn Ser Glu Asn Arg
1715                1720                1725

Ile Ser Lys Phe Lys Arg Lys Asp Trp Ser Leu Ser Lys Ser Gln
1730                1735                1740

Val Ile Ala Glu Lys Ala Pro Glu Pro Asp Leu Met Ser Pro Thr
1745                1750                1755

Arg Lys Ala Gln Arg Pro Lys Ser Leu Gln Leu Met Asp Asn Arg
1760                1765                1770

Leu Ser Pro Phe His Gly Ser Ser Pro Pro Gln Ser Thr Pro Leu
1775                1780                1785

Ser Pro Pro Pro Leu Thr Pro Lys Ala Thr Arg Thr Leu Ser Ser
1790                1795                1800

Pro Ser Leu Gln Thr Asp Gly Ile Ala Ala Thr Pro Val Pro Pro
1805                1810                1815

Pro Pro Pro Lys Ser Lys Pro Tyr Glu Gly Ser Gln Arg Asn
1820                1825                1830

Ser Thr Glu Leu Ala Pro Pro Leu Pro Val Arg Arg Glu Ala Lys
1835                1840                1845

Ala Pro Pro Pro Pro Pro Lys Ala Arg Lys Ser Gly Ile Pro
1850                1855                1860

Thr Ser Glu Pro Gly Ser Gln
1865                1870

<210> SEQ ID NO 5
<211> LENGTH: 20
<212> TYPE: DNA
<213> ORGANISM: artificial
<220> FEATURE:

```
<223> OTHER INFORMATION: PCR primer

<400> SEQUENCE: 5
tggtgacaca gggacagtgg                                                     20

<210> SEQ ID NO 6
<211> LENGTH: 19
<212> TYPE: DNA
<213> ORGANISM: Artificial Sequence
<220> FEATURE:
<223> OTHER INFORMATION: PCR primer

<400> SEQUENCE: 6
caccccaact agcacgtgg                                                      19

<210> SEQ ID NO 7
<211> LENGTH: 21
<212> TYPE: DNA
<213> ORGANISM: Artificial Sequence
<220> FEATURE:
<223> OTHER INFORMATION: PCR primer

<400> SEQUENCE: 7
acagtccatg ccatcactgc c                                                   21

<210> SEQ ID NO 8
<211> LENGTH: 20
<212> TYPE: DNA
<213> ORGANISM: Artificial Sequence
<220> FEATURE:
<223> OTHER INFORMATION: PCR primer

<400> SEQUENCE: 8
gcctgcttca ccaccttctt                                                     20

<210> SEQ ID NO 9
<211> LENGTH: 727
<212> TYPE: PRT
<213> ORGANISM: Homo sapiens

<400> SEQUENCE: 9
```

Met Pro Pro Pro Ala Asp Ile Val Lys Val Ala Ile Glu Trp Pro Gly
1               5                   10                  15

Ala Tyr Pro Lys Leu Met Glu Ile Asp Gln Lys Lys Pro Leu Ser Ala
            20                  25                  30

Ile Ile Lys Glu Val Cys Asp Gly Trp Ser Leu Ala Asn His Glu Tyr
        35                  40                  45

Phe Ala Leu Gln His Ala Asp Ser Ser Asn Phe Tyr Ile Thr Glu Lys
    50                  55                  60

Asn Arg Asn Glu Ile Lys Asn Gly Thr Ile Leu Arg Leu Thr Thr Ser
65                  70                  75                  80

Pro Ala Gln Asn Ala Gln Gln Leu His Glu Arg Ile Gln Ser Ser
                85                  90                  95

Met Asp Ala Lys Leu Glu Ala Leu Lys Asp Leu Ala Ser Leu Ser Arg
            100                 105                 110

Asp Val Thr Phe Ala Gln Glu Phe Ile Asn Leu Asp Gly Ile Ser Leu
        115                 120                 125

Leu Thr Gln Met Val Glu Ser Gly Thr Glu Arg Tyr Gln Lys Leu Gln
    130                 135                 140

Lys Ile Met Lys Pro Cys Phe Gly Asp Met Leu Ser Phe Thr Leu Thr
145                 150                 155                 160

```
Ala Phe Val Glu Leu Met Asp His Gly Ile Val Ser Trp Asp Thr Phe
                165                 170                 175

Ser Val Ala Phe Ile Lys Lys Ile Ala Ser Phe Val Asn Lys Ser Ala
            180                 185                 190

Ile Asp Ile Ser Ile Leu Gln Arg Ser Leu Ala Ile Leu Glu Ser Met
            195                 200                 205

Val Leu Asn Ser His Asp Leu Tyr Gln Lys Val Ala Gln Glu Ile Thr
    210                 215                 220

Ile Gly Gln Leu Ile Pro His Leu Gln Gly Ser Asp Gln Glu Ile Gln
225                 230                 235                 240

Thr Tyr Thr Ile Ala Val Ile Asn Ala Leu Phe Leu Lys Ala Pro Asp
                245                 250                 255

Glu Arg Arg Gln Glu Met Ala Asn Ile Leu Ala Gln Lys Gln Leu Arg
            260                 265                 270

Ser Ile Ile Leu Thr His Val Ile Arg Ala Gln Arg Ala Ile Asn Asn
            275                 280                 285

Glu Met Ala His Gln Leu Tyr Val Leu Gln Val Leu Thr Phe Asn Leu
    290                 295                 300

Leu Glu Asp Arg Met Met Thr Lys Met Asp Pro Gln Asp Gln Ala Gln
305                 310                 315                 320

Arg Asp Ile Ile Phe Glu Leu Arg Arg Ile Ala Phe Asp Ala Glu Ser
                325                 330                 335

Glu Pro Asn Asn Ser Ser Gly Ser Met Glu Lys Arg Lys Ser Met Tyr
            340                 345                 350

Thr Arg Asp Tyr Lys Lys Leu Gly Phe Ile Asn His Val Asn Pro Ala
            355                 360                 365

Met Asp Phe Thr Gln Thr Pro Pro Gly Met Leu Ala Leu Asp Asn Met
    370                 375                 380

Leu Tyr Phe Ala Lys His His Gln Asp Ala Tyr Ile Arg Ile Val Leu
385                 390                 395                 400

Glu Asn Ser Ser Arg Glu Asp Lys His Glu Cys Pro Phe Gly Arg Ser
                405                 410                 415

Ser Ile Glu Leu Thr Lys Met Leu Cys Glu Ile Leu Lys Val Gly Glu
            420                 425                 430

Leu Pro Ser Glu Thr Cys Asn Asp Phe His Pro Met Phe Phe Thr His
            435                 440                 445

Asp Arg Ser Phe Glu Glu Phe Phe Cys Ile Cys Ile Gln Leu Leu Asn
    450                 455                 460

Lys Thr Trp Lys Glu Met Arg Ala Thr Ser Glu Asp Phe Asn Lys Val
465                 470                 475                 480

Met Gln Val Val Lys Glu Gln Val Met Arg Ala Leu Thr Thr Lys Pro
                485                 490                 495

Ser Ser Leu Asp Gln Phe Lys Ser Lys Leu Gln Asn Leu Ser Tyr Thr
            500                 505                 510

Glu Ile Leu Lys Ile Arg Gln Ser Glu Arg Met Asn Gln Glu Asp Phe
            515                 520                 525

Gln Ser Arg Pro Ile Leu Glu Leu Lys Glu Lys Ile Gln Pro Glu Ile
    530                 535                 540

Leu Glu Leu Ile Lys Gln Gln Arg Leu Asn Arg Leu Val Glu Gly Thr
545                 550                 555                 560

Cys Phe Arg Lys Leu Asn Ala Arg Arg Gln Asp Lys Phe Trp Tyr
                565                 570                 575
```

```
Cys Arg Leu Ser Pro Asn His Lys Val Leu His Tyr Gly Asp Leu Glu
            580                 585                 590

Glu Ser Pro Gln Gly Glu Val Pro His Asp Ser Leu Gln Asp Lys Leu
        595                 600                 605

Pro Val Ala Asp Ile Lys Ala Val Val Thr Gly Lys Asp Cys Pro His
    610                 615                 620

Met Lys Glu Lys Gly Ala Leu Lys Gln Asn Lys Glu Val Leu Glu Leu
625                 630                 635                 640

Ala Phe Ser Ile Leu Tyr Asp Ser Asn Cys Gln Leu Asn Phe Ile Ala
            645                 650                 655

Pro Asp Lys His Glu Tyr Cys Ile Trp Thr Asp Gly Leu Asn Ala Leu
        660                 665                 670

Leu Gly Lys Asp Met Met Ser Asp Leu Thr Arg Asn Asp Leu Asp Thr
    675                 680                 685

Leu Leu Ser Met Glu Ile Lys Leu Arg Leu Leu Asp Leu Glu Asn Ile
            690                 695                 700

Gln Ile Pro Asp Ala Pro Pro Ile Pro Lys Glu Pro Ser Asn Tyr
705                 710                 715                 720

Asp Phe Val Tyr Asp Cys Asn
            725

<210> SEQ ID NO 10
<211> LENGTH: 228333
<212> TYPE: DNA
<213> ORGANISM: Homo sapiens

<400> SEQUENCE: 10
ggcccgcgga gtccagcgaa gtttggcgga acatggcgga agcgtctggg gcacgcagga      60
gcgcggggcg gcggcggccg gagcccgagg agctgtagca gccttagtcg ccgccgccgc     120
ggggcgaggt cgccgccatg gcccgctgga tcccgaccaa gaggcagaag tacggggttg     180
gtgagtgcgc gccccacctt gtcccggccc gacccacgcg gccaagttcg cggacagcgg     240
ccctgccagg tttgcgcaga gccggcgga ggaccctggc cggggctcg gcccggctgc       300 gcagctctgg gagccgggga cggtaggagt cctctccagg gagcgccgat ggggaagtcg     360
cccagggttt ggggactccg agtgcttcca agtgcagctg agcttcggga ccgtaatccc     420
gctcttgcat cccaatctcc ggcacttcac accagggaaa tgtcaacgcg aggggggcgc     480
gcctgctgct cttttggggc cgcagctctg tggctcgccc cggtgcgccc agcgtgggtt     540
tcacctggga gtaggtgacc agcccgggtc ggcacatgga ctggtgctca ttgtcccagt     600
gctttctgcc cccgctttc gtaggttctt ctcagacgcc ccttaagtga ggagttgagg      660
gtggaaagcc gccctgcccc ctttcctcca gagactggga tcttgatgac agttgtgagc    720
tggatggaaa ctagagtcgt ggcgtggaag tgatggaagg acaggaagt tgtggcacgg     780 gaaggggtg gctggcccct ggggctgttt gtgcgcactc atcccctaac ggagcctgtc      840
tggagagggt gtaaggctgc cttccggatc ctgagtttca tcctggagac gagaaggagg    900
cattttatta aggaaactgt gccagacccc gtgctgggca cttggcattc agaacagcgg     960
tgctggagag ccccgggttg tgcgcagggg ttgctggtgg tggtgctttg gctccgaaac    1020
aatagatgtg cggggatttt gacccaggtg gaaagtcagg ctcctttggc tttttatcaa    1080
ggattgaagt tattgagggc ctgtgggaag acttctgccc tgaacggggt gattacaatg    1140
gcagttagac ctggggtgat tccctacaat aaacacggct gagtgtgttg cgaatttat     1200 cacttcctct cagatccatt catttggcct gtttgtaatt tagtctttga ctttactccc    1260
```

```
ttactgaggt cctgtttttc ctcacctcac tggttaatga agtgcagtct caattaagag    1320
ctactcaacg tgtctagggg cttttcaact ctgtagccag gagtcagggt ttttgttgt    1380 tgtttgtttt gttttttaac agtctcatat ttactatatt attcttaggt tgtgatcctt    1440
tatatattta ttatttttg ttttccctca attcaaaaga catttctttt tttgctctta    1500
agttgctttt agaatcttag tctctcccct agctgcatct cagaaatggg tagagatgtt    1560
gcttctgcct cagggctctt ttttttttt ttttggttt gtttgttttt gagacggact    1620
gacgagggag tctcactctg tcgcccaggc cggagtgcag tggcgcaatc tcggctcact    1680
gcaagctcca cctctaggtt ccagcaattc tcctgtctca gccccctcc ccgagtagct    1740 gggattacgg gcttgcatca ctacacctga ctaatttttg tatttttagt agaaaccagg    1800
tttcgccatc tgggccaggc tggtctcaaa ctcctgacct caggtgatcc gcctgcctcg    1860
gcctcccaaa gtgttgggat tacagtcatg agccacctca cctggcccct agatgaaagc    1920
atatttacaa tgcccaatca ctacagaaat gttatcaact ctaattttat caggattaaa    1980
agctcttttc aaaactattc agttgagggt aattaatgca aacatgtttc aaaaatgtgg    2040
tttttattgc catagtccta ggagcaagta taattgtttt taatattttg tttttatgtt    2100
ctggagtcag tttactgtgt cacttatcag tcaagaaaaa tatttgggcc aggtgcgatg    2160
gctcacgtct gtaatcccaa caatttgggt ggcagaggca ggaggattgc ttgagcccag    2220
gagttcaaaa ctagcatagc aacatggcaa acgggtcttt acaataaata cgaaaaaaat    2280
ttagccgggc atggtcgcct gtgcctgtgg ttctagctac tgaggaggct gaggtgggag    2340
gatagcttga gcctgggagg ttgagggtgc accgagcccc catcacgaca ctgcactcca    2400
gcctgggtga tactgtgaga cccgatctca aaaaaaaaac tatatataca tatatatacg    2460
tatatatata tatacacaca cacacacacg tatacacaca catatatgta tatatgtata    2520
tacatatata tgtatatatg cgtatatgtg tgtgtgtgta tatatatatg tatatggaaa    2580
tatgggtgga aattgtgtgt gtgtgtgtgt gtgtgtgtgt gtgtaaaaa tatttggatt    2640 gcatttccag ggcctaggtg ttagggaaac tgctccagga tataattctg aacacttatt    2700
tcaccagaca tagattctgg tttgtctggg tttgacaaaa ggaccacag ttgggataaa    2760 ttaactgaag agagaaatct ccattgctta ttgctaaaac tcattgtttt tgtcacctcc    2820
ttgcttatgt ttatgtcacc tccctgcttg gaagtctctc gtggtcaaca ggataaagtc    2880
tgagcctccg ttccaaggtt cctataatct ggttcagcct atcttcagca ttatctctcg    2940
aggcttcttt cactagctct ccaatgcaga ccaactgccc ttcccactgt tgtgcaacat    3000
accctgcaga gtccctcctt tgggactttg ctcccattgt gcctgtccct gccaggagtg    3060
ccctcccaac tctgcctcag acagctcacc ttccttgag ggctcaaatc cattcctact    3120
cccttcttca aatttgctat ttgtcagact gtcccaaacc tccttgcttc ttcctcgcag    3180
ttcctggact gtgccatcct tgggttcagt gaatcagacc attgtggttt tgtattccta    3240
gcactcaaca ggtgtaccag gtattagtgc attcagtttg cttgtccttg atgttgggt    3300 gccgttctaa agtacactaa cctagcttgt ctggtaattg aatgcagttt tttcctcttc    3360
tttttcttcc cattaggcat aacatctcat tcacccccaat atgagttgaa ttttgtttgg    3420
ttagatggag gaagggagag cctccactct gtctttatct ctgcaagtaa gagaatgaga    3480
tattctgctg agaaaacaag gaagcatgga gcagacagac tttcttaaat atagttggga    3540
aaattggctt tctggacttc tctaagtgtg tactggtcag atttggtttc tggatgaagg    3600
```

```
aaccgtagga tagtcatgtt gaagcatttg gatgactcag agctagctat gactttgcct   3660
gttgtgctct aagaggagtg tgcctctgca gagctagtct gtgtgaggat agagctttgg   3720
actcagtatg aattgtgcct gctgaagctg gcagtcgcta ctgtcatatt ttatcttggt   3780
gccactcttg gctgttcctg acatatccta gatgtttcta cagggactga aatgcagcct   3840
gtctgggctt tcttagttct taaacagcag tgttggctca ggctctagca ttaagtggat   3900
ctcaatggtt tctgtgtgtt atcaagtgaa gtgactgatc tatttgattc tttaaactta   3960
tggtgctcta gtaccccagt gttaagtgct cagtggctaa gtgttcttcc ctggagacgt   4020
ggaaaatgtg ctttttttctc atcttttttc tttctttgtt tctctttttct ctctcttttt   4080 tctgtttgag catatgaaga tataaaacac ttttaagcaa acattagtga taaatatcca   4140
gaatagtctg attataaaaa catttatttt taagtttgct tccacacaag ccattatgta   4200
aagaatagcc ccagattagg ttgactatgg attctttgca aagcttttttt ttcttttctt   4260 ttctttcttt ctttctttttt tttttttttt ttttgagac agggcctcac tccacagccc   4320
agactagagt acagtatgat catagctcac tgcaacctgc catctcagcc ttccaagttg   4380
ctggaactgc aggtgtgcac caccatgcct ggcttaagtt ttttgatttt taagttttta   4440
aaatattaaa cttttaaaat aatcatttta aagatggagt ctttctatat tgtccaggct   4500
gatctggaac tcttggcctc gtgtgctcct tcagccttaa gcctcccatg ttgctaggat   4560
tacaggggtg agccatgagc ctggctgatt tttttttctt ttcttctgag acagggtctc   4620
gttctgtaac ccaggataga gtgcagtggc aaaatcatgg ctcactgctg cctcaacttc   4680
ctgggctcaa gtgaccctcc agcctcagcc cgctgagagc tgagagctac aggtgcgtgc   4740
caccacaacc agttgatttt tgtatttttt gtagggatgg agtttcacca tgttgcccag   4800
gctggtctgg aactcctagg ctcaagcagt ccttctgcct cagcctccca aagtgctggg   4860
attacaggca tgagccacca cacccagcct tattctttga aaagtagctc attgttgcat   4920
gttgggattt tgtgatcacat atatttttat gatgtaacaa aaggcagttt tgggaaatat   4980
tactagttag ctcttcaggt gtttacttgt ttaaagctct ttagttgttt agaagcatct   5040
gacttaacgg agtagagctt tgaatgctga tttaagactg acttcagact tgggcttttg   5100
ttgtgttttt gtttgcttat tgtttttgtat tttgagatgg agtcttgctc tgtcgcccag   5160
gctggagtgc agtggtgcaa tcttggctca ctgcaacctc tgcctcctgg gttcaagcga   5220
ttctcctgcc tcagcctcct gagtagctga gattacaggc gcacgccacc acgcccggcc   5280 agttttttgta ttttttagtag agacggggtt tcaccatgtt ggtcaggctg gtctggaact   5340
cctgacttca tgtgatgtgc ccgccttggc ctcccaaagt gctgggatta caggcgtgag   5400
ccaccgctcc tggcccagaa tgtttttaaa tgcataaagt acgatacaaa gttccaagtc   5460
actgtagaaa taaaaattaa gtaaattaca aaggatagaa aatgaaaaca gccgtattga   5520
aataggccgt gaaggtgttt ttcaaagttc gtgatactgc agtatatgta cttctttatt   5580
aatgcataaa gtaccaagat ctagtgacag gtctaataac tagcataatt ttgaattagt   5640
cacgagcata tatgattttt caagatatct gcagtaacca tactatgata taaaaatccc   5700
tgttttattg gtgacagtat cacaggcgct agtagtgcaa ttgcggttta ttggctacag   5760
tcgtaattaa agtgagtgct gaatgtcaga aaatagagat gtaacttttt tcttgttcaa   5820
gttcgtggat cctctggatt taacagatta agtatccttg gctgaggatc acatagctaa   5880
ttagttacag tgccatctga gcaagacagt gatacttgtt gaccacctct ttgcacataa   5940
cactgtaccg gatattatat aattataatg acccgaagaa ggcctggcct taacttggtc   6000
```

```
atgggttttt ttttttttttt tttttttttt gagacggagt cttgctctgt cgcccagggt    6060
ggagtgcagt ggcgcgatct cggctcactg caagctccgc ctcccgggtt cacgccattc    6120
tcctgcctca gcctcccgca tagctgtgac tacaggcgcc cgccactgcg ccaggctaat    6180
tttttgtatt tttttagtaga gacagggttt caccgtgtta gccaggatgg tcttgatctc    6240
ctgaacttgg tcatgtttta acagcattga ggctaagaac aaaaggaaga gagaattagt    6300
attcattgag aacttctctt gtgaggtacc attctgaacc ctttatttta gtatgttcca    6360
gggacatgtg gggtcttgga gacacgttca gaatggggggg ggtccatgaa attaaaactt    6420 tcttttttgca ataatgctaa gccgttattg gcctgtttac attctcattc tctcgttagt    6480
ggagttttcc agaggctttg caaagtgcga tatggccacc gatggaatgc aggggcagct    6540
ataaagaccc agctgcctat agtgaagtca gacattaaag agacttccaa atatgcaaaa    6600
caaagccacg cttccaagtg ttttttgtttg agaaaatagt tctgttcctt gaaaatatgt    6660 attttttacaa acatgtattg gatttatcat agttatttta aattaattac caactacttt    6720
ttgaatgttt caatttgaat ttctgatatg gcaagttgtg atagatgtca cccacataga    6780
agctctttgg tggttctcag taactttttaa gcaagtaaag gggttctgag acaaacatttt    6840 gagctgctttt acctgttatt tcattaaatc attgtggcag tgatatgaaa tgctgttgtc    6900 ccctgttttct gatataggaa atgaggtttg cagaagatga gtttctcatc catggccata    6960
taatctcact ccaaaaacaa aatctttttt ttaaaattat atatatatat ttattatact    7020
ttaagttcta gggtacatgt gcacaacgtg cagttttgtt acatatgtat acatgtgcca    7080
ttgtgtgctg cacccattaa ctcgtcattt acattagtta tatctcctaa tgctatccct    7140
cccccctccc cccaccccac aacaggccct ggtgtgtgat gttccccgtc ctgtgtccaa    7200
gtgttctcat tgttcagttc ccacctgtga gtgagaacat gcagtgtttg gttttttgtc    7260
cttgcgatag tttgctgaga atgatggttt ccagcttcat ccatgtctgt ccctgcaaag    7320
gacatgaact catccttttt tatggctgca tagtattcca tggtgtatat gtaccacatt    7380
ttcttaatcc agtctatcac tgatggacat ttgggttggt tccaagtctt tgctattgtg    7440
aatgtgccac aataaacata catgtgcatg tgtctttata gcagcatgac ttataatcct    7500
ttgggtatat acccagtaat gggatggctg ggtcaaatgg tatttctagt tctagatacc    7560
tgaggaatcg ccacactgtc ttccacaatg gttgaactag caaaaacaaa atatttaacc    7620
catgttgtgt ttcccaagtt ccacttgttc atcgtcacct tggttttgcc ctgttcaggt    7680
accactgtgt agcagcttca gggctattgc tatacccatt tccatctgta ttcttttttg    7740
tttttctttt aagagatagg gtctcactgt gttgcccagg ctggagtgca gtggtgcaat    7800
ctcggctcac tgctgcctgg acttcctgag ctcaagcgat tctcccacct cagcctctgg    7860
aatagctgga actacagaca cacactacca tgcctggcta attttttgttg ttgttgtttt    7920 cgtagacaca gggtttcact gtgtttccca ggctggtctt gggctcctgg gctgaagcag    7980
tcctcctgtc ttggcctccc aaagtattgg gattacaggc gccagctacc acgctcagcc    8040
tatactattt tctatgttat attttctttta tattgtctgc ttgttttcttt ttttaattttt    8100 agcagttact gaaaagaaa gccttatctt tctaccacta cttgctgtag aaaagaaaca    8160
attgtaaaaa tgaaagcaac aaaaataaaa gcggtgtatt agattctggc tagatactgt    8220
tgctgtcaag cctagagccc cagacctgct ttttcttcat taaaaaagga ggaagctgat    8280
acccaatgga atctttctct tcagtatagt gtccattctc attattcatg gtaattatgt    8340
```

```
tctatttagt cacagtgaac actgagttag tgaatactga cccgttgctc ctaggggaga    8400
ggcagggttc ctgtgagcct ctggtcacaa gcttttcatc agccaatcaa tacataacct    8460
tattttatgt gtgtttgtgt ttaaagttac cttatttaac atatatagtt ggttcactaa    8520
cattgagccc atggcaaaaa gcactgtaac tcatgcctga atgaagaaac ttatctaacg    8580
tgtattttt tttttaaggc acattacagc tttttttttt ttgcatttag gtacttagac    8640
agcactgtag cactatgctt gggaccattt taaatagaaa aatcaccagc aaaaagcaca    8700
aaaatgaggc caaatgtggt ggttcacact tgtaatccca gcactttggg agactgaaac    8760
gagaggattg cttaagccca ggagtttgaa accagcctgg gcaacgttgt gcaaccccgt    8820
ctctacaaaa aaaaatacaa aaattagctg ggcatggtag catgtggttg tggtcccacc    8880
tacttgggag gctgaggtga gaggatcatc tgagcctggg gaggtcaagg ctgcagttag    8940
ctgtgatcgt gccactgcac tccagcctgg gtgagcgagt gagaccctgg tcaaaaaaaa    9000
ggcagaaaaa taagagaaat gtggcagtaa atagaccctg aaaagacac ttgtttacaa    9060
tatgttagcc tgaaaaaga atgcagagcg tcaccttgct cacccttagc taggaacttg    9120
tgcaggagta ttggttttaa ggttccatgt atattttagt gagtaggtga attcgcaaat    9180
atggagtctg tcaacaatga ggatctactg tagtttcaca aaacgataat tgaagccggg    9240
catggtggct cacacctgta ataccagcac tttgggaggc tgaggcgggt gtatcacctg    9300
aggtcagaag ttcgagacca gcctggccaa catggcgaaa ccctatctct aaaaaataca    9360
aaaaaaaaaa aaaattagcc aggtgtggcg gtgctcacct gtcattgcag ctactaggga    9420
ggctgaggta ggagaattgc ttcagcccag gaggcggagg ttgcagtgag ccaagatcac    9480
gccactacac tccagcctgg gtaacagagc aagactctgt ctcaaaaaaa taaaagataa    9540
ttgaaaatgg aatcacttcc tttcccatg tgtttgtttt tgttcacata ttggatgcag    9600
ttgactttac ttctagaaac attttcttct ctagactttt gatcccattt ctccacagtt    9660
ttcctcccat atccccaccc tccatcctcc ctgccttccc tccgctttgc cacaacttta    9720
agtcttgcca tagcctggct ggcttttgtg tctcctttat ctacctgata acaagtgatc    9780
tcatcccccg ccttggctct cattcccatt catttgctgc agccttccac atggatagcc    9840
ccagacccct tccctgtgct tcgggatcac atacagctgt tcactgggcg tctcccagtg    9900
tttttcttaa caggcagtcc ctgcttccag aacagaagtt tggatcctct ctaaccccag    9960
aaccgcactt tccccagttt cttgctgtct gtccagtggc ccaggcagaa cactaagagt   10020
cacccccacat tctatctgtc atcaagtgca gtctgtcctt cctccaaaat atgtcctcag   10080
attactgctg ctgatgtttc catttcaatg caagcctgca ttagcgtctg cagggctact   10140
gcaacggtat ttttttttt ttcttttggg gacggagtct cgctctgtcg cccagactgg   10200
agtgtagtgg cgcaatcttg gctcactgca acctccacct cctgggttca agtgattctc   10260
ctgccatagc ctcccgagta gctgggacta caggtgcgca tcaccacacc tggctaattt   10320
ttgtatttt agtagacatg gcatttcatc ttgttgacca gtctgatctt gaactcttga   10380
cctcaagtga tccacccgcc ttggcctccc aaagtgctgg gattacagga atgagtcacc   10440
acgcccagct gcaatggtct tctaactgga ctccttatca ctttttttt tttttttttt   10500
tttttaagat gggcatcttg ctttgttgcc caggctggtc ttgaactcct ggcctcaagt   10560
gattctcctg cctcagcctc acaagtgctg gaattacagg catgaaccac caagcccagc   10620
taagaggaac ttttttaaagg caagaacctg acattgccac ctccctgctt ccaccttccc   10680
attgcagttg ggatggcact gaagttcctg gtcatgccct cccggccctg tgggatcaga   10740
```

```
cctgccgcct ccctctttcc cttctgcatt ccagccacac cagctttatt tctggttttt    10800
gaacttgcca agctcagctt gactcaggac cttggcactt actcctccct cttatggaat    10860
gtgtttccct agatctttag atgtccggtt ctctggtctt ccttcaaata atccctgctt    10920
agagagagcc ttctctgaga agaaccctag ctgcatgatc ccacctcctt gctgacacct    10980
cacaatgtct agccctttc ctttatttat ttgttagtgt ttactgtctg tctcccatac     11040
tagaatgtaa agttatgagg acacgaactc tttttcatca gtgtgcccca gccctggaa     11100 tagcacctgg ctcatagtaa gtcctcagtg aatatatgct gtatgaataa atgaatactg    11160
accccatcat ctctttaaat tcatcttgct taccatcagc aggattttgc ccacactttg    11220
gaaaatacca ccctgtgtgt atttcccatg agagaaacat caaaggcaga gagaaaggga    11280
cattcaagta atggagaaaa tagatttaat aaactgcata agcaaaagat tacgtgaatc    11340
ctgtggggtg ggtgaggact tagaatcata aatgttgcat tattagatgg aagtgatggg    11400
atttgctttt ttattttgg gtcattattt ctggaggctt tatggaggaa ggggcactgc     11460
agacttggct acctggaaag aaaatgcttg accatgtggt gtacagagtt taggaggttc    11520
tgagtcattg gttggtgctg tgttgagcac atgaattgga aaggaaagaa ggcgcagtct    11580
catggaagaa acaagacatt tagattcatc tgttatttcc catttctaat acaaggagtt    11640
gagattcctt acaaaagag catatgtact gtacactcaa taattaaata aaaaatctga     11700
gaaatcacaa gtaatttgga gaagaagaaa agtaattta gaatactggc aagggctttt     11760
gaagccatgg ttactcaaac attagtctgt ctaaattttt cttgtggcca tagctgtcat    11820
gtagccatct tgttagctga aaatataaat taatttgtgt tttctcctca tctaaatttc    11880
aagagacaaa tcagtggggc ttgaatgtaa ggaatcaaat ctcattgtac ttaattttac    11940
cataaagcaa agtttttcta acttctagct tattgccagc agtattcaat gcaatgacgt    12000
tataatgcaa tgcatataaa agattttagt actttcaaaa gaattaaaaa aaaggaatca    12060
tccagttctt tggaatgagt tgtagcggaa ttgaaccgta tgtctgtggt caaggaacac    12120
acagtttgtt cttcactaaa tattttggct gggcaccgtg gctcatgcct gtaatcccag    12180
cactttagga ggctgaggct ggaggattgc ttgagcccag gagtttgaga ccagcctggg    12240
caacatagtg agaccctgtc tattatttaa aaaaaaatt agtagaaaga aaaatcgttt     12300
tccccttcct caaacaggta aaatcaccca gaatatgcct actctccgtg gacattaaag    12360
gacataataa gccctttggg agtcctttga ctgatttata actacaccag catacctccg    12420
gaataatggg ggttttattg tcaagcttta taaaagtgtt ttttgagaaa ttattttgag    12480
gcagagatgt ggatgagcac gttaattgtg ttttccaag taatgtttgg gccatgtcct     12540
ctcagagcct gggctcactc aaacgattgt ctgaatgctg gcagccactt cccaagcaag    12600
agacagaagt gggctttgtc tttcagaaag ctctgtgcca ttgcaaagcc actgttgttc    12660
gaatgggttc atggtcatta tccaccttt cccaaatgtg ccgtttgctc tcatatttcc     12720
acagctgatt aaaccctgtc actatccaca tcagataata gttggacccc aaagatgccc    12780
tctctttaag gatcgtgtct ttgtcttttt ttttttttt ttttttttt ttgagaagga     12840 gtctcgctct gttgccaggg tggagtacaa tggcgtgatc tcggctcatt gcaaccttcg    12900
cctcctgggt tcaagagatt ctcctgcctc agccacccaa gtagctggga ctacaggtac    12960
atgcaaccat gccaagctaa ttttttttt ttttttga gacggagtct cgctctgtca       13020
cccaggctgg agtgctgtgg cgcaatctcg gctcactgca agctcagcct ccctgtttca    13080
```

| | |
|---|---|
| cgccattctc ctgcctcagc ctcctgagca gctgggacta caggtgccca ccaccatgcc | 13140 |
| cggctaattt tttgcatttt tagtagagac ggggtttcac tgtgttagcc aggatggtct | 13200 |
| cgatctcctg acgtcgtgat ccgcctgcgt cggcctccca aagtgctggg attacaggca | 13260 |
| tgaggcactg tgccggtgtc tttgtctttt aaaacagctt gagggaagga aaacacagtg | 13320 |
| gagactaatt ccctcttgaa ataactcttt gctgactca gccaaggtgc attagaatgc | 13380 |
| accctcctga tgggtttgtt acctgtatac ctgcaacaag ttgcatcgta tttgatttgt | 13440 |
| actttctgtg agcctggaac aatgcggctc tcatgaccca gccttccctg ccagagacca | 13500 |
| gttataagac gaagtgacga ccagacacgg tgtctcatac ctgtgatccc agcactgtgg | 13560 |
| gaagctgagg cgggtagatc acccgagatc aggagtttca agaccagcct ggccaacatg | 13620 |
| gtgaaacccc atctcgacta aaaatacaaa aattagctgg gcatggtagt gtgtgcctgt | 13680 |
| aatcccagct atgcaggagg ctgaagcaca aaaatcactt gaacccggga ggcagacgtt | 13740 |
| gcagtaagct gagatcgtgc cactgcactc caacctgggc aacagagcga gactccatct | 13800 |
| caaaaaaaaa aaaatactaa gtcataaata agactcagtt gtcaaaatct aacagttttg | 13860 |
| ccctcttgta tgtagaatca gaagatatta agagccggag tttgtaagta ttacctcttg | 13920 |
| gctaacaccc tcattttatc agaagaaaaa agcccccaga gacatcagat gacttaccta | 13980 |
| aaagtcacac agctagtagc aaattttttgt ttcaacttgc tgtctatctt tctccttact | 14040 |
| tacaactctg gagaggggtt tgttaatcag atctccttaa ggttggaaga gtaaattctc | 14100 |
| ccctctccat ccaaagggga agatgcctgt gtctcctggg ttttttccag gtggaggttt | 14160 |
| tgttataagt aaggtttggc tgttaaatat cttccctttt ttaagagttc taggaaggaa | 14220 |
| gtgtgtttga ggaggtttga gcctgcaaag tggaagtgac actgtgggtt gcacggtttg | 14280 |
| gccactgact tctcacgtgg tttcagtcct tagcaccgtg gtattgacat gacatcagtt | 14340 |
| gcaaaattaa taagtaatgt ggcattgtta ctacatcaca ggcatatttg agaatgaaca | 14400 |
| tcactgtgtt ttgcaaagta aacgtttaag gggtgaagaa agggtcatgt attgctaata | 14460 |
| aaggattatg ttagtaacct ggatgtgaga gaacatttct acttttcag acctgtattt | 14520 |
| caaataaaat gtgatgtcat cttctgaaga cttaggaaaa gtttgagtga gtaagcgcct | 14580 |
| tctccctcag cttccatttc cgctctgttc ttttttttt tttttttttg tgagacggag | 14640 |
| tcttgctttg ttgcccaggc tggagtgcag tggcaccatc tcagctcact gcaacctcca | 14700 |
| cctcctgtgt tcaagcaatt ctcctgcctc agcctcccta gtagctggga ttataagcat | 14760 |
| ttgccaccac acccggctaa ttttttgtatt ttagtagaga cggggtttca ccatgttggc | 14820 |
| caagctggtc ttgaactcct gacctcaggt gatcctcccg ccttggcctc ccaaagtgtt | 14880 |
| gggattacat gcgtgagcca ccacgcccaa ccaacttctg ctctatttc tttgctggga | 14940 |
| gtggacagct ttactctgga ggaggagatg cagcctcttc tcatgcagag acaatcactg | 15000 |
| tcattctcca tcgggagcaa actcctgaaa tggggcaata tctacccacg tggaaccaga | 15060 |
| ggtgctggtg ctggtgctgg tgctgagctt tgaacttcct tcagaacaaa agtaaacagc | 15120 |
| aagttgccct tgttctttac cataagcaga aaggcctgt ctatccaatt gtgactgcat | 15180 |
| gatttgtttt agatttgtta atttacatt tgcagaatac tgaggcacat tttctgtgaa | 15240 |
| cttatgtggt tatatatact ttcaatcagt ggatactgga agcattgtta tacatttgat | 15300 |
| gtcttttata aaagaatcct aagggccaaa aatgttggga actttggagt aactgaaatg | 15360 |
| gcaatgtgct gtatcttatc ataatacttt ggagttcatt tgacttgaa aattccaatt | 15420 |
| aaagttggta taacctctat catgtattga ttaaaaatgc acatacccctt tgacttagca | 15480 |

```
actccgtttc tctgagttta tcttacaaat atactccaca tgtggggaat aatacatgga    15540
caaggttatt cattatagca ttatttatac caaaaacatg gaaactctca agtgttggct    15600
aattggggat ggatttagta atttatagca catgcataca atggaaaact atatagccat    15660
taaaaagatt ctgacgcagt gatagataaa gtgttgacaa aggtgagagt ggcatgtagt    15720
ggttgaagga tgatcttttc aaaaaatgat actgagtcgt ttgtttatct atactgaaca    15780
aaatgtatca ggaccsctac ctaataccac ataaaaaatt gattccagct gtatgaaaga    15840
taaaacagtg gaagctctta gaagaaaaca taagagcaca tttttgttac cttagaatag    15900
accatctgta atttaataca ttttgctttc tgccattcag ttagttactt atgaccatct    15960
ctttgttaat caacaaaaac caaatccaat attttacttc aataaagggc aaaataaaac    16020
atgcctgtgc tggtctcatc tctttataat cctactttt aaaacttgta taattacatc    16080
ttattaattg tagtgttaat ttgttggttg tttaaggatc taaatggcta tttcttcttc    16140
ttctttttt gtttgagatg gagtcttgct ttgtcactta ggctggagtg cagtggtgca    16200
atctcggctc actgcaacct ccgcctcctg ggttcaaaca attcttctgc ctcagcctcc    16260
tgagtagctg ggattacagg tgcatgccac catgcccggc taattttga attttagta    16320
gagacagggt ttcaccattt tggtcaggct ggtctcaaac tcctgacctc aggtgatccg    16380
cccacctcgg cctcccaaaa tgctgggatt acaggcgtga ccactgtgg ccggcctaaa    16440
tggctatttc atggtgaata aaccattagc ctcaggcttc gtctcctctc tctgtttgaa    16500
gacaataaag tatgatgtaa ttgtattatt ttgataaggt aatatttagt cccatgacat    16560
acaaaacact agtagcatta cataaaacaa agtatttcaa tagtgaaaga gaacatttat    16620
atacaattat ttctatagtc taacagtatc actaacatta catgcctttt aaaaaatatg    16680
tttgagttac tgaagaagat tgagatacag atgttgactt gtttagggca acaggttaag    16740
ctaactttag aacgctgatt actacccttta gtcctgcagg ctgtggagcc gggcagccaa    16800
gccatgcttg aaatcagaat cgtcaaggtg gatgcaagag ccattggctg cagagtgagg    16860
ttttggagag tagttgcttg tggctgggat ttttgaagtc caagtctcct aacttttatt    16920
actctttacc ttgtgaagtc atataaggct ctaagtcaag taagacggaa ggaataagat    16980
tagcacactt cctggtacag tgggcagtac gtgatagcta tctgaaagtt tgctcagtcg    17040
cagcctccct gacagtaccc tagcctggca atcaggtgcc tttgtttgca gagtggggct    17100
gattaccaag tagttaatac tggttggctc agaacctgtc ctcaaagttc agaatagatt    17160
tgagtatatt tttgattta gagccttatg gccagaaatg gcttatctt gcaagaatct    17220
tcctgggaaa aaaacatata tatatatatt ttttctttct ctttgagaca gagtctcgct    17280
ctgtcaccca ggctggagcg cagtggcaca atcgtggctc actgcaatct ctgcctcccg    17340
ggttcacgcg attctcctgc ctcagcctcc ccaagtagct gtgactacag gcatgcacca    17400
ccaccccag ctaattttg tattttaga agagataggg ttttgccatg ttggccaggc    17460
tggtctcgaa ctcctgtcct caagcgatcc acctgcctcg gcctcccaaa ctgttggcat    17520
tacaggtgtg agccaccgca cccacccctg gaaatatttt gaattcccag ggatctctgg    17580
gtgatgggac tgttactttc ttctgatcct gtgcttttgg ggtggtactc actcactggc    17640
ttagaacagc ctggaatcct aagaggaatg gatgaatgaa tgaattcaca cacaacaaac    17700
taacggaaat gttttgagtc acgccaccttgc gtgtgaat ccccttactg tggctaaccc    17760
acctcactgt tctgaggaag cccatgttca ctgagcacct tttatgttcc agggtcttgc    17820
```

```
tgggctggat ggtggtgagg atcacacagt agtcccgcct tatcctcaag gcatgcttga   17880
aaccacggat agtacccaag cttgtatata caatgctgct tctatacaaa tatatttatg   17940
ataaagctga atttctaaat taggcacagt aagaggttat caacaataac taataataaa   18000
aaagaacaat caacacaata tgccagtatt accactcttg cactttgggg ccatgattaa   18060
gtaaaataag ggtgacttga acaccagcac tgcaataccc cggcagtttg ttttgaatt    18120 ttttatttta atattttgg accttgagta cctgaagcca cagaaggtga cacaggggac    18180
actaggagac tactgtgtaa gataaagagt ctatagaaac acacatagaa gcagtaggca   18240
gggattcata atggctgctt tccttttctt tagcttgata agagtgctac caaatacatc   18300
tccagtgtca tgaattcatg gatgtgtgac cagtagctct tggccagcca tttctggtct   18360
taacacccag atcatcatag aatatgagga taggaatcca ctgatgacag aatcctgaat   18420
gactatctta tgtgcctgaa agcctgcctc aaagaaggct gatgtcttct tgaattaaag   18480
agttgcttgc atatagaata tactggagtc attttcaga agatcctac atggcttggc     18540 agagggtggc atccagttta tctttggcgg aattagattt gctgctcaag attgttttca   18600
aattgtttga tagcttcagg gaggtccact ggtaagctca caaattcaga aatagtttga   18660
ggctacagaa gaattctttt catgtttgag ctgtgatcta agccaagagc cttggaaatt   18720
ttgaatccgt cttatatttt ctttcctgaa tgagaaatgg gtatacttgc tcagttccga   18780
ttctgacaac atgacttatt tcaaaaacaa atagctcact ccgtgaagca aaccctgtat   18840
cactctcctc tggtgacatt tcgattctga tacaatgtgg tggcatgggg atagattta    18900 gaccaggaaa agagagagcc tctcatttgt ggcccaaaag actcaatttt aaagatcaga   18960
ttggaatctg tcaggagga catatggaca tagtgatttt ttctttatt tgccttttt     19020 cgcctctctt tacttttggt ttaatgtctt ttaggacttg aggtacaaaa tcccatgttg   19080
tggaggcatt agctaacagt tgtaaaacct taggaaaagt acagcatctc agtgatcctg   19140
ccttcctaaa attgctcctc aacaaataca gatggaggaa atagaaatat ctaaaatgaa   19200
acgtgttctt tcgtcttaga tgtctttatc ttcttgcttt tatcagcagc cttgagtgac   19260
aggattttat acttttggaa gattagaggg tttgttgtt tttcttgcag aaatagttac    19320
ttataccatg ttcatttatc tgcctcagtt ctgagaattc tttgccaatt tttttaatag   19380
catgtgtttg gatgaattat agacttcata gaagtaactt caggaattat cgacttcata   19440
gtcgatacaa cataatgaga ccctgtctgt actttaactt tttaatacaa gaaattttt    19500 aaaattttag gggcatttag gttttttgggg gatagtgcat ggagtgaaac taacagaagt   19560
attgatccca ggattaggaa gttgggtttg tatttcagtc tctgttacag gagtgaccaa   19620
gtggcttgac tctctttagc ttagtttttc catctgcaaa acagagataa tatttctat    19680 taccttctag attctcagag tgtgatgaat tttcagttgt tgaaaatttc tgcaaatgaa   19740
ttaagcgatg cctgttaggc cacattaatg gactaaaaac tgctaggatc taaagttgac   19800
atgccattga acttctgcc tgaagactta ctgaggaaac tttgtctaca aaggtttggt    19860
gcaaagaacc ccattacttt atggccaaat ttcttcaca tgccgatggt aatccagtag    19920
tctttcttct aacttcttgg cggctttcat atactcttca gactggctaa gtcatacgtt   19980
aataggaaga actaattttc tctccctgag gctgaacttg tgatcttttt catctggttt   20040
ccacttctca gatttcccca aatctctcag tcgtctttcc caaagtattt aaaggaagat   20100
tgattttaac agagtgctat ggactgaatt atgtccctca caattccta tgttgaagcc    20160 tcagccccta gtgtgatggt atttggagat gggtcctggg agataattag gtttagatga   20220
```

```
gttcatggtg gggccctcat gagggggatta gtgcttttt taaaaaaaat tatttttaaa   20280
aatgtctttt attaaaaagt taattaaagt acagacaggg tctcattatg ttggccaggt   20340
tggtcttgaa ctcctggcct caagcaatcc tcccacctca gcctcccaaa atgcttggat   20400
tacaggtgtc agcccctgtg cctggtctct tcttttatgt ggagagcgct ctccctctct   20460
ctcgctcttg ctgtctctca ctctctctcc ctctgtctct ctctttctgt ctttctcttt   20520
ctctctctat gctatgtgag gatacaatga gagggtggcc acctataagc cgggaagaga   20580
gccctcaccg gaaactgacc atgatggtaa cttgatcttg gacttccagc ccccagagct   20640
gttagaaaac acatttctgt tatttaagcc acatggtgtg tggtattttg ttatggcagc   20700
ctaagctgac tgagacacag ggagttgcgt gttatttgaa atacgagtcc actgttgcca   20760
gatcaaagtt caatctctgt agtttaatcc tagattttc cctcctcttt tacagggatt   20820
tgaatctagt gaaagtaatt cacatgcaca tcagatacat gcctttagca gccttctggc   20880
cttgaaaatc ctgctgttgc tgattcagtt gtcagggccc aaatcagctg gtgaactcat   20940
gagtttgcag gtctagaatt gtaggtgtgg aaggggaga gagacatggg ttactgaaga   21000
cttgtgcaaa taaatgctgt gttcatcttc accgattcac caggtatctg agtaggaggt   21060
atgcacttag cacttggaat actcagagat aatgccattg cacacttaat tgatacttct   21120
cctaacactt aagagaagtg gacatagatt ctgtttgtgg gaagtttata atgaattaaa   21180
agaccccaag tataaagcca taaataactc cagggaaagg aaggctgaac atgaaaaag   21240 ttgcaaaaaa agtccagttg gggttattgg agtttagaga agcagagatt attctaattg   21300
agggagttga ggaagcttca gggaagtagt tgaactttat agagatggac atcaggtttg   21360
ggaaggctgg ggacctggca cagcgtgagc cctggcccta acgcagttat ttgtggcaag   21420
tggataatga ggaagttgtc cattcttgct gaagcaaagg gtgggtaaag tggaaaagag   21480
ggaaatgata tagattttgt cagattatgg ggagacttgt ttaccttgat ttttttttctt   21540 cctctttaac cattcatgct gcaatagtgt gctggtaaac tagctctgta gagtgggagg   21600
aaaaaacttg agtttgtagc attcaccaat atctgtggtg taaatactcc cacagtggcc   21660
aatttcagac cagcagtgga ttaagagata gctcacagaa ttcctgaaaa ttcctgaaaa   21720
tgtaacagtt ggcccttcca aactagtaca agtttgctcc agtattctgt gaaaaacctg   21780
ggctagttcc tacatgacaa atagttacag tacctgcctg cccacagcct ggatagaaga   21840
cccagggaag gcctaggtag cctcgtttta caccatctaa gattcctgtg gccatcactg   21900
attgtccctg gatggacaca ctacctagag gccattccgt agcctggaca atgacatatg   21960
gtttgacgca aagaagtaag tactcaatca ggttccttct cttgggaatt tgaatgagga   22020
aataccaata tgttttgcca caggggcaaa agctaaaagg atgtcgtttg ggagttgagt   22080
tggtggcaac ctgaagccat gtggaagcca atgttgtgaa tggaaaccac aaggaaactg   22140
aaaaagctga ttgatagaga gagggagca gatgtggaga gaccctacag ccctagagtg   22200
gcccctgttc ttagcagctt tccaagtcca ggtctaaaac atccctttc tgaggcaatt   22260 tgagtgagtc tctgttcctt gcaataccgt ggcatcactg aagaagttta tgtggcaact   22320
cagggtactt tgcagagctt tctatgaatg cagacatacc tccttctata tagcacatca   22380
ctttattgat cgaccataag attcatggtc gatcaataaa gcaatggttc atgaagtttg   22440
atgaaagaag tttaataaaa gaagccattg ccatagcata gaagtgcaag gtgaggcagc   22500
aagtgctgat atagaagctg tggcaagtta tccagaagat ctagtgaaga tattgatgaa   22560
```

-continued

```
agtggctaca ctaacaacat attttaagtg tagatgaaat agccttctat tgtaagaaga    22620
tgctgtctag tactttcata gctagagagg agaagtcagt gacgggcatc aaaggatagg    22680
ctgaccctct tgttaggggc taatgcagct ggtgacttta aattgaaacc agtgctcttt    22740
caccattctg aaaaatctga gggcccttaa caattatgct aaatctactc tgcctgtgct    22800
ctataaatgg aacagcaaag tctggatgac agtacatctg ttgacagcat ggtttactga    22860
ctattttaag cctactgttg agacctacag ctgagaaaaa gaagattcct tgattcaaaa    22920
tattactgcc cattgacaat gcaccaggtc acccaagagc ttagatggag atggacaagg    22980
agattaatgt tttcatgcct gctgacacaa catgaatact gcagcccatg gatcaaggga    23040
taattttgac tttcaagtct gattatttaa aagaatacat ttcatgaaat ggtggctgcc    23100
ataaatagtg attacgctga tggttctagg tgtagtacat taaaaaccct ctggaaagga    23160
ttccccattc taaatgccac taagaatatt gatgtttcat gggaggaggt caaaatatca    23220
atattagtag gagtgtggaa gaaattgatt ccaattctca tggatgactt tgaggggttc    23280
aaaacttcag tgaaggatgt ccctgcagat gttgtggaaa tagcaagagc actagaatta    23340
gaagtggagc ctgaagatgt gagaattgct gcaatctctt gataaaactt gagcagagaa    23400
gagttacttt ttatgaatga gcaaagaaag tggtttcttg agatggactc tatcttggtg    23460
aagatgctgt gaacattgtt gacaaccaag gatttagaat aatccataaa cttgttgaca    23520
aagcagtgga aaggtttgag aggattgact ccaaatttga aagaagttat actgtgggtg    23580
aaatactatg aaatgctatc aaatagcatc acatgctata gagaaatatt tcatgaaagg    23640
aagtatcaat tgatctggca aacttaattg ctgtcttatt ttaagaaatt gccacagctg    23700
ccccagtctt cagcaactgc caccctgatc catgagctgc tatcaatatc aaagcaagac    23760
ccttcaccag ccaaaaaatt aagagtcctt gaaggctcag atgatcatat gcattttttt    23820
agcaataaaa tattttcaaa ttaaggtctg tacatttttt agacataatg ctattacaca    23880
cttaattgac tgtagtgtaa acataacttt tataggcaca ggggaaccga aaaatttgtg    23940
tgattggctt tactgcaata tttgctttat tgcacagtct ggaaccaaat ccacagtatc    24000
tcctaggtat gcctatatag caaatttctt aagaatagag gacaaatcac ttgcttctga    24060
ttgaggttaa aatatgccca tgaccttcat ttctttgcct tccctccctc cctgcactcc    24120
tcccaaatga cttgtgaata ttattttttc attcttttc attccagcag agctggtttg    24180
gaattcatga tgttgaaaga atagccagta ggaacatgtg gtggggtgat gttttgttgg    24240
catttaccat tacagaaaat cacaagaaaa ttggagccat tagcagcagg gaaaggaaaa    24300
tgagttcttt atctgctgag ggcatctggt gagggagggt ctgtgaagat gccgcgggtg    24360
cactgctcta gtatgaaatg ccatttgaag gaggctcaga gcacattagc gccgtcatcc    24420
ctgtctgatg ttctcaccac acgcaagttc gtgaataatt aaattgttag gaagggaaa     24480
gtcatgcatg gcgggtcttg cccgaggctc aggcagacac acaatgaggt cgctactctg    24540
ggagcccagt ggtccaggat gccagtctgg cagtgccagg gaaggatgct tcctttcaat    24600
aagcgaacat tgtgagggag cggggtggag gcaagagacc gcttagaaat cagcacatgt    24660
gaattctgct tcaaactctg ccactaacca gctatttgac cttccagaag ttgcttcttc    24720
atctataatg aaggatgatg ccaagaggat tttaactttt tgagaaataa agctcctttg    24780
agactgtaat gaaagctgtg gattctttcc acagaaaatg gtgcatatgt ctgtcgatga    24840
catttcacat acaactttag gaagtttaga aatcttgggg gactcaagga tcccagctta    24900
agaagaagtc ttgcatgaga tgatgtctga acttttttttg tatctctaca attgcatttt    24960
```

```
tctgagactt tggatcttgg aaggaaccta gaatgtcagc tgggctctca cttctactct    25020
caacaagagg caagcctgcc ctgccagcat ttcgtgcaga aggcgcaagc aacatgggag    25080
cctcctgtgt tttcctcaaa agacaccata cttcttttc attagagaca gggtctcagc     25140
ctcgctctgt tgcctagagt gcagtggcgc catgatcctc cccctcagt ctcttgagct     25200 gctgggacta caggcacatg ccaccatccc cggctaatta tatatatata tatatatata    25260
tataaatgtg tgtgtgtgtg tgtgtgtgtg tgtgtgtgta tctgtctatt tatctatcta    25320
tctatctatc tatctatcta tctatctatc tatctatcta tctatcgagt agagatgggg    25380
ccttgctatt ttgtccaggc tagtcttgaa ctcttggcct caagcgatcc tcctgccttg    25440
ggctcccaaa gtgctgagat tacaggcatg agacactgca tctggccctc tataacctct    25500
tgatgtgtgc attctaagcg ggaagaaaca gacagcaaat gcacagtatg tatagcatga    25560
tgtcagtgat cagggctttg aaaatattga tgaagcacag tgatgccata gacagtgatg    25620
gggtgaggtg ctgttgtcga gttgggatgg tcagataacg gctctgtgga ggggatatgt    25680
gggaaaagat gtgaataaaa gagggattgg gaccgggcgc tgtggctcac acctgtcatc    25740
ccagcatttt ggaggccaa ggtggatgga tcagttgagg ccaagagttc aagacaagcc      25800
tgcccaacat ggagaaaccc catctctact gaaaaataca aaaattagcc aagtgtggtg    25860
acacatgcct gtaatcccag ctacttggga ggctgaggca tgagaattgc ttgagcctgg    25920
gaggcagagg ttgcagtgag ctgaggtggc accactgcac tccagcctag cgacagatc     25980 aagactgtct ccaaaacaaa aaagagggac tgagccatgc aaatctaaag taagaacatt    26040
ctaggcagaa gatgtggcac agttaaggag cagtggaaag tgccaatgtt cctggagctg    26100
aatgagggga gggggaaggg aggagggaga ggtgggagac aggttgagag actggcagag    26160
ctgaggttgg ggtagttctt tgtctactgg aaacacaatt atctgtactc aaatgacatc    26220
taataataat ggttattgat aagccaccca ttcatttcat aggcttggtt cattaccagc    26280
aatgggctgc tttaataaga cagtggtcct caaacctcct tctgtcaaca gcacctggat    26340
agcctgcttt gcagagtacc attggaatca gatatccctg tctttaagga acttacagta    26400
cagcagaggg gacaggatgg tgtctccatt attttgtgca catgggagaa ttgctgtgtc    26460
tcataagaga agcacagaaa gtgccaaata gagtttcagg agaggaagtg agtactatct    26520
attggagagg tcaggaaggc cccagggaac aactacgcca gttttatcac ccatgcactg    26580
gggatggtat tagaacctcc cacagcattg tatagataaa ctgtttgagt gcctagaaag    26640 cttttccacac agggcctggc acacacctag taagtgctca ataaaatatg gcaagcatt    26700 tgacttgcgt cttaaagaag gtttacgatt tctgaaatat aaaatgctgt ctgtggccag    26760
gcacagtggc tcatgcttgt aatcccaaca ctttgggagg ctgaggcgga aggatcactt    26820
gagcccagga gtttgagagc agcctaggca acatagagag accacatctc tgcaaaaaca    26880
ttaaaaaatt agtctggtgc agtggtgcat acctgtagtc ccagctactc tggaggctga    26940
ggcgggagga tcgcttgagc ccaggaggtc aaggctacag tgagctacta tcatgctgct    27000
gcactccagc ctaggcaaca gagcaagagc ctatctctaa ataaattaat taattaataa    27060
atgctatcta cgtagtttat catgcagatt ttttagaaat acagcttccg ccgggcacgg    27120
tggctcatgc ctgtaatccc agcactttgg gaggccgaga tgggcagatc acaaggtcag    27180
gagatcgaca ccatattggc taacacggtg aatccctgtc tatactgaaa atacaaaaaa    27240
attagccagg catggtggcg ggcacctgta gttccagcta ctctggaggc tgaggcagga    27300
```

```
gaatgacgtg aacctgggag gcagagtttg cagtgagccg agattatgcc actgttttcc    27360
agcctgggtg acagagcgag actccgtctc aaaaaaaaaa aaaaaagaca gcttccatgt    27420
aaagaactat tcaggtcaaa atagctagct attttttttt aaatctggtt gtttgcttta    27480
tgagtagtct taattaacaa gaggatcaag attttttccaa atctaaatcc atctgtatag   27540
ccttgttcag gaaacatttt gttcttgact ttggcttgtg tttgatacac ttgaactgtc    27600
tgtgttattt attgcttctt taattagagc agcttttaag gaccaactgt gggccaacag    27660
tgtgctaagg gccacgggca gtttcatgt ggggtcttga aagagcttac attctagtcg     27720
gggaaataag aagtatacac aaaagtcaaa ttatgttgag tcttcattat gtgggtacca    27780
cctaggaagg ggactggatg tacctctgct caaaacatct ggatcccatt tcacttgcga    27840
agtctgtttt gaaaggaaat atccagatgt gtcacgtgac tgtgaccaat tcatctgaag    27900
tagctagaga gtgtctgaat aattttattt cgatgcttgc aagagagagg gtcgaaaacc    27960
cctttatgct ggactagagg aaaacctcag caagggaggt ctgtgtcagg ccagcgtgat    28020
tctagatggg gctgacacca tcctctaccc tccccagcca tggcagggaa atgctcagga   28080
aatagattaa ggcacgaggg cttggcgtgg cttaattgac ccctgagttt tgactgccaa    28140
aaccctgaat aaggatgaat ctgctgtttg gagaatattc cctgagcaat ttaaaggcta    28200
gtttctgggt ttgcagaaaa aggcaaggtt cactgtgaac ggagtcttgg aggttgccta    28260
caatggtcat gggtggacga gtttgttgga aaagcccccg tgactgggct ctcggtagag    28320
tggcagggcg tgtgtgttgg aatggaagat ggaaagttaa accttgggct cagtgggcgt    28380
ctaatcaaga gagaagtttc ctgtgcgtca ggcccagacc taggaaacgg ggaaggtctc    28440
cgtgtttcca gcctcagcct caaatgaatg ggcaccagga tgggccgcag tgacttctcc    28500
ggggtctctc tgatgtccaa agctctcccc acacccagat attttgttt cacaggaaag     28560
tcaggagcct cctgaaaaca gacatgaatg tagcaaaaaa aaaaaaaaa aaaagctgat     28620
aatctctagg tttcatcccc cttctggctg ctgcagctat ttgtaacctt tcctttgtgt    28680
gcgtctggta gtgtccccttt tttgaagcct tttaacgttt gagaaactgg agacctggtg   28740
tttttttgttt gtttgttttt ttgttttcct agttttact cttgtttagg gtctggcatt    28800
ttcatttttcc tcatgctaca tcagggttta attagcaact gtctttgaaa tagccttcag   28860
ggaggaatga actttctttg tgaataccctc ctcaccccccc aaagaaaagc agtaatgcaa  28920
attaaatgtg tatccagaat tgcagtcact ctaatcctga catcacaaac gcatttgttc    28980
ttggaaatga ctttggtgga gcctgacagt tttatgcttc ttactgtggc tgaggtggag    29040
tgtcctcttt agatgcaata agagatgggg gagaggttga tgctttgatt agtaaacctg    29100
ttacaggttg tgtgtcccttt atggaaagta cttgagacca gaagtgttt ggattttgta    29160
ttttttttcag attttagaat atttgtgtat acatactgag acatcttggg gatgggaccc   29220
aagtctaaac acaaaattca ttggtttcat atacaccttaa tgcacgtagc ctgaaggtaa   29280
ttttgtacaa ttattttcaa taattttgtc catgaagcca gtttgtgta cattgaacca     29340
tcagaaagca aaggcatcac tctctcatgg caacgctcta acagtttcag attttggagc    29400
attttggagt tcaggtttct ggattaggga tgctcagccc ttagcaggtt ctgttgtctc    29460
cctcactgac ccctctgctt ttagagaacg aattctctgc tttgctgtt cctctttgat     29520
cttaaccttg gatattttcc tctttctcct ggatgtttgg tatccaggag gcacagaga    29580
ggtgagcctg gaccccgtgt tgggtgtgtg tcttggggtc aagggatcct gggcacatga   29640
gtggggaagc catttctgag caccttgaa aaaggaaag tggcatttc acagcaaata       29700
```

```
tgggttgtgt ctaatctggt agttcccaat ttcaatctcc tatttacctc ttcaacatcc    29760
aggcgggtga cacacactgt cagtatctat aagtatacac agtgattcct gtaccttcac    29820
tgtaagactg tcagctgcca accctgacc cccaagcccc actgccactt ctcttaaagt     29880
gtgacttaaa tgccatcccc tggcacctct tttatcctgt gggaatagtc ttatcgattc    29940
agcagtcatc ggttggtcat taatcttcca caaccacgc actttatcat tgcgaaaggg     30000
gacagagagg atcaggatgt tgggttgtga cacgcgagag agcccatct gtccctggct     30060 gctccgctga ggtcatggta cagcacagag gaccagatgg gatggctaga atctgtgtcc    30120
taccctaact ttgttttat ccgccactgg ccagctgcaa atttgctctt gccagcagag     30180
gctagggcct ggaatgaaag acttcctata ctgctggctg gacatatttc tcccatgcat    30240
cagcagatga gcctttgaa gggtgagaca tgatctgtga ctagggctg tgggaaaaca     30300 tgcctgtcct ggagctgggg gaatcctgga ctccattttg gagagggagt catccagccc    30360
ccgttgggat atggttcttc aggccaggga aggccctaac aatggctcag ctggactctt    30420
tgtgtctgtt tgaaaaacag gggaattggg tgaccagttt gatttcagct ttaaaacatg    30480
gataggctag ggtgacactg ccatcaacat attccatggg aacagagggc ctttggacaa    30540
ggcagtgtct ctgggtgagg gtaggatggg ggtggggga tgtcttttct cctctgtcct    30600
ggatctgtag aggctgggga gagagagaga ggcacagaac tttcagtgct tcaagtgcag    30660
gaagtgtttc ttctacaccc cgatccccag taccctggcc atcatcagag gccgagtaag    30720
gtcactggtg caacttgtcc actatgtgac agttgccatt tattgtgaag gtaggacagt    30780
gactctcggg agggcacaga taaggagaaa ggaattcttc ccaagcaggg caggagagca    30840
atttgcaacc tactcaatcc cttggtcatt gtgttatttc tatttccagc aacatttctg    30900
acaacagtat gtatgattag aacacatctc ttttttttca cctttaaata taaaaaggc     30960 tttattaaag cagtactgtt ctgtttttaa tgaatatata ataattccta ttacaataat    31020
aacagaaagt gatagctatt aactttgata ttgcttcccc cagtttggat agagaaaagg    31080
ttattgtcat ttctatatta gattattaaa agtaacacct ctcagatttt tttcttaatc    31140
ttttcaaatc ctggaaataa atacacacac acacacacac acacacacac acacacacac    31200
acgtatacga tatgaatata tatctgcata cagtatgtat atatgtatac aacatgtata    31260
tacgtgtata caatatgtat atatgtatac aatatgtcta tacgtgtata caacatatgt    31320
acacaatgtc tatatgtgta tacaatatgt atgtatacaa tatgtctata cgtgtataca    31380
atatgtatat atgtatacaa tatgtgcata caatatgtat atatgtatac aatatgtgca    31440
tacaatatgt atatgtgtat acaatatgtg catacaatat gtatatatgt atacaatatg    31500
tgcatacaat atgtatatat gtatacaata tgtgcataca atatgtatat atgtatacaa    31560
tatgtgcata caatatgtat atgtatac aatatgtgca tacaatatgt atatatgtat     31620
acaatatgtg catacaatat gtatatatgt atacaatatg tgcatacaat atgtatatat    31680
gtatacaata tgtgcataca atatgtatat atgtatacaa tatgtgcata caatatgtat    31740
atatgtatac aatatgtgca tacaatatgt atatatgtat acaatatgtg catacaatat    31800
gtatagatgt atacaatatg tgcatacaat atgtatagat gtatacaata tgtgcataca    31860
atatgtatag atgtatacaa tatgtgtata caatatgtat agatgtatac aatatgtgta    31920
tacaatatgt atagatgtat acaatatgtg tatacaatat gtatagatgt atacaatatg    31980
tgtatacaat atgtatagat gtatacaata tgtgtataca atatgtatag atgtatacaa    32040
```

```
tatgtgtata caatatgtat agatgtatac aatatgtgta tacaatatgt atagatgtat    32100
acaatatgtg tatacaatat gtatagatgt atacaatatg tgtatacaat atgtatagat    32160
gtatacaata tgtgtataca atatgtatag atgtatacaa tatgtgtata caatatgtat    32220
agatgtatac aatatgtgta tacaatatgt atagatgtat acaatatgtg tatacatgta    32280
tagatgtata caatatgtat atatgtatat ataatatgtg tatatataca catatatacg    32340
tatatatgtg tatatataca cgaatgcagg agaaggtgat agcattgttc actttcctgt    32400
tgtagggaga gagagagata tatatatata tacacataca catgtataca tacaaatatgt   32460 atatatgtat acaatatgta tatatgtata ctatatatgc atatatatgc atatatacac    32520
acaatatcat attagtggga gattttaaa actagtttgt atttaaacaa ttaattatac    32580
tgatgatctc tggacacctt agtaatgaac aacttaaaaa cggggaactg aagttagggg    32640
tttgagtcac catgagttta ctgaagttac taccccctggg acttgccctg accagtagca   32700
ttcacttgtt ggagagtttg agattcttct ttctgtgcca gctgatacca gcaacgcatg    32760
tgccagacat caggcaaata gagttgttct aatgcctta gttccagtgg cacagaagtc     32820
agcagtcaag gttgggtgct tcttgggtgg gttatgttgg tggagaacaa tgtgtcaaag    32880
ttggtgggaa aatattattg cccagaccag cacctgcaag aagggaccc tgtctgtgat     32940 ttcagagagc catatggtag tttgagaggg tgcagtatgc atgacattaa tctaacattg    33000
aatcatgtag tgaggaaata attctttaaa aattctcttt cagtatttct ggtttcacca    33060
aagagaatgg gacatgttag taacgactct ctaacatttg caatcccagt cttgcaggcc    33120
actgcaccta ctaagattgt tctttattac ctttttattca aagggaatgg tgctggttt    33180 ccaattacta taagaaatc aatttaaata atttgatttc aaatacatct aaatgatgta     33240
cttatgagaa aaacagtgaa ttcgtttaag caaatagtaa gcaaataagt atcacaggtg    33300
gctgatggga ctgaaatcct ggaggcaggt acatgaacaa acagagcctg ggaaatcctg    33360
agctaggtca ttggtgtctc tggaatttgt tttcaagtgg gtttcatgaa tcttttcttc    33420
tatgaaagtt aaacttttta agatttttc agaatggtta tgacctgatt aagtgacagg     33480
gactctcctg cctccgtgga caggaatgga gtgtggaatc ccagggtgcc ctcaggttgg    33540
tcacacaggc tctgattatc atagggcatc cctgcagggc ccggggtggc cgcagagctc    33600
agcttctgtc ctggttacca cacacatgcc accatgacca ctgtgctctt acagttttat    33660
ttcacgctgc ttgcctccat agtgcctctg tgtggtgtct ggaccttgcc atggtccagg    33720
gacagctgga ttgttacaag ggggcatcac caatgtcacc ttagtggtgg ctaggagatg    33780
ttcctagtcc ctgactagta ggatctttta agtccctcct gtggtgttta tgacacgttc    33840
agctgtatgc tggggcaat ggacaatgca ggagaaggtg atagcattgt tcactttccc     33900
gttgtaggga taaatctaac atagaaggaa acactaaccg atttgtcaca attaaggact    33960
gtcttgtgtg gagcctctgt ggcagtgctg tggctcttct agggagaggc ttgaaggcta    34020
gagcaggaag acaagtttcc aggaagagag cttaggtggc aggaccttga aggctgggta    34080
acagaaataa taatcattgt aatcaaaata atgcatgcat atacttttta aaaatccaag    34140
gagcactaac aggcttataa tgtatcaagt aacactttcc ttcgtcttct tctcacccaa    34200
atctcactga tactcctttt taaagaggat tcttttggta ttcatattga tgactctaaa    34260
catgcttatt ttgctctctt gtgattcatc ggttttaggc attatttact gacttccgct    34320
atctgttggt agacgagtat ctgctcttct acctggctac ttccccctccc ctctgagtca   34380 caatttttt gttaaattca cattccatgt ttatgatatt atgactatgc agatattctt     34440
```

```
ggctgaataa aatatgtatt atgaccctga gcccttcctt gtacagtttt cttttctgg    34500
agttaataat tgcttcattt ctatgtcctc caatatatcc cctctgataa tctgtcagtg    34560
gcatgttttt ttattaaaga cctcatccct ggagcacttt ttctgttaat ttcaatctgg    34620
catagtcgct ctttatatct ctgtccatgg ctatcatccg agacctcctg tcctcctcat    34680
tttgggacct tccttttcct ctctccattg ttggattttg tctttcccct tcttggttta    34740
cttatttgtt tttctggatt gcatcctgta gtaactcttt gaggaaaggt tccgtggtaa    34800
cttttgagag cctaaatgtc tgaaaatatc tctattccac ccttccactt ccttgacagt    34860
ttgcacatag aacttgaaag tgttttccca tgggaataat gcatatgtag tagtctgttg    34920
tcctctgggg tccgtgtttt ttttttttga dacgttcaca accactttttg actttctgtc    34980
cccttcaact gtgacctggt tttttctttct ggaaggttct aaaatcttct ctttattttt    35040
gtgttggcat gccttggtag gaatcgtctt tccgttattt gtgctaggta ttcattgatt    35100
ccagaaagtt atgctcttta cctggaaact gtcttgtgtc atttaagata atattttctt    35160
cttactcatt ttgtatattc tttgtgaaat ttctaacaga tgttggtctt tgggaattga    35220
cccttttagtt ttcttcttct ttttttttttg tctattgtcc ttctcttttgt ttcacagaca    35280
tgatatttca tcttctctgc aggtatcaat gatcgctttg atattattat tattatttta    35340
gttttttcctc taaatacttgc actgcctctt tttctgccag gttttgtttt gtttcgtttc    35400
gttcctttcc tttcctttcc ttttctttgt gtgtgtgtgt gtatatgtag gtgtgtgtac    35460
ttcctgttag agaatttccc cagtggtttc ctggtccttg gccgcttgtt cctatataaa    35520
ggtgagaaac tgaaagttga ttggatgctc tgtgtatggc taggcatgtt gacgggtgga    35580
cttcacactt aactgccttt tttgttctct ttctctctaa gactttcaaa tgcctttatc    35640
tgtagaaatt tctctgtggc aattcagatt ctccaggaaa agattttctg atttcatacc    35700
gaggcaggac acacctgctg ctagggctct ttgtctgcag caggagggggc tgggtcaca    35760
gcacgtttca tgtgttctgt taccccccagc tctccacagg taccgggtgt ccctgaggcc    35820
ggaacatctc tcattcagtt ttgttttgtt tgtttgtttg agacagagcc ttgctgtgtc    35880
gcccaggttg gagtatagtg gcgcaatctc ggctcactgc aacctcgcc tctggggttc    35940
aaagtgatgc tcctgcctca gactcctggg attacagata tctgccatca tgcctggcta    36000
attttttgtat ttttgtagag ttgggggtttc accatgttgg ccaggctggt cttgaactcc    36060
tgacttcagg tgatccgccc accttggcct cccaaggtgc tgggattaca ggcacgagcc    36120
actgcgcctg gcctctcatt cagttttttac aggggatgaa ctttcctgtc tcccgtggga    36180
gtggagaagg gattgttatc tggacctgtg gaggggtgg gtagggatgg tggttatttg    36240
tcccatctct caaatttccc tgtttcttag cagtctacct ctccagtctg tccctaactg    36300
ggaccaagct acctatatca ctttatttct acagttcatt tttcagtccc ccccattgtt    36360
gggtatttag cttgtttgct gcttctccca gttattact gaactttatg tttaatttgt    36420
cttgtctttc tctttccaaa ggaatatatc tgataagtga aattattaga tcaaagaatt    36480
aaaatatttta aaatacttga agcttttttaa aagcttcagc tacattctgc caaatctttt    36540
ttgtttgttt gtttttttgag atggagtctc gctctgtcgc caggctggag tacagtggca    36600
cagtctgggc tcactgcaac ctccgtctcc tgggttcaag caattctcct gcctcagcct    36660
cttgagtagc cgggattaca ggcgcccgcc accatgcccg gctgattttt gtattttag     36720
tagagaaggg gtttcgccaa gttggccagg atggtctcaa tctcttgacc ttgtgatccg    36780
```

```
cctgccttgg cctcccaaag tgctgggatt acaggcgtga gccactgtgc ccggcccatt   36840
ctgccaaatc ttaaattcca cttctgctac ctaccatcat catcatctcc atcaccatcc   36900
catcatcatc atcatcatca ttagttgagt acttacaggg accatgctga gcagttttcg   36960
ttctcatctc atttaatcct cacaggaatc atgcataaag tgtacagtta ttcctcagat   37020
tggcagagga gaaatgaag gcttaaagaa gtttaatgac ctgtccagag ccccagggtt    37080
agtgggtgct tggagctggg acttatatcc aggctcacct aatggcatag taacgctgat   37140
catatcagct ccccactgcc agggctatgc tgacccatgc caaccaagac tcaccttcag   37200
ggcctttgag agtgaggaag tgtgctctga atcttacctt ttctcctgct gtcagccctg   37260
cgagttaaga gagagcattg cttttttgcta ggggttttttg ctgtttagga cactctgttt 37320
tctgtgaagg aaaaaggatg agttcgtgat ctcgctttct tcatgctggt ccactctgca   37380
ctgttattag atagaacaat gctctcccca aggtcctggc atatgattaa tgctttggtt   37440
tgctttctag ggtggctatg gatttgtctt tctttgaata attccagtat tatttcaaac   37500
gggatctgag aggcagacca tactcttgag ggccatgcct tattacttat gaattgtttc   37560
caaaccctgt cttttaaaata aatggaaata taattcagtg ggtcatatta tgttcacttc   37620
taggctgggg ggatatgaga gctctcctag gagtcaggtg gcctgaaccg gcccctgact   37680
cagatggtcc tttatttttct gagccgttga gtaaaagcgt gtgatatgcc ccgtctctag   37740
ctgtttcaca ggagttccat gagaataagt aagaagatct ctaaattcat tcttttaccc   37800
tctaatctga taggatgaag accaggaatc ataattattg ccacattaac acacttagtt   37860
agagcacatt agaaatcctt tcttcctttc taatctccct ttcttccatc tgttcctcgc   37920
ctccatcagg ggctcctggc agccctgggc tgtgtgtcct catcttccgc aagcaccaag   37980
cccatggcag ctcaatgaga ccttcataga ggctgtcggt cctcagcatt tccctgcctg   38040
caagcagatt cccatcatcc agtgaggaca aagtatgtga aatttgccaa aagtgtcttg   38100
cacgcttggt gcccttggca gctacgtcgc cagcagatga caccccaagt aatgcccttc   38160
ctaaagggct tctcacccta cctggagtac tgcttgccca ggtgcccatg aagtgcttcc   38220
atggaaagtc ctggaaccga ggagctaatt aatccatcct tgcttgagcc cagtggctta   38280
cctaggagcc aagttttgga atatgtattc agggtctcag tcccataaat aaagtacatg   38340
tgctggaatt ttttatgatt gggactattg atatgtgaag gtttttaaaa aaaatttttg   38400
aaatcttatt ttaaatatag agacaaggtc tcactacgtt gcccaggctg gtcttgaact   38460
cctggcctcg agtgatcctc ccaccttggc ctcccaaagt gctgggatta tagacacaag   38520
ctaccacatc cagccagaat gctttattta tttatttatt aatagacagg ttttttgctct   38580
gtcatctggg ctggcataaa gtggcacaat cacagctcac tgcagccttg actgccccag   38640
gttaagtgat ccttctacct cagcctcttg agtatctggg actacaggcg tgggccacca   38700
cgctcagtta attttttaaat tatttgtaga gatgaggtct cgctctgctg cccagcctgg   38760
tctccaactc ctgtcctcaa gcaatcgtcc tgtcttggcc tcctaccatg ctggaattat   38820
aggtgtgagc cactgcttct gggactggcc gtgattttta ataccaccaa caatgggcat   38880
aaaaaatgaa ataagagcga gtgataagaa tggtttgcta ttattgtcaa gagaggtaac   38940
ttacttttgt aacaaatgtg ttgattacac atttacttgt taagatggat ttgggcccctt  39000
ttgggtagat gattattttg ttttattaaa atctctctga gattaaattt ctgttaaaca   39060
gcgagaccct gtactttatg gatgaagcat tgaattcatg acctgtcaaa actgaggctc   39120
atcataacag acagtttccc tgaccatgct ttgtactatt ttgtacagca cttatcacct   39180
```

```
ccaatttctc tgttttattt actgctgtat ctccaacatg gagaacaagg ctaaattgca    39240
ctcagttaat atttgttgaa tgaatgaatg aggcattttt aactttatcc ttttttcatg    39300
ctttccacgt ttatatacta tccttgagtt ccaaatcttt gttttgtttt tttgttttct    39360
ttttctgaga cagagtcttg ctctcttgcc caggctagag cacagtggtg tgatcttggc    39420
tcactgcaac ctccgcctcc cgagttcaag tgattttccc gcctcaactg cccgagtagc    39480
tgagactaca gccgggcacc accacactca gctaatttat atattttag tagagacggg     39540 gtttcaccat gttggccagg ctggtctcga actcctggcc tcaagtgatc tgcccacctt    39600
ggcctcccaa agtgctggga ttacaggcat gcgccacagc tcccggcctt aatcatcttt    39660
gtcatttctg tgtgtaaaca aatatctcct tttcactatg tggcatatat tatggacatt    39720
cttatatcca tgagaaaaag tgcaaggaag tgtgtcactc tgaatcttac taacttgttg    39780
ttggaaaagg tacaaatgaa gtaagaacgc ttcaactagg ggagagaaac tttcatttaa    39840
aatagttatg gttgagggaa gatggactgc aaattgtaga ggctggcctg aggctcttct    39900
ctgcattgaa agacatggca tcatatttc ttcctataac acattagata taaaaacagc     39960
cagaaaggca accccatgt gttttataac aaatcaaata atacagaaat gtataaagaa     40020
aaagttactg tgttcattgg ccccacctct gctctgggcc accctggcac ccttctcagg    40080
agactgatgt gaagaaagtc atctgcccta cagcttaacc atcaaaaaac ctcataactc    40140
aattaacaaa tgggcaaaaa acttgaaaag acgtttcttc aaagaagata tgtaaatggc    40200
cacgagcata tgaaaagatt ctcagcacca ctaagcagta tggaaacgca caacaaaacc    40260
acaatgaaat atcacctcac atccattaga atggctgtta tcaaaaacaa aaacaaaaa    40320 ccaaaataaa tggtcatcca ggatgtggag aaattggaac tcttgtgctc tgctggtggg    40380
aatgtaaaat ggtgcagtcc ctatggaaaa cattgtggta gttcctccaa aaattaaaga    40440
tagaattacc atgtgatcca gcaattccac ttctaggtat atccaaaaga actgaaagca    40500
gggtctggag gagatatttt tacactcgtg ttcatagcag caccattcac aatagcaaaa    40560
catggaagca acaaaattgt gtacagatga atggagaaat aaaatgtggt ctgaccatac    40620
aaaggaatat tattcagcct taaaaaggaa ggaaattctg ccgtggtggc tcacgcctgt    40680
aatcccagca cttcgggagg ccaaggcagg cggatcacta ggtaaagaga ttgagaccat    40740
cctggctaac acagtgaaac cccgtctcta ctaaaaatac acaaaattag ccgggcgtgg    40800
tggtgggcac ctgtagtccc agctatttgg gaggctgagg caggagaatg gcatgaaccc    40860
gggatgcgga gcttgcagtg agccgagatc tcgtcactgc actctggcct gggcgacaga    40920
gtgagactca gtctcaaaaa aaaaaaaaa aggaaattct gacacatgct acaacatgga    40980
tgaaccttga ggacgttatg ctaagtgaaa taagccagac acaaaaagc actgtgtggt    41040 tctacttata tgaggtccct agagtagtca gagttaaagg gacccaaagt aaaaagggag    41100
ttaccagggg gtgggagtct ggagagtgaa tggggagtta ttgctgaatg agtgtagagt    41160
tacacttttg caagatgaaa gagttctgga ggttggttgc actacagtgt gaatatactt    41220
aacactactg aactgtacaa ttgaaaatgc tttaagatgg tgaatgttat gctatgttta    41280
ttttacaaca attgaaaatt aagaaaaaat actgaagtca tttagcaggt aaaataaaac    41340
aagaaaaatt gaatctgttt attagttaaa atgaaacaaa catagaaata aattaagaaa    41400
aaagtaaaat aaaatttaaa aagagggtag tatgtatcct ccacactagt cttaatgctt    41460
atatgtgcca aatgtgtgta taggctgctt tttttttttt tttttttttt ggacagagtc    41520
```

```
tcactctgtc acccaggctg gagtgcaggt ggcatgatct tggctcactg caacctccat    41580
ctcccaggtt caagtggttt tcttgcctca gcctcctgag tagctgggat tacaggctcg    41640
tgccaccatg cctagctaat ttttctatt tttattagag acggggtttc gccatgttgg    41700
ccaggctggt ctcaaactcc tgacctcagg tgatctgccc gtctaggcct gggattacag    41760
gcgcaagcca ccatgcctga cgttacccat gttttatttt tttatttttt taattttaag    41820
tttttttttt ttcgagagag agtctcgctg tgttccccag attggagtgc agtggcgtga    41880
tctcagctcc ctgcaagctc cgcctcctgg gttcacgcca ctctcctgcc tcagcctcct    41940
gagtagctgg gactacaggc gcccgccacc acgcccggct aatttttgt attttagta    42000
gaaacgggt ttcaccgtgt tagccaagat ggtctcgatc tcctgacttc gtgatccacc    42060
cgtcttggcc tcccaaagtg ctgggattac aggcgtgagc caccgcaccc ggctcctcca    42120
tgttttaaat ccataccatg acatctttc caggtcagca aatatagatc tgactcactt    42180
tcctttaaaa ggtgactaat tatctgtggg atgtgtgtac catgatttat ttcacgtttc    42240
cttttttctga accttcaggt tatttccagt tttgttgcca ctacagtgtt gcaataaaca    42300
gccttattca tattaccatt ttattgtggt tgttctgact tctgccgaat ttcaaaaagt    42360
gttgctaggt caagagtagt gccagattgt ttttcaaaaa gtccagagca gctcacgttc    42420
acaccacatc tggtgagaag cctgactgcc gacctcccat gagggccagg tactgtaatc    42480
tgcaggtaga aaatggcttg ctgtgatctt tcaaacatat agttaggaag ttgagtagct    42540
tttataaatt tattacttgc atttttttg gatgtgataa aagataggga gtctaatttt    42600
gttttttttt caagcaaata gccaattata cccatgctgt ttattaaatc atttgtcctg    42660
ctaaattaaa atacataatt atatgcattt tggatatttt cttatttgat tccattgatt    42720
tatttttta tttctgtgtc agtgctagat tgctttgggt atgtaaacct tatagaaagt    42780
tccaatgtct tgaaagcaaa atcccttgcc atttttccct tctcaaaatg ttgtgaactc    42840
tcagatactt tttccttctt atgacgtttt aaaccatttg ttcagttatt taaaaaagtc    42900
caagtgaggt tctaatccta tttaaatcta ccacatataa tctggtgtgt gtatgtattt    42960
gtatgtctca ttgtgttta tgaataaaga tatatcctca tctttgtcaa gcaaactaca    43020
aagtattaga taatactttc tctagttttc taagcatcca ttaataattt atagtatgga    43080
catgaagatg tttttctgtg cttttgttgt tgttgttgtt gtttgttttt ttgagacaag    43140
gtctctctct gtcacccagg ctggagtgca gtggcaggat catggcctac tgcagcctcc    43200
acctgccagg ctccagtgat cctcccacct cagcctcctg agtagctggg accacagaca    43260
tgcaccacca cacctggcta acttttttgta gagatggagt tttgccctgt tgctcaggct    43320
ggtctcaaac tcctgggctc aagcgatctg cctgccttgg cctcccaaag tgctgggatt    43380
acaggtgtgc gccaccatgc ctggccattt tctgtgtttt tgaaacacac atttacttat    43440
ttaatgaaaa tagaacatca tatactaaga tatttcagca tagttttgtt ccacttagaa    43500
aaagttatgg caatttatc agtaactgtc taacttaata cccatacatg atgcaggata    43560
ggtgtgtccc caaattgggg cttaacctgg gagggttctt ggcttcactt aggatggagt    43620
tcaagggtga gccagtggtg ttaaacagtg actttgattg aagtggcagt gtacagcagt    43680
ggcagagggg ctgttccttg tggctacccc ataggcagtg tgcccacaat ggcagctctg    43740
gttctacagt catatttata ccactttgag ttacagacag attaaggggc agagtatgca    43800
gtaatttcta gaaaaaggat tgtagcttct gtgtctttgg gttgttgcca tgggaagggc    43860
agtaacttcc atgcgttgcc gtggcagtgg taacctgaca taaatatgct gaggcaagtc    43920
```

```
tcccttaat ttttcatttt caagctattt taaactattt ttaaccttt ttcacatgtt    43980
tattcttcca gatatatttt attaccattt ttgtgtcatt ttctaaaaac cttttttatt    44040
tcatttggaa tttaatttag tctatgtttt atttagagaa ttgaactctt cgtaagatta    44100
cttttttcc tacaggaaca tgatgtgtat ctattttctt ggttcttctt tcaatctttt    44160
aaacaaaaaa aatttgtggg ctgggcacag tgtctcacac ctgtaatccc agcactcggg    44220
gaggccaaga cggaggatc acttgagccc aggagttcaa gaccagtctg ggcaacgtag    44280
taagacctca tgtctaccaa aaaaaaaaaa aaaaattgt gatgcaagaa ttttacactc    44340
agttgaactt gaaggcaacg aaaagtcgca gatgcaggaa ccagaaagaa tgccacacat    44400
acgtttcttg acttaaacaa attgcttgga gccaggtgca gtggctcacg tctgtaatcg    44460
cagcactttg ggaggccaag gcaggcagat cacctgaggt taggagtttg agattagcct    44520
gaccaacata gtgaaacccc atctctacta aaaatacaaa aattagccgg gcatggtgat    44580
ggtcacctgt aatcccagat actctggagg tgaggcagga gaacctcttg aacccgggag    44640
gcagaggttg cggtgagctg agatcttgct actgcactcc agcctgggcg acaaagctag    44700
actctgtatc aaaaaaaaaa agtgcagttc cggtgaattt aagttttcat ttcttttaaa    44760
attaagtcat agaaatactg atttaccttt cttcagactg gaagaagaaa tgagattgaa    44820
aagaatttt cgtttctttg ctttgaattg attgcgacta attgtatctc aaaagaaaa     44880
ttttatttgg ttgcttacat atatatatga agaaggaaaa tatatcagag ggtcattcta    44940
accctctgat atattcatat ttaataattc atagacctga atgtttcatt tgtttatttg    45000
attgattatc attccttcat tgcataaaag gtaattggtc atttgttttt attcctccac    45060
tgttttatt gttcactgta aaagtataat ttaatacagg gtaaaattta ttataaagat     45120
cactaatgtg gcccttgaaa aaaatggttc cagcttgctc atcctagact gcttttaatt    45180
ctctatgatt ttaagcaagc tactttattc aggtcatagt tttctcgtaa gtgaaaactg    45240
caattggatc tagaattacc ttcaataaga atcagcaagt atagagccag ggttggacat    45300
aaacagtctg agtccagagc tggtgtgatt aaatattatg taatactgca gacctcttaa    45360
tctctcagag attatgtttc tttatctgta aaacgaggac tatgagctct ttcttctctg    45420
ctggtttgca tgaggctcac atatagtaat gcaggagttt tgcaatgtca tctctgaacc    45480
aggagcacca gtggtatctg agaatgtgct acaaacacac attcttgggc tgtattccca    45540
acctactgaa tcagaaacta ggtttgggac cttgcaacct gggttggagg aagcctctca    45600
cgtaattccg atgtgtgcta aacgtcgcga accactggaa taataccctat atgtaggttt    45660
gtgttaacgt gccatcaatt atgtaaacag gtttcctttt gtcattatga tcctctcctg    45720
catacatata taaatatctg tctaactggt ttttgttgtt ttaattaaac attgaatgca    45780
tgaagaatat ttataccagg ctgggcatgg tgactcatgc ctgtaacccc agcactttgg    45840
gaggccaaag tgggaggatt gcttgagccc aggagtttga gaccagcctg gccaacatgg    45900
tgaaaccttg tctctactaa aaatacaaaa atttgccagg tgtggtggtg catgcctgta    45960
acccagtta cttgggaggc tgaggcagga gaatcacttg aacctgggaa ggggaggttg    46020
cagtgagcca agatggtgcc actgcactct agcctgggtg atgatgtgag actccatctc    46080
aaaaataaat aaataaataa ataaatttac accatttgcg aagagtatga agaagaacag    46140
tagcaaaagt acctacatat ccctgtcaaa tgaattgcaa acaacatgat tctcagtata    46200
ttaatcctat actcatgctc ttccctaatt gtctgacacc ttggccccac cctggatgta    46260
```

```
aacataccct cgggttagtg tgtttcattt cctccttttt tttctgtagt tttatcatcc   46320
atacacatat gtatatgcaa attcatttca cttagttttg taagacttgg tattatatct   46380
aaaggcatca tcctgtgtat attttttcta taattttttca attctctcta cattctgtta   46440
gtgtcatgca tgcactcatt ttccctgcca tatagaattc tatatctgaa tatgccataa   46500
tttatttctc cgttttcctt tccatggaca ttaggggtga atctcttttc aaagggctat   46560
cacacacagt gcttccgtga actttcttgg acatatttcc tggtacactt gtgcaagtgt   46620
ttctctgggg catagtcttc agattactac acttgcactt cgtgggaaga aatgcacttt   46680
ttatcataac caagcaattt catattgttt gttgtagtat agagaaatac aatggattct   46740
tatacattga ccaaaaaatt aggccctgaa acctccctaa aaactcacat attagttgta   46800
gtaactttgt ttttgcaaat gccttaagat tttctatata gataatcatg gtatttgctc   46860
ataaacacaa ttttatatta tcctttgtaa ttaatatgcc ttttatttct ttttcttgcc   46920
ttattgcatt agctagaccc acccttaaaa tgtgaaatag agcgattcaa gcagatatct   46980
ttgccttgta cctggtatta gaggagcaca tttaatattt aacagttcat tatggtgttt   47040
tctagatgtg tatgatggat ttttttttcta cttttgctgac aggttttttat tatgaataga   47100 gatcagattt taccaaatgt cttttctata tctattaaga tgatcatatt ttttttcctt   47160
tttcatcata atatgttggg tgatgttgat attggaatgt tcctcgggtt atttagaggt   47220
gtgtgtttag ttttcaaata ttttgagagt tcctaagtac cttctgata ctaattggta   47280 attcaattct attgtattca aagaaaatgc tttgtatgat ttgcatcctt ttaaattaat   47340
taggacttgt tctgttgcct gatctatgtc atttctgggt cttttttctaa aagtctcttt   47400 tctcctaact atgagtaata tttttcttct tctttggcta cttggtaatc ttgaaccaga   47460
tgtcagtcat gaatttaatc ctcttgggag gattctgcaa tgcagaatgc aatgcaatgc   47520
aatgcagatg caatgcaatg cagaacaagg ctgagctagg aaacgtattc aaggtttgca   47580
tttaagcttt gttatgcagg accaacacag ccttttattct ggggccagtt tggctacatg   47640
tctaagtcta tttgggatac tataacaaag tctcatagac tgggtggcta gtaaacaaca   47700
gaaatagatt tctcacagtt ttggcagctc aaagtccaag gtcaaggttc cagcattgtc   47760
aggttctggt gagggcagtc aggttctggt gagggcaacc ttctgggttg cagactgcca   47820
acttatcact gtgtccttgc atggtacaaa aagggcaagt gagctctctg ggccttttta   47880
taagagcacg aatcccattc atgagagctc caccctcatg acttaattac ctcccaaaag   47940
cccacctcct aatacctaat actatgggcg tagatttcaa cataaacatt taggggtaca   48000
ggagacaaac attcagtctg taacactgca ctaccgagta cttagtaccc ttctgagctc   48060
tcagcccagt accctcatat tccaagcttt ctctactctg gttgtgggat ctgtaagctg   48120
ttctcatcca tgtgcgtggg ttgggaacaa tgcctcttgc tcttttccag tgattttttt   48180
cttagcctcg ggtattttca cacacatgca ctgaccagta ctcagctaaa gacttgggga   48240
accttctaca catctctagc actctctctg agcagccctc ttctctctgg ttctctgccc   48300
tgcacattct agccaccttg acccccctga attctccact ctcctggtct cagagtgacc   48360
actggctgcc tgcacaatag cctggaaacc ctgttcaagc agtaagtgca ggcaggtgta   48420
gacttcactt atctgtttct ctcctctcag gtatcactcc ctgcattgcc tgctgttcag   48480
tgtctgaaaa ccaacgtgtc atgtacattt tgcctagttt ttaatgctta aagcaggata   48540
attcatctgg tccctgatgg gttgcttccc tagtccacct gggcaacaag tagaattgat   48600
atatgtattt tttaggtaga aaacaaatcc caaattcaaa ctgatatttc caacccacgt   48660
```

```
catcccagaa tcagttaacc tttttgattg tgtacttgtc tttgatgctg aaagatcttg   48720
gttccaaaga catgaccaat agttgctcgt tgtttcttct cattttattc ttaaccagaa   48780
gagttaggta aaacaccagc tcactttact gatgagggaa cagaagcctg caaagattga   48840
atcacttgcc ctagagtcca ggatggtagt ttttggcca cattatggaa aatatcttca    48900
atggcacagc tgtaattttg ttcgccttgg tctatcactt ttctttcttt tttaaaattc   48960
tagatatttt ttagtgcttc acttttaaa aaattttgtt ttattttaa ttttttataag    49020 tacatagtag gtgtatatat ttatggggta cacgagatgt tttgatgcag acatgcaatg   49080
tgaaataatc acatcaggtc tgtcactttg aacttcacac acacacctat gtacacatgt   49140
cctatccttc tgtttcctca ctgcaatttc agtagggtgt gattctggag tatataaata   49200
cccaggaagt tgagattcag ttctaaaatc ctcctgagta ggatccagag gttaaaggag   49260
tcaggccaga gcttgtcctc agactggccc agggccggaa gctgctgttg tacttgcatt   49320
ttttaggttg ttattgtcaa agtaatgact tgtgtagcct ggttggggat cattgctttt   49380
ctcagtgaaa tgtgtttgtc tcattcatgt acatatagag aggataatcg gtgacatcct   49440
caactatcat ttaaaagtgc tttttctaga ttccacagta acctctggca tttatcttca   49500
gattctctat tccttagtga tgatttctgt ctataacaga gtcttagctc aacagagtct   49560
tagatgtgac cgtcttaatc ttagatctgt tcacctttg tttcataagg atgtgtacca    49620
agaagaacct gataaggaga ctttatttgc tttggaaaag atgttctggg ctgggtagtg   49680
agctgttttc cttcattatt aaagactgca atagttgcta tcagatttt ttctgtttta    49740 cttttttccta ttttgtttaa taaggaagat attcattgag aaaaatggag gctaatagaa  49800
ctataggcat gaataacatt agcatgtgta cctttgatat tatatacagc ctgagggtcc   49860
tgtggtgagt acatggctga ggccatcttt agtattctgg ataataccct ggtttctcaa   49920
tgaattgttg cagaaatgct tggaagggggc agcaagaaat ggtgaatgta ttaaaatact  49980
ccccgcacct ggtgctgttt cttaaaggag ctctgtattt agcggcctgc aataaaatgg   50040
ctttgctcta atcaaagaca tctgcatttc attgtccatc aaccattgcc ttggaaggac   50100
cattgaggct gatttgttct tgacctctcc agtccttcct gattcactgt tttcattgac   50160
cgactcccac tggtttattg atgaggggtt agtgtccatc tttgaggatg taggtgtcac   50220
catgccctga atgggaagct ggacacggcg agaaagggga aggagtggag gggaggagac   50280
tgctctttac tcactgtctg ccaggtgtta gtcatcattc tggccctgca caaattctcc   50340
tttttgggcc tcacaaaacc ataggaagaa tgtactgttg cctcccttt tcagaggagg    50400 aagctgtggg aaaaaactcc tatgattata caccatagac ttttgttct gtaattttgt    50460 ttttgttttgt ttgtttgttt gagacaggat cttgctctgt cgcctacgta gtgcagtggt  50520
acaatctcag ctcactgtag cctcgactgc tacaatctca gctcactgaa gcctcaacct   50580
cctgggctca agcgatcctc ccacctcacc ctctcgggta gctaggacca taggcacaca   50640
ccattatgcc tggctaattt ttataatttt ttgagacagg gtctccctat gttgcccagg   50700
ctggtctcaa actcctgagg tcaagcaatc ctcccactca gcctcccgaa atgctgggat   50760
tacaggcgtg agccactatg ctgggccttt gttctgtaat ttcgaattgc cttgtttctg   50820
ctttcctgct gtaagcattt catataaatt taatgtcata ttcatgtaaa tgatgtggct   50880
tctaagtcat cacttgctgc cagtgaggca atcaagaaac aatatttgag tttatatctg   50940
agaaataccc ctccagttca agatatttat ctattccctt cacaaatata tgtaatcttt   51000
```

```
aagatagaga ttttttttctt ttcttttcct tttttttttt tttttttgaa acggagtctc   51060
actgtcgtgc aggctggagt gcagtggcac gatctcagct cactgcaacc tccacctcct   51120
agattcaagc gattctcatg cctcagcctc ccgagtagct aggataacag gtgcgtgctg   51180
ccatgcctgt ctaattttta tattttagt agagactggg ttttaccatg ttggccaggc    51240
tgatcttgaa ctcctggcct caagtgagcc acctgcctcg gcctcccaaa atgctggaat   51300
gacagacatg agccactgca cctggccaag atagagattt ctaaatagta atcaatgcat   51360
tgattatgaa atcctctctt ctcctaaact atctagaaaa tgaagttaag aatcctgtaa   51420
gagcctgctc ttatggagta ctgttggtga gaagtagagc tgatgtccta acctgatagc   51480
ctccgtcctg gatgggtctg agcagagagg tggcgtgatg gtcatctcat tgtagaaaga   51540
ctgatttgga acctacttgt aattatcatc ctaaaaccac agatttgact tcttggtgtt   51600
atacctatta ttgaatatga ttttcttgtc cttatagtac agtgtaatta cagagcataa   51660
gaaaatgaaa tctgtttggc cctcttggat atcattgcag gaaagccaag atgaagatca   51720
aagatgagtt gtgcctcttt agttttata gaatgcatat ctgaaactag gcagatcaag    51780
atcataatgg aaaagaagaa ttgtaaccat cttttttta tttttttga aacagagtct    51840
cactctgttg cccaggctgg agtgcagtgg tgcgatgctg gctcactgca gcctccgcct   51900
cccaggttca agcgattctc ctgcctcagc cttctgagta gctgggatta caggcatgag   51960
ccaccacacc cagctagttt ttttgtgtgg ttttttttt gtattttag tagagatggg    52020
gttttaccat gttggccaag ctggtctcga actcctgacc tcaacttatc cacctgcctc   52080
ggcctcccaa agtctgggga tgacaggcat aagccactgc gcctggccat agtcatcttt   52140
ggaatattat gaatgatata tgtctccaat gggtatctca ttctgtgttt gctggatctt   52200
tcttttgtag attctatcag gtgactaata aaaatataa tgtagctatt cttcagggga   52260
ttgtaatttg aggattcatg taataatctc attcattaga aatattcatt acttggccgg   52320
actggatgtc ccatgcctgt aatctgagca cttggggagg ccaaggtggg tggatcacat   52380
gagcccagga gttcgagacc agcctgtcca acatggtgaa actttgtctc tacaaaaaaa   52440
ttttaaaaat tagccaggtg tggtggcaca tgcctgtcgt tctaggtact tgggggggatg  52500
aggcgggagg atcaccagag cctagggagg tcaaggctac agtgacccac gattgtgcca   52560
ctgtactctg gcctggttga tagagtgaga tcctgtctca aaaaaataaa aaataaacat   52620
aaaaaagaa atatttatta cttctagcc tacagacttt tcattgtcaa aactgatcac     52680
tcagtttgca gccagtaagt ctgttctgtt ggtttcttat tgcataatcc caggacttca   52740
gttttcttct ctcatgtaag cctggtttaa agaaagagc caaatcaaag attcagtaaa    52800
atgcaaacta ttttgtcttg tctacttggc tctgcaaaat tatactttcc tgttataaac   52860
agtaagctgc ttagggaaga attccagcaa tttgtctttc ccagtgctgt tcatggcagc   52920
cagcgaggca acgtatgtac agcaactccc ggttcttgtt taatttcctc agtcaaaaca   52980
agagattgtg gtggtgcctg ccggttcaaa aatggcacat gtttcttttg cctcttctca   53040
ttaccccgtg aatcagaagg cgttagaacc agagggctct ttaaaggcaa tcctgttta    53100
cagataagaa actgaggcct aggcttagta gctcattcaa ggtcatgcat tgtgtaagtg   53160
gtaaagttga gtcttgaatc cgttttgctt accctgaggt ttttcttggt ttcccatttc   53220
tctagctttc tctataacag ttattcatgt tctagaaaga aactatgggc ccactaagtg   53280
cattagctgt actctcattc ttgaaatagc atcagactag cggacaatgt gatcaccagt   53340
cactgatgtg tgtgatgaga aagcttggtt tgggaagtag gatggtcatt taaagagaga   53400
```

```
aatctaggct cttctctttg tttctgggct attccagggc atatcttcac cactatggac   53460
tggcttggtc aaatgtgatg aatagaccag ctttataaca gctttgctgc ttgcaagctg   53520
ggtttaaccc ttctgagtct cagcttccgc attaaataat gtgacacctg gcatccactg   53580
tatacaatta ctaagatata tatgaaagta aactatgaaa tacgctggaa atgtgaggta   53640
tattatgata tggagggcat actaccaaac ccaagagtta gaatgaatag atgacggcgg   53700
tgattggaaa tcttgtttgt gcttttgccc agagacatga aacagattgt acaaacatcc   53760
tctaagcggt gacttttcat tccagtgaaa ggcattcttg aagggatgtg cttctaacat   53820
gaatctcttt gaaagcttag gttggagagg cagattctct cttgtgataa accaaatgga   53880
tggagaagtg attttagtaa ccctttcttg agtgatggga aaccacagcc tctgctctgg   53940
aggaaagcag aagtgtgttt gagtttgggg aagaagtggt gaataactga attttttgat   54000
ggattttata gaagagataa aaatatgtgt ttttaaaata tattctttc tgacatcgtt   54060 attatacctt gagtactttc tttgggacta gcctgtgcc ttgtaatgag aaagacacaa   54120
aagtaatgtg taacgagggc cccaatcata gggatttcct tctaattgat ggcagacaat   54180
tacacaagat tgtctatgat taaaaaccca aactgcgctg gaagggaaaa ttgttgtgga   54240
atgtcagaga agaaagagat ccacgcaggt aatcgggagc tagtagccat ttgttgaatt   54300
gcattgtgga tgtgagattt ggattgttac aaatcaagac aggcccttgt tctaggcaga   54360
aacaaaccat ggactgagct cagaatttag gggagaacat aggagtcttc actggagagt   54420
aggctggaat ttcgcagata gtggagacaa agacagataa ttacgggctg gacaattttt   54480 ggaggtatt tgggtcaggc ttagagatct aggttttaag caaaccggtc tttggtgtgt   54540
gcgtgtatat gtgtgtgtgt gtgtgtgtgt atgtgtgtgt gtgtgtgtgt gtgtgtgtgt   54600
ttccagcagt ccttggtagg tgtttgtgtt tggagcttcc agtgcaaggt gctgcctttg   54660
agagcttctg cttactttc caatgaccgg aaccaggaag aggtgaagct tggtcattac   54720
acaatgcatt gtgactcagt gacctcacta cttcctgttt tcatttgaga aggggggccaa   54780 tggaagggac catttcagta caaggccatg aataggagt aggagatgtc aaggatatga   54840
ggtctgccaa actagcaggc agagcatttg cgtaaaccag cagacgaatg aaggagttga   54900
actccactgg aatagcagcg gtggcccagt tacccatgag aaagtctagg aattgggaat   54960
tactcctact tctgaatcgc gtgcgatttc tcctaaccta tgtcaccagc caatcctggt   55020
tgtaaattca tagcctagtc cataagctca atagtaaaat aaattccaac atactttgtc   55080
caggcttctg tgccaggagt gcaggagagc actacttgga tgacttcctt tatcaaggag   55140
aggccactgg aaaacaggtg gctggacgtg tgctccttcc tgctcactga gaggttgact   55200
gtgatgtaag ccaagctgca ggtgcagggt gcactgcagg cccagggaag agctgggaag   55260
agccgggaag acccaccact ggcaatgtca aggacgcctt tcttccctgt gggatatact   55320
gatggactga gtgactatcc attcatcagt gtggatggcc actcatcagg cctgcagaga   55380
tgggagcctt atgggttcct tggattgtca agtccatggc tagagctgaa tctctaaggg   55440
agttcttttt tcctggaaag atgtagttcc ctcatcagta gagtgagggt aagaagtaaa   55500
tctacttaaa aaaaaaaaa aaccagcttc cgtcaagtgt aatttatata ccataaaatc   55560
cacccgtttt aagcatataa ttcactgatt tttagtaaat ttacagagtt gtgtaaatat   55620
caccgcaacc cagttttagg atgttttcat ctccccaaga agctccttag ggccttttgt   55680
ggtcaatcac cattccctcc tcacagcccc aggcaaccaa taatctccta tattgccttt   55740
```

```
gatagatttg ctaaattctg gacattttga ataaatggtg tcataaacta tgtggtcttt    55800
tgcatctggc ttctttcctt tagtgtaatg ttttgaggtt cattcacgtt gcagtatgtg    55860
tctgtattcc atttctttc attgctgcat agtattccat tgcatggata taccatactt     55920
tgtgtatcct ttcatcagtt aataaattat ttccattttg ggggctattg tgaataatgc    55980
tactgtagtg gatttcagtg gctgctgtga caaattatac acttgatgtc tcaagacagt    56040
gggggtttat tctctcacag ttctggagat gggagttagg aagtcaaggt gcaaacaggg    56100
ctgtgctccc tccggaggcc ctcggggagg ttctgttcct tgcttcttcc agcttctggt    56160
ggatactggc cttctctgac ttgcagtcac atcagttcaa tctcagcctc catctgcatg    56220
tcgccttctc tcaggtgtgt ctctcagctc tctctctttc tctcttataa agatatatgc    56280
gattgcattt aaggccaccc tgataattca gggaagagag ctcctctcaa aatccttatc    56340
attggtcatt agaaaaatgc aaataaaaac tgcaatgaga taccatctca agccagttag    56400
aatggcgatc gttaaaagtc aggaggctgg gcacggtggc tcacgcctgt aatcccagca    56460
ctttgggagg ctgaggcggg tggatcacga ggttaggaga tcgagaccat cctggctaac    56520
atggtgaaac cccatctcta ctaaaaacac aaaaaaaatt agctgggctt ggtggcgggc    56580
acctgtagtc ccagctactg gggaggctga gcaggagaa tggtgtgaac tcaggaggtg     56640
gaggttgcag tgagccaaga tcactccact gcactccagc ctgggcaaca gagcaagact    56700
ccgtctcaaa aaaaaaaaa gtcaggaaac aacagatgct ggagaggaca tggagaaaga    56760
ggaacacttt tacactgttt ttgggactgt aaactagttc aatcattgtg gaaaacagtg    56820
tggtgattcc tcaaggatct agaaccacaa ataccatttg atccagtaat cccattactg    56880
ggtatatacc caaaggatta taaaacatgc tactataaag acacatgcac atgtatgttt    56940
attgtggcac tattcacaat agcagagact tggaaccaac ccaactaccc atcaatgata    57000
gactggatga agaaaatgtg gcatatatac accgtggaat actatgcaac cataaaaaaa    57060
ggatgagttc atgtcctttg cagggacatg ggtgaagctg gaaaccatca ttctcagcaa    57120
agtaacacag gaacagaaaa ccaaacacca catgttctca ctcataagtg ggagttgaac    57180
aatgagaaca caaggacaca gggaggggaa catcacacac tggggccttt tgggggtgg    57240 gggtctaggg gagggatagt attagaagaa atacctaatg tagatgacgg gttgatgggt    57300
tcagcaaacc accatggcac gtgtatacct atgtaacaaa cctgcatgtt ctgcacatat    57360
atcccagagc ttaaagaata attaaaaaaa aaaccttaac ttaatcaact cttttgcctt    57420
acagggtaag atacacaggt tccagggatt tgatgtggat ttcttttggc cgggggcac     57480 ctttacagcc caccactgca gctctgaaca ttcacataag gttcttatgt agacacatgg    57540
cttcatttct ctttgtaggt acctaggaat ggattgctag gacctatggt aaatttatgt    57600 ttaactttt gagaagttcc ccaactgttt tcagaagggg ctgtatcatg ttacattcct     57660
accagcaatg cggagagtt ctagtttctc cacattcttg ccatttgtct gccttttctt     57720
ttttctttat catagccatt ctagtgggtg tggagtggta tctcactgta gttttaattt    57780
gtattttccc atgactaata gtgtcgaaca tctcttcgtg tgcctgttag ctattcatac    57840 ataattttg gcaaaatatc tattcaaagc tctggcttgt cttaaaattg ggttgtcttc     57900 ttttttttgag ttatgagtta gtctatcatt tttcacaacc cggcccagcc attgccagcc   57960
ctaaagactg tggtggctga ggtcaccttg attaggaagt gctggggtaa cccagttgcc    58020
cagggtgccc tgggctgggg ccaggcacca tcgttcacc gtgccctgtg tcagtttgtc     58080
actggagggt ggatgggcct cacaggtggc ctttttgccat cagatactgt gccatggaag   58140
```

```
ccaggacatg gctcgcctgt gtactagaga tcatcagttc cgtgttcttg caggctggct   58200
gttgtctgat gaacaagggc actgactaac aaaatcccac aatatatttt cattgtaact   58260
ggattgtttc tttcctaaca cttatcacaa ctttaactag ttatttctgt gattatatat   58320
ttgatatctt tcttccttcc actcaactgt taagttccct ggggacaggg gccatgtcca   58380
tgtgatttgc ccctctatca ctagtctcta acacagttcg tgatgtgtag caggcaactg   58440
atccatattt gttggatggg ggaaatgagg atccatttct gtgctttaca gtgggcaatt   58500
cacatgaaat tattaaatag agagttgttt gttgaccgaa ttgttcactg tgacatgcat   58560
tcttttttt tttttttga cggagtct cattttatca cccaggctgg tgtgcagtgg      58620
cgtgatctcg gctcactgca atctctgctg cccgggttca agcagttctc ctgcctcagc   58680
ctcccaagta gctgagatta catgcgcctg ccactacgcc cagctgattt ttgtattttt   58740
agtagagatg gggtttcacc atcttggcca ggctggtctt gaactcctga cctcatgatc   58800
cacccacctc accctctcaa agtgctgaga ttataggcgt gagccaccgt gcccagccaa   58860
gtgacatgca ttctaatttc ccttttttat ttctcatttc cagcgatcta taactacaat   58920
gcttctcaag atgtggagct ctccttgcag atcggtgaca cagttcacat cctggagatg   58980
tacgaggta agtctggctg gccttctgcc agatgagggc aagggaaaaa cagtgtaagt    59040
tacttattaa aaaggcactt agagtaaaca tcaacatgct tgacttcctg aaacagtgct   59100
agtaaaaatt caggaagtac ttgggtgaca caattttgaa cagagtgtga tttcaaaaca   59160
gccagctgag tacatgagca caaacttgca cagacaccag ggtgaaagct catgcatatg   59220
tgaagggtgc tggtgtggcc aggccacttg ggcacagaag gatcagtgac agagctggct   59280
cgcgaggaga cacttgggat gttggctgg cagtagctca aaggaagcac tgctgattaa    59340
gggtctcttt ctgttcagca ctaaatgttc ccaggttggg ggagaaatga gggagagtct   59400
ttctggtgtt gctgagattc ttttagaaaa ttaggtcatg actgcagcag gtccagaaag   59460
cctgattgta tatctccttc aactaggtca ggcgagggcc gtggttccat taacctgtta   59520
gtgggctgcg gggcagtact taggactgcc tatttgtctg ccaagcattg gtcatgtctg   59580
tacccactcc actgcaggct tccaacttca gctcaggttc tctaaatcct agaagaagtc   59640
ttcctccata tatccacatt tttaatccaa acctctggag cacaacaaaa gcatagccag   59700
gccactgaag ttgaggacca aaccaagaac tatgtttagg gtccagttat tctctcagaa   59760
ggttagggta caaatgaggt ggaaattagg cagatttgac agggaccgtg cattttccgg   59820
gtctagcccc catgtaaacc cttgtgatgg tgaaacggca gagatggtcc gcgaggaccc   59880
cgtgcaggtt cctagggtgg gatgggatga cacaggatga gaaagaagag atgggaaggc   59940
aggaggaaag gaagcaggat ttggccacag aacagctaaa ttatctgcat ggttgcatgg   60000
aagactctgc tattactgca gcctcccttt agttttggc agagggctgg ggtttcacat    60060
tatcctttc ccttccacac aactcaatgt aatcatgtag ctcccagggg cagagagaag    60120
acagagaggg ctgtgtgaac tcttcccttt ttctttctac tgcttattct caccatctca   60180
ggcccagcca aagcatcaat tcaaagtctc caagacacta gggcagtcgc cttatctttt   60240
ccagaatctt ttgcttatgg aaaccacagc tcttccaatc tttttattta tttatttatt   60300
ttttgagacg gagtctcgct ctgtcgccca ggctggagtg cagtgacacg atctcagctc   60360
actgcaagct ccaccttccg ggttcatgcc attctcctgc ctcagcctcc caagtagctg   60420
ggactacagg tgcccaccac cacacccagc taattttta tatttttagt agagacggag    60480
```

```
tttcaccatg ttagccagga tggtctcgat ctcctgacct cgtgatccgc ctgccttggc    60540
ttcccaaagt gctgggatta caggtgtgag tcactgcgcc cggcctacag ctcttccagt    60600
cttatcagct catacctctt ttgtcaggag gccaggttaa ttcactttgt ctagcctcaa    60660
tggatgcata ttttcctatt gtgcaggtaa aaagcataag ttcaattttt ctaactcttc    60720
catgtgggct tggaaagaat gtatatttaa ggattattgg gtgcaaagtt cttttttttt    60780
tttttttgag atggagtctc attctgtcgt ccaggctgga gtgcagtggc acaatctgag    60840
ctcactgcaa cctccacgtc ctgggttcaa gcgattctca tgcctcagcc tcctgagtag    60900
ctgagattac aggcatatgt catcacacct cgctaatttt tgtattgtta gtagagacgg    60960
ggtttcatca tgttggccag cctggtcttg aactcctgag ctcaggtgat agccccatct    61020
tggcctcccc aagtactgga attacaggtg tgagccacca tgcctggtgg caaagttcta    61080
tatatggtaa ttaggttcta atttctgagt cattttcag gtttgctata tgctaacttt    61140
tttttcctgc tttctctgtt actgatagaa ctgtgttaac tcttccacca tgattgtagt    61200
ttgtgtctct ttatggtgat gtcagctgtt tgctttatgt attctgagac ttgttttag    61260 gtgcctgcta atttagaatt gttgtgttaa acagttctaa cttttaattc ctatttatta    61320
aacctttatc attgtcttac tctgtagtaa catgctatgt cttactctgt gttgtgtaaa    61380
attgcagcca actcactggc aagtcccagg gcttcaattt tgtcctcct ggctccacaa    61440 ggccatcaga aatgctgctc agcttctcag ccactcagga atcctttctt tttgttgttg    61500
ttgttgtttt ttgtattttt tggagacaga gtcttgctct gtcgcccagg tggagtgcag    61560
tggctcaatc ttggctcact gtgatctccg tctcccgagt tcaagcgagt ctcctacctc    61620
agcctcctga gtagttggga ttacagacac ccgccgccat gcctggctaa tttttgtatt    61680
tttagtagag acagggtttc ccatgttggg ccaggctggt ctcgtggcca actcctgacc    61740
tcaggtgatc cgcccacctt ggcctcccag tgttgggatt acaggtgtaa gccaccgcac    61800
ctggtcagga attctttctt aaatcagcag atggatgccc caagcggaaa gcagccccag    61860
atgctgagct ggtctttta ggttttggtc tctttcagat tttgacctgg taattcttca    61920
ctgccatgtt agtttgtgtg tgtgtgtgtg tgtgtgtgtg tgtgtgtgtg tgtgtgtgtg    61980
tgtgtggcgg gggcggggtg gggcagtgta tatgtttgtg tgtgttgttt tgtcaagctt    62040
ttctaattgt cctacagagt gtgggaggga agaatggaga cttggtctga aataaagtag    62100
gtaatgtctt ttgtttttg tttttttttt ctttgagaca gggccttgct ctgtcaccct    62160
agctggagta cagtagtgtg atcataactc actgcagcct tgagctcctg ggctcaagct    62220
atcctcttgc ctcagcctcc caagtagctg ggattatagg catgtgccac cacacccagc    62280
taatttattt atttattta atggacacaa ggtctcacca agttgctcag gctgatccca    62340
aactcctggc ctcaaatgat cctcctgcct cagccttcca aagtgttggg attgtaggca    62400
taagccatag cacctggccc aggtgatacc tttaaaatat tcttcaaat ttttttcat    62460 ttttatgtga cctcagcgta tttctaagaa atagttaatt gaaacacttt gtcctgttag    62520
ggttcatatc aatagtaatt ttaaggatga gtgtggtggc tcactcctgt aatcccagca    62580
ctttggtagg ctgagatggg aggatccctt gaggcctaga gttcaagacc agcctgggca    62640
acatagtgag accttgtctc tacaaaaaat ttaaaactta gccaagcatg gtgacatgca    62700
cctgtagtct cagctacttg ggaggctaag gtgggaggat tgcttgagcc tgggaggcag    62760
aggctgcagt gagctgacta caccactaca ctccagcctg gcaacagag tgagtccctg    62820 tctcaaaaag aaaaaaaaaa gtaattttaa gtgtctcact atactttacc aagagttctc    62880
```

```
cagttggcct ataaacattc ctcaagacag catccctatg gaccaagcta aggggggtcac    62940 tgagcttagt tgaatataaa tataatcaca gatacattca tttcaaatac catgcacttg    63000
agtccaaaca gtccaaaacc cacagtgctt ctagtatatt acagctcaca ctacgatatg    63060
cttgtaggat gtgctggccc atttgacagt cacacaaaaa tggttaactt cttcagttat    63120
ggtgatccgg atgctgtagt cctgcccgca agaaaccgct cttcttaact gctaccataa    63180 cattttttgct gcgtcagccg tagaactttt tcatctcaaa ggacgtcagt gcctgttctt    63240
taaaagtaag cgcatgtcaa ggcgtgaagg ggagggaggt tgagaacact tgagcctgca    63300
ccgtgagctt actgagttca ttaaccacca aggggcaggt cagcttgaca gagagattac    63360
tatattggat tatatttttc attagtgttt atttctggg attaattttt aaaatcgtgc     63420
ctaccttgcc agatgtccca tgataggtcc ttgtatctgc taagcactta gagttcttgg    63480
cttgattctc aaattccttt attatttaag gcagctcgag gcaagggccg gagtgctttg    63540
caaacatgaa acgcgatggg aatgctgagt aatcacttgt cttctacccc tcttctccta    63600
gtccctctta actttagaaa aataaacaca atgaaaacac cgacagtcct gccgggtgga    63660
actgaagggt gacactggca ctgtattgtg gccctgggat tcgtgtcttc cagcttcctg    63720
tcggagctga ctttggggcg ctccctctgc actctgcccc accctgccct cgagatgtct    63780
gcataccaga tctgtgtgtg ttttttccagc gtggacatga atccacccag acatgaaaca    63840
ttttttctgc ccaccgcccg ggacagaata ctattttttga ttctccttttt tctgtttcct   63900 gccgtgtggt tggctgaaaa atttcagaaa gtattggctc cttgaaggca aagcctgttc    63960
ctccttcatc tgcagagcct gtgcctccct agctcctggt atacggcagg tgctcagcaa    64020
caatctattg aatgatgaag gtaaaatagg agaccaaggc aagctggtgt agagagtaag   64080
ggggtcaggg gtcacctcca caaaaccctg ggtattacaa ggcagaggtg ctgttccttc    64140
tctatgaggg aaatacaggg ggtgctaatg tttttttggtc ctctgcaatt ataggaggat   64200
ttagtcattg ctgaagttttt tgttttttatt ttatttatct tttttttaga dacagggtct   64260 tgctgtccccc caggctggaa tgcagtggca taataacagc tcactgtaac cttgccttttt  64320 tggactcaac ggatgctcct gcttcagcct cttgagtagt tgagactact ggtacatgcc    64380
accatgccta gctaatgttt ttaatttttt aggagaggtg aagccttgct gtgttgccct    64440
agctggtctg gaactcccgg cccttagcga tccttccacc tcggcctccc agagtatagg    64500
gattacaggt gtgagccatc gtgcctggcc ttgtgggttt ttttgtttgt ttttaataac    64560
agctttcttg agatataatt caaataccaa tcaatttact tatttaaagt atacaattca    64620
atggatattt actaatgcag agggttgggc aaatatcatc actatctact ttcagaacac    64680
tttcatcatc ccataaagaa gctctgtacc catcggtagt catgcctccc ctggctctag    64740
gcagcttcaa attcatttca tgtaagtgga atcacataat atgtggtctt ttgtgactgg    64800
ctgccttcat ttggcatcag gacttcatct ctctcgccct ctctcttgct ctgttggtca    64860
ggctggagtg cagtggcatg atcacggctc actgcagcct tgacctcctg ggctcaagga    64920
atcctcctac tccagcctcc caggtagctg ggactatagg tgcacaccgc tacacccagc    64980
taaattttta ttctttgtag agacagggtc tcgctatgtt actgaggttg gtcttgaaat    65040
cctgggctca ggcagttctc ctgccttggc ctcccaaggg ccaagtgtcc cagtgtgttg    65100
ggattatagg catgagccac tgcacctggc ccaacttcat ctcttttcat tgctgagtaa    65160
tatgtattat gtaggtacat tatattttat tcattcatca gttggacatt tgggtcgttt    65220
```

```
agatgtttca gctactgtga ataatactgc tgcaaacatt tgcgtgcaag ttttatgtg    65280 gacatatgtt ttcatctctc ttgggtaggt acctaggagt ggaattgctg ggtcataggg    65340
taactcaatg tttaatattt tgaggaactg ccagactgat tgagctttgg ctccaaaaca    65400
ggcgaccaga gtccagatga acgagcttct atccatcatc tttttcact catttgactc    65460 tctggccttg cccctgaact tcatttgttg ctaaatgaag gaagaagca gaactgactg    65520 agaagctatc tactgctcat ccgttacagg tctccaggaa ttatttgtct ttagagactt    65580
tatcaggaaa cagaattcct taaggactga agcgagcgtt cttgcctttc ttcatctttg    65640
gcactggctt gcccacagtc attttttgtgt ctttgcttct tttactgtgg aatgtatttg    65700
gcagcgaggt agctgtttat tactgtgaac gttcctttcc accccagatc catggcagaa    65760
agtgcactga cttctggaga tgcccggccg tgaggtcatt tattcattca acattatttg    65820
ctgagcacca agtatgtgcc aagtacattt attgagcatg agagatgttc tgggtactct    65880
gtggtctctt aagtgacaaa atgcaagttc ctgctctcat agggtttaca ttggagggat    65940
agacaaaacc aagtaaacaa agtaagtaaa caaaacaatt cagatatgtg cttacaaatg    66000
ctatggggag aagagggtgg tattgcagag gccagaggtg gaggacagcg atggagaggg    66060
agacggaaga ctattgtagg ttggtagttt tgtccttgtc tagattgact gtccctgggc    66120
aagatattgc agctgtcttt gtgacaagga catttcatct aaattggagt cacttttga    66180 gtcaagagtg atcaaatgta agtgctttga aaagtgcata gtaccttgta tgtgtcaggt    66240
ttcagcatcc tgttaccatg gagctcccct ctcctgtgat taacgtcact ccagtcacaa    66300
gtggttttag gcctggagtc tgaggttcct ctagtgctgg tttcctgtgt ttaattcata    66360
tccatcgatt aactctttt ctgctccgta aaccactcac aagctcacga gaaagggcgg    66420
ctggtatgct ggtgttagca gtgatttctg gggtaaatac aacacaattg accgctgttg    66480
gaacaaacac aacgaaatgt ctcaaaggtg agctgaactg tacagaggca ggcacagcac    66540
atattatttc agggcaattt gtaaagactc gaaggatagc acaaatgctt ggactggaac    66600
cagaggaaac aggcaaacct gaaaagttaa agaaacaaa agaagggtt tgtatacgta    66660 caggagttcc ccagaatacc catgttattt cttctatata gaagaagtct agttttgaa    66720 tgcactttaa tcaaaaaatc tacttccctc taatatgaaa aggaataaaa atgtattaag    66780
acttgagctg tatgtgtttt gaatctcatt tttataaagc aggcctttgt gagtagggac    66840
agtgggcagt gttatgacag gtaagttaca tggcaatgaa ttttgtctgc atgtttgcca    66900
aaactttcta acagagatat aaaaaagaag agagtgggct gggtgcggta gctcatgcct    66960
gcaatcccag tactttagga ggctgaggcg ggcagatcac atgaggccag gagtttgaga    67020
ccagtctggc caacatggca aaaccctgtc tctactaaag atacaaaaat tagccgggca    67080
tggtggtgtg cacccataat cccagctact taggagactg aggcacaaga atcgcttgaa    67140
cccgggaggc agaggttgca gtgagctgag atcacgcgtg ccattgcact ccaacctggg    67200
tgacacagca agactctatc tcaaaaaaaa aaaaaaaga gtgcttttaa aagatttttt    67260
tcaaacagag gcttaatcat catcctttag agatgtggta ataggaaccc tgcattggat    67320
tatgatacag tatggtatct aacgtttga gaatgtctgt ctgattgtca cattctgtta    67380
tgctctatga caattaattc tgtaacactg aaatctcttt attgttcctc ctttctactt    67440
gtttctttct ctacttggtc atccatgcac agtggtcaga agccaagaga gagacaaaag    67500
attcaaaatt gctgttaaaa atcagttctt aatagaatgt gtaaagtttt actggatata    67560
agcttcaata ggggtgtcca aggtatttgt aacttccgtt tacttttgtt acccgctaat    67620
```

```
taaaataatt gaaagtttat tgtaattcaa aatctatata gtctccacga tctaggtata  67680
gaaatactgc ctttctcata cataaatggc agtgagccta acagcttgga ttttatgacg  67740
ctgcgtgcaa atattttggc attagcctgg aaagcagata aggccatgtg catttttgtt  67800
gagtgtgctt ggtcacttcc cacatctgtt tgacctttac cttaagtaca gcttgtgagc  67860
tactactgct ggtgacatat gttcctgaga tgtgttttc aaaagatatg tgtggcagta   67920
ggagggtgtt taccagagaa attaattaaa aggagtgtca gtgaaaagtc ttatctcgga  67980
tttaatcttt aaaaaaagcg aatgccttct attttttcctt ttcaggtatg tttcagtatg  68040
cttctaaaat tctaaaattc catctttatt tattttttg agacagagtg ttaccctgtc   68100
tcccaggctg gagtgcagtg gtgcaatctt ggctcactac aacctctgcc tgctgggttc  68160
aagtgatttt catgcctcag cctcccgagt agctgggatt acaggcacgt gccaccacgc  68220
ccagctaatt tttagtagag acgtggtttt gccatgttgg ctaggctggc ctcaaactcc  68280
tggcctcatg tgatctgccc accttggcct cccaaagtgc tgggattgca ggtatgaacc  68340
accaacccta aaattccatc tttaaaaatg tacgtgattc aggtataggc atatatggaa  68400
ttttctactg tagagttcac aactgttttcc tgagtggtac cttcattcag ttattctgtc  68460
atgagtaagt acttggaatt acctatttgg gcagctccta tgcacctaag gaggcaaact  68520
cagtctgaaa gcaaatatgc ttttgggagt actctggagg aatattccca ggagctttta  68580
gcattccaca gattttggac cgcaacagat cttggttgga tcaagtggtt gaaatgggag  68640
cagagtcctt ccatcccatg cacacacata cctgctcaca gctgtcttca caccctgat   68700 tgctgtagca ttcacattat ttggtgcata acctttattt tttttaaatg cgttaggtta  68760
tgtccatata acatcacggt tgggctggct aagcctcatt aaggattagt gtaaggagaa  68820
agccttagag gaaagtttaa aattgattga gggcaaatga tcatacttct cctcttgctt  68880
atatctggaa aaaaaagtta aatatatgcc tctgcttcat ccatagtaat ataagagtca  68940
gttattatct ttaaaagcat atattgatga aagaatttga aatactaaat aaatggaagc  69000
tatcccatgt tcatgggtag ggagactcaa tgtcaaaatg tcagttcttc tgaagttgat  69060
ttatagattc aaagcaatcc caattaaaat cccagacagt tattttgtgg atatcgacag  69120
atggattcta aagttatgtg gagaggcaga ggactcagaa caaccaacat gaagttgaag  69180
aacaaagttg gaggactgac actacctgat ttcacaactt actataaagc tatagtaatc  69240
aagactgtgg tattggcaga acactagaca aacaaatcta ctgaacagaa cagagagctc  69300
acaaatagac ccacacaaat atagtcagct gacctttgac aaagaacaaa ggcaatacaa  69360
tagagaaaag atattctttt taacaaatcg tgctggaaca acctgacaac cacatgccga  69420
aataataatt tagacacaga cctttcaccc ttgacaaaaa ataagtcaaa ataaattcaa  69480
gacctaaatg taaaatataa aggtgtaaaa ctcttagaat ataataacat ggagaaatgt  69540
aaatgacttt tgatatgggg gtaacttttt agatataaca ctgaaaacac agttatatga  69600
aagaaataag tgataaactg gactttatta aaatttaaaa cttctgctct gcaaaagata  69660
atgtcaagag aatgagaagt taagccacag tatggaagaa aattttgtaa aagagaaatt  69720
tgagggtggg cccagtggct cacacctgta atctcagcat tttgggaggc cgaggtgggc  69780
agatcacgag gtcaagagat agagaccatc ctggccaaca tggtgaaacc ccgtctctac  69840
taaaaatgct aaaaattagc cgggcgtggt ggtggccagc tgtaatccca gctacttgag  69900
aggctgaggc aggagaattg cttgaacctg ggaggcagag gttgcagtga gccgagattg  69960
```

```
tgccactgca ctccagcctg gcgacaaagc aagactttgt ctcaaaaaaa aacaaaacaa   70020
aacaaaaaaa aaaaacattt gataaaggac tattatctaa aacgtataaa gagctttaaa   70080
atccaacaat aagaaaacaa cccacttaaa acatgggcaa agaccttcac agaaacctcg   70140
ctaaggaaga tatatatcca tatggcatgt aagtgtgtga aaagatattc agcatcatat   70200
atcattagag aattgaaaat taaagtaatg agatactact gtgcacctat taaaatggcc   70260
aaactccaga atactgacaa caccaaatgc tgccaaggat gtggagcaac aggaactctc   70320
attcattgct gatgggaatg caaaatggta cagccacttt gggagacagt tgttagtgt    70380 cttagaaagc taaacacact ctcatcacac aatgcagcaa tttctgtcct tggtatttac   70440 ccaaggagt tgaaaactta cacccacaca aaagcatgca catagatgtt tgtagcagct     70500
ttattcataa ttgccaaaat gtgggagtaa acaagatgtt cttcagtagg tgaatggata   70560
aacacagtgt tacatccaga caatggagta tcattcagcg ctaaaagaa atgagttatc    70620 aagccataaa aagacataga tatgcatgtt actaagtaaa aagagtcaat ccacatgatt   70680
ccaactatat gacattctgg ataaggaaaa actatgagaa tggtaaaaag attcgtggtt   70740
gccaggggtt agagggaagg agggatgaag aggtagagca cagggaattt ttagagcagt   70800
aaatctactc tgtatgatac tgtaatggtg gaatcatgtc attatacatt tgtccatacc   70860
catagaaggc acaacaccaa cagtggaccc caatgtaacc tatggactt  gggtgataat   70920 gatgtgtcag tgtaggtttg attgcaataa atgtaccact ctggtggggt atgttgatag   70980
cagggatgtc ttgtcagggg acaagaggta tatgataact ttctgtacct tctgctcagt   71040
tttgctgtgg acctaaaatt gctctacaaa ttaaggcta  ttaaaaattt ttaagcatat   71100
aaggagactt ctgtgtcata aatattaact ctgtgcttga gtacacccat tctgtttcac   71160
ccatggagtt gaatgattca acagaaatgg tcatagtagc aggaaacaga ctgcctaaaa   71220
aacttgtgtt ttattgatgg gtcttagaaa cccatgaaaa cttcacttct cttccttgcc   71280
tcatctccag gtataattca agctacaaat aagaatggac aaggcaacac aggaaagttt   71340
ctagttacag aaagattctt agtcttacta ttatattctg tgtatctgtt cctaatgttt   71400
gtcatgcaac caagaatatt agatatgtgt gtgtgtgttt aacttttcca ataggaatat   71460
aggattttaa acaactgtat ctagcaattt ggttaatctt ctaaatggca ggaacaatga   71520
gtattacatt actaaccttg aatacttgtt tagttttcac caatgccagt gtaagaatct   71580
gttacaggcc gggtgcaatg gctcaagcct gtaatcccaa cactttggga ggctgaggcg   71640
ggtggatcac ttgaggttag gagttcaaga ccagcctggc caacatggcg aaaacccgtc   71700
tctactaaaa atacaaaaat tagctgggtg tggtggagtg tgcctgtaat cctaactact   71760
tgggagactg aggcaagaga atcacttgaa cctgggaagg agaggttgca gtgagccaat   71820
attgcaccac tgcactgcag cctggtcgac agagcgaatc tccatctcaa aaaaaaaaa    71880 aaaaaaaag aatctgttat agttggaatt gaaagataca aagggtgaaa ttttttctta    71940
gtgtcacttt cattgctgac actaagtgtt taatcaggcc ttagataacc aatttgggta   72000
acttttgagt ttggccccat ttggtctctg ccaaggccct ggttactcag tgccatgttt    72060
ctcgattatt ctagccacag tcttagggtt tttctatcac tcaaattgtt tcttcttgac    72120
tttttttttt ttggtcctct ttctttttaaa gtcatctttt ctaccatttt cttggagtag   72180
ggaagttatg ctggaaaata aaattatgtc ttcatatcag gtactatagt ctggacaccc   72240
ctagcatggt attctagctg ttttgtgtgt ctcagctttg gttgttggca gtaatttaag   72300
tagttgagag aggttctgtt cttttttgagg agcacagaca cattcttcaa aaaaataagt   72360
```

```
aaaaaagaac tccaaataga gcccccaca gcacaggaac cagaagacag acctaagcac   72420
tgccgttggt ccctgaactg tgccattgtg taccttccgt gtctgacatt ttacatccct   72480
ctctatgcca ggcatcgagc tacggccttt catgtactgc ctctcagttc ttacaatcct   72540
gggagaccag aattattgat gctcttttaa tcaatgtgga gatttaggtt aagaaacttg   72600
aagaaattca tgcagctatt aaatggcaga gctgtgattc ccactggggt cctgtggaat   72660
cctagtatat tgttctttcc acaacatgca gcctttagc aaatgacgtt tatacttttg    72720
gacacgacat aaagttttcc aaggggtta gggttgtttt gcttttgaaa tagccacctg    72780
aaaagttcag cagcacccca aatgtgtctg tattgcggtg agctctttct gaacttagct    72840
cccctccatg gctcttggca cacaaacttg ccactcttac ccagtggtct cgttgctgtc    72900
ctggagggag atcagggatt ggggttatac tctcaaattc cttgaggtcc catagcctct    72960
agcataactc tttataaaaa gtgggcctca tgttggttga ttaattgtac atctctctca    73020
ttcgtctttc gaagtcatgc tgatgataac aaaaccagca taagagtgag ttgcagcaaa    73080
ttcattgctc ctactgacaa aaccacatgc tacctcctgt catctcagct ttcttgactg    73140
cttggataag ctagagaaat gcaccacaga agaggaaagt tagactttta gcaagaagga    73200
ctaaccgctg gcaagattac tttgctttaa aaaggaaaga aagaaaaacc acatccagaa    73260
aatataaagc gaattggcca aaaagtagat gatgttgtcc aggctacagg aagtgttatt    73320
tccttcctct cactgagctt ccagggctct gtgaaggcac agagggaggt ttccttgttt    73380
tgcagtggaa atttggatat atcatctctc tattttgctg actgtgattt ggtcctcttc    73440
ctcatccctc actgcctgga ccaggtctct ctgcttgtct cagaaggtat ttactggttg    73500
caaatagaaa tctctgctat caccctctgt gataggcaac cagaataaac cttcttggca    73560
ttctttgcta cagatgttat ggggtaacaa gattaaaaat attgtaatgt ttttgtggaa    73620
tgaaatttaa gagatttaaa ctgtaattac ttaaaattga caagggaaaa aaatggagtc    73680
ccccagagct ggttactgtg gagctaggat ggagaaccag gccttttggt gtcacacaag    73740
ctctctttat aaagaagcaa tggctcctct attctgggca ttctggccgt gtaggcaggg    73800
tgctttagcg ctgcctgtct ctgcccactg ggcatgggat cccaggagaa caagaagggg    73860
tcactcagac cctgctatcc aagtgtgtct tgtgggtgca ggtttcattg catattcctt    73920
acagcagtct attctatacc tagccagtgg ctcaagaaca cctgtctttc tcattgctat    73980
attcatcaga tgtttactca gtgcctgctg catgccaggc actgcgaagg acagttccct    74040
gttttgatca ttaaaaaaat taaatagacc ggacacagtg gctcacgctt gtaatcccag    74100
cactttggga ggctgaggtg agtggatcac ttgaggtcaa gagtttaaga ccagcctggc    74160
caatatggtg aaatcctgtc tctactaaaa atacaaaaat tagctgggct tggtggtgca    74220
tgcctgtaat cccagctact caggatgctg aggcaggaga attgcttgag cccgggggg    74280 cggaggttgc agtgaggtga aatcatgcca ctgtacgcca gtctgggtga cagagcgaga    74340
ctctgtctca aagaatgaat aaatgaatga atgcatgaat gaataaataa agccagaaga    74400
cttatctcct tttcacttaa gatggtgtgc ctatgcgtgt gtgttttata ctgatagaat    74460
tccatgccaa agctcacctg acctgagggg tggcgcattg agaaagtgtc ctgtctactg    74520
tgccccagca gggccgtggg ctagcttggt ataaggtaaa gcaatgagct ggcaggtagg    74580
aggcctgtgt ttgtatcccc agcttaggta gtaagtagct gggtgatatg ggacaaacct    74640
tttcagttcc ttaactatgt tttctttctt taattaattt atttactttt tatttatgt     74700
```

```
tttaagaggc agtcttgctc tatcacctag ggtagaacac agtggcacca tcatgactta    74760
ctgcaggctc aacttcctga gctcaagtga tcctcccgcc tcagcttcct gagtagttgg    74820
gactacaggc atacatcatc accaggcctg gctgatttaa aaaaaatttt tttagagaca    74880
aggtcttact atgttgccca ggctggtctt gaactcctgt cctcaagcga tcctcctgcc    74940
ttggcctccc aaagtggtgg gattacaggt gtgagccacc gcacctggcc tcctttgttt    75000
taagtaaggt tgttatattt tagtgagctg tgagttcttt ccaatatctg gctatctcaa    75060
atccacaaaa ttgagctcag ataattaacc tggaagactc atttgtctca ccaagaagta    75120
caaaagaata gaatcatctt ttaccatctt tgcatcccctt gactttctgc ctttgaactt    75180
attttcaaaa gccccagtga gttccatgtg gagtgcggac atcttgagac ctgaggctca    75240
ggaaggcggt gagtgtgctg tgcacaggga gaggtgcagc cactgtctgt aaggaaggat    75300
tttagaccca gcccttgtc tgtcctgtga cgagtttgca cccagcagtt tctgctcact    75360
ggcttcccaa gagacaatca gcttctattg gaaggacagc tcaccgggga tgggaggaca    75420
ggatatgccc gtggaaacct gacgagctta cctggcccac aggggatgga gcctttgccc    75480
ttggcctcat ttactgtgtt ttatccagta agataccaga ccagcaacac ttaaaggaaa    75540
aacaacagga tttagcacct gctccttctc tggggtgccg cccaccccccg cccagtcccc    75600 acaaacacac acataatgca ggtgtataga aacatagctc ttttatgtgt gtacgtgggg    75660
taaaactaat ttatcttgtg atcagaaagt agggagagat tttataaaac actccataat    75720
ttcagcatct gaatgatgct tttcttgttg ggaaatcatg cgtccctctc agtaattgct    75780
tctgagtctt cagcatattc atgactttct cttttgtgtg ccagagtcta caagcattac    75840
cattaaaagc ccttttgtat ttagttattt gtttacagat ctgtttcctt cctccttgaa    75900
gacaatgtct ggcacactgg tgttcaataa atgttttcat gtataatgaa tgaatgacca    75960
cattagtaat gtaaatcctc agcctaaatg tacatcctca gagagacaat tttctttctt    76020
tctttctttt tttttttttt aaacggacag aatcttgctc tgttgcccag gctggagtgc    76080
agtggcgcga tcatagctga ctgcagcctc caacttctgg gctcaagaga tcctctgacc    76140
ttggcttccc tagtagctag gactatgaat gtgtgccacc tcacctggct agttatttta    76200
tttttagttt tttgtggaga caggattttg gctatgttcc ccaggctggt ctcccacctc    76260
agcctcccaa agtgctggaa ttatggatgt gagccaccac gcccagagag aattttctaa    76320
ccatgttttc taaagtagct ccatcctcag gagttggcct ttcccaggtt agcctctttt    76380
attcctttat aacttttagc cctatatgaa gttactttttc ttgtttatat gcttgtgtgt    76440
ttacatatat atttttttct ttccattatt aagtaagatt taggacacgg agacattgaa    76500
taccctgctt tcctaacatc tgtaactaat tgctcactgg agaaattaat ctccaatctg    76560
cagttgaact tctggaaata gcaaaacttg ttcagaatga atttttggagc atgcagtagt    76620 aattaagatg aataatgtct ttgggaagac aaaataccac gtaaagtaat ggagaaatag    76680
ttctgtgctt tttcacacat gactcaaact tgtttcagag gcatttccaa acaaaaatat    76740
tcagtcatat ttcagcaatg caattccatg ttactttgag gtggttactt tatagagtaa    76800
tattcatctg acggtgtcaa ttttttacatt aaagaaaaag tgcagtaaaa tttacaagca    76860
acaaaaggca ttcatcttag gtttacaatt caatgtgttt tatcaaatga atgcagcttg    76920
tatgcctaac attccgatca agataaaaca catttcccctt accccagaaa attccgcggt    76980
atctttatcc acacagttcc cacccctcagt aaacagccac cgatctggtt tagatcactg    77040
cgagttagtt ttacctgtga gtcaacttca tatcagtgga attagatgtg tctattgtgt    77100
```

```
ttgggctctt tcacttattg taatggtttt tgggttcatc catgatgttg cacatccgta    77160
gttcattcct gtgtattgcc aggtataact atattacgta ttatatatca tagttatagt    77220
atagtaagta atatatacat ataacactgt cagtactccc attgatgtac attttgatgt    77280
attccagctt ttgactatta aaataaagc attcacaaac attcttataa agcactggag      77340
tgaggatgtg gccaggtcat aggataagtg tacgtttaac tttataagaa accaccagca    77400
atgagagaga gttccagttg ctccatctcc ttaccagtga ttggcacagt caatcttttt    77460
aactttagcc attgcagtgg gtggatagta tttcactgtc ttttttttt  agagttataa    77520 tttgcataga gtaaaattca ccgttttag tgtacaattc tgcaggtttt gacaaatgca      77580
tacaatcttg aaacacaacc gtggtcaagc tacagaacca ttccgtcagc ccccaagttc    77640
tcctgtgtcc cttttcagtc atccccatgc caccctgagc acttggcaac tactcatgtg    77700
ttttgtatcc ctataatttt gcctttgcct agttctggcc taccagggtt tatcagcggt    77760 atattttta  aaatgttatc agtcatatat gtttataaat ttaaacatca agaccatttc     77820
tacaaggttt ataacgaaaa acaggagacc cttcttaact cctctcgaat tctgaggagt    77880 ttcaacttt  tcagaagtct ttcaactctt tcagccaatg ttttatgcca taaatctctt     77940
catttctaaa ttcatttctt actatggaag ataaggattt cactcttctg tacaccccac    78000
caacgatgca gatacccatt aatccctcat agaaaagcaa atatagatac aattttttt     78060 ttttttttgag accgagtctg gctctgtctc tcaggctgga atgcagcggc atgatctcag    78120
ctcactgcaa ccccccacctc caggttcaag tgattctcct gcctccacct cctgagtttt    78180
ttttaaacac ttaggatttg ggttattatg cctatgtagt gtaagcagca gaggctgtgg    78240
gatttacctt gattacattt cctttcttga ataatatgtt tttctagagc taattccttt    78300
ttttcttcat tctctgtgaa tttacctcta tttcatactc aaggttgctg acaggagtat    78360
tgactgcctt ttaatatgtt gagacaaata agatcattta tcagtttctt ttttttcttg    78420
gattcattcc tcatgggacc gtctgtcctc ctcccttgtt tgggacgttg tgctttccca    78480
gtgacagctc tttttctgag ggctctcttt atcatctgtc ttggggacag aaaaatagga    78540
actaactagg taattcaaca gagctagggg tagtatgcat ttgtataaat acagattaat    78600
acctgttaat tttgactgat ccacatgtat aaaaagtcat gaattcatgt ggataccttc    78660
aatcccaatc cggcagcaca gggttcattc gagatttttc ccttctgggg cttataactc    78720
cattctataa tagtaagaaa cctagcttcc catattttta atagatttag ctatttgatc    78780
agttccctgg tatgtaactg atcactcatc ctcattagca tgctgtctcc catgggaaca    78840 ccccctcac  cccgttttag ctcagctatc cgaggccagt gcaccacccc caagtcctat     78900
gtgcggatac cccctcgccc cacttaggct ctgacacccc gtctgctccc ttacacggat    78960
gcccacctcg gtcccctgg gctctgacat gccatgccag tctggacccc tctgcggatg      79020
tgcagccttc ccccactgcg aatgcccagg tcactctgct ccaccccatg gctcagtact    79080
cagctgccca ggagggacgg cagaagggc aggatccatc tcctgattct gtcctgattc      79140
ccattcccca aggttttcct ttcttcaatc ttcctatacc aaagactact gtcctcctat    79200
ttgcttaagc ccaaaataca aataccttg agaatttgcc tttactcccc cattcatggc      79260
cacccccagc aaaatcatga gcaactcctg ttgattcata tatatcattc gtctgggtgc    79320
ggtggctcat gcctataatc ctagcacttt ggggaggtcta ggcaggcgaa ccgcttgagt    79380
ccaggagtcc gagaccagcc tgacagcatg gggagatgcc atctctataa aaaatgcaaa    79440
```

```
aaatagccgg gcatggtggc atgcacctgt attcccagct accaggggtc ggggttgggt    79500
gctgaggtgg gatccatgga gctggggtgg cggaggttgc agtgagccat gattgtgcca    79560
ctgcactcca gtctgggtga cagagtgaga tcctgccaca agaaaaaaac aacaaaaaaa    79620
acctcatcaa tgtatatatc ctacattttt ttcatctctc ttcctcttca ctgcacccac    79680 cactccccctt tggtgttcct cttgctacta cacctcacat cccacaatcc attcccatat    79740
agcagcaagg atgctctttt aaaagcctaa ggcagccagg cacagtggct cacgcctgta    79800
atcccagcac tttgggaggc cgaggctggt ggatcaattg aggtcaggag ttcaagacca    79860
gtctggccaa cgtggtgaaa ccctgtctct acttaaaata caaaaaataa gctaggcatg    79920
gtggcacacc tctgtaatcc cagctactga aaggatgaa ccatgagaat tcttgaacc    79980 tgggaggagg aggttgcagt gaaccaacat tgcaccactg cactccagcc tgggtgacag    80040
agcaggactg tctcaaaaaa caaaaaacaa caacaacaaa aaaacataa ggcatgatga    80100 catttgaaac cctccaacgc ttcctgctgt acttagaata aaacttgaat ttctccatgg    80160
catataatac ctgtgtctga taattaatct tggctacaca ttagcatcac catctccatg    80220
gcatataata cctgtgtctg gtaattaatc ttggctacac attggcatca ccatctccat    80280
ggcatataat acctgtgtct gataattaat cttggctaca cattggcatc accatctcca    80340 tgcatataa tacctgtgtc tggtaattaa tcttggctac acattagcat caccagggga    80400 cctttttagaa gcattaagtc tgggcctcac cccagaccag ttaaatcaga atatttggtg    80460
gtgtggacta ggcatcagtg tttgtaaaag ttcctggtgg gtctcacggg tgcccagggt    80520
tgagaaccag gcctcctcta actaccttcg tattgcctct ccccatttca gtctcttgcg    80580
ctgaactctg gcaatgacat ttttcttctt tctttgaact tcaggcttat tcttgcctca    80640
caacttcctc gcttgatttg tttctgtctg gaagtttctt tgcccagatc tgttaatggc    80700
tcattccttt tagcttctta gagtaatctg tccttggtca ccgtatctaa aataatgtgc    80760
catgttacca accattctct gccatattac ttttcttgag cacttcttcc tcttagcact    80820
gtcattatct caggtcattc tacttgtgta tattttttaac attagagtgt aatcttcatg    80880
tgaactcttg ctttccatta tgtcatggtt cttaattagt gtttaataaa gatttgtaga    80940
atgactgcat gtagcgagga gaagaatcag ggaagagatc tgttggacag aaagtgtgca    81000
ggagccagag agacatttgg ataggtgaag tgaaatggag cagataagag tcctgactga    81060
tggagattac ttgagaagcc agatttaaag taaataattt tgacagtgga attagcaact    81120
ctctgttatt ttcagttgga gaggacagat ttttattctg gattagagca atcccaagaa    81180
agcagaaaag acttgtgagc ctagcgaaag agcaaccctc agcatagaat acgttggtgt    81240
tcaccatggt tgccatgaat ttgctttttg caactgtcat ttcccctaaa tgtaggcaag    81300
agtggccctc tggactcatt atcccctcac gattcccttt attttaatgg tgtaataact    81360
taaagcatct gagatcctgc ggaccacttc acaccaccca ccgattgcag ctactgtatat    81420 gcccatcact tcctctttgc attatgcctt cttttttttt tttgagatgg agtctcgctc    81480
tttcacccag gccagagtgc agtggcacta tctcggctca ctgcaagctc cgcctcctgg    81540
gttcacccca ttctcctgcc tcagcctccc tagtagctgg gactacaggc acccgccacc    81600
acgcccggct aatttttttgt atttttagta gagacggggt ttcaccgtga tagccaggat    81660
ggtctcgatc tcctgacctc gtgatccgcc cgcctcagcc tcccaaagtg ctgggattac    81720
agcattatgc cttcttaagt ctaatatcaa gctatatta attatgattg tcttactgta    81780
aatacgcggg attaattgga aaactggatt cttgcttgta tgacaaccca ggtatgtaat    81840
```

```
gtggaaatga gcaaacatat ttgtgaacta ttaccatatt ctgtgcagtt attaaaattg   81900
aatttatgga gttctgacag tatacgctta aaactccaga gatagatctg ttctctcata   81960
cctgatgcaa ggaaaatgaa cattcacgtt tacaaattca gcatgataat tttgtgcctt   82020
taggtagggc ttacacacac accacaattc tagagaagac ataggaggtt aaaaaaaaaa   82080
gttttttcaa caatgacagg cttaggaagc ataattccgt gatgaatggt tgtgcaaaat   82140
actgtttaca aacgtacaga taaattcttc tttgaaagtg gaatgaagtt tgtattgtga   82200
cagcttggct ttatagggca cagaacgatg aaaactgttt ggaaaagatg aatatcttgt   82260
ttctcagcct gcccgcctcc cactctgccc ttttcccagg gtgaattcga agccatttat   82320
tcatgcaaaa gcccattttc atgttttcac agaaccaagc aagtatatac agatgggtac   82380
agaccttgag acctggggag aaatgcttag cttagtatcc ttcttattcc tgaatctctt   82440
acaccttggc atcctaaatc gggggaagtg tttcctgttt agatatcttt ttctcagcca   82500
tgtgccttga tgcaagccac aattccacag catagtaccc cacgcctccc tgtaaaatgt   82560
agcaaatcct ttcaatgtct gaatgccaca gtttaaaata tttatgaaat actactttta   82620
caatatttgt gaaatattta ttgaatatat gcccaaagaa gataagttca gttttctacc   82680
cataacatgc acgaagtaga gtatgtgtct attttttggt tgatttcatg tagaacaaat   82740
tacaagagag ttctaggatc ctattggcag atgccagaag ttttaattac agtttgcatc   82800
tactcactgt gtatatatgg ctaccttata cgtgtatgcc gttactttca gtggcaaaaa   82860
ctgcagtttc ttttgcacca acctgatacc acaaggttta cctgggcaag atgaccacac   82920
tgatgcttta gttgatgggc atggggaatg agggaaatta ttacagtgaa cttcctacag   82980
taggtgttca gcaaatagtt aatataaaaa atctgtttat ggacagagta aattgtctac   83040
tctccacaag atagagggtt ggaaaacatc tatagggagtg tgtaccttta ttggaatttt   83100 ttttttttg gaaacggagt ctcgctctgt tgcctaggct ggagtgcagt ggtataatct   83160
cggctcactg caacctccgc ctcccaggtg caagagattc tcctgcctca gcctcctgag   83220
tagctgggat tacaggggca caccaccaca cctggctaat ctttatattt ttagtagaga   83280
cggggtttca ctatgttggc caggctggtc ttaaacttct gacgtcatga tccacctgcc   83340
tcagcctccc aaagtgctgg gattacaagc gtgagccacc gtgcccggct ggaattttta   83400 aaagaagtt aaagccttta cctaaagcct cagcaaacaa acgcataaga tcttttatg   83460 ggggtggcgg ggggatgttg cttttagcat taccaagaat tgcacgtaat tttgttttat   83520
tatttcatta tttggattat ttttaaagtg caaatatttg tcttcataag atctgctagt   83580
tcaatttaaa attttccag aatagtggtt cttaacctgg gaactcagaa gagttacagc   83640
aaatataatt tatttaaaaa tatatatttt aatagtataa ggtgacatgt agaaagcatg   83700
tatacaatga aagtccatat ttattcatgc aaaaacattt attaaatgac tgtaaggtat   83760
tagggtgata agaaacgggc tgtcttgttg gttttttttg ctattgttct attcttcctc   83820
caaaggagta gagatgaggc taggttctaa gtgaatttta aatccaattg ttattaagag   83880
aatacagctc taaatacag ttagattttt cttgtgtaat aaactaaaac attcatcttc   83940
taacgtactg ttaattgtct ctgtcaactg ttgtatccca gtattgctaa tagaacatga   84000
gagtatatat tgctaataac tttatgatat cccagaaaac ataaaatatt ttgtgttctc   84060
ttttgctctg acaggttggt acagaggata taccctccaa aataaatcta aaaggtatg   84120 acttatcatt cactttttaa tttcatttga aatctgtctg ctagttttgt attgtgctat   84180
```

| | |
|---|---|
| gtgaccctct cctctgctct ctgctgtctc tagacctagt ttgctttctc tttgatggct | 84240 |
| cttctttgga tttgaaagca aattctctga cctcagtgcc taaatgtaat agtgtaaatc | 84300 |
| ccattgactg tatttcctac cagccaattc aaggagaaaa tcctggaaga cttcttgctt | 84360 |
| cctgtccctc aagttaagca agttggtaac acattcattg ccctagtggg atctcttttg | 84420 |
| cagggagggg tggacccacc cttctccctt tgtcctttac ttccaatgct acaattccaa | 84480 |
| actaaaggat ctccccattt ccacttgatc ctttccttca ttgtaaattg gataaacaag | 84540 |
| agtggttttc atattatgag cctcacatcc caataataca ttatgaaatc aatatggtgg | 84600 |
| attataacca attttttcca aaaaatgaaa ccgaaaagta gagaacatga gatgcaatgg | 84660 |
| taagtactgt ttcacgaaac ttttatttta ggtatatact tttatttatt gttttttatta | 84720 |
| tattttatgt atttgatatg taatattggt tgccataaga atgtatcttt tactgtgcaa | 84780 |
| caaaggcaca gtttgaaaaa tactgaccta aatggttcct tttgccagtg ccaaaactac | 84840 |
| taatcgtcag gctaaagaaa atctattaat tatgttaata cctccctcag tttcttttag | 84900 |
| gtcttgtcag cacttttcct ttgatactgc tcgctggggc agcatgacat gtcagcactt | 84960 |
| tcttttgaaa gagcagagtt gatagggcct tattatttca caattagttc acatgccaaa | 85020 |
| tagcaaatta ggaaagggat gagagaaacg ttttagaatt tatcaaaaga gggagtgaaaa | 85080 |
| aacaaaacca gacccacggt tcttacactt cacggacagc atgagaaaga cgtaatcctg | 85140 |
| cacagatagg ctgatgttac acacccaact ctccaaagag tacggggccc aggaaaaacac | 85200 |
| cttctacaa ggtatagttc attagaaacc aggactgctt ctgcattgtt gatgcttaag | 85260 |
| tcacactcag tatttgcaca tgtatgtgta cacatacaca ttttgttaac tttgacagtt | 85320 |
| tattcatcta gcaaaataaa ggaatgtttg cttttaatgc aattcccaca gttttggtcc | 85380 |
| tttttctca cctcaagcca gagaatgaat ttttctaccc acagttattc tagtgtcgca | 85440 |
| tgtctttatt tcaaaccaaa ttattttcat ttaatctctt gctgacttca gtttctctgg | 85500 |
| gccgtcaaat aggggtccaa gacagcaggc atgccagagt aaatgagaac atgacagaac | 85560 |
| taaagtgaaa gcttttcttc tgggatcctc agtgacacag agtacttgat tatggccact | 85620 |
| cttgcttttt tagccctatt ggtgttaatt ttactcatag ttatggaagt ggtagttact | 85680 |
| tcaaagcacc attagagtta acaattttga tgttctgaat ttgttaaaca gtaagaatac | 85740 |
| ttatgtcact taattcccaa tccttttta agaaaaaaaa agttaattta aaacaataa | 85800 |
| acaaaaagcc attctcaaac aaaattatgt gatgaactta aggaacaaac gaaactcttg | 85860 |
| gatttttcac tgcgaaattc aattacgttc aaccaaggtc ctagatcagg tcttcttttt | 85920 |
| catagactac agtatgtaag gatccttttg aacatggcag accttgcttt ctaaagtatc | 85980 |
| ctatgatttt ttaatatagt catttcctca tttccacagg caattggttc caggacccccc | 86040 |
| acaataccga atccatgga tgctcaagtc tctgatataa aatggcatag tatttgcata | 86100 |
| taacctctgc atttcctccc gtgtacttta aatcatgtct agattattta taatacctaa | 86160 |
| tacaatgtaa atgctatgta agtagttatt ataccgtatt gtttagggaa taatgacaag | 86220 |
| gaaataaacc tctgcttact ttttttttct atattttaa tcatcagttg gttgaaccca | 86280 |
| tgatatggag ggccttgtgt atataaaaat cagtctagct aatagtgcca ttgttgttgg | 86340 |
| ctttgaacag tagatagata gggttccccc aggatctaaa tgataaattc tggatttttt | 86400 |
| ttaaatttt ttgtgttcat taaagagtgc ttaaaacctt taagcttaaa atctcaccct | 86460 |
| tcagaagaaa tctttcggta agagtttctc tttgttctct tggtaagtaa agaaaaactt | 86520 |
| tctaattcaa tgaaatgatg acacagacaa gggacatgca tttatttgat gattgttta | 86580 |

```
agccgaaata tccttcttgt ggagagattc agggaaaata caggcaaatc aaattcagtt   86640
gccatgaatt ctgctctgct tttgacaccc cgtcattaag agatcagctc attagaaacg   86700
ctctcctgtg ctgtgtccct catttctccg tctttaaggg gaagagctac ttgaaaggcc   86760
tgttgtttta atggaaattc ttggtgtcat ttataagctg acccagccat ttagagtgat   86820
gataaaagga gctagttgat gataaaagga gctagtggtt ttacaaattg aagaagccaa   86880
gcgcttttcc gaaactgatt attgatcctg gtggaattgt gggagtgtgg ataagggcaa   86940
catctagaaa atcattagtt tattttcta ctcaagtgag tgggttacaa tgaggaagga   87000
gaagcagaac tgagagacag gctgtaaatc agaaacacat gacctaggtt tactctgact   87060
ttctgtgtgt catcatggca taggagtcat tctataagca tcagatttgc cagagcaatt   87120
ctatgactgt aaatggccaa gtgtcatcat ggaaaggtga agcctactga tgacaaatac   87180
acacatacta tgtaacaaat acacacatac tgtataacaa atacatgcta tataactaat   87240
acatacatac atatatacat acatacatac atatttgaga caggatctca gtctgttgcc   87300
caggctggag tacagtggcg tgatcacagt tcactgcagc cttgaccttc tgggctcaag   87360
caatcctcct gcctcagcct cccgtgtagc tgggaccatt ggcatgtgcc accatgctgt   87420
gctaattttt taaattttg tagagacggt gtctcagttt gttgcccagg ctggtcttga   87480
acttctgggc tcaagcgatc ctcttgtctt ggcttcctaa agtgctggga ttacaagcat   87540
gatccactgt gccttgcctc aaatattctc ctaatatgaa aatcatcatg tctgaacatc   87600
cagtgtaaat tgtctgctta tgatctgctt agatgtcaca agattcatca ctctgcattt   87660
atgtttctga atacttctat cttgaatgtt ttccacttat taggagcgac tagtcaccag   87720
attgtgaatg catgaaaatt ttaattggtc ctttaccttc tgatttcaaa aaccttcagc   87780
agggatgttc ctttgtagta gcagtgttac attttacttt tgacttccag aattggatcc   87840
ttgtaactaa acagtttatc cgtgcccagc gcctccgcaa cccccactcct gcttttttat   87900
gagttttgga cttttttat tgtggtaaaa atatatataa cataaaattt accatcttaa   87960
ccatttgtaa gtgtactttc cagtggcact aagtacattc tcattgttgt gcaaccatca   88020
acaccatcca tctccagaag tctttcatct ttccaaacta aaattctgtc ccctttagat   88080
actaacttcc tattgttccc tatccccgc aagcccctca gaaccccat tgtactttct   88140
gtctttatga atttgactac tccaggtgta agtggagccg tacagtattt gtccttttgt   88200
gactggctta tttcacttag tgtaatgtct tcaaggttag ttcccaacat cccagtttag   88260
ttccccacag agatgatagt cagcaaatca tttgccgtgg cgcagtggca cagtggcaca   88320
gcggcacagc aggcagaaga aacacccaga gttccttagg cctcctaggg acaggcctag   88380
agcttccgaa ctgcagaaat caggcccag aggaatcaca cgcagttttt gaactgaaca   88440
ccctcctttc tcattgctat attcatcaga tgtttactca gtgcctgctg catgcctggc   88500
actgcaaagg acagttccct gttttgatca ttaaaaaaat taaatagacc aggcacatgg   88560
ctcataccctg taatcccagc actttgggag gctgaggtga gctgatcact tgaggttaag   88620
agttgaagac cagcctggcc tggccaatat ggtgaaatcc tgtctctact aaaaatacaa   88680
aaattagccg gcatggtgg tgcatacctg taatcccagc tacttgggat gctgaggcag   88740
gagaactgct tgagcccgga gggcggaggt tgcagtgagc cgaaattgtg cgactgtact   88800
ccagtctggg caacagagca agactctgtc tcaaagaatg aataaatgaa tgaacgcatg   88860
aatgaataaa tagtcagaag acttatctcc ttcttttca cttcgatggt gtgcctatgc   88920
```

```
gtgtatgttt tatactgata gaattccatg gccaaactca cctgacctga ggggtggcgc   88980
attgagaaag tgtcctgtct actgtgcccc acagtagaca cacatttaat ttttgttttc   89040
aattatttga tcagttttcc aaaatggttc tgaatcccac ctccataatg aaagaggtca   89100
ttgtcacctt gtgtctgtgt gtgttcttgg tctcatcagt aacgggatta gaattccac    89160 tcatattccc cacgcctgcc cccgtctcaa agcgaggagg agaagggatg tactttttat   89220
ttggggcttt gtgtctggtg gggaagcaca tgcaggatcc actctgtcat caccaatgct   89280
aggggcagtt taatctcaaa tgttcttgct gtttcctgtt ttattggcaa cggattaaaa   89340
gagagaaagc agagtgttgt acagacaaat atagcacatg caactggaca caagaacaac   89400
cctgtcaatg ttcactggtt tcctgtctga gtggagtaag gatcagtggg tatatatgcc   89460
tccgggcact gggacatccc ctcccacctt tatgatcagc cacccctgac atgtcatgtt   89520
catggagttc acaccaactc ttccaggaat agggctggga gcagttagcc aacagtgcca   89580
ggtataagct ccatgtaaga taccatgaaa cagatcagca tcactgtctc cggatgacat   89640
ctcctctgtg tgtgagcata tcacacagta aacagcagaa gctttggtac acataacact   89700
cacatctggg acttgcttcc tgttggttag atctggtcct ctgttctctg atttctatcc   89760
accagtttct cctcttttctc ttaggtcttt ccaggcctaa gtcttcccca tgggcagtgt   89820
tacaatactg atgtagaact gcctcttagg gatatagaat ggagagcagt ttgacactgt   89880
gaggtgctga aaataaccag gtaactaaca cccgttgatt ttgagtgcat ttggtttaag   89940
tgggagtgct gagaggaact actttagaaa aatcactatg tagttgaccc gtgaaaaata   90000
tgagtttgaa ctctgcagca cttccacatg gattttttt ttttagccaa atgcaaatca    90060
aaattacaat attcttggga catgaaacct gtgtaaaagt atatgcgggt tgtgcagggc   90120
tgcgtgccat acttgagtat gtgtggattt gggtatatgc tttgtgggaa ggaggtttct   90180
ggaaccaacc ccttgcatat tctgagggat gacttatttt atgggctact gagtactgca   90240
tagtttccat gtcaccccct tatgtgaaact tatgggaagc atctcatggc aagtagcatc   90300 tgagggttt aggagttcac aattacactc cttcccatta tgttatctct gagctgacac    90360
agcatgtttg cctcttcatt cacaaaatat cctatgctct ctgaacccaa attttaattt   90420
ctaccttttt gatgtttcca ccatgctttt gtggaggtag ccagtcaacg taagtggtgt   90480
cctgccaacc tgatctcagg agtttagcta ttgcctgggt gttcccattt attctcttta   90540
ctttgggctg aggtgttttt gtttggtttt tgtttgttt ttatggccat ataaccaaaa    90600
ttcttttctc tgtagggcat tttccctgaa acatatatcc atttgaaaga ggcaactgtg   90660
gaagacctgg ggtaagttcc aagctaggaa gattccccaa aaatgatgaa gatgtaacat   90720
tatcattaat gataatcttt aggcattaat gccttatgta cgttaatagt tctctcatct   90780
caggccaggc gtggtggctc acgcctgtaa tcccagcact ttgggagacc gaggtgggca   90840
gatcatttga ggtcaggagt tcgaaaccag cctggccaac atggtaaaac ccccatctct   90900
actaaaaata caaaagttag ctgggcttgg tggtgggtgc ctgtaatccc agctactggg   90960
gaggctgagg caggagaatc actcgagccc aggaggcaga gctcgcagtg agctgagatc   91020
ataccactac actctaacct gggtgacaga gcaagactct ctctcaaaaa aaataaaat    91080 taaaaattt ctctcatctc atcagttcta cttctcctat gagagagaaa tgaagaaaaa    91140
cttttcactc atacaattcc ttcctctgtc ttctctttct ataattgttc ctccttttcca  91200 ttacttctcc agaatactaa acacagaagt agcaaaaact gagggctttt gcctctacat   91260
tacatttatt atctgttcac tgattgtgtg tgtgtgcgtg tgtgtatgtt tgcacacatg   91320
```

```
aacatttggg actctgactg ataagatctg agaagccccc aattcaggat ccttgagaga    91380
gagatgatta agcaacagcc tgcatttacc agctctgagc cttggatgaa tcacttaaac    91440
ttaagtggat cctgggtttt tcacagcata ttagggaaaa caatctgacc ctactttgat    91500
catgagcttg tcatgagatt cgaatgaggt aatgtatgca aatgtgccct gaagataaga    91560
tctgctatat tttgggtatt catatttctt gcccacctca tcttgcccac ctcatttgtc    91620
ctgggaagta ctgcctctgt gacagctaag aagagtgagc tacttagtct aagtgggaga    91680
gagagaggtg acttaggtga tggtgagtct ctggacagga gaattctgga ggcagtacgg    91740
agaggctggg gtaggactgg aatcctgggg ctgatggaga ggagagtggg gccgaggaga    91800
gagtggacag ctgggtcaca gaaccatgca gcctcacagc tagaaagagc attcccagtt    91860
gtagttcagc accatcattt cttttctttt gttttctttt cttttttttaa ttatgatggg    91920 caagctttat tttgtatgaa cttgatttca caaaattaga atggcaattc cacttaaaat    91980
taactgttta aaaagtgtaa atgtcacggt atagatctgt tatccaaaac tccaaaaggc    92040
agtgaaattg gtaacagata ttcctcctca tctttggacc catacaacag cagaattgat    92100
gaaactggtt cccaggcaag tatgtgccac ttgctcccgt gcctcaggga ggagaggatg    92160
ttatgacaca ggcgtttttg ttgcagtgac ttgtggataa ttgctcctta ttaacactgc    92220
taaaattatg ttcacatgtt ttactttgtg tgggagccga tgactcttgt cctttcgttt    92280
tttgagtatt atctttcaaa tgagcgttgg cctcaaaccc gctcattcca aaatgcatca    92340
cagatgggaa tttaagcctc ttcacaaagc aaaccactgg aaattcatag gtagtatgca    92400
acattggtct gtaactgata atagggcaac atcatttctt tggaacgtaa ttttcttgat    92460
tccacaagaa gtgacaggat aagaaaactc atagttaaat gagaacagtc ttgttacagg    92520
acagttatct cccaggtgta tgtcatcaat tctaatttcc gtgttgttac caagggcct     92580 tattttcatt ctgactaaca accaatcatc agaacacatt gaaactgttg ctgggtcaag    92640
ttcaaaagga ttccaaaaca gtaaaaaaaa agaggaaggg cccaccaaga gcacagaggt    92700
cttcatcgct ccagactccc agatacagca cagggaacaa gaaatggcag aaccatcatt    92760
tcatagacaa gtggtcaaga tgtcctcaaa gccgtacagc tctttggtgg cagaaccagg    92820
accaaaaacc aggtctcctg ccctgctgga gaagtcctct ttccggtggg ccgtgggctg    92880
cctccactgc cacccaccat gttggaggaa acgtaggtgg ggaggcacat tcaccaat     92940 tagggttata caggatgccc agttacattg gcaattcaaa tagtaagtaa tttttcatag    93000
taagcatttc ccagatattt catgggtcac acttattcta aaaaatctta ctataccaga    93060
aattcaaact taactaggtc tcctatattt ttcctcattg agcctggcag tcctaccacc    93120
agttccaatt tgtttgcttg ctcttgcttt ctcctttttt cttttgtcta atcataaaaa    93180
tgccagagag gatttctgtg aataaatgta gtacctacct ttatgagagt cttctgtgag    93240
taagcaagga ttttgttaag tgtacgtttt ctgtgttgtg aaactgcaga tgagaagaaa    93300
acatgggact attccagaaa ggggtgctgc ctccgtatcc cccacctcta ccctggcctc    93360
tgccccaacc aggtcctggg tggagtcaca gccccaggac actcgtgcca cacacacctt    93420
tccatccagc ctcccaaatg aaacagctgc ttggtggaac cagctaaaat gctgcatatt    93480
ttgcttccat cttt gagaat cactgaagcc agcctggctc agtaatcgag tctcctggag    93540
aaatctacac tggggaggtc gaggctgggc cgcaggctca ttcagttgca ggaacggagc    93600 ccatttgag gactgtgctg ccttactctc cttctcttct cccagatgct tggatgcgat    93660
```

```
aaagtcccct gcacaactcc tgcccccagg cctaaccagc ttcattctca accttgaacg   93720
ttgggaagtc tgatccccat caagtaaagc agtgctgatc agcctagaag aaagtgaccc   93780
tcgtttggtt ctttgtaggc agcatgaaac cgtgattcct ggcgagctcc ccctggtgca   93840
ggagctcacg tccactctgc gagaatgggc tgtcatctgg cgaaagctct acgtggtgag   93900
tttccccttg tggcttggag ccccagggtc actctgggtc ctcagcctgt aggtcctttg   93960
cagggtgttg gcccctgatt gctgacttca tggagtggga tgcattctcc ctggatcaca   94020
caaaggctga taagcagcag attctcattt ccccagagct gggtcactga tagcgggtag   94080
tggagtaact gggcgtaatc attctagcag tcttttctca aatgataaac atgctgattg   94140
tgaaagtact aatgataata atcactgcaa acacttctgc agtctttcct aagtgccaga   94200
aactatgaat cctcacaaca ttcctataaa gtaggtgcaa ttattattaa tttgttaata   94260
aggaacctga gtcatgctct tagcctcttc atgtatacca gtgaactgaa atttatcgat   94320
atttcagggc tcagctgcat gaggatgaca ttctttacct tggcccacat accttacaga   94380
ctcagaaact tgaatagtgt taagttgtgg tctgagagtc acctttttgg gcagactcac   94440
agtattcttt ctcccaacac tggtttgacc tcataatgct aatacagtgt gtcagttcac   94500
agggaaatta caaggagcca gcacatcctc tccgtaataa acaataagct caagttgtgt   94560
gcaggaatca gcaccaagta aatctagcat ttaacatgat gaaactgaga acagctgtct   94620
tgcaagagac caaggatgct caaagtctat ggcagcaag tctgcctcat ctccagtgta   94680
gaaagctctt tccttaatgt ttttttttt tttgagacg gagtctcact ctttcgccca   94740
agctggactg cagtggcgct gtcccggctc actgcaagct ccgcctcttg ggttcatgcc   94800
attctcctcc ttaatgttaa cattggaatc cacaaagact ttttatttta tttatttatt   94860
tttttgagat ggagtctcgc tctgtcactc aggctggagt gcagtgacac catctcagct   94920
cactgcaacc tccgcctccc aagttcaagc aattctgcct cagcctccca gtagctggg   94980 actataggcg tgtgccaccc cgcctggcta atttttttttt tttttgtat ttttaataga   95040 gacaaggttt caccatgttg gccaggctgg tcttgaactc ctgacctcaa gtgatctatg   95100
tgtcttggcc tcccaaagtg ttgagattac aggagtgagc caccatggcc ggctaattttt  95160 gtgtgtgtgt ttttagtaga gatggggttt taccatgctg ggcaggctgg tcttgaactc   95220
ctgacctcaa gtgatccaac tgtcttggcc tcccaaagtg ttgggattac gggcgtgagc   95280
cactgtgccc cgcccacaaa gactgtttat tctaaagttg cttctttgcc tatagccctt   95340
gtagttcagc atcactgggt cttgcctctg ttagtgggtt ccagccttct gtggctgacc   95400
agaaattcct atggcgaatg tatattctct cgttagatgt gtgtacaagt tcagggaggt   95460
tgtagaccag acttgatggc ctgggaaccc tcctcttttc tttatgtggc tttgtttgtc   95520 tcaattttg ttcagtcatg tgttgattca ttttaactct gaaaagccaa tcttaataag   95580
ttactgggaa tacctcactc tagaccctaa atactgaagg cagtaatcaa aagctaattt   95640
tggcataact tataagagtt catggaagat atttcatttt cattcagggc tgttgtttcc   95700
cttggttaat cacagcagta gaaatcacca acccctttgg tggaaaagca catggtattt   95760
ctctacttgg tcatccttca agaccttgtt tagacgcttt cttcttcata ttgtattttc   95820
taaacatagc aatctataac gtttccctct ggacaataga agcacttact gctaaactca   95880
tcatctgacc cttggggcac actgcttcat aataaaggtg atctttttgat ctctttatgt   95940 ttagttgaag agagaatgca cattaagttg ctaaatcaca aggaggatgg agacactgct   96000
gtcagccccg tggccttcat tgatcatctt gcacttatat tgagagtact ctctggttct   96060
```

-continued

```
ggtttattga ttagttagtt gggtggatgt aacaaggttg atggatgagg aattgcgtgt    96120
acgtgggttg gttccttaac atgttctttc tggaaattga tgagtgttga aatgcattag    96180
ataatcagta ttgggaaagg agttttttttt tttttttta aagatgtatg agactggaga    96240
gtatgagtga ggccgacttt ttttcttgct aaaacacaac tggtgtgccc agtttattac    96300
ctatgtcttc tacacatcca caagtaattg tgccaggtct accattgaat agaatgaaga    96360
aagaagtgaa tgggggccag gtgcagtggc tcgtgcctgt aatcccagca ctttgggagg    96420
ctgaggacgg cggatcactt gaggtcacga gttcaaaacc agcccgtccc aatatggtaa    96480
aaccccttct ctactaaaaa tacaaaaatt agctgggtgt agtggcttgt gcctgtaatc    96540
ccagctactc gggaggctga ggcaggagaa tcgcaggaga atcgcttgaa ctggggaggc    96600
agaggttgca gtgagccaag atcacactgt tgcacttcag cctgggggaa aagagtgaaa    96660
ctccgtctca aaaaaaaaaa aaagtgaac ggggatgaag aattaggact catgtatttt     96720
ggctgccaaa atctcttagt agttaaaggt gataaggtct tgttgaacat ttccttggtg    96780
ggagagtttc atgttgtagt agcagaattt ggttaaaaaa aaaaaaaagg ccaggcgcag    96840
tggttcacgc ctgtaatccc agcactttgg gaggctgagg tgggcggatc acaaggacag    96900
gagttcaaga ccagcctggc taatatggtg aaaccctgtc tctactaaaa atacaaaaat    96960
tagctgcgca tggttgtggc cacctgtagt cccagctact cgggaggctg aggcagaaga    97020
atcacttgaa cccgagaggc ggaggttgca gtgagccaag attgtgccat tgcactccag    97080
actgggagac agaggggagac tccgtttaaa aaaaaaaga aaaaaaaaa aaaaaaagcc     97140 atcccctctt cgagggcagc acatttctca ttttaattta gatatctaat aacataatta    97200
ttttggtatt tgtgaataat ttaaaatgtc ttatagccgc tgttgattga ctaaaagaca    97260
ttctttgtag aaattctcag tcagtcgata ggactgagaa acctgcttct gctcttgata    97320
catgctcatc cagtaaggaa caatccacta agatttgtta ttatggttag tgcaaaagta    97380
attgtggctt tcaccgttac tttaaatggc aaaacccaca attattttg taccatccta     97440 gtattaattg tggctttctc tttttttttt ttcctgtccc ttcctaaagc attgacagtt    97500
aacttgaggc agaacttctg aacttcttac tgaaacgttt ctgtatcaaa gtagcaaaca    97560
tcaatattat gtttcactag gaaacaagta aaaacccaaa tctctggttt tcgtgtccca    97620 tctccttca cctgctgtat gctgttattg atgttttttgc tttctgattc tgtaagttcc    97680
ttcagtccat gtaaagataa atacagattt tactagtatg tagcaatact tgtattattt    97740
ctctcttgca tttcccctg tagattacaa caccagacgc tctgtttgat gtctttaaag     97800
acacctgtgg ccagctagtg gctcacgcct gtaatcccat cctttggga ggtcaagcct     97860 gggggattgt ttgagtccag cagttttgaga ccagcctggg tgacatagca agaccctatc    97920
tctacaaaaa ttagctgggc acagtggcac atacctgtaa tctaggctac tcagaaggct    97980
gaggtgggag gattgcttga gctcgggtgg ttgaagctgc agtgagccat gattatacca    98040
ctgcattcca gcctgggtga cacagtaaga ccctttctca aaaaaaaaa aaaaaaaaa      98100 aaaaaaaaa gatacctgtg atgtcttaga aatcccacat ttctatagta catttccttg     98160
ttctttcctt ttcagtctca gttcaccaga aatgtacgtt gtggatccac agtctcatat    98220
gaggggaaaa tgcagtccac taaccagatt aaccccagcc atgtagacgc tggtgattat    98280
tctagaaaag aaaaatattt gcctagctgt gatttatttt tagcagttat acggtaacca    98340
tgtagaataa tcataaatat gtcttaaagg ggaggggagt atgtacacag aacagaggtg    98400
```

```
aacccactta tccaaaatgg agagaacaga tgactccccc cgtggtctct ctgttcctta    98460
ggtatattat tattgttttc tgttggatta tcttccccag tgggtgttgg ccttatgctc    98520
aggagaggaa gcgggttta ggagacagac actggcccag gaattgggaa gctgagtatc    98580
ctgtgcgggt cctgttctga ccagttctgt ggccttgggc aagtcacttg aacacttcaa    98640
gtctgctgga tgttgttcct ctgcaaaagt tgatgtaaaa gctgccgtgt tgaccgcgta    98700
gaactctgag agtatggaaa gagagagtgg ctgtgatctg tgctgctgac agaccacaag    98760
gactccgcca atgggagcat gtgcttttga tgttatctta gctggaagca gtagccatct    98820
ggacaccctc cctctgggaa gccttggcat agcttctctc ttacccgact gcctgcccaa    98880
gactctgaag ctcccttctg tatggcccct tatccaaggt cgcttccttt ggaacaatta    98940
tcttaggcaa agtggccttg agcactcagc agccaagcta aatttctcac catacataga    99000
gaacctgctt ggtttaaatt caagtccagg aggcccgggt cattccaaaa tacagagaaa    99060
ctgcaaatgt atggcagttt ctgatggtct ttccctatac tgctgtgcct cagttggaac    99120
tagtcactgg gtgtgttttc attggttgtt caggaaagga gggaacattg tgatcaagga    99180
gacctcctgg tgacgtacca agaccttgga cattggagtc agacagactg cctagttctt    99240
aagttctggc ttctccctta ctgggtatgt actattatat tcagaaaaaa atgacaaacc    99300
cagtaatagt tactgaaaat aaaccaaaac agaaagaact tggatgcaga aggctactag    99360
ctgatcctgc tgcctaagac aagtcccttg atctccttaa gttttctttt cttctcttaa    99420
gtggggattt tatgtgctat atgccttgca aatttattgt aaggattcag cgggatagtc    99480
tgtataaaac cccagggtag tacctgtcac actgtggtca atacatgaca gcccctgact    99540
aacccctcac aactctgctc ctagaaagag ctgattgata atgagaagtg taagagaaga    99600
gctggatcac actagaagat ttagtgacgt ttgccttgag gtcatgtaag ggtgcagttg    99660
cccacctact gtggttattc cccatcttcc agcttcgggc agaagggtg gcagataat     99720 gtctagcctc cctccagccc cgtagtaact taactaggtc gatgggtttc agattttcta    99780
tccactattc ttcccagcct tggaaagcag ctccagcgag ctgatctttg gcctcttttc    99840
ctttctgtca acacctcttc ctgcttccac acggctgagg tggaatcagg gcagatcccc    99900
gtgctagatg ggcggatgcc catgcagtga cttagacacg gtcggattcg tgtaatgtct    99960 aactttatc ttgtcgataa caactcagtt atacttttg aatataaaca attctacatc    100020
tcaagtcaaa ggatcatact ttttcaacta aaaatctggt cttgaaactg aagaattgca    100080
gtgtattcgt ggacacagta gggcaagagt tttcaaatac aggactgtcc tgtaaattct    100140 aaggtgttg gatgccataa acatgctgtg caccatctca ccctaagatt tagtttcgtg    100200
ctattcctca tcttcccatg ggagaaaggg ttcagtgaat tgtggtcaat cgggctgttt    100260
tgttcgtgta actttggaag actggatcta atcctactcc ttatggaaaa gagatagaag    100320 atctttttg gtgatagaag gtattgaagg catagtgttg aatcaagtga atttattatt     100380 atttttttt ttgagatgta gtttcattat tctcgcccag gctggagtgc agtagtgaga    100440
tcttggcgca ctgcaaccte tgcctccagg gttcaagcga ttctcatgcc tcagtctccg    100500
gagtagctgg gattacaggt gcgcatcacc acgcctggct aatttttgta ttttcagtag    100560
agaaggggtt tcaccatgtt ggccaggctg gtctcaaact cctgatctca ggtgatctgc    100620
tcgccttggc ctcccaaagt gctgggatac aggtgtgagc cactatgccc agccaatcaa    100680
gtgaatttaa ttgctaacat gtagtttgta caaaggactg atctccctc acttaaaatt     100740 tgccagcaat aaagaaccct gtggcagtct atagttctgg aaaaatcagg agcagaaaaa    100800
```

-continued

```
gtgcctataa ctgggaagag ggggtagggg aacttgcaga acatactgaa tggcccttc   100860
ttcccatcat cgcatatcca ggcagtttaa agctgctgga ttctaatctc tttgaaccgg  100920
tggttattac tggctgctgg aacgtaatct ctgaagtaca attaagctgg tctcatggtt  100980
tgaaaccagc atcttattcc ttattaccaa gaacagaaaa ttcccatagc aaactttgtc  101040
ctcttgtcag ggcattttat ctgggagttg caagccctgc ttcagtgtgg ctctaacaag  101100
agagccaaga tgtggcgtgg gactgactga tgggcaccag acatgggtgg tgctttgggt  101160
attttccag ttttgatttc ctctgacctg gttgcctggc tgtcaggatt tcttttcctt   101220
caggaggcaa aaaatggcct ttaacttgaa tggtttcttt aaaaatcaga cctttgctgg  101280
tcagactgca cttttatctg acacagagaa aaggcactag aatggatagg aagcgtgttt  101340
ggggcagtgg gaattctctt cttcccgggg tccctggagt cagtgtagct caagaacaca  101400
gaaggaccca acaccccat ctggacccag gtgttacagc tacgtggaaa aggcatgaga   101460
ttgattgcaa tgagctcgac accgggaaaa tttgattcaa cgccaactga gtgtgcaagc  101520
aagtgagatg atcagagtca gatgcagtta atcaggaagc tgcctgggag gagtaattga  101580
gtttaatgtc tcagtcatag actcaaagac gcttatcctt gggaatggat tttagttcca  101640
gtctctttat tttacatgtg agtttaccct agagggaata tgcccgaagc cacatagcaa  101700
gttaatgata gaattcgaga tagaagccaa gtacccatac tttcagccaa gcctgtttcc  101760
ccctaagtca taaaatctgc atggaagagg aaaggttggt gaacagagtg aatattgatt  101820
cttttataca tggaatggta gaagaccaga gaaagggttt ttgactgtgg tctgcattgt  101880
ttttctcttt tttgttttt ttttgtttttc agagataggg tctcgttctg ccacccaggc   101940
aggagggcag tggtgcagtc acagttcact ggtgcctcaa actcccaggc tcaagcaatc  102000
ctcccacctc agcctccttg gtagctggga ccacaggcgt gcaccaccac atctggctaa  102060
tttttattt tttgtagaga cagagtctta ccattttgta gagacagagt ctttagccca   102120
tgcaggtctc aaactcctag gctcaagcag tcttcctacc ccagcctccc aaagtgctaa  102180
gattataggc atgaaccatt ctacccatcc ctgtggtctg cattctttgg gaaaatgaag  102240
aatagagtcc aggttttcta atacccattg cagctgggcc atcatctaaa tggcccctca  102300
aatttctata atactcctgc tttcctgtga gtattgaagg caaagctatt ttttcttgtg  102360
actttgtgtt tatctctaga cattctaaaa aaagaaaaaa aagttataaa catcggagg   102420
ccgaggtggg aggatcacct aaggtcagaa gttcgaggcc agcctggcca gtatggcaaa  102480
acactgtctc tactaaaaat aagaaaatta tctcattgtg tggtgtgtgc ctgtgatccc  102540
agctacttgg gaggctgagg caggagaatt gtttgaaccc aggaggtgga ggttgctgtg  102600
agccaagatt gcactactgc actccagctt gggtgacaga gcgagactcc attaaaaaaa  102660
aaagttataa atatttggac taaaactaca aaagtgagg cttcaggtat ctccgtatct   102720
ccaagtagaa gagggagaaa ttttaagcaa atgcaggaat atctttgcta tcttgaaaaa  102780
aatttagatt gttttatttt gtggacacat tcttcattca cattgaaagc agagtattac  102840
agagtgttat tttaaattta agctgtcaaa gtttgttttt gagtccctat tgtgttccag  102900
gattgtgctc ttttgtggag agggtcacag aaattcttgg atgatgtgac agtggcggat  102960
aatgcagaaa aggctgaagt gagtgatgac gagagataac cgagaaggct tctacaacag  103020
gcgggcctgg gcagtatggg attcaggaaa gaaagagctg gaaggagagc aactggagag  103080
agaaaataga gcctcagagg agcttagcat atgctctttt tttttttttt ttgagatgga  103140
```

```
gtttctttct tgtcacccag actagagtgc aatggtgtga tctcggcttg cagcaacctc 103200
tgcctcctgg gttcaagcaa ttctcctgcc tcagcctctt gagtagctgg gattataggt 103260
acccgccacc acacccagct aattttgta tttttagtag agacggggtt tcaccgtgtt 103320
ggtcaggctg gtctcgaact cctgacctca ggtgatccac ctgcctcggc ctcccaaagt 103380
gctgggatta caggcgtgag ccactgcgcc cggccagccc gtgctctttt ggtgagtgtt 103440
tggttttctc ttcacctgtc ctcatatgct tcccccaaaa cccatgaagt gtcagggacc 103500
aactattatg tgaaacatct tgcttagaac gctcttagga atgtagcaac aaagtccatc 103560
tccttgaagt gaatggggaa attgtttcct ttggtgtgtt atagcttgtc tattcagaat 103620
tcacttggca cagtatatca gagaagaatg actgtcttca tccttccttg ggggacaaag 103680
ttggcagaca aggctggtat ggacgggcaa taattaaatt gccacggata gtgtctaatg 103740
taactgagac taagaacttg tgcacatgta ccccaaacaa agcactgtgt cacacagagg 103800
atccccggag cctttgaacc cttttcttta c catattatga gaagcaatat cttaacatta 103860
gaaaacactt tgaatagcta aaagtggaca atgcgttgc aagaaagaaa acaagagtct 103920
ctttctgctt agcagttttg aaaagcaaaa actgacaggc ttaatttctc acttcttttt 103980 ccaatttga agaaaatgaa atggaaacat tttataaag attgaaggaa aaaagcaggg 104040
tttttacctt tgcttattaa aaatagtatc ttaaaagccc tcatttttat gttttgctaa 104100
ggactggggg atgaggaaga ggcaattcag aaaatgctaa aagcagtaaa tgtaggtagt 104160
ttcaaaattt taaacaggct ttgccttctg tgttttttta agatcagtgg tgttaacaga 104220
gcatattgca atcacagata aatgggttgt tcatctcttt cctttgtgtt gccacagaac 104280
tttgaacttg tgttagggtt tcaacacact ctgctaatct cagttttgtt cattgccccc 104340
tactttacac caaggcctct ttcctcctca tttattcttt gttaaggagt attttggatg 104400
ttttcagccc tgtttctagt ctacacctgg tccaggaatc tgtgtcctta ggatcgtcat 104460
agaaggacat cactagagaa tattgtgtgc tgtcaacatc tctctctgtg tgtgcattgt 104520
tttttggggg gttttttgtt tgtttgtttg tttgtttatt ttacagaaac aaggtctcgc 104580
tatgttgccc aggctggtct caaactctga gactcaagtg atcctcttgc ctcggcctcc 104640
caaagtgctg ggattacaga tgtgagccac cacgcccagc cagtgtgagt tgtttttaca 104700
gcagataaga agaatgtttt cttataattt cagaagtata tggttatata actatatcat 104760
gactttcaac tataaagaag aaagaaatgg ggctgggcgt ggtggctcac gcctataatc 104820
ccagcacttt gggagactga ggcaggcgga tcatctgagg tcgggagttt gagaccagcc 104880
tgaccaacat ggagaaaccc catctctacc aaaaatacaa aattagctgg gcgtggtggc 104940
gcatgcctgt aatcccagct acttgggagg ctgaggcagg agaatcactt gaacgcggga 105000
tggggaggtt gtcgtgagct gagatcacgc cattgcactc tagcctgggc aacaagagca 105060
aaactccgtt tccaaaaaaa agaaagaagg aaatagattc atagtatatg tggattcagt 105120
ggaattctgt ggggttttat ttaactaaca tttcaaaagt gatacacaga agactttct 105180 ctgaacgcag tacctaaagt aacatccttc ccctatatac gcaagatcat attgtcctat 105240
ttattcttct tatactttc atcatcagaa attatctcat gtgtgtatat atattatgat 105300
ataatatatg gcgtatatat ttactttctt attgctgtct taccttctct ggaatgttag 105360
atccttgagg gcagaaactt tattaccagc acatagtgga tgctcattaa cttaaaaaaa 105420
attaaaatga agacatcaat catttaggtc agggtgtcc aatctttggg cttccctagg 105480
ccacattgga agaagaattg tccacatatg agatacacta acatgaatga tagctgatga 105540
```

```
gctaaaaaac aaaaattgca aaaaaaatat gataatgttt taagaacgtt tatgaagttg 105600
cattgggctg cattcaaagc catccagggc cacaggttgg acaagcttga tttagaagtt 105660
tgtgatggct taggtgtcaa gtatttgatt cttaaaatga ttgaaaaaca aatgattagt 105720
tagttgtaag gtaatttagt ttggttacag taagttacta gtgaaaccaa gattaacagt 105780
ttaatatgtg gatggtctaa caattgggga aatggggact ttaaaataat atttaaaatt 105840
atattttcta gtatttctta tctctgaaat tataattatt tctccattca taattcactc 105900
atttagtaca tttgctagag tgcctactta taccagctat attctaggga cacacaaatg 105960
aacaaactct ctgtcctata aaggcctacc agctaagcag ggaggcagat gagccagtgt 106020
aacccagggt tctccatgct atcatgggaa caaattctgg gcactgtggg tgggaccgct 106080
aacatgaagt tgaagtttca aggtagagac atctaagttg agactgaaga aatcagaatt 106140
accagttggc agagggtgta gtgtgagtca gaaaaggata ggggtggggt agatttggag 106200
gaagaggaca aaagaagaaa taacatattg agaggatctg gagccttgga gagaaatgga 106260
tgtgactttg catggaaggg aacatagatt gttggggtgg agactggtat gaaatgcagc 106320
tgggaatgtg tggaagagtc aagatatgga aggatcaaga tatgtgtctg gaggacattg 106380
agactcactg gagggcttta aacccaggag gggcatggct agagttttag ggtacatgga 106440
tgatttgata tgtttgtgag tatgacccac tgtttaccct acaatcacca gtttccacag 106500
ttgcaagagg ggagggtgta gaaatggctc gggagaaagc cattcctatt aatatatttt 106560
cttaaaatcc ctggatgcat gcagcttact ctatgacacg attgattaaa taacacctta 106620
taaagaatca ggctaggcgc agtggctcat gcctctaatc ccagcacttt gggaggccaa 106680
ggcgggcaga tcacttgagg tcaggagttc gagaccagcc tggccaacgt gatgaaaccc 106740
catctctact aaaaatgcaa aaattagctg gtgtggtgg catgctcctg tagtcccagc 106800
tattcaggag gctgaggcag gagaatcact tcaacctggg aggtggaggt tacagttagc 106860
cgagtttgtg ccactgcact ccagcctggg caacagagca agactccgtc tcaaaaaaaa 106920 aaaaaaatc aaccaggcca ggcgtggtgg ctcaagctta taatcccagc actttgggag 106980
gccgaggcgg gtagatccat ggtgagaccc tgtctctact tgaacccagg aggcagaggt 107040
tgtagtgagc caagatagtg ctactgcact ccagcctggg tgacagagca agactccatc 107100
acaaaaaaaa aaaaaaaaag aatcggccaa aagatgttcc ctctcatctg tctgacattc 107160
ccgttaaaaa caaacaaata aaaaaaggat gttcccatcc tctgtcacac ctttttctaa 107220
gaatcttttc ttcatcatat tttctcatct tagaacaaca agctcaccct cttccgccag 107280
ctgcagcaga tgacgtacag cctgatcgag tggcggtccc agatcctgtc tgggacgctc 107340
cccaaggatg aactggcaga gctcaagaag aaagtcacag ccaaaattga tcatgggaac 107400
aggtaggtaa accagggatg gcttttcact gaaaacttgg cgaacagtgg gcatgttcac 107460
gctaatgaca ctgtttgcag cgacctttga tcttagagtt gccaagaat aatgcttact 107520 gctctcatt tgtctttgaa gacatttaat tttgttgaaa aaatgtcac agttccctcc 107580 atggccaggc tctgtgttgg atctctgatc ccatggaggt gacagatgat caggaaagat 107640
gggtcttgga ctgaggctgc tccactccaa ataaagaaaa caaaaacaaa aaacctggct 107700
gggcacagtg gctcacactt gtaatcccag tactttgtga ggatgaggct cgaggatcac 107760
ttgagcccag tagtttggaa ccagcccaga acacatagcg aggccccatc tctacaataa 107820
atatttggaa attagctggg tgtggtggtg cacacctgtc atcccaccta ctcgggagga 107880
```

```
tcacttgaac ctggaggttc aaggctgcag tgagccatga ttgcatgcct gcactccagc 107940
ctgggcaaca gagtgagacc ctgtctcaca aactaaacta aactaaaatc cctgaaaatg 108000
accaagcctc tgaagttgac attttcagat acttgggact gtatctattt ttattctaac 108060
agtggattcc aaatcaatac cagactcatt ctctttattt ctcttcatct cccctaacc 108120 gggaccattg tctatggtgt gtgaaaagca gacttgcagg agtagtaaaa catgtttgta 108180
gcctgttgat tatggctaca atcacctcta cagagttaat cacttcatta atcttctgat 108240
taactcaggc acatatccag gctccagata tcactgcctt taggaaaatg agaaattcag 108300
tcctatatcc aaattggtgg tggcctgggg ttttgcctc ctgaccagca cttttttaaa 108360
aggcaaaagt ggttcctcgg ttagctgtta ttggtgattc ttttggaatt agtttcattt 108420
tctaaatttc ttcaacttgt gcatatgtga ttttttcct cctcctctac cttgcttttc 108480
tagtgtcgga attcttggat atccctcaga gacctattaa aatatagatc attatgccac 108540
ttatttaaat gtcatagact ctgacaacta tattctgaag tagccgaagt gaacatgcca 108600
tgcaggattc agattcaagc agtatttagg aaacaccttc tatgtacatt tcatatacat 108660
tacttgatta taatcttaaa acatagggtt gaggtagctg ttattattta catcttatgg 108720
ataaagaaac agaccaagtg agcttaagtg atttatttcc cagtcacata gataataaat 108780
gggaaaggtt aaatttgaac ccaagacttt tgactccatg tctaatgctg ccttcttagg 108840
gttaagaatt aatagtgccc ttccctatta cttgaccacc cagaagacca tacctacagt 108900
ggctgcactg ccaggcttgt ggtgtcagag gacttattaa aaggccaatt aggccaggtg 108960
aggttgctca tgcctttaat cccagcagtt gggaggctg aggtgggcag atcaccagag 109020
gtcaggagtt cgagaccaac ctggccaaca tgatgaaacc ccatctctac taaaaatata 109080
aaaattagct gggcatggtg gcatatgcct gtaatcccag ctacttggga ggctgaggca 109140
caagaatcgc tggaactcag gaggtggagg ttgcggtgag ccaagatcat gccactgcac 109200
tccagcctgg gtgatagagt gagaatccct ctcaaattaa ttaattaatt aataaaaggc 109260
caattgggta ggataaggaa actccattgc acataggaca cctctgtcat ttggtgtctt 109320
gccatgacat tggcctggag gtcccgtgat ctctggcaca ggatgttcac accccacaaa 109380
cggcagaaca tgacttcttt cccgttccag ctcttggaag tcgctcagga aatggagctg 109440
ctgtgtcagt gccttcctga tccagtctcc gagcagccag catggccatt gttcatgagt 109500
ctgggtggcc tgtgggtctg gccgccatgg aaaggaacct gccagatcaa atcacttgat 109560
agagatgctg taaaacaggg aggagggaga ggaggcattt ttgctttctt cccaaagact 109620
tggcacattg cagtgttatc cctgagcggt cttgctcttt ggtaccggga atgcatgctg 109680
ggtattcgga tagcagtatc ctatttccac cacagtcctc aacttcttga gcctaagcaa 109740
aattttttct acttctgtgt gcactttggg cacaaaagcc ttgagggag ggattgcacc 109800 cacgatatgg ccgttagtat tcccaagcat atgcagagct acaacttcac acacagccag 109860
gtgtttgctt ctactagttg ctgcgataag agctgtgtta gtccattctc acactgctat 109920
aaagaaatac ctgagactgg gtaatttata agaaaagtgg tttaattgac tcatggtctg 109980
ttggctgtac aggcagcata ccagcttctg cctctgggga ggcctcagga aacacaatca 110040
tggcagaagg ggaagcaagc acgtcttaca tggccagagc aggagtaaga gagagagagg 110100
tgggaggggc tacagacttt taaacaacca gatctcgtga gaactctatc acgagaacag 110160
caccaaaggg atggtgttaa accatttatg aaggatccac ccccatgatc caatcacctc 110220
ccaccaggcc ccacttccaa cattgggtg aatgtgagat ttgggtggga acatagatcc 110280
```

```
aaaccatatc aagagctaac atttatgctt aagctgagag tttactgtat gctacatata  110340
gtattaggta ctgtacatgc attatcttat taaattctca caacagggcc aggtgcaatg  110400
gcttatgcct ataatcccag cactttggga gaccgaagtg ggaggctcac ttgaagccag  110460
gagttcaaga ctagcctggg caacatagca agacccatc tctacaattt tttttttttt  110520
aattagctga gcatggtaat ataagcctgt agtcccagct acttggaagg ctgagacagg  110580
gactgcttga gcccaggagt ttaaggctgt ctctaaaaaa aataaaaata aataaattct  110640
cacaacaacc ttgaagggta aggaatgtat acaaatgaag aaaccaaagt tgtgcagaat  110700
taagtaaatt ctccagggtc ataatgttag caagtattca agccaagatt caaatcctgg  110760
tctaaatgac accagagccc atgctctggg catgagatag cagcaagcca ggacttactt  110820
cactcgtctc ctttatgacc atcttaagtt aaggaaatca aggcaagccc tcaaataatt  110880
gttcattggt ccttcatagc aatgtaataa acagtgagac cacgcccact tggtctgttc  110940
ctttactcat aaaatggaaa taataacatt tacctccacc ctacctcatg gcattataat  111000
caatcaatgt ttgtgaagtg tatataggag gtatgtgtgt atgtatttat ttatttattt  111060
attgtttcag acagggtctt gctttctcat gcaggctaga gtgcagtggt gcaatcctga  111120
ctcattgcag cctcaacttc ctgggctcaa gccatcctca cacctcagcc ccccaagtag  111180
ttgagactac aggcgtgtgc tactacacct ggctaatttt tgtatttta gcagagacag  111240 ggtttcaaca tgttgcccag gctggtcttg acctcctggt ctcaagtaat ccgcccacct  111300
cagcctccca aagtgctagg attacagacg tgaaccacga cgcctggcaa aggaggtgtt  111360
tattaaacac aggttgaatc ttaattttgt ttgctctatt tacttcatag ttcctcttca  111420
taataacaga agattacagg caagaagcat tggccagagg aatttagtca gaatcagtgc  111480
caattttact tttctcttca gggtctatgg accatatttg catatccttc tacgactttg  111540
gctaatatca tctcatgagt tttctaacag tgttgaaagg tggcagaaac tgaaatgaga  111600
aaagtcaatg aggtgtgctt ccctgggctt gtccagcatc tccctttcta actatggatc  111660
ctctgggctc cttgacaagg actcctcagt aaaaagtctg cccctggtga ggagaaccag  111720
ctgactactc ctttctctcc agaatgctgg ggttagatct ggtggtgcga gatgacaatg  111780
ggaacatcct agaccctgac gaaaccagcc ccattgccct cttcaaggcc catgaggtgg  111840
cctccaaaag gattgaggaa aagatccaag aagagaaggt acagttcctc aaatgtgaaa  111900
ttctgcccac tgaggttcca ttttttgcctt ggttttttaat gaaagaaagg gaaatcattg  111960
agaacaaaac tacttctgta gttttcgtcc tcattttaaa agtgaaacat agcagaaagg  112020
atgaggcagg tatatatata tatatgttct gatatggaaa gatcgcaaag atacgtatta  112080
agtgaaaaga tcaggatcca taatggtata tatgaaatgc tattatttgt gtttcaaaaa  112140
atgtatataa atctatgctt gcatatacat agactaactc tgaaataata gacaagaaat  112200
aattattaat ggatgcatct gggaaggaaa acggggtggg agggagactt cttaaatgtg  112260
taatctcttg cattcattgc atatattgca atttcaaaat aaatagtatt tatttttatt  112320
ttttatttat atgtttattt ttgagacgga gtcttgctct gttgcccagg ctggagtgca  112380
gtggtgcagt ctcagctcac tgcaacctct gcttcccggg ttcaagcaat tctcctgcct  112440
cagcctcccg agtagctggg attacaggca cccaccacca cacccggcta attttgtaa  112500 tttttttttt ttttttagatg gagtcttgct ctgttgccct ggagtggcca gatctcagct  112560
cactgcaacc tctgcctcct gggttcaagc tgttctcctg cctcagcctt ccgagtagct  112620
```

```
gggattacag gcgcccacca ccacgcctgg ctaattttg tatttttagt agagactttc    112680
accatgttgg ccaggctagt cttgaactcc tgacctcctg tgatccacct gccttggcct    112740
cccaaagtgc tgggattaca ggcgtgagcc accaagcctg gccaattttt gtattttag    112800 tagagatgga gtttcaccat attggtcagg ccggtctcaa actcctgacc tcaggtgatc    112860
caccctcctc ggcctcctga agtgctggga ttataggcat gatccactgc acccaggcta    112920
aaataaataa tatttaaaaa taaagtgttt gaaagacttc aaaggtaata attggacatt    112980
aaagaaaaat tagaatccat gcatggtgcc tcatgcctat aatcctagcc ctttgggagg    113040
ctgaggtggg cggatcattt gaggccagga gttcaagacc aactgggcaa atagtgacat    113100
agtgagaccc catttctaca aaaattttt taaaaaatta gctggacgtg gtagtgcatg    113160
actgtagtcc cagctaccca ggaggctgag gcaggaggat cacttgagac tgggaattta    113220
aggctgtagt gaactatgat cataccactg cactccagcc tgggcaacaa agcaagaccc    113280
tgcctcttaa aaaaaaaaa aaaaaaact tactcatatt ttgatttctc agacccaaac    113340
atattgacat tttaatatgt tttttttcca gtctttctgt tctaatgagt aaagatttgt    113400
gtcaattttc tttggtttgt tggtttgtag tgtttacttc tttagcatgg tcatgataat    113460 attttgtgttc tgaatccaat ggcaaaccac acctgaaggt aaagcctttc tagtggaata    113520
ttttgttttt aatgagagtt atttctttat ccaggataat ggatcatgat gtttgtgctt    113580
ttgagcttca ttcagaagct attgtgtaag acaagcacct cttggagcta ccaaaaccct    113640
ggaattatca cctttagaca gcatttgttt gaatgtctgg gattcaaggc cctgaacagg    113700
acagtcttga tcactgaaaa tataatgatt atattttgct cactgcattt gtccacttac    113760
atacactttt tcttagcaaa tgcacttcct ctcgggtgtt atctgtgttt tgttttttgt    113820
tatttattga ttaatcaact gattgattga gacagggtct cactttgttg cccaggctgg    113880
agttcagtga ctccatcata actcactcac tgcagcctcc tctgttccca ggtagctggg    113940
actacaggca cagctaatta aaaaaaatt ttttgtaga cagagggct tgctgtgttg    114000 cccaggctgt tctcaaattc ctgggcctct agtagcactg ggattacagg aatgagccac    114060
tgtgcccagg ctttgtctgc catttgcagg cttattatt tatttattta ttttgccaa    114120 catttcccat ttgccaaaat caagatgttt ttctctgttc cctcttgtt cagtcaatcc    114180 tgcagaacct cgatttgcgg ggccagtcca tcttcagtac catccacacc tatggcctct    114240
atgtgaactt caagaacttt gtctgcaaca tcggggaaga tgcagagttg tttatggccc    114300
tctacgaccc agaccagtcc acttttatca ggtagcagag acccacatcc cctgctgctg    114360
acctaacaaa gatacccagc cttcccctga cccctacccg ggcagctctt tgccagattt    114420
gagaagagaa aatagggaag catggaagat ttcaagcag tagaatgtaa atcatatgg    114480 tctatgaagc cttcatatgt cactactaga acaatgaggc cagtttgtat actctctggg    114540 attagagat cacataaaac tcattagggc ttggagatgg gaacaaagaa ttcaaaacag    114600
tgtgtgggag ggtgagaaag ggatgaatag gcagagcaca gaggattttt agagcaacgg    114660
cagtattctg tatgatgcta tagtggtgga tgcatgtcat tatgaatttg tctaaatgca    114720
caggacgttc gatgccagga gggaacccctt atgtaaactg tgggcttgg gtacatgatg    114780 tgtcaatgta gcttcatcag ttttaactaa tgttactact atggtcgggg gaatgttggt    114840
agcaaaggag gttgtgtctg agggagaga atatgttatg ggactctatt ttcagctcaa    114900
ctttgctgca aagccaaaac tgctctaaga aaataatgtc tattaaaaaa catttttttt    114960
aagactctaa ggagtgtgat gggcattgtt cagccctaca gtggtactac tgtttagcag    115020
```

```
ctaagaaaat ggagaattta tttttgagaa gatagttaaa agtaattgct gacaatttgt   115080
ttctttaaaa aaaattttt aatgtcaatg tggattacag gggatagatt tggaatgact   115140
gttataaaat taaattcttt ttttatcttt tatttattgt ttatttttg agacagagtt   115200 tagctcttgt cgtacaggcc cgcatcctgg gtccaagcga ttctcctgcc tcagcctccc   115260
aagtagctgg gattacaggc acctgccacc atgcccaacc aatttttgta tttttagtag   115320
agatggagtt ttaccatgtt ggccagcctg gtcttgaact cctgacctca ggcgatccgc   115380
ccgccttgac ctcccaaagt gctgggatta caggcgtgag ccactgcgcc ctgcctaaaa   115440
ttaaattatt aatttagcaa agctgaaact tttattcaaa gattttgaga tggaaggaca   115500
acccagaccg tagcatccca taagctctac catgtctgtg cccaccagga gcagtgggtt   115560
tcctgcatct gtgtggggca tgtcttgcgg agccacagca gggacgcttc tctaatgcca   115620
ggacacccag cagtggccat ctgtgtggtc ccagttccca actcagctgt tttcacaccg   115680
gcctgttgaa tttcactgag catttctggc ctttcctcct tcccttgtaa gtctatactg   115740
agggtagcct catctccaac cccagttagc ctctcattaa gagcaatttt ttttccttt   115800 gccagtgaga actatctaat tcgttggggc agtaacggga tgcccaagga aatagagaag   115860
ctcaataacc tccaagcagt gtttacagta agtcctccct tctgtttaat cattctcttt   115920
gtttgtgata tgagcatatt cacataatga atatgtggaa aacatacaaa atgaaaagat   115980
gaaaggaaaa atcatcaatc tgcctagcag gaataaccca cccatttatt caacatgtac   116040
ttcaatgcca ggcactgatt tagacacttg agatacatcc gtgaaaaatc ggggaaaaaa   116100
aagcagcttt tgtcctgatt ggtaagacac ataataaaca ataatcaatc caggcacagg   116160
ggctcacgcc tgtaatccca ggactttggg aggccaaggt gggaggatca cttgagctca   116220
ggagttcgag accagtctgt gcaacatggt aaaaccctgt ctctactaaa gaatttaaaa   116280
aaggaaaaat gaccttaaag tacaagagga gtgatgctgg caattcggat atgccaaaga   116340
gaagcgtgct ccctttaagt gaaaaggtaa aactttataa atacttatgt ataggaaaaa   116400
acagcacata tagagttcgg tactgtcttt ggtttcaggt atccaccagg ggtctcagag   116460
catattcatc acagacaagg gggggctact ctatcaatgt gccacaatat atgtaactag   116520
tcacctggag tctttatttt tccattaaca gaagccttgc agacctagag tagaaatgca   116580
gggtggacgt tatcattgat gtatatcttg agacctgag ttaactaaat tacagggct   116640 ggatttggaa tgattatgtt aaaagtgatt cttgcttcag taaagagagc ttgggcagct   116700
gtttcatata accaatttga gatgtgatta gttttttttc tgaagtcgaa ctgaatgaga   116760
gatatcagct cattcctggg tttactcacc catccttaag aaaacaaata atggctgggc   116820
gcggtggctc atgtctgtaa tcccagcact ttgggaggcc aaggaggctg gatcccttga   116880
gcctagacgt tcaaggccaa ggccagcctg gataacatag ggagaccttg tcaaaaaaaa   116940
aaaaaataca aacaagtgta gaaccctagc tgcaagagaa ataggtattt cattgacaca   117000
tctgtcatga ttcagtatac actgataagc tctcaataga gacctctcat aaatcaggtg   117060
aatagtccca taaagcagtg cctgtctcat agttgcctca tgggcttgtt ttgaagagga   117120
aatgaaatgt cacagacttg tgtggatacc caataaatgt cagtgttaca caagttttta   117180
cttcatttga tgttgaaatg catcctgtgc tgagatacgt ccaaagatat acaatcgcaa   117240
tgatgagggc cctgatttt caatacccctg cttaagctga tgaactggag acttccaacg   117300
ggctgtgatc tgatttgtaa atttgaagta ggaactgggg aacaaaaaag cacttgttta   117360
```

```
caagcacaaa gtcatgtttt ctgatgccat aatagctctt ggatggagat gggggagaag   117420
agagtcgttc taatacttca gcattgagaa ataaggtcgg aacaggattt tgttgtagag   117480
ggtaaagaaa aaagagacac aggtgacaca gtggtccagc cccacctcct ctcacacttt   117540
ctctgcccct ttaggacctt agcagcatgg acctcatccg gccccgcgtc agccttgtgt   117600
gccagattgt ccgcgtgggc catatggagc tgaaggaagg caagaagcac acctgtggac   117660
tccgaagacc ttttggagtg gcaggtacaa gagagaccca gagacaaatg tgaaatagtg   117720
cagtgctgtg gaaaatagca tggcgatttc tcaaaaaatt aaacatggaa ctagcaaatg   117780
atccagctgc cctgcttcaa aacaatcaaa agcaaggtct ggaggagata tttgtgcatc   117840
catgtttgta gcagtattat tcacaatagg caaaagatgg aagtaaccta ggtgcccatc   117900
agtgcataaa tggactaaga aactgtggtg tgtacgcaca atggaataat actcgcctta   117960
aacaggacgg gaattttgac tcatgctaca cactgcgtgg atgaaccttg aggactttac   118020
actaagtaaa taagtgagac acaaaaggac aaatattgta tgatcccacc tatatgaggc   118080
acctagagta gtcaaattct cagagacagt atagagtggt gagtgtcagg ggctggagag   118140
ggggaatggg gagttagtgt ttaatgggta cggagtttcc atttgggaag atgagaaagt   118200
tctagagatg gaaggtgatg atggttgcac aacaatgtga atacacgtaa tgccactgaa   118260
cggaatactt taaaatgggc aagatggtac attttatgtt atgtgtgttt taccacaatt   118320
ttgaaaatag aggaagagaa ggaggaaagg aggaagaaag gtggaagaag gcacagagat   118380
agtaagagat ggatcacgtt gtcattgtca gtatcagaca cgcagcattt actgcctggc   118440
actgcccgtt ttctttgcat gggttctgtg tcctcacctg gcccacgctc ctttctttcc   118500
cccttagtgc ccaacactgt gtcttataca caatagaacc taagttgtga ctattggaat   118560
cctccctgtc tgggtctgcg tattgatttt agtggaataa aatactcgct gggaagtggt   118620
ttgccggtct aggaaattta ctcttcgaag acaatgttgt gtttgtttct aaatgctttc   118680
agagatcctc cttggcttac atcaaacccc agaacctgct taaacgccca gcatcttcct   118740
ctgtagtttg ttcaattgag gaaatacatt ttgggcctta cattgacatt tggttgctc    118800 atagattgaa agcgatcaag gaaatgttat aattctgctc ctggacctt ggttccatac    118860 ttactaaaaa gtaacctgat gttaaatttc tcaagaattt agcaactcgg gcggggcacg   118920
atggctcatc cctgtaatcc cagcacttg ggaggccgag gcaggcagat catctgaggt    118980
caggagttca agaccagcct ggccaacatg gtgaaactct gtctatacta aaaaaataca   119040
aaagttagcc aagcgtggtg gcatgtgctg tagtagtccc agctacttgg gaggctgagg   119100
caggagaatt gcttgaacag gggaggtgga ggttgcaatg agccaagatt gtgccactgc   119160
actccaacct gggcaaagga gcaagactgt cttttaataa aaagcaaaag aatttagcaa   119220
ctcgatcttg tagagttttt aaagtgggta gtctgcaaaa ttgatccagt aaaacccaga   119280 cccccttcctt agcacctcat gagtcacttt tttgctgggc taggtacact gggaatcacc   119340
attggcaaag aaattttaaa aaagtccctg cttagtacct ttcttcctgc agtgtttgat   119400
gtttgctgat actgtccttt tccatagtaa cttactgagg catgaagcaa ttagtttctt   119460
taatgaagtt tatcttttc ctagtgatgg atattactga tatcatacat gggaaggtgg    119520
atgatgaaga aaagcagcat tttattccct ttcagcagta agtactttgg catgtgtccc   119580
aggtgacttg agacctggat tagccattca attgtctttt aacacagaaa caggtgttag   119640
aaaccatttt ctcagagaag gaaagattct aagctgcaag attgtcagat aggagctgaa   119700
cagaagactt tattcaaagt ccttgatgtt ggactcccat tgaagagggt aaactgaact   119760
```

```
ttcctgattc tatagaaagc atcaaaggaa tataaaaggg cacatatctg tctgctctgg   119820
aatgcagaga gggtgccgtc cttgtgtcag caatgccaaa atatatgtgc agtctattgc   119880
atgaaacagg catcatggat gacacggaat cacgtgggct agcataggc ttctcagact    119940
gcatcatgca tatgaatcag gggaacttgt taggctgcag gggagttctg cctctgacaa   120000
gctcccaggt gatgctgatg tagctggtct gagggccaca ctgtctgtag cgagggttta   120060
ggagatgaga gagtgaaggg ctgacccacc catgggccag tgttcctgca tgttggggga   120120
aagccagcct gggagcatgt gaaaggatcc ttgcagagct ttactgaggc cctccatatt   120180
gagctgcagg agctggagcc atgggtaggc cattgaggag ctgttgggag cagattcaag   120240
ccgtgtcact ctgaagaagt gcaggtgtga acgtcatgac ctgctccagc acctgcacag   120300
gcagtggagg cctagtggag gccaagagca ttgccgggac caagtcccac caggggccat   120360
cgtgccagtc agagggcatc atctcagctc acttgcagct gccactgcag acaagtagaa   120420
caaactgaga attccacaaa ccagccagag tcatatattt gagttaatat atcacttttt   120480
acaaatgata tcacaaatta gtggagaaag atacattatg caaaaaaaa aaaaaaggt     120540
ttttggagaa agttagctag ccatttaaga tcccgaagtt agattccagt ctcacaactt   120600
atgccagtgt aaattttaga tgattaaaca tacaactgta agagctagaa tcttaaaata   120660
ttaacgggaa aatagaagtt ttatgtggta gtcatgggag ggaggccgtt ttaaagattc   120720
agccaaaaaa agaaaaattg ataggtttaa ccacccaaaa actgtaaaga acttaataca   120780
tagaaaaaaa tcgatacagt cttgcactg tgtttgagaa aggatgaata tttgtaaat    120840
ataagaatt aatagaaatt aataaggaca tgaagggaat acacacacat acagaaatgg   120900
tgttgtacat ttattgagga tgagtgaaat gcaaatcgaa acatcaaggt ttattttta    120960
tcttgaccac actttagtgt ttgggtagat ataaggagac atacattact tatagagaat   121020
atgaattgtt acaatgcatt agaagtctta aaatttagat atttcaaaaa atgtactcca   121080
tgattaacag tgattatttc tgttgatgta actcttggtg attttgctcc tgtttttgtt   121140
ttcctgttgt ctgtttttta tacaaaaaat atgtattata tgtaatatat aaaatataac   121200
aattttaatc tttcaatgtt aagtccacac cttcggacca gtttctaaac ataatagtgc   121260
aaatagccca tgctaagtag tacttgtctc ttttatccag aggctgctat gaattatttt   121320
tttaaaatat ggccattgca ctccatcctg ggtgacagag ccatacgctg tctcagataa   121380
aataaaatat aaggtaaaaa tagataaaat aaaatagtta aaaataaaa tgcacttacc    121440
ttgtatgcta ccacctatat attgaccttc caagacgaga caaatatttt atgtagcaca   121500
gtgctaaagt taattatgtg ataactttca tctccatgaa tgctgctctt gttttgtgca   121560
taatataaaa cactgcatgc acatacctat ataaatatgt attgtataat atataaatat   121620
gtttaagtat atttaataaa catgttgaat ttaggtccgg gcgcataggc ttacgcctgt   121680
aatcccagca ctttgggagg ccaaggcggg cagatcacaa ggtcaggaga tcgagaccac   121740
ggtgaaaccc tgtctctact aaaaatacaa aaaattatct gggcacagtg gcgggcgcct   121800
gtagtcccag ctactcggga ggctgaggca ggagaatggc atgaacctgg aaggtggagc   121860
ttgcagtgag ccaagatcac gccactgcac tccagcctcg cgacagagc gagactccgt     121920
ctgaaaaaaa aataaataaa taaataaaa taaataaata aatatgttga atgtaatacat   121980
atgttaatt gttaattaca tttataaata tgctaaataa aatacaatca tgcatcactt   122040
aatggcagtg atacgttctg agaaacatgt cactaggctc tcttgtcatt gtgtagacaa   122100
```

```
catagagtgt acttacacaa acccggaata tatagactac tacacaccta cgctgtatgg   122160
tatagcctat tgctcctaga ctgtaaacct gtccagcaag ctactgtact gaatactgca   122220
ggcagttgta acacagtgct atttgtgtct ttaaacatat ttaaacatag aaaaggtaat   122280
gagttgggct gagatgttaa aacagctata atatcactag gcaatagaaa tgtttcagct   122340
ccattaataa tctttttttt tttttttgaga cggagatttg ctcttgttgc ccaggctgga   122400
atgcagtggc gtgatctccg ctcactgcaa cctcacctcc tgggttcaag caattctcct   122460
gcctcagcct cctgagtagc tgagattaca ggtgcatgcc attacaccca gctaattttt   122520 ctattttttag tagagacggg gtttcaccat gttggtcagg cttgtgtcaa actcctgacc   122580
tcaggtgatc cacctgcctc ggcctcccaa agtgctggga ttacaggtgt gagccatcat   122640
gcctggccag ctccgttata atcttatggg accatggtca tctaggcagt ctgtcattga   122700
cagaaacatt gttaggaata tgactgtata ttgaataaat ataaatgtac catatatatt   122760
atagtactat gaatgtgtta tatttgtatt taagattata tgtacataat aggagtgacc   122820
ttcatggata tgaaaggtgt ctgaaacagc catctgtata tttgctggtg gtgatgtgcc   122880
tcctgcttaa tttctgaacc agcttttcctc cagcaaccat atcacagtac ttagtcctga   122940
gattgtcccc actgtataat ccgtgccttg agtccctgac gaaccctgcc ttaatttcat   123000
tactgctcac tgtgcagcca acagccgcag tggagtattc atgatgcaga ctgcagcctc   123060
tggcattgaa tgcctaagat ttatggcaag cgctactata atctacttca aaactttac    123120 agtgttttcc agtaggagag tgttgtatgt atattctgca agtccattta gagagaatca   123180
tttgtaaaaa acaggaactc aagactatag caatcccatt tgccagtcac atattgcagt   123240
gtgttttatt gtcagggtac agggaaccct gcagagaaaa ctggcctaca tgcagtggac   123300
agaggagaca ggagactatt gtactgcacc aggccgatgt gcagttgctt atagtgcttc   123360
tgccttcagt agaatggagg ctgtatttgg ttctttgatc gcccttttaca agccgcagcc   123420 tgataaggtc actcaagtgg agcttgtttg gcagcaccta tgccaagatc tagcttgtca   123480
tcacatggaa atctgagaac atctaccaga caccaggcat atacactgtg cttatatata   123540
gggggttgac actagacagg agccttaaca ggcatgcgat cccagcccat ctcttacaga   123600
tggagaaact gaggcccaaa gggagcctct tgcagagctc actatcaagc agaagtagac   123660
ctgggggctc ctgcccttc cgtgggtgct ctgtcttcaa ttctattgca gcagcctctt    123720
ctgcctctga aagagcatgg agtgttgcct ctgattttag ttgctaaccg ttggtcacca   123780
gttttgtgta ctcttgggtt ttttttcctcc ctctttgcct caagtcattt ccaaggtgaa   123840
tttagtattt aagatgacac aaaatggaaa aataaaggaa agatagaaag ataggggtac   123900
ttagtgttga tatctccaaa ttattcctat atgactcacc attatctgag gttgtgctgc   123960
agagacttcc tttctccccc tcccaccttta cctcttattt ctctttccca agaattgcga   124020
tggaaaccta catccgccag aggcagctca tcatgtcgcc tttgataaca tcacacgtga   124080
ttggggagaa tgagccactc acttcagtct tgaataaagt gattgcagca aaggaagtga   124140
atcacaaagg gcaaggtaca gtccagtgcc agagctggga gggactctgc tgagggtggg   124200
ggacattcac agctgggtcc ttggactcct gcccttatt atctttctct gatacaaaac    124260
agcctctgct ggggaccatc cccctcagct tccaaccaca ggcttttaat actgaactgc   124320
attgagatgc acccagcggt gatttgatca cagttgtgtt ttgtaaattc tttggaacaa   124380
atttttatcc catgagtctt tactctttat tcatttattt atttatttat ttttgagact    124440
gtctcatgtt gtcacccagg ctggagtgca attgcatggt cttggctcac tgtagcctcc   124500
```

```
acttcctggg ctcaagcatc ctcctacctc agccttccaa gtagctggga ctacagacat   124560
gtaccaccat gctcagctaa cttttaaatt ttttgtagag atggagtctc actatattgc   124620
ccaggctggt ctcaacttct ggccttaagt gatcctccca ccttggcctc ccaaatccct   124680
ggaactttag gtatgagcca ccgcccctgg cctccatgtt tttgcctacc cttcattccc   124740
aatgtcgacc ctagataata attatgctct attctgaata agtttatccc atcacatttt   124800
ttaaaattga gaggaaggaa accaaagtaa tacagatgaa tatgtattaa tacaaaataa   124860
tgtaaaaatt gtagttttta gtatctccat atcatgttct gttgatagag tgtgttggtg   124920
cacacctgta atcccagcta ctgggaaggc taaggcatga gaattgcttg aactcgggag   124980
gcaaaagttt cagtgagccg aggtgatgcc actgcattcc agtctgggca acaaagtgag   125040
actctgtcta aaataaaaaa aaagaaaga aagacagaaa aatggtttgt tctcagaggt   125100
ttaatagcta tacacttctt ttttctttta acattctgcc ttcttttct atgtaattca   125160 ttattgggaa tttaatgaaa atacaagatg ggaaattaaa ttttcttaag tagcaagaaa   125220
ataatcccag catattcatg taattattgg atttttttca tgatttgtta tgcctctttt   125280
gccatatatt aaattgctat atactatagt gtttcattgt ttcatgtata tatctttttt   125340
acccctagga tcacagatgg ttgtagcttt actatatatt ctggtatctg gtagggtcta   125400
tctttacccc ttttttcccc caaagttagc atctgttcac atctctgtca aattctcaaa   125460
gaggtcctgt tgtgatttta atggaagtgt cattaaaatt ataagtcaac tgggggagaa   125520
tttacatctt tacagtaagg ttgtgactat acaactcaaa tgttcttctc accagttacg   125580
catgtgtttt atacatcata caaagaacta aacgtttatc ttttatttct tttaaggcct   125640
ttgggtatcc ttgaagctct tgcccggtga cctcacccag gttcagaaga attttttcaca   125700 cttggttgat agatcaacag caatagcccg gaagatgggc tttcctgaaa tcatactgcc   125760
aggtaagcac tttgcatggc tcacctgttt gcttcctcct gttcagcgat tatttcttat   125820
tggacggtgg aggcaacttg gatccagaag acttggttat ttacattcat tggtcctgag   125880
acacctggga cacaaacaga gacacctgca atacttaaac acttaggtgc ttcctaattt   125940
gtcattatta caaatataaa aacctctgct ctgactatcc ttaccatgaa gtcttttcca   126000
cgtttaagac tatctccccg agaaaattcc tggaagttgg atatacagtg tgcaagtaca   126060
gtacactgat atacggtgtg caagcccaag ataatgcttt taaacataac tcaaatttc    126120 ttactctctc ttttacgcag actctctcaa atagcacagg gtgctctgtt caggagacta   126180
attggcctca tttgtgtgtc cctttcttgt tatgacatcc ccagcatgtg ggcgccttgc   126240
tctctccatt ctctgaagct ccaaaagcgc tctggctctc cctgttcttg ttgtgacaag   126300
aatgtcagca ttttcctgtt tcatcttctt tctagtgatc tgcatatgtg tgtgttctct   126360
ggaatttgct gacttcgccc atttaatttt aatctccata ctaagaaaag ggaattggtc   126420
ccttgaattt tatacatatt gctataaact aattgatatt aatagaaatt ctagaaaaac   126480
aaccatggct tggccgagca gggtggctca cgcctgtaaa atcagcactt tgggaggctg   126540
aggtgggcgg atcatgaggt caagagatcg agaccatcct ggcaaagatg gtgaaacccc   126600
atctctacta aaaatacaaa aaattagctg ggtgtggtgg cacgtgcctg tagtcccagc   126660
tactcgggag gctgaggcag gagaatcgct gaaaaccgga aggtggaggt tgcagtgggc   126720
cgagatcgca ccactgcact ccagcctggg caacaagagc aaaactctgt ctcaaaaaaa   126780
aaaaaaagaa aaaagaaaaa caaccatacc atgttagaaa aattctagaa aaccaactta   126840
```

```
cctattgcac aaaaattcag gttattttag gccaggcatg gtggctcacg tctgtaatcc   126900
cagaacttta ggaggctgag gcaggcagat cacatgaggt caggacttcg agtccagcct   126960
gaccaacgtg gtgaaaccct gtctctatca aaaatacaaa aattagctgg gcgtggtggc   127020
tggtgcctgt agtcccagct actcaggagg ctgaggcagg agaatcgctt gagcctgaga   127080
ggcagaggtt tcagtgagct atgatcgcac cactgcaacc cagcctgggc aacagagcaa   127140
gactctgcct ccaaaaaaaa aaaaaaatta ggttatttta agtaataca aaatcttatt    127200
tctcctttga gaaattaagg ggcagtgata acttgttgct gcccacattg tctacatgta   127260
gtgggtctta aatgagtatt tgtggaagga atgaataaaa atgttataaa atggagatca   127320
ctcttttttc cttttctcat aaaagaagat agttttttgc ttattttgtc cattacatag   127380
ctattttacc ctgatataca ttcatcaaca ttctgggaaa atgttttgtc ttcttgttaa   127440
ggaaaaaaaa aattagtagt aatattctct acctgaaggt tgttttacta ctacaacaag   127500
acacaaatct gaaaaaataa agtagagaag tttattcttt gatcaaggtg acagcagggt   127560
tggcttctcc tgaggccttt gaataaggtg agtttacctt ttaaatctgg cttgtaaaag   127620
aacatttagt tttgttttgt tttttaagtc aataggattg gttcatagga tgccaagggc   127680
tacattggtt ttaaaattca tctagaatac ggccaggcca gatggctcac atcggtaatc   127740
ccagcacttt gggaagctga ggtgggtgga tcacttgagg tcaggagttc aagaccagcc   127800
tggccaacat ggtgaaaccc catctctatt caaaatacaa aaatcagctg ggcgagttga   127860
cgtgtacctg tagtcccagt tactcaggag gctgaggcag gagaattgct tgaacccggg   127920
aggcggtggt tgcagtgagc tgagattgca ccaccgcgct ccagcatggc gacagaacaa   127980
gactccgtct caaaaaaaaa aaaaaaaaaa ttagctggga gtggtggcgc atgcctgtaa   128040
tcccagctac ttgaaaggct gaagcgggag catcacttga acctggaagg cagagtttgt   128100
agtgaggtga gatcatgccg ctgcactcca gcctgggcaa cagagtaaga ctccatctca   128160
aaaagagaa aaaattcat ctagaacaat cgtttccagt gctagtatgt ggatcagcta     128220
atcaagatct ccttgaagat ctccttgaaa atacagattc ccagatttct agagaccgat   128280
tcagagctcc caaggtgatc tggtggtgag tcaggtctga gaaattcagg tctagaccca   128340
actccctggg ctcagaactc cttcctgttg tcccatcacc acgtgaactc gttccagttg   128400
cctcctaaac tcttccctgt accccttgc cctctagcaa ggagctttga ctctcgtctt    128460
cagcatcgca ggagtgattc tgtccacgct cttttctctgt tctcacctct gccagcccca   128520
ctccagcctc tcaagagtag ctctcatgag agtcacccat gatcatggta tcgctacatc   128580
tgatgggagt tttctagcct agcgatcaac tctgacctct cagcagcatc tgacattgtt   128640
gaaatatttc cttcccttct cattggtgac ccctcacttt tctctgcttc tccatttccc   128700
tggggcttct gctagaaccc ctttgccacc ttctcatatt ctgcttcacc tctaaatgtt   128760
gaagttcctt gttatttggt cctgagaccc tgtgtgagtg tgcttgggct gccatagcaa   128820
aataccacgg actgggtggc gtcaacaacg tttattttct cacaacaaag gacagggact   128880
ggaaattcaa caccaaggtg acagcaggga tggcttcttg tgaggcctgt ctccttggct   128940
tgcagatggc catcttctcc cttcgtcttc acttggttgt ccctctgtgc atgtctgtgt   129000
cttaatctct ttgtatgagg acaccagtca tattggatta gggcccacct atatgacctc   129060
attttacctt acttactctt ttaaaggccc tatctccaaa tacagtcata ttctgcgtta   129120
ctaggggttg tggcttcagc atatgaattt ggggaggaca cagttctgcc cagaacagcc   129180
ctctttctgt ctcacctgtg ttttctccct agggggtatca tccactcact tggctttcat   129240
```

```
ctgcctgtca ccttcaaatc tgtagctcca ggaccaagac ctctttaatg aattctagga   129300
ccctatagcc agctatttcc tgcctcagga ctcccctctt tttttttttt ttttttttga   129360
ggcaaggtct tgctctgtag cgcaggctgg agtatagttg tgtgatgata gctcactgta   129420
agcctcgatc tccgaggctc aagcagtcct cccacctcag cctcccaggt agccaggact   129480
acaagcatga gccaccacat ctggctaatt taattttttt tttttttttg tagagatcaa   129540
gtttcattat gttgcccagg ctaatcttga actcctgggc tcaagcagtc ctcttgcctc   129600
tgcctcccaa agtgctgaga ttacaggcat gagccacaac actcagcccc tccttgcttt   129660
aattggctaa ttcttactca gcatccccat ttggacctca taattctgtg catctaggcc   129720
tgaggcacct ctcttgtgtt ttatctaaga aaatagcacc tccatccatt catccatcca   129780
tccatccacc cacccacccca cccatctatc atccatccac ccaccccatcc acctaccat   129840 ccacctaccc atccaaccgt ccacctatct atctaaccgt ccacctatcc aacctctatc   129900
catccatgta tctatccatc catccatcca tccatccacg tacccaacct ctatccaccc   129960
atccatccct ccctccaccc acccacccat ccatccaccc acctatccat ccactgcaca   130020
agcaagaagc cagaaagtca cccttgatat ctccttttcc tttataactc acataaatta   130080
gtagataaga cctgtcagca ttacctttga aaggactctc aagtctctct ctcccttctc   130140
tccatctgca ttgtcactac ccaaaattgga gctacgatga cctcttccct ggacaactgc   130200
cgtagcttcc tacctggttt tcatgtttct gttctttctt tgctcatttt ctcttctcct   130260
tactgcatcc tgaatgttct attctgtaag cacacctgat ctcatcccgc tcctccctcg   130320
ctgaaaacat cttactgact ttcatttatg ttgagggtaa atattaaaat tcttaatttg   130380
cccaccggcc tcaggggat ctgacttata tctgtctctg cagcctcatc tcacaccaga   130440 cacccccctca ctgtgaggat gtcagtcagg ttgtctccta cctctgggcc tttgcacagg   130500
ccactctccc tgactgtgct aacagctgaa aggaaagatt cccatacct gcagacgagg   130560 tcaggacctg gtattgtgca ttcacagagc ctggcacatt cctccattgc taatggtggg   130620
tttacttgtg cagattattt gactggtgct tctctctggc actagactgt aacctgagtt   130680
ggggcaaggc tggtgagtgg ctcaccatag ccacccagac acccagcaca cgcctgctgc   130740
agagtaggag ctcaagcact tttaaaatg aatgttacct ccattacgtg attataccat   130800
aatttattca actaattccc tgtgcttgga aatcgagact gtttccatgt ttccactttt   130860
ataaacaccg caatgaatat ccttacagat aaattattgc ccacattttt aatactttga   130920
gacaaatatt accagtggga ttgctgtatt aagacttttg acacattttc agtttctcca   130980
ttgacaaaga gtgtgtcaag taagattttca aactgtgctg tgtgaataag ccccttttttc   131040 ttcatcctca gcaagtgata agcagtatct tattttttc cagttgagga aatgatgaaa   131100
acgatcagtg ctctaaatat gcactcctgt tttcttatag tgttaaaagg ttttgttttt   131160
tacattgggt ggcagtttaa tatagtgcag gtgttggaat cattttttca atactttttt   131220
catctaggag tttaatatac ttcacattta ttccaagttt cttttatgta cctcaataac   131280
atttaatatt tttcttcaat atgtgggcca cacattatt aattaaaatt ttttttgctg   131340
ggtaacaaaa aagaaaaaga gcagcagaaa gcattctttc attgataaaa tcaagtaaac   131400
tgatttaaag aaataaaaag tactctaggc tgggcatggt ggctcacacc tgtgatccca   131460
gcactttggg aggctgaggt gggcagattg cttgagtcca ggagtttgag accagtctgg   131520
gcaatgtagt gagacccctt ctctacaaaa aatacaaaac attagccagg tgtggtgatg   131580
```

```
tgtgcttgta attccagcta cttgggaggc tgaggtgaga gaatcacttg agcccaagag   131640
gccaatgttg cagtgagccg agattgcacc actgcactcc agcctgggca acagagcaag   131700
atcatgtatc aaaaaaaga aaaacatact ctataggctt tcagaaagag tgtctacctc   131760
atcaggttgt tctgtagatt aacaagttag tctataatcg attacattaa tacatataag   131820
acattttgac cattgcctgg cacagcatat aataagcact caatagacaa ttgccttcat   131880
tattatcaga tgtattcaaa atatcacact ctccaaggca ctattgaaaa accgtctgcc   131940
actgtaacct aacaatatat actatgtatt tattattaga tagaaatttt taatagagaa   132000
agaattacta cttaattttc tgtaaaacta cagtgcaaag acatcttggt atgcatgaa   132060 aggtaaaatg tgataagctg aagacagcaa acgcatatga aagccttttg tcggatgagt   132120
agttcagtat aaaaccagac catttcgtgt tgtctttacc ttttatgtcg tatgacattc   132180
tgaaacttag aatgacttct ctcagcaaca ctcacagcat gcttatcatg ttgcaggaga   132240
tgttcggaat gacatttatg tcaccctgat ccacggtgag tttgacaaag ggaagaagaa   132300
gacgccaaag aatgtggagg tgacgatgtc tgtgcacgat gaggagggca agctcttgga   132360
ggtgcgcggc atggcccaga aatcctgcta ccatcgcatc cgtctttaca atcacgatag   132420
aatcttggcc gtatttaat tcttctttgc atcaggatgg gtttgatttt tcctgagaaa   132480
agaaatataa agcctgttaa atttgtgatt agcagtgagc agtttcacta aggaagctat   132540
ctagactctt ctagactctt attttatat ttctcctgtg ctaagaaata gctccagcca   132600
ctaatgattt tatgtgtaag cttccaatgc agatgttatt tatcgttttc aacttagtta   132660
gccactttca agcttgatca gttcctctta ggcttgagct aagtggcctg ggtgctcgaa   132720
tagcatcaga aagcatgttt ccttccctgg gtgagcagaa ccaaaggaga tgtgctcatc   132780
agagactgaa actggaagag ccctggggta ggcatccgct accactgctc tttagtttgt   132840
ttgtttgttt gttttttga gacggagtct tgctctgtcg cccaggctgg agtgcagtgg   132900
cacgatctcc actcactgca agctccgcct cccgggtgca cccccattctc agccttagc   132960 ctcccaagta gctgggacta caagcgccca ccaccacgcc cggctaattt ttttgtattt   133020
ttattagaga cggggtttca ccatgttagc caggatggtc tcgatctcct gaccttgtga   133080
tccacctacc ttggcctccc agagtgctgg gattacaggc gtgagccact gtgcccagcc   133140
tactctttag ttttaatgaa caggaaactg taagaaactt taaaggatg agttattgtc   133200 tctgggaaac acaggagtta gtggcagagc tgggagggta tctaagtatc ctgaattcca   133260
gtccagtgtt cctccaactc tggcagcttt ttcttttctt ttcttttctt tcttttgttg   133320
ctgttgttgt tgttgtttga tggagtcttg cactgtcacc caggatgaag tgcagtggca   133380
caatctctgc ctgctgcaac ctctgcctcc caggttcaag caattctcct gcctcagcct   133440
ctggagagct gagattacag gtgctcgcca ccatgctcga ctgatttttt ttatattttt   133500
agtagagacg gggtttcact atgttagcca ggctggtctc gaactcctga cctcatgatc   133560
tgcctgcctc agcctcccaa agtgctggga ttacaggcat gagccaccat gtgctgcctg   133620
ctttgctttg ctttacttta ctttcttctt tcttttcttt tcttttttt tctctgtctt   133680 tccgctccct tcccttctct cctctccact cccctccccc acttttcctc tcctccccca   133740 cttccccctcc cctcccttct cctcccttc cccctccact tccttcttc tattttcctt   133800 tcttttccat tttctttcct tcttttttt ttttttttt tttaattaag acaagatcta   133860
atgcaggtat ctgccagctt tctgcccaca taaagaagtg agtcccaatt ctgacatcaa   133920
agaggatagg caggaggtgg tcacaggagg ctgcatggcc tctgctgaac tccacctctt   133980
```

```
ctcgtatgag ccgtagttaa ctgctttggt aaccaaggac caagctcttg attgacttga   134040
ctcactgagt gtcctgttgc atagttgttt gaggctacaa tgaaatacaa tttcatcact   134100
tgccatggat gttataatct attaaggaag cagatagcta ggcagtttac taaggcaagt   134160
cgtattctgc atgagaggga gaaactgaat gctatgagcc actgtatgaa agtgctttat   134220
ttgtgctgtt gataagagca catgagctca tttcacgtag acaccttctc ctggttggtc   134280
atttcgtttg atagtgcccc accaaggcct ggttctacta agctcagtgg ttcatgacca   134340
ggaaaagatg cagccctgag ttgagtgaat atgctgtgcc aatacccctaa gtccctaaaa  134400
cagaatgtag acaggaaaag agaaatgctt ttctgcaaat agcggcgcgt ctgcagttgt   134460
cacctaactt ctcgtcatcg tcatgttccc tgagagagaa gaggaaagaa tcagaggaga   134520
atgcatgcct ggggagggaa gagaaaatac aagttacagg aaagaagaat atttaggcgg   134580
tgctgggttc cttagctgct accaaattga tattatagac ccttgaataa agtggtggaa   134640
attcagtctt ctctgttctt catcccccaa acttaatcag ccgatcagtg ccagtgtagg   134700
gcatgtgtgg acgtgtttgg gggtgagggg cttgtgcatg gtatatgggg tcctcttact   134760
tttctaaaca aaattattcc cttctaattt tttccttcca tctgaagaaa gcaattcacc   134820
ctggtgctgg atatgaaggc atttcagaat acaaatcagt agtctattac caagtcaagc   134880
agccctgttg gtatgagact gtcaaggtga gaatgagtca tttgtaaccc ctgttatctg   134940
ttaaacctca gttagattcc tatcttctgt ttaccccccaa attattccta ctttattttg  135000
aaattttttag ataagttgcc tatggtgtgc agtaagaaat gaatcagtaa ttataattct  135060
gtattaagag catttatcat taagaaactc agtgatgtat gagaatttga atagcaaagc   135120
ttgtggttga cgtgatggat ataatagact gccaagatgg tacaaaacca aacagaaatt   135180
ttcacactgt gcaaacagtt tcctaacatt ttttttatttt tggcctctca ccaagtgttc  135240
tgggcctctt ttcaacttca atatgtgtat tacacattcc aaagtgcttt tcagatcagt   135300
catctccttt gagccccaca agggctctgc aactagaaca agcaggtgtt gtaacgccat   135360
cttttcatatt aggtactgaa gttcaaagtt cagtgacttc ccaggatcct agagctgact  135420
ggtatcaggg cccaaactag agtccacttc ttctgaatcc cgggctccat cagctctttc   135480
tggttgtcga agtcacacga gttcttcata gaaaaaaaaa ttttttaatt gcattcatat   135540
atctcaattt agaattaacc attttcaaca gttttctata gttcatatgt tttgaatgat   135600
gctgttgata caaatttata ttgtgctttt taaaactact tatctcaatg catataaatt   135660
cttcagatat gtattttaga tacttgcata aggttccaaa gtataatcat gccatgattt   135720
gactgcacac cacaaatctc tgctcgtttg agtgccctaa ggctctgttt cttctctccc   135780
ctgtagatag gtaagcagca gaaaactgct ttatgagccc taattattac ctttcccct   135840
ctttatggaa taatcaggtc ttatagatcc aattattact atatttatac acatcttgca   135900
gtctgaaaga tcctgtgtgg acctcaaaat accagtattt cccctctgaa gtattactgt   135960
ttcttacttc agaaaatgct agaaattcac agtatcccta tgctcagaat ctatgataaa   136020
cagcaagatg atctgagatt cttttgattt gaaaatagct cagtctcctt tgaatgaaac   136080
ctataccaaa tctcactctc tagtaatttg tgctgtggaa agtataaaat tgagcctaat   136140
tccatgaaat aaaccatgct tgcaaagtac tgtgtgtctg taaactatta atttcttact   136200
atgcacagg tatccattgc tatagaagaa gtcacacgct gtcatataag atttaccttc    136260
cgacacaggt catctcagga aagtaagtat taagacgtct atgacatatt tccacttaaa   136320
```

-continued

```
aaaaatttgc tctggcttga cagccatctt gtgaagctgg agaacaagat atttggaaac    136380
tagagacttg gcagctgtat tttgtaactc actggtgcta aggaaatcag cataatgaat    136440
tttgctgggc gtgcaaggtc tgtgttgtca ctctatatta ggatttcctc aaaatgtgtt    136500
ttgtgaacac taatattctc aaagacagca gtcctcaatc tttggcacca gagactggtt    136560
ttgtgaaagc cagttttttcc aaggaccagg ggtggggtga tggtttcagg gtaattcaag   136620
cacattacat ttattgtttt ctttattctt attacattgt aatatataat gaataattta   136680
tacaactcac cataatgtag aatcagtggg agccctgagc ttgttttcct gcaacgagac    136740
agttcagatc atcaggcatt agatttccac aaggaatgtg caacctagat cccttgcatg    136800
cacaggtcac aataggggttc ggctcctgtg agaatctaac gctgctgctg atccaacagg   136860
aggcggagct caggtgataa tgcgagcagt ggggagcagc tgtgaagaca gatgaagctt    136920
tgcttgctcc tccgccgctt acctcctgct gtgtagccca gttcctaaca ggccacagac    136980
tggtatgggt ttatggcttg gggtttgagg tcccctgctc taagatgcta ctagatgctc    137040
tataacaaaa agtgttgtat ttcacaatca aataggtata ggaaaggcta tatatacatt    137100
gtatctccct cctagacgtt cacaatgcgt gttgccatgt tgcagtagca agaaaactct    137160
ttattcactt gtctccccaa attatcattt ttctcatgaa aaaactcttt caagtcttag    137220
gtcacagttc ttgaaatggc tacactaaag tgtaagcaga gaagaaaatt gattgttttc    137280
agattgatca caaaatttct ggaatcgtct tattctcatt tcgcactgca taaaaatgta   137340
accccctcctt ccaaaaatgc atgtgttgaa caccatctac acaacaggct gcaggcgagg   137400
ccctggtcta tgacagccag ctggacactc ccacgcagag tctttgtggt ctggttagga    137460
agatgaacga aaaagtgggt ggttatgtac ggaatagtat gatatgtaca ttacaagggg    137520
caaagacttg taatggaagc gtagcacagc accttacccca gtctggggga tttatgcata   137580
tgacctccta catcttagct gagacttgaa ggtgagtaga aattagccca gtgaagggtg    137640
atgggagaag tgtgtttgga gaaccaaatg aactcagtat ggctaaagca ggaccagtgg    137700
agcaataata gtatcaggtt gaatcgtgtg aaattggcat ttttttaggtc taaatggcca   137760
aatatcagcc atttcatatg gttctgcata ataactaaca attgtcaatt aacaattaac    137820
aaaggtcaag tttgtatgaa gtattatgtg aagctatatt tgtacatggt cctgtttagt    137880
atccacaata atataacaag gtacattcta cttttatcta catttataca caaagaaact    137940
aaggcatgga gaggttaggc acttgcctgt ggtcacaagg ctagcatatg accaggctgg    138000
gttagcaccc agacaatctg attctagctg ggctggagcc ggatcatgaa ggctgaagat    138060
gttttttcagc catgttaagg aggtgcaatt caagggtggt ttctggtttt gaggttttgg   138120
gagggggttgg tctatgttca taacagcttc acccatagta ctccaacact agaatagcct   138180
aaatccccat caataggaga atggataaac aaattgaggt atgatcatac aatggatgac    138240
tactccacca ctgtggggac ccaagggggca cagcagacca cagagccgtg cctatgataa   138300
aaacaggcca caggttaccc tactcagagc cactgaagca ggggacccgg tgagttcaga    138360
gactggcccc gaagaccaag agagaggagc tctgcctcct catgaagctg caccctcctc    138420
ccagctgcca cagggcatgc agatcttctt tcctggcact ggagctggta ttctggggag    138480
gaagggtaaa gaaactttgg gcagcaccat aaaccctaga gtagaataaa tatcttgcag    138540
agcctgtttt agagcaacat aaattgagat ctctcattca agtgttttga agcagcgtgg    138600
ttgacatgat tggattggac tttggaaacc tcattccaac atagagaatg tgtttggtgg    138660
gagagcctag agacagagag atgcgctggg aaggtcttgt agaaataaag agaagaggtg    138720
```

```
agtgtggcct gaagtcagga aggacagcaa gatggagaga gaagagacag gctccagagc 138780
tgtttaggac atggagttga cgtggggtgg agttggtgtc aacacccaca tttctgattt 138840
ggatgactgg gcagatgcta gtctcattta ttaggggatg taggaagagg agagcatact 138900
tgggggtgcc aggcagtttc agtggcacat ggtacgtggc ttattgcagt ttgctcagtt 138960
gtgcttatta gaatatggtt gaacgctgca cccccgagca aaatgtgaaa tcgtgtcata 139020
gccatcgcct cctggtgtct ctctgcactg ctcagacatg tctttctgcc ttttcagcca 139080
gagataaatc ggagcgagca tttggggtgg ccttcgtgaa gctgatgaac ccggatggca 139140
ccactctgca ggatgggagg cacgatctgg tggtttataa ggtggtgcta acagaaaatg 139200
gctgagaaaa atactccctt tcaaatgagc atttaagact cctttcatat ttatttgtac 139260
aaacatcaga aacctttcta gagctttctg tacttgccca ttaacatcta gaaacccaga 139320
gggctctggg ccctccagct ttgtggtttc ccacctgctt tctggagaga gtgagttgca 139380
ttattactga gtcttctaag gaggctctca cctccttaga cctctcacgg gagaggtcct 139440
gtgaatggtg ttccctagca gtgaatggta aggggtcggc ctctcatgat ctgctctttt 139500
catcatcctg catggcacat ggacaggtgc actgttgggc ttcagtagtg tgtggtggat 139560
atggttttcc catcaccatg agccacatac tatttctgtg ctctgggggc cttatttcct 139620
tccctgaaag ttttgtcttt gttcttgcct tccaactgat gctgagctcc cacttctact 139680
gagattttag agtataaagt agatgctgga agatctcatt tagccaacaa tatctgggga 139740
tttccccaca gttggctgct cttttgagat gcatctacct gaggaatatt tttcttaaca 139800
tcttagttta tgaatcattt tggaagggat ggcaagctaa ttcttcttcc atcaacccaa 139860
taaagtataa ttgtccccat tttttaatta cacttcaagt tttagggtac atgtgcacaa 139920
cgtgcaggtt tgttacagat gtatacatgt gccatgttgg tgtgctgcac ccattaactt 139980
gccatttaac attaggtata tctcctaatg ctatccctcc ccctcccccg ccccgccac 140040
aacaggccct ggtgtgtgat gttcccttc ctgtgtccat gtgttctcat tgttcaattc 140100
ccacctatga gtgagaacat gcggtgtttg gttttttgtc cttgtgatag tttgctgaga 140160
atgatggttt ccagcttcat ccatgtccct acaaaggaca tgaactcatc cttttttatg 140220
gctgcatagt attccatggt gtatatgtgc catattttct taatccagtc tatcattgtt 140280
ggaattgtcc ccatttagag actgaagaaa atgaaattta accttattct gaaatatgtg 140340
tatttactct aacagagact aggatattct ggtttctagt tcacaactta ttctgtttcc 140400
attcaatcat gaaattattt ctgggctcaa tgtttacaga aagatatcag agtatctcag 140460
aggtggaagg gatcttcagg ataaattgat aagtccacgc ttctcatgct gaaaatgcat 140520
gatagaaatt gtttttattt gcatataaga gattttggcc atcatttggt gttcctaaca 140580
tgcttccttt tagggtgaca acaaaaaaat ggaagatgct aaattctacc tgaccctgcc 140640
tggaaccaag atggagatgg aagaaaaaga gcttcaagca tccaaaaacc tggtcacctt 140700
cacccccaagc aaggatagca ctaaagacag ctttcagatt gccaccctca tctgctccac 140760
aaagctcacc cagaatggta ggagtggtga atacactgac acaaataagc ttcttgctca 140820
gcctttctgg gctccttggt taggctcaca gggctggact atatgggct gggtcttatt 140880
aggtaggatg ttggccaatt ggattctgct ctctgctttt caagtggtat tctgggtagt 140940
gctgatcaca ttgcacagcc tcttctgaag tttcatcgtc cacttagag caggatgaaa 141000
aacatttttag tatttaatat cttaaaacct ataaatgcat ttattaacag caactgtaaa 141060
```

```
attcaaaagc cgtatgttcc ctgatagtgc attctgtgta gtatgtgcag gaagagatgt  141120
tggtagtaag aggaggagct tggcaaagaa atataatcag tttcctgtcc aaacaggtat  141180
ggcagggctt cctgtttgag ttctgtcctt ccctcctata ttctcttctt tcccattttt  141240
ttccaagcag tcagggattt tccataaatt cagctgaata gttcaaagag ggattcattt  141300 ggttttcct tcaaatctct gatatcaatt ttaacctctc ttgtgtagat tatgacatgt  141360
gctagccaat atcaacttct tatttattta acttaagtaa tgtgtaagga accctactgg  141420
atgtagtaaa ccaagaatga gctgcctagg ggacttgcgc tagaaattct gtctcccata  141480
tgccgtgtag agactgttgc ctttggcctt gtagacagtt tgagtgaggt acaggcaaga  141540
gctctgcctt aagggtgcc aagatagaca aaaagtgta gttatagggt aaacccaggg  141600
atcagatccc tgatctttag aagggctcag tgttaggttt gtttcaacaa gtcgtggttg  141660
acaaaaagat aaggattgta tttcaacttg gacaagtggc tagactccac agagtgaagt  141720
ttagggctaa tccgtatgtg caagtaaaag catcctcacc aaaatgaag ccagaaacat  141780 aaaagacgtg acaaaaccgt cagcaacata ccccgtgtta tggacaaagc gaatccatta  141840
acaatgaact gctggtaggt taatgggtac aacatttatg gaagataatt tagaaggcat  141900
atcaaggagt ttaactgtct tcagacccctt tgagcctgtg atttgattcc tggaagttgc  141960
acttaagtaa acaatgagag atggacacga agatttatgt acaaggatgt tgtttcccta  142020
ttatttgtaa cagggaaata ctggaaacaa cccaaatgtc tgatagtcag ggtcagttta  142080
accacgtttt ataatataat taagtgatga aatatatgca gctgctaaat atggtatttc  142140
aaaacatagt gaaggacacg gtgaacttt taacactata tacagtatga tcccagtttt  142200
atttaagtat atgtgagcaa cctgcaggca gattgcctgg cttcaaatcc cagctctgcc  142260
atttactagc tgtttcatct tgggcaagtg acttgatatc tctgtgaatt ggtttccttg  142320
tctttcaaat gggagcaata atagtatcta tttcaaagaa tgcagtaaat taaaacacgt  142380
aaaaactcac attcgatcta tatagtgaac actataatgt cagctatcac gatcatcatc  142440
actatttgta cacagaaaac gatgaatagg actaacccaa agtttgataa ttcttgtttt  142500
ctttattctt tttggtattt tccaaatttt taactatgaa atgtcaaaat gttatttttt  142560
aaactaagta tggtagtata ctatataaag cattaatgtt cttttaaaac tatcaaggga  142620
tatttgagag ggataacact tattgaacat ctagtagatt atcctttctg gactacagat  142680
taaagaagaa taaagaaaac aagaataaaa gtttgtgaaa ttaactagta atgaaaagca  142740
aaaggaattt ctgttagaga taaccatatt gttacattgt ttgttatctc cctgtcaaaa  142800
atgtagggtt tcctgacaac ccgcagttct caatgtagac ccttcgtttg ctgatacatc  142860
tacttcaccc catcttctga atgttcttaa ctagcctgta ctgtcccgat atggtagccc  142920
ccagacacat gtagcttgta aaatttaaat taattaaaat tggagggtgg ggagattggg  142980
gagaagttgg acaaaaggta caaaagctca attagacaag agggataagt tcaagagatc  143040
tgttatatat cctcgtgtct atagttaata gtatagtgta tacttgaaaa ttggtaagag  143100
agtagatttt aagtgttctc accaccaaac aataagtgag ataatgtgtg tgttaattac  143160
cttgatttac ccttctaccg tgtgtgtgtg tgtgtcagaa catcatgttg tacactgcaa  143220
atacatacaa ttttttatttg ttaattaaat tttattaata aaattaaatt ataaatcagt  143280
ccgctagttg ccctagtcgc atttcaagca ttctggtctt ctgcagctgg tgagttttgt  143340
gttgggcaga cggatataca ttttcatcat cacagaatgt tcctttggat gacactgtat  143400
gctttatttt gtcatcctta ttcctgatgt tttgattaaa aaaaaagaca aactcatcat  143460
```

```
aacacataca aaaaaagtca gaagtaatat cttattacaa agaagggtta aaaaggcaaa 143520
ccttgtctga gtcagagagg agtgagctgc catccaaaca gactgcgagc agggagaggg 143580
aacagggtac agagagggaa agacggagac ttggcaaagg catcacgagc atcagggaaa 143640
atggggtatt ccaggacaa atgattgcag attattcatg catttgcttt cttctgactt 143700
gatggaaatt ataagaatg aatttgattt aataaaaagc tgaagaacat taataagcca 143760
tcagctaatt ctgtgagggt gttgactgag tagagagggt agcagtgttc tcactgagag 143820
ggtgaacaaa ggcatttctc cttcgcctga ggagagttat tcagactcaa aaggttaaaa 143880
gccactggag ttttaacaaa cagatcttgg agactctttt gtttacttga tttgtttttt 143940
agaaactaaa acagaccaat ttgtgtggga tcattggttt ctgggcccac tggaaggtaa 144000
gaatagattt gtttcccagg aaaaagagag gaatgtgcag gtccccagag gtgcgtggcc 144060
ttgggccagg aggttcatac tcagtcagtc attgcaccct ccagcaccaa ctttgccaga 144120
tcatctccag cttattgatc agaaaattga gttttaaagt ggcaaaaaat ctttcttaag 144180
ctcctaagtc gtggacttgt attttgaaag cagctctttg tagctccaaa cagtttatag 144240
tttatcgttt tgcagttaca gagtctccaa gatctgtttg ttacgaactc cagtgacttt 144300 taacctttg agtctgaata gctttgtctt tcttttctct ttaaaagtat gtgttcttaa 144360
attctctcct ttagggtaga aggcagttac taccctaaat gtggggattg ttattctctt 144420
gcttctcttt atagttttgc cacatctgta gcccttaagg tatattgttt cattttgcat 144480 ttttaattt tatgttaata aattaaatta tgagtcagtc ccttagttgc cctagccaca 144540
tttcaagtgc tcagtaatct cctgcagctg gcaacttttg catgccacct tacttatttt 144600
tcggtggtga gaacactcaa aatctattct cttagcaatt ttcaagtata cagtatacag 144660
tactatacag tctacagtat taatgtagtt aataattgaa ctgtctaatt gaagtcttgt 144720
gtcacgtgtg aaatcatgta acttgcgctt ttactcagca ttactgaaga tttgaaatat 144780
cctgaattct tacacatttc tgacaagaat gtaaaatgag gacagtgact ttgcataata 144840
tttaatatgg ttgaagatat tcttcctgat gccccagaaa tcccaccta gttttctatc 144900 ccagagaagc tgctctacct gtataccagg agacgtatga gaatgttcat ggcggaattg 144960
cttatgatag caaaaaaact agagacaacc cacgtgttta tcagcagcag agtggataaa 145020
caaattgtgt acacccatac aattgaatag acactataca gcgagaaaaa aaattaacta 145080
gagctacatg gataaacctg tataaatctt agaaacacag caagcatggg gctctttctg 145140
taaccccgtg tcactgctct cctggcccta agaccttaac aattcaccag atgccaaaat 145200
attttcctat gtgagcagtg atctggcatg cagatatcac taggaaataa acctctgggc 145260
tgatagatgg gtactttgcc agagctgaag ctgctgggtg aatattcacc cctggtgaag 145320
ggactaaatc cttttcctcc agcagctatg agtcaagtga tggaatgagt gataccttcg 145380
actagcctgt gacagaaata agagctggag aatatgaag tagatggtgc ctagtggatg 145440
aatgaatata ttaatgattg ggttgagcat attatcagtt tccttagggc tactggttcc 145500
ctttccgttc attcatttat tccttcatca acatgtatt gaacacctaa tagatggcta 145560
gtactaaggc aagataaaag aatgaatact atatgattcc tgccttcaaa tggctgagaa 145620
ctatgggaag agtcaaggag ataccaagta catcttacca aatacatagt atttctgggt 145680
atttcaggca aagggaagaa tatacacaaa gacacagaga tatttcagaa cctgccatgg 145740
ttgggctgta gtgattggat ttctctgact gctaaagggt aaaagagaat ggtggtggtt 145800
```

```
ggaagtatgc aggagtgata taggtggggc cttattacat tctctatgtg gcattggaag    145860
tttatcctgt agacacgagg aatccctagg cactaggttt tggagggtgt tgataaacac    145920
cctcaagaag gactttgact atttatgaaa aatacatgtg taactactta tatatttcta    145980
caaattcatt gattgaaaaa tatcagccgg gcgcagtggc tcacacttgt aatcccttty    146040
ggagggattt gggaggcact ctgggaggcc gaggcaggag gcttgctttt gaagctcagg    146100
agttcaagac cagcctgggc aacatggtga agcccttct ctacaaaaaa tacaaaaatt     146160
agccaggtgt ggtggtgcac ctgtagtccc agctactctg gaggctgagg tgggaggaat    146220
gcttgatcct gggaggtgga ggttgcaggt tgcaatgagc tgagattgtg tgattgcacc    146280
actgcatgag attgcactac tgcacccag cccgggtgac agagcgacct tgtctctcaa     146340
agaaaaaaaa agtatgtatt gctacattta ctagatagtg ctctgaatag aaatagtagc    146400
ttgatgtact aaactaggtg ataatacagt aacagtccag ataactgcag tttctctgtg    146460
acacacacac acacacacac acacacacac acacacacac atatatgtgt atttcttaat    146520
agagacaggg tctctctatg ttgcccaggc tggtcttgaa ttcctgagct caagtaatcc    146580
tcctgtcttg gcttcctaaa gtgttgggat tacaggtgtt agccactgtg cccagcccct    146640
ttgacatttt taatagctca acattttatta aacctgtaag tggcttaaag tttcaaaatt    146700
ctccattgta agtcaaaaaa tgtcttaaga ttttatccc agacttatgc taagggttat      146760
gaatctgttc cacctttgt ttgaaatagc cacctgtctg atttgcttgt ctatttcttc      146820
aaagaactct ggggaaaaca gtatgataga gtagcaagga gttggttttt caaatcagat    146880
aaatatgtaa taaaattcca tttctacctc tcctaagaca tgtaatttaa cttcacaaag    146940
cctcagtttc ctcatctaaa agatgaaaaa aataaaatct gtgcagtcat gatgttgaaa   147000
taaattaatg catatatata tatatatata tagagagaga gagagagaga gagagagaga    147060
gagagagaga gatacacaca tacctatgtt cctctttccc tctgaatcca cccagacata    147120
ggtagtgata agggacaatt taaataaggc agcaaattaa agtaggaag gttacattag      147180 catgcttctt agctttactt cttatgacca tgatgtcatt atttgagaaa tgttagtttc     147240
agtcagatat tctaagttct tatgcattaa tagttaattt ttttctcttt gaagaatgaa     147300
agaggaccac aaggttttct ctgacttaga taggagatag taaattaaaa gaatatataa    147360
ggcatcttga attagccact attgagagca attacctgtt ctagagaatt ctttagctat    147420
gtcctgaaat ggtctgggtt gttctcacct gtatctaatg tttgtggttg ttcttcctag    147480
ttgacctgtt aggcttgtta aattggcgtt ccaactccca gaacattaaa cacaacctaa    147540
agaagttaat ggaagtggat ggaggagaga ttgttaaggt atgtttatat attcatagtt    147600
agaaatacac atacctacat atatatacct atctaattat acctaattgg ttccacattt    147660
aaaattaaat cattcattgt aaatataaaa tctacgttgt taaacaagtg tgctagtttt    147720
ttaaaaaatg ctatttttaaa cctctttgat ttaaactagt tgtacccaga tttctgtggt    147780
gtggggctga atgaaagcat caaaataacc tctccgtttt tcttatcttc agtttttgca    147840
agatacacta gatgcactct ttaacataat gatggaaatg tcagacagtg aaacctatga    147900
cttccttgtg tttgacgcac tggtaagcag ttaaacatat taactagtgt ttattgttgc    147960
aactttgtag ttttcaatat ttcactatta taagtgattg tgtgaatatc ttctcacata    148020
aatatttgtt tacatctctc tggttattgt tttaggctga attcctagaa gtactattag    148080
aaacaaatga cttatatttc aggcctttgt ttgtttcctg ttaggtctca tttttgata    148140 tgctctttct cattagagaa gataagatgt tttatttta ttagaaatca ggaatcattt      148200
```

```
taactcacat taccatgatc tggagcattg ttacatgttg gatttgtgtg tgcactggtg  148260
tgtttatgca agggagactg aattcacaag tcagaggtga atctgagcct cattaggcag  148320
aatattcaac ccagcagaaa attgaatttg tcgcacaaag cacttaaacc tacaacccat  148380
tgcaagaatt gaaatcagat cagggataag tgatatcaga atctgggaaa gccagaggtg  148440
agggtggagg ggaagaagct gaaaggctca aagcaagcat cgttttcacc ttggtggggt  148500
gaaatttcag gacaggattt tacctgaatg ccacagctga ggaggaaggt cagttgcagc  148560
tttaggcgat ttaccagctt tgagaaacta gtcagtttag gaaatgatta gggtattaaa  148620
gctaaggttt aagataaaga aagaaaaggc caccttacttg agatccaact ggttggactt  148680
gggtttatgg gaaagagaga cagtggttat ggttgctgtg ggacaaggtc tggaaacaga  148740
ttcctgaggg acatagcagc tggcagtggg catagatgga aatcccaaat gcctctttct  148800 tctgaccct ctgtcttaaa cagggtagtg tggctgattt taggtcatgt gcctgatagc  148860
agtgcaagag aatatacaag aggtaattgg gagataaaac tctggtgcag ttgttactgg  148920
gggcactcat agtgtacaca ggagaaaaat gtcatggaat gtttcattag ctgcatcctt  148980
ggattagaga aaacacccttt ccagagcctc cttcctcctg cccgttaggt tacctgggca  149040
tcgactcccc tgtctttgag atagtcagct ccctgaggcc aaggatgctg gcttgagttg  149100
gtttcttcac agcatttaac atagtgcctg acacataata gtctctctat ttatgctaaa  149160
taaatacaat cctcaagact tgacatcagc tctggaatag tagagtggga atgctgcaga  149220
aaagatccag agaggaaaga aggcaccgag atgttaaaat gcggcttgtt gacagaatac  149280
ttgggattgt gcagtgctgc tatttctatt tttcactttt ggcaggtatt tattatttca  149340
ctgataggag acatcaagtt ccagcatttt aatcctgtac ttgaaaccta catttacaag  149400
cacttcagcg ccactttggc atatgtgtaa gtatgatctg aaggaactac atgttgttgg  149460
atctttggat ttgtactctt aggactggat tgttgagaaa cgagacggac ctattactat  149520
tcagtaaata cgcctgttaa ggcagaactc ttattctaag cttccgggtg gaaaaggga  149580 accatctaag tattctaact ctggaaaggg ggctaagatc agggccttca ttctggatca  149640
ggcgaaattt ccttaaggat ccagaatagg ccaggcgtgg ttgctcatac ctgcaattcc  149700
agcactttgt ggggaggatt gcttgaggcc aggaattcaa gaccagccta ggcaacataa  149760
caagaaccta tctttacaaa aaattaaaaa gttagccagg tgtggtgaca cacacctgta  149820
gtcctagcta ctcgagaggc ttaggtgaga ggattgctta agcccaggga agtcaaggct  149880
gcagtgagct gtgatcatgc cattgcactc cagcctaagt gacagagcaa gacttagtat  149940
ctaaaaaaaa aaaaaaaatc gagcaaaatc aataacaaat gactcaaccc aggatctcag  150000
aggttgaatg tcagtgggat tggcgtggga catcaaggag atcaaaccat gaattaaaca  150060
agaccaagtt tgatagaaga aaaggtcatg ccctcaaccc tgtaccacaa atgctttgta  150120
aaatgtattg cttacaggat atgagaagat ttcgttttcc catcttttgc ataagaggca  150180
gtggtctcta ccttttttgt agtgcagcct gccttctatc attggtttat gggcccctga  150240
ctaaggaaag caactgatgt ccactccgca ttcctcccca gagcactcag ctcaccatgg  150300
cattgtgtgt gcctgccaca cccacccgtt gccttccagt tattgtgcag aatgtgataa  150360
atagtgaaag gaatgtagct ggattggtcc atgatcttct tatgacagtg gcttaagcca  150420
catcctgtag attgctgccc actgacttgt cagcaagaac accagtgaca gtggccgttc  150480
cacccaggag cctcacatcc aggtgggcaa tagctacaaa tgaggaaatc ccatcactgt  150540
```

```
gatcataccg agccaaatgc agcactccag gtggtagtaa tctgggttta cttgcaagac   150600
ttgatcaatt ctatatgttt cctttttaaa aaataataat tcggccgagt gcttgaaccc   150660
aggaggcaga gatcacgcca ctgcactcca tcctgggtga cagaatgaga ctccatctaa   150720
ataataataa taataataat tataagtgac tattattata ttattatgta tgactattat   150780
tgtatataac tattattatt attctaggaa agctcaagga tccccagaag gaaagtttaa   150840
gtttaaaata tcagtgccct ccaaagtcta agggatagca caaatgaag accattccta    150900 gcccaaaaac tctagaaaga cacaaagagc aacctataac cccagaacag ctttatctgt   150960
tgaatgctta gaaccatgaa tgttctggag agtgagctcc tctttcttca ctccataaag   151020
tttctatctg gctccatatt gatggatccc aatgggttga ggcagaataa aaggaattag   151080
gcttctttta agtcaactcc tgtaggcagg cataatccct catttatggg agcatctgaa   151140
gatgtcagaa ttgcatacca gagattaaaa tatcctagca atttgggtca cttcaaccat   151200
ttcatttcat aaccctccgg tttaatccca caagggaaa gaaacctttt ctagtatttc    151260
tcagcagaag gtagttccaa acctagatgg cagatgagga aacttaattg gaaagagtt    151320 aattttgctg ttcagggcat attctagaag atataattag ttatgacttc tacttccagg   151380
atgccatgtt cccctcttag ataacttacc caagcctcag agtatcctgt tgctcattgg   151440
cttaattttt ctttctcatt cttctaagga aactctccaa ggtactgaac ttctatgtgg   151500
ctaatgcaga tgactccagc aagactgaac tgcttttgc tgcgttgaaa gccttgaagt     151560
acttgtttag attcatcatc caatcccgag tgctctactt gaggtaatgt taactgcagt   151620
gaagatgttt agattatcag ctgtcactct gtgtgctttt tccctcactc tgcacagtgg   151680
tgttcagctc tgtgagcagt tagttcttag aattgcctta tttcagaact gcagggctga   151740
agatggattt gggctgcgtg tctgttggag aagactcatg agaagttttt gtagatcagc   151800
aaaattctgg ggcagtaatg acctcaggac ttggggaagc agattcctgt ggaaagattg    151860
tacctaatac agcagatgac ttcatgacaa tattgagtgt gcaaatctag gatcatgatc   151920
tgctgtcgct agcagaagca gcagtcatct caggggaggt gttgcctgag atgagtgttt   151980
ccttgttgac actgtgctta gctacctggg caactaagca ctagagacag gattattccc   152040
tgtttggatt tctagcataa cagttccatc aaaaacagaa gaaactgcaa aagagcaagt   152100
acctttgcag ggaacattca aaccccagt gactttccta cccttcagaa atagctgtat     152160
ttccaaactg ttaaaatttt tttctaagga agaaagaaaa ggtttgtaga attgagcata   152220
tgtattttta aagaaacttt tattgaaaaa aataaaatta aaggcaaaca acctgcaaaa   152280
aggttacata tagtacagat gaaagtttaa tagcttttct cagttaaagc ttttataaat   152340
caataaaaga atgataaata gccctaatgg aaaacaaaaa caggtaattt acaaaagaaa   152400
aacttaaatg gtcaataaac tttttaaaaa atttcatact atcaaaagaa ttttgataca   152460
gacgcacaca catgcatgca cacacacacc atctttacc tatacatttg aaaaagatta    152520
gacatctttg tccttgatga gattgggcaa aaattggtcc tgtatttcag ttttgatgct   152580
aatggagata taaattcttc aggatagaaa tagatagtct gaataaaaac aaaaaagaag   152640
atttttaagg gaaaggaaaa agtgtcacat ttgtccagta atacctcatc tagaaattta   152700
tctaatggaa aaaaaaaatc ttatcaggta tgacaaaaat gaatgtgaaa gtatgtacat   152760
tcagtcattt caaatgtagg gtatgttaat gaggaaagac gaccatgata gattcttttt   152820
tttttttttt tttgagatgg agtcttgctc tgtcgcccag gctggagtgc agtggtgtaa   152880
tcttggctca ctgcagcctc caccttacag gttcaagcga ttctcgtgcc tcagcctccc   152940
```

```
gagtagctgg gactacaggt gcataccacc atgcccagct aattttttg tattttagt    153000 agcgatgggg tttgacatgt tagccaggat ggtctcgatc tcctgacctc gtgatccccc  153060
cgcctcggcc tccgaaagtg ctggaattac aggcatgagc cactgcgcct ggcccgatac  153120
attcttaaat gataaaacaa aggtattaag catgagtaca gtatgatctt ccttttaaaa  153180
taatacagat ttgaaatatg tatagtaaag aagactggat agatcacatg ctaaagtgtt  153240
tttttgttgt tgtttcttta gagttttta gggtttttg ttttgtttt tgagacaggg    153300 tctggctctg tcacccaggc gagagttcag tggcatgatg ttgggtcact gcactctgct  153360
tcccgggctc aagcgatcct caaccttag cccccaagt agctgggacc aaagggcacg    153420
tcaccatgcc cagctaatgt ttatatttt tgtagagaca gggtctctct atgttaccca   153480
gtctggtctc aaactcctgg gctcaaggga tctgcccacc tccgcctccc aaagtgctgg  153540
aattacaggc gtgagccacc gtgcctggtc tgaaatgtca atagtatgaa aacttcatgt  153600
gacagggttg taatttattt tttcattctt tatgttttta ttctttcagc atttgattta  153660
catttattat tctatttta tttgctattt tttatattt tttgaatttt taaatgaata   153720
tgtacctttc tgattgtttt taaaaaatgt ttaatgactt gaaacccatc tggctgaatg  153780
actgtccctc ctttccaggt ggaagtgggc agtgttttcc ccacacataa tttatgctca  153840
gtctctgtat ttgctttctt ttcagaaggt cttctttaa agttgtttca ttatattttc   153900
cagttatggt acatttccat gtattcagaa tggttggggc atggagtgtt cgaccaaggg  153960
aatattctct tacccaaaag tttgtatgta tagtaaaccc tgatgtccaa aaatcagtat  154020
caactttaaa ccacagaaag aaaacctgag tgtgaaatta aaatatattt tcttatggat  154080
ggttcactag ttcatttcct cttcatttgt tgaggcacat cagagtcctc attctagaca  154140
ccagatagga cagtaaagga tggtgagtgt ggaaaacaaa aggttagggc gacagaggac  154200
ccatgaaatt gactaggaga gttgcttcat tacacactgt ctgtgatggc ctgcgtgtgg  154260
ttacttttcc cttatatgtt attaaagaag aacctgagct ggggaagaga ctggcaatgt  154320 gcgtccctg gttgcttaga tttaatggtc acttcagtgc actggccatg tctggaggct   154380
gcagtggaat gtcacctggt ccctgggccc cctgttgcct tccgcagagc ttaaatctct  154440
cttatgagct cattacctgg ctggatttca cctcaatcag caaaacacca agaaaaaatt  154500
gtaaattgct cccaatagga tgttgagaag cttgatctta atcccttagc cccctatcat  154560
tagtacttaa aaaaaaatc aagtcacata cgtagagtgc caagtgttct gcattggtgc    154620
agggcttttg cagcatatgt gaccaggctc ccactatgat ggtgtgtgtg ggttccatgg  154680
agttcaggga ggcaaggagt aaagaaatca acccctaaat gaaggcagtg ttggagtggt  154740
ggaaccagca gggaaggctg cctgagctga gctgggtgga ggaggaggtg gtatcatgtg  154800
agctgagact gaaagatgaa gaagcagcct ccagagatgt caggtaaggg ttagtgggag  154860
caggacctgc cccaggcagg gacctatagg gcaccaaatg tggatgcgtg aggagtaacg  154920
agaacccagt gtcgggagag agagcgggag tggccagcaa atagtaaatg atgtggggcc  154980
ttgtaggcca tagtgaggag cttggatttt attccaagtg tagtgggaag ccgttggggg  155040
acaactagag aagtaataaa atctggctta tatttaaat gatcatctca tctcccacat    155100
ggaaaatgga ttatcgaagg ctacaggtag aagccagtga ccactttaag aggccattgt  155160
ggtttaaatg tgagatactc cagccccatc tcagaggcag atggagagaa tggactgatt  155220
cgagctcgta ggatttgctg ttgggtttga tggggcaatg agagaaagag aagaaacata  155280
```

```
gataacatct aggtttgggg tggatctagg ttcgaggtga tgctgtttgc tgacatttgt 155340
aatacttaga gttgagcagg gaaatcaagc gaattctgtt gtaggtgtgt taattttgag 155400
atactttggg gactacattg caaataaagt tcttttctag ttctgtaaaa tgggtgaatt 155460
gagaattacc attaaccctc tgattaacga tctcagtgaa gttcatattc tttgggtact 155520
atataaggta taggtgaatg gaggagatga atttaaatgt acatgtgtgt atttgagtgt 155580
gtgcatgaaa ttttgaattc aagccatcct attcttgacc agttagtggt gaaattgcca 155640
cctattatat gtgcatatgc actttcattt gggacttttg tgtgtcttgg aaagtgccca 155700
aatatctctt gatttctact tatgagaaag aacccacttt tgagttggtg gacagatctt 155760
ttggagacaa gtagagtact ttaattaagg caagcatgta tcagcgaaga ctaagggtc 155820 ttgtcctgga aggcccttat ggtagagcag gccagcatcg gcacgggcag ttcagtggct 155880
aaagtggaac aaatggtttt gtaggctggg ttggggatca gagcctttcc gggttgagcg 155940
gcttctctaa cccattgcct gaaacttcag atgactgggg cttaattagg tgagtcagaa 156000
tgattagggt gatacgatga aggagaagtg agggaggcaa caaatctatt ttaaaatttc 156060
ttttaacaat ggaaagtcca actgcttttg tcttttcct attaagattt tatgggcaga 156120
gcaaagatgg agatgagttt aataattcaa ttcgccagtt atttcttgct ttcaatatgc 156180
tgatggacag gcctctggag gaagccgtca agatcaaggt cagcctggca gcatcatggg 156240
taactcttct taggctgtgg taaggatgtt ctggaccgc ttagaattgg ccatcatgag 156300
ggagaaacaa agtgaatcat ggttcatgca tagcttatga attttagtat gatttacaga 156360
aaataaagga aaaaaaatcc attttaactt ctacagagct tgtatttca agtgtcaact 156420 tgccaaagac aagctaccca attagacatc ccttgaaagg ccattgtgaa ccctgtttga 156480
ccccatgatt tcagcaaact gatcccaatg cactacaggt gacaaatttt tatttttgt 156540 ccctcatttt acccagaagt gcaaagtcac catctttatt atcataattt ttttaaaaaa 156600
tatgaaatat ataatccctg aaggctcaaa tgtgaacttt actattaata tttattttt 156660 gctctttatg gccatgttgc aagagaggct tcaagaattt aaccacctcc ttaggcagag 156720
aaatgaactc caagtggaca gagcctgctg gcagtagaaa ccagaaagct gtacccctg 156780 gcatcttcag gaaaagcatt ttaggagatc gtgtagagca atgccagctt tccttttat 156840 tgtaagggta tctgtgtcca gttccctata taagttccaa gcacagcctt tcttcctgg 156900 gatcaagcag taaatactgt atttgtcttg cctggcaact gaatttgcct ttggtgtttt 156960
tcttacaggg ggcagctttg aagtaccttc ctagcataat taatgatgtc aaacttgtat 157020
ttgatcctgt tgagctcagg taaatagcaa aacaaaattt tgttccttaa ctctaacaga 157080
aacagctccc ctgcttggct ggagcctggg ctgctacacc tggcttttat ttttctaaga 157140
agtattaact gaataccttt ttgtgctcag ttctgtggaa gatgcaaaag aacatccaaa 157200
acctgccctg agagaggttt gcactttctc tgggaaaaca agacatgcag acataaaatc 157260
gattacaaaa gatagtgtat aatgacatgc ttccagccct acccctaagt atcccagcag 157320
tgcaaagtca gactgcaatc aacatgagag tggagttgcc aagaaagcca ttttcataaa 157380
ggcgggtctg gaaagtgatg atggacgtgg gtgttctttg gcaatttaaa tactcagctc 157440
taaggcagag ccctccagta agtgaggata aaatctccct tgctgccatg tcataaactc 157500
tcaggtcatt ttgtagtttt ccaggtaaat ctctccatgc ccaaatctca gagtggagga 157560
gaaaagttta taatgatgcc ttcaatttgg cagaacgaag acactactaa ccctgaggtt 157620
tctctcccag cgtgctcttc tgcaaattca ttcaaagcat tcctgacaac cagctggttc 157680
```

```
ggcagaaact taactgcatg accaagatag tagagagcac tcttttttcga cagtcaggta  157740
agtctccttc aaaacttgct gcatgaggtt gcagtgagct gagattgcac cattgcactc  157800
cagcctgggt gacagaacaa gactccatct caaaaagcta aaacaagctg ctgcatgctg  157860
aaatgacagc cccattttctg cagctaacac ttgggttttg ttgtttgttt gttttttctt  157920
gtttttttt ttttttttt tttttgaga cggagtctca ttctgtcacc caggctggag  157980
tgcagtggcg caatctcggc tcactgcaac ctccggcctcc caggttcaag caattctcct  158040
gcctcagcct cccaagtagc tgggactaca aggacctgcc accaagccca gctaattttt  158100
tttattttt attttttagta aagacggggt ttcaccacgt tagccaggat ggtcttgatc  158160
tcctgacctc gtgatccacc cgcctcggcc tcccaaagtg ttgggattac aggcgtgagc  158220
caccgcgtcc ggcttgtttg tttttttaaga cggaatctca ctccctcacc taggctggag  158280
ttctgtggca ctgtctctgc tccctctaac ctctgcttcc caggttcaag tgattctcct  158340
gcctcagccc cctgagtagc tgggattaca ggtgtacatc accacaccca gctaattttt  158400
ttttttttt gtattttttgg gagagggggg gtttcacaat gttggccagg ctggcctcaa  158460
actcctgacc tcaagtgatc tgcccaactt ggcctcccaa agtactggga ttacaggcat  158520
aattaccgtg cccagtcagc acttgacttt tcttttttaa aaatgtcatt aatattcttg  158580
ccagttgttt gttggcaaca ttaatattgt tgccagttgt atgtaaggac ctcctggag  158640
agcggtttta aggagaatct aaagtcagct cggtatttcc aacagttcct aaaagagcaa  158700
aatcatgtgt tccttaatct ttaattagaa caatctgcaa gtggttcatt aattagaaa  158760
ttttgtcttt aaaacaggaa cctcaggaag taacaagcaa gtaggaaaag atgaccctttt  158820
taaagaaat tattcttctt tagtctatac ttattgcatg accttaaaaa ccaggggaca  158880
gggaaacagc aatgtgttgg atcccacagg agagctggtt acatgcatcc cttctcaacc  158940
ccacgttcag tgatatcaca ttagtagctg gaaattgacc atggtggaag tctttacacc  159000
agggtaactg gcaaacatga taaagcaagc gttttttttgt tttgttttgt tttgagatgg  159060
agtctcactc tttcgcccag gctggaatgc agcagcatga acttggctca ctgcaacctc  159120
cacctcccag gttcaagcaa ttctcctgcc tcagcctccc aagtagctgg gattacaggt  159180
gtgcaccacc atgcccagct aatttttttt gtaatcttag taaagccagg gtttcaccat  159240
gttggccagc ttgtctcaag ctcctgacct caggtgatcc acccaccttg cctcccaga  159300
gtgctgggat tataggcatg agccactgca cctggccaag ctgttttctt taggggtag  159360
gctggcagaa gccagattac tagtattctg ctggagagg agtggggcat ggaggggaaa  159420
aactcttaca ctgataaaat acttttcatt ttgtaagtag agtctagcaa atagccacca  159480
agtgtttctg tcccaaagct gatataaaca ggaggtccag cacctgggcc ttcccaataa  159540
actcaagact tgctagagtg aggcagccac ggagacttct tctggggcta actacctggt  159600
caggggctcc cagagtgtaa cctcatttta tgtatgtata ttgcctggag atctgaagac  159660
cagcaggact cctcaacgtt aaacaagttg agtggattgt tggtgggaga gccttcctgg  159720
ctttgcccct ggctagttat gtaactggac aaatgagtgg ccttctctaa gtctcagcct  159780
ccagttctgt ggaaggaagg acttgagcta gatcgtatca gtagcctcct tgggctctga  159840
tattttctga ccctatgaat ttgcactttg aaattgcaaa tgttcctaag acacaattgg  159900
aggtagaggt aatgcctgca aaaggttagt gaatgctcat aagtagaaaa catttattac  159960
taaagcaaat tattactaaa catttttaata tgctttgatc acttttttaag gatacagaaa  160020
```

```
aggtaattga gatagtaaag ataaggtgtt tgagcagaag agcaagcatg cactggatag 160080
ttctacttag agtgtgatca cggttaacag tcatttctgt agcattcaga gtacctgaac 160140
tcattataaa atgtgttaca atagcaaaga tctcagaaga cataataggt cataccttac 160200
tttctgaaat ccacacgcct gcacagacat gagcagaatg tcattgacat gtactaggga 160260
agctcagtat ttataggaac tttatttata ggaacttctt tcagtaaatt ttctccatta 160320
ggtgaaaaaa ttttgaaaa aaaaaatgta taacttgctt ggttttattt gtttcatatg 160380
accctcaatt tcgtgcatta ggttggcgtt ttgaaaagct agagaaattg ttaaataatt 160440
taaacatttt gctaagttcc caccttcacc tgtgagaagg gtcattttt ttttttttaa 160500 ttcattcatc tgcgcattga acaagggtaa agttccgtgc ctaaaccag gtgttcctgg 160560 gtggcctgga ggggctgcat ccctgcaggg ctgattgcag agcttagagc tactggtact 160620
ggtcgaggaa gagttgcagg aaggagacag gcagttcagg aggtggcact gctgtgtgtg 160680
agctgtctgt gttttccttc tcagagtgca gagaagtgct gctgccactg ctgacagacc 160740
agctcagcgg ccagttagat gacaactcca acaagcctga ccacgaggca agctcgcagc 160800
ttctgagcaa catcctggag gtgctggaca ggaaggatgt ggtgagttga gtcatcactg 160860
atgctgcaca gagttcacac tgtccccttt gcaccagaca ggagtgactc cgtggccttc 160920
ctattctcag gtagtttcca gctccggtat tagggcaggc tgtgcccatt ttagagataa 160980
ttagggaggc cagagcctcc agtgcaaagt cagattactg ctggggcctt ctgcaggctg 161040
attttcctgg cttgcccagt gtgcgcacta ttgagatccc tgtgactttt ttttttgag 161100 agggagtctc gctctgtcgc ccaggctgga gtgcagtggc gcgatctcgg ctcactgcaa 161160
gctccgcctc ccgggttcac gccattctcc tgtcccagcc tcccgagtag ctgggactac 161220
aggcgcccgc caccacgccc ggctaatttt tttgtatttt tagtagagac ggggtttcac 161280
tgtgttagcc aggatagtct cgatctcctg acctcgtgat ccacccatct cggcctccca 161340
aagtggtggg attacaggca tgagccatcg cgcccagccc ctgtgactat tcttaagaat 161400
caaagacctg actgggcatg gtggctcagg cctgtaatcc cagcactttg ggaggccaag 161460
tcaggaggat cacttgagtc caggagttca agactgacca gcctgggcaa cttagtaaga 161520
ctttgtctct ctaaaaaata ataataataa taaaaaataa agaatcaaag gcctttctgt 161580
ttttatgcag acacctcttc cttcttatcc tctgatgcct aacaacctga tatttctgag 161640
ctgctgagaa gttctcattt ccatatcctc ttggacactg atactttctc tggaacctaa 161700
tggaaattat gttttctcat cttgcgtttt ctctgtgacc tggcccccat ccctcttgaa 161760
aacacagggc taaggccggg cgtggtggct cacgcctgta accccagcac tttgggaggc 161820
cgaggtggat ggatcacgag gtcaggagat cgagaccatc ctggctaaca cagtgaaacc 161880
ctgtctctac taaaaatacc aaaattagct gggcgtggtg gcacgcgcct atagtcccag 161940
ctactcggga ggccgaggca ggagaatccc ttgaacctgg gaggcggagg ttgcagtgag 162000
ccaagattgt gccactgcac tccagcctgg gtaatagatt gagactccaa ctccaaaaaa 162060 aaaaaaaga aaacataggg ctgaacctgt ctggattcac catgtcctag aaatagtgca 162120
gcccacaggc ctagcagagc ccccacacag gaagctggag aactttgcag aatgtgttca 162180
ctcgaacagt tgagggctga gaaaaaaaaa gcatcttacc acaaattata gttaccacgt 162240
ctatggtggt tcatggcac aggtgttccc acagaacagg aaaaccactc tttgtcatca 162300
cctaaagtct ttatctttcc agtatcttgg gattctgtcc taccaaagga tatgaatact 162360 acacctttc ccatagctaa accgttagtt cacttgtcag ggtccaccac cgtttgacta 162420
```

```
cagcccacct tttctcctgc tcatggtttg cactgggatg tctacatttc tgtgaatcca  162480
cattgcagcc tcagaagtat gtgagggtac cattgccatc tctagctgct ccgccaatct  162540
ctgtccctcc acttccctaa gccctgtag cccacttact ctttgcactg cttacttgat  162600
atttattcat tatagatcat tccccctttt tttcattaag tatgtttata gaaaccacat  162660
tataaaatgg aatacatttt ctcaaagcat gttgcgattg gagatttggt tcctaaccaa  162720
ggactttgca ccaaatacgt aaatgtgacc aatcacgtca taaactcaat acttttttaa  162780
aagtaactct tataattcaa taattcctta aaataataaa gtaaagctcc acgccctata  162840
aatttggcag caatgtacct ggcacattgg tttagccagg gatcagtgtt ctagaaatca  162900
tatgtttatg atccaaagtt aatgtaaaac acaagaatca gagcattgga ttctagtccc  162960
aatattacca ctctgcagct atttgtcctt agtcaaatat ctcagtgcct cagtctccta  163020
acccagtcca ttgtatgtag gaattgttct agacgacctc tttagtctct tccacttctg  163080
accctattgt ttaatacatc acatctctac caaccttctc accacccaga aagactcttt  163140
ggaaatgact tgaatgtatt taaatcctgt gcaaggagat ttaagttagc ttttattttt  163200
ggtattccca atattatgtt ccctgtaatg agcagagaca ttcaaaatta tcgatcttgg  163260
agctctggta aagtagtaag tccaatcgtt ttttgtccat catgatggta cctttttttc  163320
ttcataaaca ttttgaaata tgtgcactag ttcaatatct cttctcttat cctctcatct  163380
ccttagttaa ctcaaagctc taattactga tatttgttct tcctgccttt tgttttattt  163440
ttttaaacat tgcaggattc cctcctctcc ccacagctct gttttggaat tgtcctggtt  163500
ctttcaagtc cagctgcagt aagcacctct gtgaagttgt ctctggtgtg gtcctgccaa  163560
attctactca ttcttttcat gctcccttg agtttctttt gaggatttta tcactttgta  163620
cattgagtta ggaatgcagc tcacaaatcc ttgggaagct gctcttatgc tccaggcact  163680
gggatcagct agggctatga cagtgaacta gagaagcaag cacccctaccc ccaggagccc  163740 accttctagg gagattcttg tgttatgctt atttaaatgt atgtcccagc tgggtgcagt  163800
ggctcaggcc tgtaatccca gcactttggg aggctgagac aggtagatca cgagatcagg  163860
agttcgagac cagcctgacc aacatgataa aaccccatct ctactaaaaa tacaaaaatt  163920
agctgggcgt ggtggtgcgc acctgtaacc ccagctactc tggaggctga ggcgggagaa  163980
tcacttgaac ccgggaggca gaggttgcag tgagccaaga tcacaccact gcactccagc  164040
ttgggcaaca gagcgagact ctgtctcaaa aaaaaaaaa aaatttatg taccactcac  164100 ccgcaccccc acaatagaaa tctctaaagg ctcagaggag ccttattcat ttcatacctt  164160
ccccacaagg cacagcgtgt aacttgcaca actatttagg gccacactaa ggaaatgtta  164220
tgtaaatgga agtgaaagca gcatctcctg gagaggctga ttttatgaat cactttcatt  164280
cagggaaatg ggaaacaagt aaatgactaa taaaagtga aggaggaaga gaagaaggga  164340
cagagggaag cagagaggga gggtggaccc caggtacttg atactgtaat taaaatacat  164400
atagccatac cataattgag aagtcaaaaa acaatagatg tgggcataga cgtggtgaaa  164460
ggggaacatt gttacactgc tgggggaatg caaattatta gtacgacgac tatgaaaaac  164520
agtatgaaaa actatgaaaa acagactatg aaaacaggg aatgcaaatt attagtatga  164580
caactatgaa acatgtttaa agaactaaaa gtagaagtac cattcaatcc agcaattcca  164640
ctcctgggca tctacccaaa ggaaaataag tcattatatg aaaagataca atgcacgtgc  164700
atgtttatag cagcacaatt tgcaatagca aagatatgaa acccatctaa gtgtccattg  164760
```

```
accaatgagt ggataaagtg tggtatatat gcatcatgga atattactca ctcataaaaa 164820
ggaacaaaat aatgtctttt gcaataactt aggtggagat ggaggccatt attctaagtg 164880
aagtaactca agaatggaaa atcaaatatt atatgttctc acttataagt gggagctaag 164940
ctatgagaat gcaaaggctt aagagtgata ttatggactt tgtggacttt ccggggaaag 165000
gctaagaggt gggtgagcga taaaagacta cgcattgggt acagtgtaca ctgcttgggt 165060
gatgggtaaa caaaaatctc agaatcacca ataaagaact catccatgta accagaaacc 165120
actcgtaccc ccaaaactat tgaaatcaaa aagaaaattc ctacagccat agacaaatcc 165180
tacctgatct gacttctatg tggaatctaa aaaagttaga ctcctagaag cagagagtag 165240
aacattcttt accaggggca ggatggggag atgttgatca aagggtagaa agtgtcggtt 165300
ataggatgag caagttctgg gaatctaatg tatggcatgg gtggcaatag atgtgttaat 165360
ttgaccgtgg aaatcattac acgattacgt ggatcaaatc ttcatgttgt acacgctgga 165420
taagtacagt ctttgccagt taaatttgta aagataata aaaatgttaa gcaaaaaaat 165480
acaaatagca atgatttagt tatttgaagc attaagcagg agtttcaaag tatctatcat 165540
aaagcaagga cagatagagg ctatgaaaag tcaagttgca tgtgggtaag tcggagccaa 165600
atgagggtaa tatctagcta caaaaaagga aagaaggtga aagaaagaat gtgtacatca 165660
gccctactaa ttccaataag aaaactgtta ctgtcccct tttgcagcta tgaaaactgc 165720
aagctcagcg aagttgaata attgctcaaa gtcacacatg acacagtcag aatacaaaat 165780
ccttgtatta gtctgctcag tcagtcttct ataacaaaat accacagact gcgtggctta 165840
aacaacagac atttattttc tcacagttct ggagactgag tttctgagat cagggtgcca 165900
gcgtggttaa gttttggtta ggtctctctt cccagcttgc agacagctac cttcttgctg 165960
tgtgctcacc tggtgagagag agagatccac atctgtgata ctcatttact aagagcattt 166020
atcccgtcag tccagggccc caccctcatg acctcatcta accttcatta catctcaaga 166080
gctgcatctc ctaataccat cacgatgggg gttagggctt cacatatgaa tctggaggag 166140
acacaaacat ttactccata acaattccct tgacttgaat ttcttgtttt tttccctcca 166200
acacagaagg tggtaagagc tttgtatttt tgcctttaat ttcccacaca tgtgcctaat 166260
tgacctgagc aattcttta tttttatttt tattttatt tttttgagat ggagtctggc 166320
tctgtcaccc aggctggagt gcagtggcgt gatctcagct cactgcaagc tccacctcct 166380
gggttcccgc cattctcctg cctcagcctc ccgattagct gggactacag atgcccgcca 166440
ccacgcccgg ctaatgtttt gtatttttta gtagagacgg ggtttcactg tattagccag 166500
gatggtctcg aactcctgac cttgtaatcc gcccgcctca gcctcccaaa gtgctgggat 166560
tacaggcgtg agccaccgca cctggcctga cctgagcgat tctaatctgc tcaacctcag 166620
aacagaatac gtcatgctaa tgggggtccc ccaaaactat ttgttgagtc agtggccaca 166680
gtgagctctc agtgaacctg agcaatctga gttattaaga aggcactcat ccctgcacag 166740
ccacattcat cttttaagtg ttatgactga tcattttcaa ctatttcctt cataaagtta 166800
tatattattc tgtgagacca ttttccactt ttggacaaga gattgctttg tagggaaaag 166860
ccaaaaagag atctaaagac aaaactcatc tatctgaggt tccttaaaga aagtgaaact 166920
gagtcagaag gaatggagtc aaatcctgtg ttccctgcag ggtgccactg cggtgcacat 166980
tcagcttata atggaacggc tgctgagaag gatcaaccgg acagtgattg ggatgaaccg 167040
gcagtctccc cacatcgtga gtatctcttt gttggatccc acggccgctg ctgtttctct 167100
gtccccttg cctatcggga ggccttcggg gccagtggct tgagactatt cttcacatgg 167160
```

```
gcctctcaca tcatgggtca ttggttataa ccttagcaga tcttgattct gacatggatt   167220
ttctgttgag agaaaataat ccagcctagg caatatagtg agccccatc cctacaaaaa    167280 atttaaaaaa ttagctgggt gtggtggtgg cacgtgcctg tggttgcagc tactcaggag   167340
gctaaggtgg gaggatcact taaacgtgag atgtcgaggc tgcagtgagc tgtgattgca   167400
ccattgcatc ctagcctgga caacagagca atagcctgcc tttgaaaaag aaaaaaaaaa   167460
aaaaagcagc aagcagggag ggaagggagg gagggaggga gggaggaagg aaggaaggaa   167520 aaaggagag aaagaagaa aagagaaaag aaagaaaatg atccagtatg aaccacccag     167580 ccccttttgat tcaaggaaga aaccaaacat tttaaagaac ctgtggttag catgcttgtg  167640
gaaaggccat tgttggtctg gcctcttatt ttctgtgcac tctatctaaa cagatgccgg   167700
gtaacaacta tgatagaggc cataggtagc tgttgaaagg ctaagtggtg tcatcattaa   167760
agtgaagcat cttttacttc ctatattaaa agcttcctat attaaaatcg aattagattt   167820
taattagagg acataggaaa agaactattt caaattccta tcagataaga aaattcatt    167880 tatttcacaa atacgtattt aaaaactgcc ataaaacagg cactgctctg gacactgaag   167940
aggtacccat aaacaaaaca gaaaaatcac tgcctttgag gagctgacat tccaacaata  168000
atgacagcag ttacagcaaa ataaactaca tagtgttagg aggcaacagg ggctagagag  168060
aaaaaaaatg agcaggataa gggaagtgag ggtggggagt cacacccttta aataagatga  168120 ttaggaattt taccagagag ggtaaaattt gggtaaaaac ttgaggaagg taagggagtg  168180
agccatgtgg ctatctggga agggtcttcc agggagaggc cacagccata gcagaaaccc  168240
taagacatgc ctggtcagaa cctgtagggt gatggagctg atcctaataa gaataaagag  168300
aaacgattgc aagtaaaaact gtcttttctgc tggattaaaa cccaatctct gagccgagga  168360
gttcgagact ggcctgggca acacagcaag accccatctc tacaaaaatt ttttaaaaaa  168420
ttagccaggt gcagtgatta gtgcctgtac gcccagctac tctggaggct gaggcaggag  168480
gatcgcttga acccaggaga tcaaggctgc aatgagctat gatctcgcca ttgcacttca  168540
gcctgggtga ctgagtaaga ccctgtttca aaatataaaa taaaacaaaa taaaataaaa   168600
atccaagctc atccaaaaca tattataaaa ggatttagat cttgtattag tggattatca   168660
gttaactaga ctagtcctac atcttttct caaggaagta tctgagggaa caaagactaa    168720
tatgaaaatt ggagaattcc tcatgtaaaa tcaaggcttt tatctttaga acagtcgat    168780 tgttggcaag gaaatactat ttttttttt accaacagaa agagggaata aaacctaaaa    168840
tctatcaatt acttttt att tctaggccct gataatattg ctgttaatca cttgtgcaaa   168900
aataaaatct atagcttaac tgatctgtct tttccaccca ttgactattg aagggtaaga   168960
atgacttagg aagctgggtg cggtggctca tgcctgtaat atcagcactt tggaaggctg   169020
aggcgggcag atcacctgag gtcaggagtt cgagaccagc ctggccaaca tggtgaaact   169080
ctgtctctac taaatataca aaagttagcc aggtgtggtg acacatctgt aaccccagct   169140
actccggagg ctgaggtagg agaattgttt aaacccaaga ggtggaggtt gaggttgcaa   169200
tgagccaagg tcacgccact gcactccacc ctgggtgaca gagtgagact ttgtcttaaa   169260
aaaaaaaaaa aaaaaaaaca aacaaaaaaa aaaacgtagg agagaaaact agtcaaatca   169320
cttatatgtt ttatatgttt aaagttggg catgttttaa cagcattgct tcactaatcc    169380 cttttataatt tactgaaatt actaacagat ggagtgcaat ttagcagatc aagatggaaa  169440
aaaacaggat tgaagaacat tgcgttatgc taaaactgat atacttttag agtatttttac  169500
```

```
atattttgtg aaatttaaga aaagacaatg taccattaat tgctattgcc aagccatttc   169560
tatcatacat tataaagaaa gattgatatg ggaaatgata tattggctat agataaattac  169620 atacttgaat tcaaatttcc tgagctcctt ttaggaatca aattgcatgt tgtctccctt   169680
gtttaaactc actcaaggac atcagctcca tatgtttgaa gggaagggca ggactggatg   169740
taaaggcagc agtactcccg ccgtgcttcc gctaacatga aatgagagtg ggaatgactt   169800
agatccacgg agtgatggcg gtgccaaaag aagcaaagtg aagtgggaat gataagcata   169860
agaaggaaaa aaagtgaggg gaaaatgtac agacagacac agacagtcgc gaagagagat   169920
gtggaaaaag aaaatctaca tggcttgata cagtttattc cagatattca agaatggtta   169980
aatattagga aatacattta taaaataaca tcaattcaat aaaaggaaaa aagccttata   170040
attttcttca tagatgccaa aatggtatct gattattgtt acattttttc ccaaatcaag   170100
aagaggaggg aactttttag cgtgaaatca ccaggcatca tgatactcaa tggtcgttaa   170160
aaaagggaat caagatattt aggccaagca caatggctca cacctgtaat cccagcactt   170220
tgggaggctg aggcaggagt attgcttaaa gccaggagtt tgagactagt gtgggcaaca   170280
tagcaagacc ctgtctctac aaaaaaatta aaagttagcc aggcatggca gcatgtgcct   170340
gtagccccag ctgcttagga ggatgaggca ggaggcttgc ttgaactcag gaaattgagg   170400
ctgcagtgag ctgtgaaggt gccactgtgc ttcagcctgg gtgacagaat gagaacctgt   170460
ctctatttag aaaaaaaaag gtatttaatt tcaacactgt tgtttagctt tttctataat   170520
ttctagccaa tgtaataaga aaagatact aaacataaat attgtaaaag taaaaataat   170580
tgtcattatt tttagctgaa atgaccagca tatctacaaa acccaagagg gtttactcaa   170640
attttagtaa aactaataaa caatttatta aactaacctg tttatttatt ttgttttgag   170700
acagggtgtc actctgtcag ccaggctgga gtgcaggggt gctatctcgg ctcactgcga   170760
cctccacctc ccaggttcaa gtgattgtcc tacctcagcc tcccaaatag ctggggttac   170820
aagtgtgtgc cctgacaccc agctaatttt tgtattttta gcagagacga ggttttgcca   170880
tgttggccgg gctagtcttg atctcctgac ctcaaatgat ccacccgcct tagcatccta   170940
aagtgctggg attacaggca tgagccactg cacccagcct ctaacctgtt ttaaaataaa   171000
tgatatttaa tgcctgttct ttaacaatgg aagctattta gagattataa ataagaaatt   171060
ctatttaatt tagtcacaaa aatatcagag taaaaataaa tactagttac aaataaatag   171120
ccaaatagaa ataataatgg ggcctggcat ggtggctcac gcctgtaatc cctgcacttt   171180
gggaggctga ggcgggcaga tcatgaggtc aggagatcga gaccatcctg gccaatatgg   171240
tgaaaccccg tctctattaa aatacaaaaa aaaaaaaaaa atagccagtt gtggtgatgc   171300
atggctgtag tcccagctat tgggaggctg aggcagggggg aatcacttga accccggagg   171360
cagagctttc agtgagctga gatcgcgcca ctgcactcca gcctggtgac agagcgagac   171420
tccgtctcga aaaaacaaa aaatacataa taatggagag cttgcctgtc agacttagtg   171480
gacacatatc agcagaacag aaccatgata agtgaaaagg agactttgga ttatatgaac   171540
atttcattac ctttctaaag ggaaaatgaa ggttttttagt aaatgttatt tagaaaatta   171600
gttaacaatt tggggctggg tgcggtggct catgcctgtg atcctagcac ttcgggaggc   171660
tgaacctagc agattgcttg atcccaggag ttggagacca gcctgagaaa catggcaaga   171720
ccctgtctta aaaaaaatac acaaaaatta gccaggcatg gtgacatgcg cctgtaatcc   171780
cagctactca ggaggctaag atgtgaggat cgcttgagcc ccaggaagt cgaggctaca   171840 gtcagccatg atcgccactg cactgtagcc tgagtgacag aacgagaccc tgtctcaaag   171900
```

```
aaagaaaaag aaaattagtt aacaatttgg aaaaaatttg ttcaacttca tgctataccc   171960
acaaaataaa tgtcagagtg aagtgttcaa ttaaaaaaag ttgtatcata aagcactaga   172020
ataaaataat aaatagataa ctgatttgag gaggaatagg attcatggat tttttatagt   172080
taaaatacaa gaaaacaatt ttactagata aaattttaaa tccctctata tgaagattat   172140
atatatatat atatatatat atatatatat atatgcaa attaaatgtc aagtcccaag    172200
ctttaaaaat tttgtaatat aggtgacagg tggctaataa acttaatata caaaagctat   172260
tataagccac taagcaaaga tattgtttta gtagaaaaat gagtaaagaa tgggtgcaaa   172320
cagcaacatg agaaagctaa atggccaaaa agttcatgga cagactgttt aatttagaga   172380
aaaggaaatg aaagtgcaaa gtgagattaa acctctgagt attaaacctc agtgttaaat   172440
tctgagtatt aaacctctaa tactcagaat aggcaaggtc ttggagaaac aaattgtgtt   172500
agacaccgtt gggaaaacaa gctatatgat aatttggcaa tatatatata tcaaaggcct   172560
tagtacaata agtttatact gctttataat tgaaaaaata aacttttttt ttttttttt    172620 tttttttgaga caggctctgg ctctgtcacc caggctggag tgcagtggca gaatctcggc   172680
tcactgcgtc tctgcctccc aggttcaagc aattttcctg cctcagcctc ccgagtagct   172740
gggattatag gtgcccacca ccatgcctgg ctaattttg tattttaat agagatgggg    172800 tttcaccatg ttggccagac tggtctcaaa ctcctgacct caagtgatcc gcccaccttg   172860
gcctcccaaa gtgctgggat tacaggtgtg aaccacccca ccaggcctaa aaaataaact   172920
ttttaaaaca aaagagacag tctaaggcat acgttcagaa agagatagac atggacagtc   172980
tttcattgtt ctgcttgggg aatctttccc tctgttttag aaacagctgt atgttcatct   173040
gtcctgtgct aaattccttt gtgttatttt catagctgca tgaatacagg aggttagcac   173100
ccctggatct ttactccctg tctaaaaaac taagtctata attcacattt ttttggtcta   173160
ggggatagca ccttgaatat gtaattcctg aactcacaaa tggaagcagt gttaatgaat   173220
catctagtta ttgatttttt ctcttcaagt cagggtcaca attcacgtgg gtagtatgtt   173280
ggaacaactg gctgaagggc tctggagttg gagaagcggt atcaggttgt attagtccgt   173340
tctcatgctg ctaataaaga catacctgag actgggtagt ttataaattg ggtagtttat   173400
agaggaaaga ggtttaattg actcacagtt cagcatggct ggggaggcct caggaaacct   173460
acaatcatgg cagaagagga agcaaacgtc cttcatcaca tggcggcagc aagaagtgcc   173520
aagcaaaaag gaggaaaacc ccttgtaaaa ccatcagatc tcgtgagaac tcactcacta   173580
tcacgagact agcatgagtg taaccgttcc catgattaaa ttacctccca ctgggcccct   173640
cccacaacac atggggataa tgggaactac aattcaagat gagatttggg tggggacaca   173700
gccaaagcat atcacaggta ttctagcagg gagttttcat catcatcgct tgccctcctc   173760
tccttcatgc tcagtgttgc cacctctttt cctgctagcc ttcctccccg ttaagatttg   173820
tttaactaat ctaagtattt cagacatttc tccatggaat tctatactac agctctgtct   173880
caacaagaaa cccaaagccc cacaagttgt tacatcttca ctggtaatct cattgaggtg   173940
tcctgtctat aggattccac acttcttagc tgttaatgag atttcttcac tcagacctgg   174000
aaggaggtgg tttgaagcag aaaccgcaaa gcacgtggcc tttggacctt tagaatgcag   174060
cgtgtttcca gtgtggtggg atacctgcgt ggctcagtgg gtgggaaaag ccaagttcat   174120
ggggctcaca tagtgttttt gtcagttggt ggtctaagga gtcttggatt tgtgctttcc   174180
ttttccttcc aggggagttt tgtggcttgc atgattgccc tgctgcagca aatggacgac   174240
```

```
agccactata gccactacat cagcactttc aaaaccagac aagacatcat cgtaagttgc    174300
ctttactggt cctggtaacc tgaagacttc ttaaatttgg tttaaaaaaa tgactgaagc    174360
tgagcatcgt gagtccaggg ttctcttccc acgcacctcc ggtgctatgt ggctgtccac    174420
agtgattaca gaaaggagag agctgattcc tactttctct ctttgatagg atttgaaaaa    174480
gagtacaaca catataccaa gaggttatca cacactttaa tctctcttgg atttagagag    174540
agcccttatt tagcaacatt tgggagatgt ttttttgctct gaaaacagga cttaatactt    174600
ggtacagtaa ctactcatgg caaggatttt agaaggcagg ggtgtgcaaa gtctcctaag    174660
acgtggttga taccatcatt ttggagaggg caacaaaaag aggtaatccc tgcccttttac   174720
aactggtccg tgtggcctgt taggaacctg gccgcacagc aggacatgag cagcaggcca    174780
gcaagcatta actcctgagc tccgcctcct gtcagatcag cagaggcatt agattctcat    174840
aggagctgaa tcctattgtg aactgcacat tcgaggaatc taggttgcca gctccttatg    174900
tgaatctcac taatgcctga tgatctgagg tggaacagtt tcatcccaaa accattcctg    174960
cccccatccg tggaaaaatt gtcttttcctg aaacctgtcc ctggtgccaa aaaggttggg   175020
gactcctgct ttacaatatt tgtaagttat cttcagatga aaatattttg ttctctattg    175080
ttttaagcag gaaaattgtt ctcatagttg ctgtgaagca ctcatctaag aagctgagtt    175140
aggcctccgg ctgtggcttc acggcacctt cccttcaggg gattattagt ggcccttcag    175200
acgtccatga aggtgttatt agactttgca gagcagtgga caggatgtgc cgctggatta    175260
gcacactgtt gtcatgttga cactagtctt tggataactt cccatcatct gtgcgtactc    175320
cagtctcttt gttctagatt ttccactttc tgcctctgtc atgctgagta gatggccagt    175380
gccccccatgg attcgcagct ccttccttgc ccattaccca cctttctgcc atgcccacat    175440
ggtggacaaa catacaagga attggaagga aagtgctgtt tgttattatt agttggttcc    175500
atggtggact ctcaatgccg tgttagacta cgtggcttta gctgaaggtc tccatgagcc    175560
tctgcttggg ccatacccctg gcaggcagca tggcatggga accatagcaa tatgtagatg   175620
tgcctgtgga gaccaggcgc aagaggccca gtatgggggg tggggggtgg aggaggaagc    175680
ccaaggttag ccatgtgttc tctacaggca ggtggtgtag cgggtaagag cacaggcctt    175740
agaacacgca gctctgggtt tgaattctga ccattccact cccttgtatg caatttgggg    175800
caagcggttt aacctcactg aacttcagtc tcctcatctg taagatagta cccacccttga   175860
gggttaatta agtgttgctt ggctccatgc atgggaaatg cccagcttcg tgcaggtagg    175920
catgtagcta atgcctatga ggactagctg tttgtaacaa taattgtatt attattgcta    175980
tataaagtaa aattaacaat aaaaattcta gggattttgt ttcaaatttc cttcagagag    176040
caggcaaaat agggaggttt taaggtcaaa ccgtgacaat ttggctccat tgttaagtaa    176100
gaaaaaaagg ggcgtacctc ctgtttgcca gcatggtgtt gagctcctcc agctgtatta    176160
tgtaattaaa agaggatcat tatcctcacg agggaactaa gacctggaga atgagggaa    176220
cttgcctgaa tttagtcccc ggtggctgag ctaccgtgca cagctaggcc tttgcctccc    176280
agtggccttt cagtccctca tgctgccttc tgagtgaacc gcatgaaggc ccttgggaag    176340
tggtggataa aaccaggctt tgggattccc tgtgagttcc atcatgccgt tcattaatt    176400
tagatttcca ggagttaaat agagagtctg tatctgaagc aaataacaag tatctaaatt    176460
caatccttgc ttcacaaacc atgaattctt atggatttag aagaaaagtt aacagaatgg    176520
ccaataaatt ggtggaagca cttaaaatat ataatgaggc cggatgtggt gactcatgcc    176580
tgtaatctca gcactttggg aggctgaggc aggtggatca ctggaagtca ggagttcgag    176640
```

```
accagcctag cccacgtgat gaaacccat ctctactaaa aatacaaaaa ataattaccc   176700
aggggtgatg gcagacaccc gtaatcccag ctcctggggt ggctgaggca gcagaatcgc   176760
ttgaacccgt gaggtggagg ttgcagtaag tcgagattgt gccgctgcac tccagcctgg   176820
gcgacaaagc aagactccat ctcgaaataa ataaataaat aagtaaataa aatatatgat   176880
gaaacgaatt tgaattcatt aattatgtct aggatttcag aactgagggt gggtatgtct   176940
aactcgccat aaaaccaggg gagaatccac agttgcacac acacactggc cggccaggga   177000
gagtcattcc ccatgccgtt cagcatccaa agtataggaa gttacccagc ttgaccagca   177060
tctcagaaaa atatggttag caataggacc tgggcctcct gtctctcaca tactgtgtcc   177120
aggcagaact gtgtaggtta gtgccagaga aactggacag gactttcaag aatcccagtg   177180
gaaaaggtct aaatttagct aactaataaa aatgccttca aaacatttta gctttgattt   177240
caactctgat tgttctattt ctgaattagt ttttgctcac agccccttt ggagcagaag   177300 agctctgtat gcttaagtga ttagttatta gtcatcacca gccactgtta cgatccattt   177360
tgaaggaccg tttaggacct ttcttccagg ctgcacatga taacgtccct ggcgcaggaa   177420
gagtggtgat tctgcttctt gtgtgtatca ctgtgtcctt ttctaaccat aataaaggag   177480
aattgaactg aaatctatta aaagtatcca tttccccaca attgttggtg aattatgttt   177540
aagtgcatga gatacattct gacaacctgt ggcagcagag gaagaaagag ataagggttg   177600
caaacttggg gtccaaagct ccaagttctc atccagctct tctccttccc actttctttt   177660
tttccttttt tcttttcttt tcttttcttt tcttttttt ttttttttt ttttgagata   177720 gagtctcact ctgctgccca ggctggagtg caatggcaca atcttggctc actgcaacct   177780
ctgcctcctg ggttcaagcg attccctgc ctcagcctcc cgagtagctg ggactacagg   177840
catacaccac catgcccggc aaattttgt atttttagta gagatgggat ttcactatgt   177900
tggccaagct gccccacctcg gcctcccaaa gtgctgagat tacaggtgta agccactaca   177960
cccaaccctc cttcctactt tctatgccct taagtgagtc ctttagtttt tctcagcctc   178020
agttgtacca tttgtaaaat gtggatgatt ctttttgtcc tcatcttcct tatagggtcc   178080
tacaatataa aaatcaaatt gcatcacagc cagctgtaag aatgctttgt tattcctaaa   178140
acccttgaaa gatgggctgt tactgtgggg ctaggaacat cctgttctga ggttgtggtt   178200
ctgcttgtat acacgccaga ataaagacta tgaacgtaac ccagttttcc cccaaccact   178260
cctctgttct ccgcaggact tcctcatgga aacttttatc atgttcaagg acctgattgg   178320
aaagaatgtc tatgccaaag attggatggt gatgaatatg actcaaaaca ggtgagacag   178380
cccatggctg gccctgaggc atttgtctga atacctaagg ctgctgtgtg aactttggga   178440
aatgtcttta aatccctttg cctcaaaccc atcatctgta aagtgaggat cttcctgctc   178500
cagaggtcct aatttatgtg ctcgtgatct tgattttccc agggtaattg cctttgctcc   178560
acctcgggct ctctactccc ttctctagcg tcgtctcttc agtgctctca tggtaattgt   178620
catcctcaac tctccactgc acctttccgt ggctccacgt ggcctgtgtc atcctgatat   178680
tcagggctca ccagttagtg tctgttctat gaccggtcca tgatgtattt aaccagattc   178740
ttcttatgaa catttagatt cttttccattt tctattaatg tgaaatagca ctgtcatggc   178800
cttccttgct ttacatattt aaaaatatcc atggttattt tatcaggata tactcctaaa   178860
ataatttagt agttcaaaag tttggtgaaa ttatagggct tttgatacac agtgccaaac   178920
taactagttg cttctgctac ttccctgtgt atgctacctg tactccaacc aaactggcct   178980
```

```
ctgcccagtc cctgaacaca tggtctgctc tgcctcacac cggtcttccg ctagcagtgc 179040
cttccccata acctctggct gtcagcattc cagctattcc ataaggttct tctgaagcgt 179100
cacctccaga ggaagccttt ctgacctgga tgtcatctct tcttccttcg attttccata 179160
ccccattcaa accttcttat agaattgttt tcagattcta tgttgggtaa tagatgtaca 179220
tgttgttaat ttccccaacc aagctgtaaa tttcttaaga tcagaaactg tgtctttcaa 179280
cacagacgtg agcctgtgcc ttgcaattgc tagcccacaa caaatacttg ttaacagaa 179340
gtgaaatgaa ctgaatatat attatattaa aagagtgtta gagtttaatg agataaataa 179400
accattattg taagcattat tattaactct acatgatacc caattctgag taattctact 179460
ctaacacctg attagaagaa gccttctctg ctatgtacag attagattta aaaaattaca 179520
ccagaaaccc taagcttaaa cagaaggatc ataatagagt ctatatatat taccctcctc 179580
tgaggcttaa gagtcctggt ttgcagtctc agatctacct tcaattacct aaattgggat 179640
gtggccctga gtggctcttc ttgtttgttc tgtaaactga cctcctgtgc cccatctgcg 179700
gatggtgtta tgctgttgtc tgcaaggaca ctgttagatt atgaggtctt atgatgccaa 179760
gttcaggttt ggtttggttt agttcttaat ataggtggga aaaggtttca aaggacatac 179820
agttggcttc tttatctggt gttttccttc cgcagggttt ttctccgtgc tataaatcag 179880
tttgctgaag ttctcacaag attcttcatg gatcaggcaa gctttgaact tcaggtaggc 179940
atgtgactca cctacctgct tctagaattc ttggccatgg caagagaact atatgaattt 180000
ggaaaatgtc tcctcagatt tcactgtttt cacatgaaaa aggttttcct gtgtttttc 180060
atttcctaaa gcacatatgc ctgtcacact gtcctccaaa cacaacaaaa tagggctggt 180120
ttcttctttc tataaaggta acatatgtaa aaaaaaaatc ttaagagta atagtagaag 180180
atcaaaaata taaatagtcc tccttgtcgc tataaacatt tggagttgac cctttgtata 180240
tttacacaaa tgcacataga cacacatggc tacaaataag cacacaggta actctcctac 180300
cgacaaatga gtttggttct aaagaacagt tcttatgcac agtttgttga agtccaaag 180360
gaattgcaaa acggatgacc gctagctcta ttttcattca ttcattcatt tacttatcca 180420
ttcatccatt taacaaatgt tagagtactt acatgtacag ggccctgttt tgcgccctgg 180480
taggggcatt tccctggtga aggcagataa gttccttgct gtcatggagc ttaccttcca 180540
gagtactctg cattttgtgg gtgatgtgct ttctgtgttc tttgtctttg cgtgtatctg 180600
tggaactgtt atcagtggag gtccttgact acagattgtc caagttcttg acgttttgaa 180660
caaaatgcac aaacaaagca atgaaagaat gaagcaataa aagccagatt tattgaaatg 180720
aaagtatact ccacagagtg ggagcaggct caagcaagta gctcaagagc actggttaca 180780
gaattttctg gcgtttaaat accctgtaga agttttccca ttggttactt ggttacaccc 180840
tatgtaaatg aaggagtagc atgtgaccag tctgaccctc ccaccaattg tgggagggga 180900
ctaatcagag gtactttcaa ttttttcatct gccacagagt gcaaaggggt agcctctgat 180960
ccttttgtta cttgggtgtg gagaggtggg gttttccttt tgattcagtt ctaggaagtc 181020
agtgtgaatt ggccttcagt gccctgcctc caggccctgt tttcctgcct cagaacttta 181080
aaagttgaaa atcataagta gaggaaagta tacacacata cacacacaga gatgcatgca 181140
catatagatg aatatatatt gtatgtatgt gtatgtatat ttgccaaaat ggaattgagc 181200
tgtgcagttc tttggtactc tgttaatctg ttttcctttt tcaatgatct gtgatctttt 181260
caataatgtt gaatattttc ctgtttttaa tggctgaata tcatctgttc tatgactggt 181320
ccatgatgta tttaaccaaa ttcttcttac gaacatttag attgtttcca ttttctatta 181380
```

```
tattaaataa cactgtgatg gacttccttc ctttaaatat ttaaaaatat tcgtgcttgg   181440
ctgggcacgg tggctcacgc ctatagtctc agcactttgg gaggccaagg cgggcagatc   181500
acctgaggtc aggagtttaa gaccagcctg gccaacatgg cgaaactcca tctctactaa   181560
aaatgcaaaa actagctagg cctggtagtg ggtgcctgta atcccagata ctcgtcagga   181620
taaggcagga cgcttgaacc tgggaggcgg aggttgcagt gagccgagat tgtaccactg   181680
tactccagcc tgggcaacag agtgagactc tggatcaaac aacaacaaca aaattcatgg   181740
ttatttcatc aggataaagt cctaaaagtg tttactaatt caaaagtttg gcaaacttt   181800 aggacttttg aaacatagtg ccaaagtaca tactataaat agatacactt cttggcagca   181860
gttttccttt atcccaggag taagaaaaa tataatagct taaattttt taaaaagctt   181920 aacattaagt ctcaaaactt ttaggattga ataatcaaaa cctaagaaga atgtagattg   181980
tattttgttc tttcattaat ctcttgttaa tgactttta ccatgtgaca ttgttttatt   182040
atggccctta ttaatgttat ttttcatttc cctttaccca cacaattaat tttgaacagc   182100
tctggaacaa ttacttccat ttggcagttg catttctcac ccatgagtcc cttcagcttg   182160
aaaccttctc acaagccaag cgcaacaaaa ttgttaaaaa gtaagtgtcc ttttaaagtt   182220
aagatcggga aggggcttct tccatttgtt tacattgaga gcaatatttt aggtatcaca   182280
gaaattacta tttagtggct acccatgttg ttagtgaggt aagtcttcaa ctaattactt   182340
aataggcctc acattcaccc aggttcagct ctcttttctt aaggcccaac catcttccca   182400
tcagtcatcc catgctttt atcaaatctg tacctggaga cggaccttgg ctgtcagctt   182460
gcccatcccc aagaacagct gcgcctctgc tggcagcttc cccaaattgc aggcatagta   182520
cctcctcatt catagcgctt cacaaagcac actccttcag cacagttgct ccacctccct   182580
gccatttcag cagagaaagc caggtctcag acattgcatt aaaatgccct ccagattcct   182640
ggtttggaat tcaaaatgga attatgtgca gaagtgataa gagatttagg gaagcatttc   182700
atttcattga gagactggaa tccaaagacc atgtcgttaa aaataacttt gaggaatgta   182760
ttatttgaag actttgaaat tttagttgtg ttccccttgt tgggatatct gcgatatgta   182820
ggaaaattat ttagtgtccc tctacttctg gttcctccct caaaaactgc ctacatatac   182880
aaaaacagca agtattttt tgctcccaag gaccaatatt tatccctttg tggacagtat   182940
cactcccatt gagagtgcat ggtgtagagc cttccaatgt gaatattttg aaaaacacgc   183000
tagaatggat gtatattacc ccaatatcag tctataaagt atataagtat ttagtcacct   183060
gttaggcatt agtcacagta ctgtatgatc atacttcatt caccttcctt ttcatcagtg   183120
tttgccgtgt tttgtttggc tttgtctgtg cctcactctt ctccctgaag tgagtttgtt   183180
aatctcatct tctcagctat ttttcagcgt ttccatttgg ctttattgcg gcacaaggtc   183240
ccccggcctc tgtgcgcctc attccttttg ggggctcgtt taggtatgaa cctcatctct   183300
taaggttggg ccttaagagt gaccaagaga gacacagact gtttttactt tccttcttat   183360
tgtgtttatg caattcattt ctactgaaaa tcctccttct agtttatgat cttcttccta   183420
gatatgggga catgagaaag gaaatcggct ttagaatccg ggacatgtgg tataacctgg   183480
gtgagtgtct agccttgaac aggcctgatc acaacctctg agtgataagc atcccacgat   183540
aaagtctttt ttttattttta atccagataa ccctgagatg tatttgtctg tgtgtctgga   183600
agtgaaagtt gatttgtggg tttcattgac aatgaactgt ctcttactct ggcatccaca   183660
tgctatcaga atctgagtca ctcacttctg aattgagttg ttttaacctt ttctttctt   183720
```

```
atggaacttg tggaggaaga ttttaacact ttactttcag tgaaataatt ttttaatatc   183780
ttcattcact ttcatttcag gtccccacaa aatcaaattc atcccatcca tggtgggtcc   183840
cattctggag gtcactctga cccctgaagt agagctccgg aaagccacaa tccccatttt   183900
ctttgatatg atgcagtgtg agttcaattt cagtggaaat ggcaatttcc atatggtaag   183960
aagtggcaga ccgcgtaata ttagtaaatg gacatatagt caaatcataa ctcatttctt   184020
tctatataga gaagcagtaa ccttaataat gcaagtccat gttgatctga aagttcactt   184080
tacatttcat tttataaagc aattagagat agagtcagac agtgcaaccc agagcctgga   184140
aaagattttt ttgctacatg tcttttcctaa ggcaacacct gtctgtagaa aattaaagga   184200
agttaacttc atgcatttta atcctagctg tttcagtata gcctagagaa taatgtagtg   184260
aattgaattt aaaaacctat ctattatagt acggctgaaa gcagtgcaat ggattaagtt   184320
ctaatccatt actctgtagc tttgagaatg tcatttccct ggtatgtctt ctctgtgcct   184380
ctgttttctt atctacaaag tgtattaata ttgaaaggac gatttcgcat ctatgaacct   184440
ctgcaaaagc aatctcactg cagagactta gacatgaaac tgaagtaaaa tagaaaaaca   184500
agaattatta ttctattttt atatgaatag ttgtaacaga aagcaatgtt ttggataata   184560
tgtttttaat caaatgtaat gcaaaggaca aagtaacatg agactttgtt agaagatttt   184620
gatagggcct tggtgcacag tttatgagtg accctctgtg atcctccctg tctgtgctgg   184680
aaacagttca caactcagcg aatggggttgg ccaagtctag aaagttggcc atgtcttctt   184740
ctaaggatgc aacattatcc tgtgaaattc tgcctctact ttcagtttga gaatgagctg   184800
atcacaaagc tggaccagga ggtagaaggg ggcagaggag acgaacaata caaggttctt   184860
ctggaaaaac tgtgagtatt tcaggaacga aacctgaagt cagtggtgtc atttagtaat   184920
agagaaaaac aggggtcctg tttcaccaat agagcaattg agtagtctca gagtcactag   184980
ggccaccccc actgtggtct tcagtatggt tatggggtgt atactgtcca cagctgacat   185040
tgtttatctc gtgggagtca aatgctggta ttttcctggc cagcctggcc ctagagaaca   185100
cagcagatgg aggcaaggag gaggtgcaga gtggtggcat tttgcccagt gtttgaattt   185160
ttgaacttca acaaaagtat tagcacttct aattataact gcaaagtaac aatttaaagg   185220
aaaaaatatt tcaaggtctg ctgtgtatgt aaaaaatacc ttaggaccca taaggacat   185280 ataaccaaag cagttctgtc tccagccagg ttggtctttt tcctgccctg tcatccaccc   185340
catccaacac atctgtacct ctgtctgggc tcccattatc accactgtcc cctcttcccc   185400
caccaccaca ctcacctata accctcttgc cctccttggc acatgtggag taatgaagag   185460
tgggaaagtg attaaaaaca cataggtgtt ggcctcagtg agagattgaa cttcaaaccc   185520
tgttttcgcc acatattaag agtttggctt tagtccagtg attctgctta tccaacactt   185580 cattttttt ccctctccaa gaataacatc tatttttga tatcatcatg agaattacag   185640
gagatgatgt gctaacatag catctgttgc agagttcatg actaataaat attggctgct   185700
ctggtgttca tggttgttat tattacaatt tgttttggt gtttgttttt aagagatagg   185760
gtctctctct gttgcccagg ctggagtgca gtggtgcaat gatagctcac taaagccttg   185820
aactcctggg ctcaagcagt cctcccgcct cagactccca agtactagga ctacaggcat   185880
atgtcgccat tcccagctgt ttcttatttt tacttgtgta gaaatggggt cttgccgtgt   185940
tgccaaggct ggtctcgaaa ttttgcttta agtgatcctc ccacttcagc ctccctagta   186000
gctaggactg taggcgtgca ccaccatgcc cagctggttt tcattttat ttttgtgag   186060 acagggtctt gctatgttgc ccaggctggt ctgaaactct tggcctcagg caatcctcca   186120
```

```
gcctcggctt cctaatgggc tgggatttac aggcatgagc caccacgtct ggcctagtat  186180
tattattatt attatttaca ggcctaccct tcattcaggt tgtaactact ctagaccatt  186240
gctttctcat gttccctgaa cttttctagt gttgaccaac tgcatctcca gctgggtgct  186300
tgcctcagtc acttagttgt tcacctgttc gcctgttgtg tgtgagtttt gtggatgaga  186360
gtctgtgttt gaggacagtg ctcccaactg tattcttttt tgaagattct ctaaggaacc  186420
agcactctga ataccgagaa atggaattga attgtatttt cagtagagat ggggtttcac  186480
gatgttggcc agggtggtct ccatctcttg acctcgtgat ccacctgcct cggcctccca  186540
aagtgagcca agtgagccac cgtgatggat gcctgtagtc ccagctactt gggaggctga  186600
agcaggagaa tcacttgaac ctgggaggcg agattgcagt gaactgagat tgcaccact   186660
gcactccagc ctggctacag agcaagactc cgtctcaaaa aataaaaat aaaaaaata    186720
attgaattga tgaatagtct gtattttaaa ggactagaag cctttcttgt tttgttttta  186780
atagtgacaa gacctttttat tggtcttttt tatcctgttt ccattaagtc tctccatttg  186840
agcttcaaac ctcccagttt atatcttttg caattctgat cttatatgga attaaatgaa  186900
gttatgcaca tatacacaca atattttatac atgatatgct acttttttaa atcctacagc  186960
tgatttgttt tacataagga tcttactttg ttttcttcat tcttcctaga tcactaactt  187020
agaaaaaata cggatacata ggtctccagt gcccaagaat aaccctaaat ctggattaat  187080
gtgttggacc catttctttc tctttccctc tccctctttt cccaggtttt cttttaatta  187140
tctaataagc cccagaactt ggctctgtgt gggtccaaag ggacaggatt tagactgaaa  187200
gtttagcctc agtttgcttc tttataactc tgcattttttt tctgaagcta acacttttat  187260
ctaaagagcc gcattgcagg agatgtacta ggttcccagg ttcctctagg ctgggcatcc  187320
atacgaggca ttcagaatg ttcagaggat gccctgagtg ccaggcctta gggagaataa   187380
agacatagga aaaatggtct catacaacta attagagtcc tcacagagca cacgaaacc   187440
ttttgagcaa gggtttgttg actgaataaa acacaaacaa aaacagacat tgaaagaagg  187500
acattgtgtg ctcagattct aagtgatgtt gggacttgag ctgagtccta aagaaaactg  187560
gaactcgagt ccacaaagaa gcgcagcata agtgaaggtc acaggatagg aaggtgttgc  187620
atgaggtgtg tgtgtgtcgg cttaactgtg tcacttaata tctaacattg acgttctgtg  187680
tcatcaaatc ctgccccagc cactgctgag accctggtca gtgctggtca gtgctgctgg  187740
aatgatagca tggaacctgg gcttttgtct ctccctccgc ccctccaggc tcctagaaca  187800
ttgccggaaa cacaaatacc tctccagctc tggggaggtc ttcgccctcc tggtcagcag  187860
cctcttagag aacctgctgg actatagaac catcatcatg caagatgaga gcaaggagaa  187920
ccgtatgagc tgcactgtga acgtgctggt atgtgacatg cctccggtgt gatgggaggg  187980
tactgtcagg ccgcccctgc accctacagc tcagctctag gtagatccca caaacacaga  188040
ggcgccctga ggcacctttg tggagccggt gtcttcctaa gtctaattgg aatggctggc  188100
tcagctcaca ggtatcagca gccacagacc ctgaggataa atttggtgtg tttttgattg  188160
tttgtttaa ttttttattc agtaggtttg ggggtacagt ggtttctggt tacatggata   188220
agttttgggg attttttttt tttttttgta gacggagtct cgttctgttg ccgggctgga  188280
gtgcagtggt gcgatctcag ctcaccgcaa cctccgcctc ctgggatcaa gcaattttcc  188340
tgcctcagcc tcccaagtag ctgggattac aggcacgcgc caccatgccc agctaatttt  188400
tgtatttta gtagaaacag agtttcacca tgttggccag gatggtctcg atctcctgac  188460
```

-continued

```
ctcatgatcc acacgcctca gcctcccaaa gtgctgggat tacaggcgtg agccaccgca   188520
cccggctgga taggttattt ctttagtggt gattttttgag attttagagc acccgtcacc   188580
cgagcactgt acccaaaatg tagtctttta tccctcaccc tcctataacc ttccccactg   188640
agttcccaaa gtccattata tcactcttgt gcttttgcat cctgaggata aatatcccct   188700
tttcttatgg ggatatttgt taaagggaaa cagtgatctc tttggaaaag tgaaacttt   188760
gaaaagcaac aatagtggtt tgtctatttt tgtgtcaata gctcttgatt tatgttggga   188820
ttctgtgatc ctttttttttc ctggcagaac ttttataaag aaagaagag agaggacata   188880
tacataaggt aagctgaagg aaatttcttg cttctgctgt ttatttcatg gctttgtgat   188940
tgatttcttc agtaaacaaa tactttccca acaccgtgtt tgctgctttg agagacccct   189000
aaaagtacat gatacgctcc attcaccctg aaccgacaaa ctctttagac agatacatga   189060
ataagtacga caggaaggag tgcctatgtg aggtcatgtc agggatcagg ggaaggatag   189120
acaacttctg gcctgggtgg gcaggagagg ctgtacagga agaggcagga aaacccaccc   189180
aagagtctta gcttgaagtc tgcgaatccc tgaacatgaa acaaacttgt acgtaaccaa   189240
cgtgcatgtt gttggggaga gattccatag ctttcattag cttcccagag gggtccaaga   189300
cctaatattt aaaaacatta aacaccactg ccttaaagaa agaagagaaa ctagtctagg   189360
tggagtcaga gaaacacgga ggcaggaggt gcacagtgta ttgaagaaat ggggaagatc   189420
cgacttcttg gctcaagagg aaggaattgc ttctgtacag tagtggggag gggggtcagg   189480
cagggaagca ggctgggggtc tggttatgga atgagctgaa cactaaatca actctcgagc   189540
ctgggcagca tggtgaaacc ctgtctctac aaaagatacg aaaattagcc gggcctggtg   189600
gcacgtgcca gctacttagg aggctaaggt gggtggatca cttgagccct ggggcttaag   189660
gctgcagtga gccatgatcg gaccactgca tactgcagcc tgggcaatac agcaagccc   189720
tgtctcaaaa cagaactaaa aaacctataa aactctcgag tgacaaaatg cttccttctc   189780
cccttcttgc cagatatctg tacaagcttc gagatttgca ccgagactgt gagaactaca   189840
cagaagctgc ctacacgctt ctcttgcacg ctgagcttct gcaggtgaat ggctcagaga   189900
gcttgtttca acagggtgga gtacagtgtc ctttcagact aaattctata catttcatga   189960
ttttgatggg aaagaacttt attccaggaa tatccttta tacaagttttt tttagttctt   190020
tctaaatagg cacagctaat ttgtagatca agtatgggaa aatgtcagtt atctttttatt   190080
taaaaatcct tagaaagcag agcacgactt atgaaccttt ggtaattgac actctaatta   190140
aagcaataaa acacacattg atgaatacat aaaaaaattt gtaaaactgc agaaaactgc   190200
agaaagatga gttataagtg aatatagtac catagaagta ctctattttt attctctccc   190260
taaataaatg tatgttgtgg tttagatata aatacatcta tatgttatga atcccaagta   190320
attatttcta gccctgagca ccttctctaa ctttggattt acatataaac tttgattggc   190380
caatatgcag ctcaaactga acaaggcggt aacaggaacc tttatttctc actctttgct   190440
cctccccagc ccatcctacc tcactttgtt accatgttac taataacatt cccatccatt   190500
tagttgctca ggcaaccctca tagtcatctt caatttctct cttttactca ccacctccca   190560
cattctccac aagcgagaga tgtggcccct ctgttcagaa catgccccta acttatcgc   190620
ttttcttttt ctttctttat ttttttttttt aaagagatga gatcttgcta tgtttcccag   190680
gctggtctca aactcctggg ctcaagcaat cctcccactt cagcctccca gagtactagg   190740
attacaggca tgagccacca tgctagccaa tccacttttc tttatctccc tgactaccac   190800
cttggtccat cccgtaagca tgtcacacct tgagcactac agcagcctcc tgtttggtgt   190860
```

```
ctctgcctcc agttttgttc tcagctatta atattctttt acagtttata ttttatacta    190920
aagtaatata tgggcattgt ccgaacatat gagttaaaaa taggattcct atgcctcacc    190980
acttcccaaa ggaaattcac aattcatatt taagtttagg cattaaaaa gcttattgta    191040 taatggactg ggcctggtgg ctcacgcctg taatcccagc tctttgggaa gctgaggcca    191100
gcagatcact tggggtcagg agttcaagac cagcctggct aacatggtga aaccccatct    191160
ctactaaaaa tacaaaaaat tagcaggcgt ggtggcacct gcctgtagtc ccagctactc    191220
aggaggctga ggcaggagaa tcatttgaac ctgcaaggcg gaggtttgca gtatgctgag    191280
atggtgccac catactccag cctgggtgat agagcaagac tgtgtctcaa agaaaaaaa    191340 aaaaaaaaa gcaacctact gtatatagct taaaagtga ggcttgttga ctgtggattt    191400
cgccattgta tgatcagaaa gaaatcccca gtgtctgtaa ctgtaggtct tttcatttgg    191460
gaaactcagg aaggtaaact ctcctatcct ggtgtaagat atgaggtatg aatgcagctt    191520
ttttcccccc cagattgcta ttcaatagag atgctgtttg ttaagtatag ttcacatttt    191580
gcttattggt ataagatccc atctttatta ctaaattctt attttggggg gagggaatct    191640 cttttctagat tgtatatgct tttacgtggg tctctgtctg ttcatgtacc agtaccatac    191700
tgtattaatt attaattctt gatagtgtgt tttatgacct ggtagttact cttgattgct    191760 cttcttttc agagttttcc tacctattcc ttttgttaa ttttccata tggactttgg    191820 aaagatgaaa tttaaaaatt aatttagtga gaatttacat gttaatgaaa tagaattttc    191880
ttatccaaaa gcatggtatg actttccatt tgttcgagtc tgcttttgtg cccttcaatg    191940
gcgtgtgaaa gttttctgca tataagtctt gcatattcct tgtaatgttc actcttagaa    192000
atgttctttt tggacttatt tttgtttggt tccattcttc tattctgtat atttagtctc    192060
cgtgtatctg aaataaattt tatttcaagt atattaattg ttcttcctgc tgcgtaactt    192120
aattctctta ttgtgtgtcg cagtttctta gtcaactgcc ttgcattgtg aggaatacaa    192180
ccataatgtt tgcaaattgt ggtagtttta cctcttccta ttcattttta tactcctaat    192240
ttgttccttt tatctgactg tgttactgat gccccagtac aacgacagtc atgtcagtta    192300
gcgaccttgc tttgtcgctg gcattttggg gggatgctgt gagtgctcct tcatttggca    192360
tgatactctt gttttggagc tggcatgtgt atatgtgtgt atatgtaact tttgtgttta    192420
atacataatc taaaatacaa aatcaatgag tcaaatatat atacaatatt tcttgatgt    192480 tgggggggctg aatatttgtt gtattaaccg tgtgtcgctt ttcttccttt tcagtggtct    192540 gacaagcccct gtgtgcctca tttgcttcag aaggacagtt actatgttta tacccagcaa    192600
gagcttaaag agaagctgta tcaagaaatc atatcatatt tcgacaaagg caaagtgagt    192660
attggattgt ttttgtacta ggggaaagag gaaaatgacc gcagtatcgc aatacaattc    192720
tgatgctcac cacttggagt tagcactgac tacccaggtt cagggcactg tctccaacga    192780
gactgccccc gcttcagatg ccatcttcaa atttggggt ccccagtcca ttcacagttc    192840
tgggcaactg ggtatacatc tgggggggctt ccactgcccc ctcaggttta atagtctgct    192900
agaacaacca atagtacaca gtgaagtgct atatttaacc attccagttt catcaggaag    192960
aatgtaaact ggggccagcc acatgaaggg acccataggg aacagtctgg gagaatctca    193020
agcgtggggc ttctgtgtct tccccctgtg aactcggggc accttcccag caaatcagtg    193080
tgttcctcaa tcaggaagct cacccaagcc atgggtgtac agagttttta ttggggtttc    193140
tttttttttt ttttggtaaa tatggggtct caccagttgc ccaggctggt ctagaaccta    193200
```

```
gaactcctgg gctccagtga tcctcctgta ttggcctccc aaagtgccaa gactacaggc  193260
atgagccact gtggggtttc attatacagg caggattgaa tgaatcgtta actacacaat  193320
gaacttgatc tttagccttc cttttgtccc tgaagattgg gctgatatcg catggctcac  193380
agccctaacc ttctagtcac atgattagta tttctggcat ggcagccccc atcctgagac  193440
taggagacca ccatgagtca cctcattagc atagatttgg gtatgatcct ggggtggggg  193500
caccaggaat aacaaagaca ctcttattat ttgagaaatt ctaagaaaat tcaccggaac  193560
tcaggaccaa gaccagatac atgatttaat atacaacaat aactcacagc tactgtttat  193620
tcttcccttg tgtattcttg aattctgaga tttcagaggg ggacagattt tgcaaacaat  193680
gattttaaaa gatttaattt tgaagtgttt cccaatggct tgtgggctct gcacacattt  193740
cctcagaagc cagaaacaat ggaacatagc accttgtgaa caggaatgaa gcaggaggtg  193800
acccgatgct gcaagttgaa tagtatccgt ctaagagaca gctcatgaaa taccaaaggg  193860
gttagaaggc tcaatctggg ctgctagcct cagacactga ggacgtgctt tagcctgtaa  193920
cttacatggt tatacatgct cggaggcatt tcctaaaact catccactaa gtagggaaat  193980
cagtgccctg cattgaaata cagttttgcca aattccacac tatcggggaa acccaccccc  194040
aatatttcaa cataggttct ttctattttc cataagtgtt ggccggctga taataaaga   194100
gaaagagtac aaagagagga attttacagc tgggctgccg ggggcgacat cacatatcgg  194160
taggaccgtg atgcccacct gagctgcaaa accagcaact ttttgttaag gatttcaaaa  194220
gggagggg tgtaccaaca gggagcaggt cacatacttc aaggggcaaa aagcagagca  194280
aagatcacat gcttctgagg aaacaggaca aagggcaaaa ggcagaaact cctgaagagg  194340
gtctatgttc agcggtgcac gtatagtctt gataaacatc ttaacagaaa acaaggtttg  194400
agagcagaga agcggtctga ccaaaaattt accagagtgg aatttcccaa ccctagtaaa  194460
cctgagggta ctgcaggaga ctgtttattc ttccttatct caactgcata ggacagacat  194520
tcccagagtg gccatttata gacctccccc caaggaatgc attcctttcc cagggtctta  194580
atattaatat tccttgctag gaaaagaatt tagtgatatc tctcctactt gtacgtccat  194640
ttataggctc tctgcaagaa gaaaaatgtg gctgtttttg cccgaccccg caggcagtca  194700
gaccttatgg ttgtcttccc ttgttcccaa aaaatcgctg ttattctgtt cttttcaag   194760
gtgcactgat ttcatattgt tcaaacgcac atgttttaca atcaatttgt acagttaaca  194820
caattatcat agtggtcctg aggtgacgta catcctcagc ttacaaagat aacaggatta  194880
agagattaaa gtaagacagg cgtaagaaat tataaaagta ttatttggga actgataaat  194940
gtccatgaaa tcttcacaat ttatgttcct ctgccgcagc tccagccggt ccctccattc  195000
ggggtccctg acttcctgca acaccacaca acagtactgt tagccttttt ccatctccac  195060
aaacaacatc actacaccta cacacacaca cacacacaca cacccataca cacacctgta  195120
cacacacatt tcagaaccaa agtcccacag aaacttccct tcccctcca accagacttg  195180
catgctttcc gaacctgggc tggcagagct tcctctctac tttgaagtgc tgtaggtgct  195240
tgacctgtta aacacagtat tgcttttttg ggcgacacat ggtacttatt cttaatgtcc  195300
gtgcaaacag aactacagaa gacgcccctg gcaaagctgc caatatacac tgtctttatg  195360
atgtcaggaa atgaaggttt cactgatcta agggataaag cgagtgagga atatctaccg  195420
aaactcaatc ccccagacca cttgctcatt cccagtgact cgccagtggc ttttgccact  195480
gaatcaatga ctgccttgtt ctccactttt aaccttactt tccttttttct gaagatgtgg  195540
gagaaggcca tcaagctgag caaagagttg gctgagactt acgaaagcaa agtatttgac  195600
```

```
tacgagggcc ttggcaacct cctggtgagt ctgggtcaaa atatgttagg cctctgacag 195660
ggttgctaaa attagcactc atgaaaatgt ttccgtaagt tgaaagtcag gatgaatggt 195720 gttttttac aatggaaaag tcaactttgc ttgaaatgag aatgaaaaaa gatgtagtcc 195780
aaaggctctg atcaatattt ctgccaaata tccttcagag aaggttcagg acatctctgg 195840
aagtggagtg gggttgtctc gacagtgtgg tggaatattg agtttcagat agtagtgact 195900
cgctttccac atccctcagg atctctgtct gcagctctct cattcttcct gaagccattt 195960
ttctttctgt gggccctcca tattcccagc catcagtaaa gcaaaacaaa aatgagtgcc 196020
cagtgttagg cagccaccat tctgaaagct cagtggaggc agccaccatt ccgaatgccc 196080
agtggaggca gccaccattc cgaatgccca gtggaggcag caccattccg aatgccagt 196140 ggaggcagca ccattccaaa tgcccagtgg aggaggcagc cattctgaat gcccagtgga 196200
aggcagccac cattctaaat gccccagcgg taggcagaca ccattctgaa tgcccagtgg 196260
aaggcagcca ccattccaaa tgcccagtgg tagacagcca ctcttctgaa tgcccaatag 196320
aaggcagcca ccattctgaa tgcctgatgg taggcagcca ccattctgaa tgcccagtgg 196380
taggcaacca taatattaaa tttaataatt tctagtagag gagttagaaa agatcaggtc 196440
acccatagtc atgaaataat catttatttg aggagctggg tgtcaagatc actttgtaaa 196500
aagtttacca gtgtgctatt accagcccct ggcttcacat gcaaaaaact gacttattaa 196560
tttcatcaac tgggctgggc acggtggctc atacctgtaa tctcagaact ttgggaggcc 196620
aaggcagatg gatcacttga gcctaggact tccagacgag tctgagcaac atagtaagac 196680
accatctcta caaaaaatat aaaaaattag ctgggtgtgg tggcaccttc ctctagtccc 196740
agctactttt gggaggctga agtgggagga tcacctgagc ctgggaggtc aaggctgcag 196800
tgaactgtaa tcatgctact gcactccagc ctgggcaaca gaatgagacc ctgtctcaaa 196860
aaaaaaaaaa aatttcatca actgaactga gctgaaatat tagtaatgta acatgttaca 196920
taccggtcta agaaaatagt attttgacga gaccatcacc tagatagaag agtaatggca 196980
tgctaaccat tgtaggggag ggggctcagg tcattgctca aagctgtcca cgtctggctg 197040
gctattttgc tttctttaag gctgacccttg tgagccaaag ctggaaagcc cctcatcttg 197100
tgaagaatta aagataaaga tggtagcaga tactgaaaaa ccgaacatca ccaccacctt 197160
ctgggcactt ataatttacc agacacttc atccagacca cctgcatgaa ctacacagtc 197220
cttcttttta aaaatgttct ttatttattt attattttt caaaacaggg tctcactctg 197280
tcacccaggc tggagtgcag tggtgcagtc atagcccact gcaacctgta actcctggc 197340 tcaagacatc ttcctgcctc agctgctggc taattttta attttttgta gagatggagt 197400
ctcactatgt tgcccaggct ggtctcaaac tcctagcctc aagcaatcct cccacctctg 197460
cctcccaatg tgcaaggatt ataggcgtga gccactgcgc ctggccttgg aaggttcttt 197520
atcttctccc atgggtgtct ggttaagtgc agccgccttc tgtgaatctc agaatgcact 197580
ttttaacctt ttgtagtccc tgagcccact ttgagaaact gctgaaagtt gtgcactgcc 197640
ccgttacgca gaagaattcc aacgtgcaca cacttcagca tacaccctca gggagtcaca 197700
gccttccaac gtccattcat ggagcccagg tccaaaacct gtgatccgag aataggataa 197760 ccctttctg cccataggt gttttccaaa gaccttcat tgctctgggt tacgtgggaa 197820
acaacaaaac aaagtctgac ttttttttc ccccaactgt gtacttataa cctccccttg 197880
gaatgtcttg ttttgttttc cagaaaaaaaa gggcctcatt ttatgagaac atcattaagg 197940
```

```
caatgaggcc tcagcctgaa tactttgctg ttggatacta tggacagggc tttccttctt   198000
tcctacgggt aagaaacctg atggtggtct cccaggccat taggaggagg gaagagactc   198060
atttcttttc cagatgggca cagggtgtt agcagctgcc gacccgtgtt ctcgctgtgg    198120
gaggtagggg agggaaacca cttcctgagc agccggcctc ttcacccac acccccggac    198180 acccgtggtg ttctgcaggt cttttgtgaa atgacttttc ccaggtgcag tgaaaaaggg   198240
aaaaacagaa ccatcccccg cactggtcag ctgctacggg tcacgccagg gaaaagtgtg   198300
gactgatgta tttcgttgtt taccatgttt ctagccagag ctaatttgaa aataggtatc   198360
ccaagaacca gactgcagga gtatcccaaa ataaaacatt ttattataat aataatgaca   198420
aggatggtat ttttcttcca tctcaaaatt gtgtataatg cgatattcaa tttatagttt   198480
aataaataaa aattcttatc tcttacgaaa agtttctttt agagctgagc tttgcttaaa   198540
catttattat ccatctgctt tctcctaatt tgaaaacaag cgataaagca agcaatttac   198600
attcctaaca gtgcctaatg agacagttta ttcattcagt cagtaaatat ttattgaaca   198660
tctactgtgt gccaggcata gggaaggcat tagaaagatc ttgctgatta cagtcaaaca   198720
tagtccctac tctcatggat tttacaacct aaactcatga ggggagattt taatcacaca   198780
tgaatgtaaa atttaatctg catgtcggac gcagtggctc atgcctgtaa tcccagcgct   198840
ttgggaggct gaggcaggca gatcacttga cgtcagggt tcgagaccag tgtggccaac    198900
atgctgaaac gctgtcccta ctaaaagtac aaaaattagc tgggcgtggt ggtgcatgcc   198960
tgtaatctca gctactcagg aggctgaggc aggggaattg cttgaaccca ggaggtggag   199020
gttgcattga ccgagatca caccactgca ctccatccta ggtgacagag cgagactcca    199080
tctcaaaaat aaataaataa ataaactata accaagaaag atacctgtg ctataagaat    199140 ctgtaaccag gaagtattta cccaagtgaa atagaaactt acccttttac aaaaaatgta   199200
caggaatatt tatagcagct ttaatcatag tcaccaaga caggatccaa tccacgtgtc    199260
cctgaactgt tgatgggata acaaaacttc agtgtatcca cacaacgaaa tactgcagca   199320
gccaaaggca gtcagctcct gatacacaca actgcgggca tgattcccac ccacatgcag   199380
cttgctaggt aaaagaagtt acacttaaaa ggctgcgtac tctgtggttt tatttatacg   199440
aaattcttgc ctaggcaacg cttcctatca ggacagaaag tagatcagtg gttgctggcc   199500
agggggaggt tggctgcaga agggcctggg gaaattttttg gtggcagtga aactgttctg   199560
tatcttgatt gtggtcctgg ttatgtttgt caaaactcac agaattttac actaaaaggg   199620
gtccatttta ctgtatgtag attatgtctt aatattatta ttttatttat ttatttattt   199680
atttatttat ttatttttt ttttttgag acagtgtctc gctctgtcac ccaggatgaa    199740
gtgcagtggg gaatctcgg ctcactgcaa cctccgtctt ctgggttgaa gcgattctcg    199800
tgcctcagcc tcccaagtag cagggattac aggtgtgcac gaccaggccc agctaatttt   199860 ttgtattta gtagagatgg gtttcacca tgttggccag gctgatctcg aactcctgac     199920
ctcagttgat cccctgcct cagcctccca aagttttgga attataggca tgagccaccg    199980
tgcccagcct atgtcttaat aaaaaaaga atcagggcct ggcacagtgg ctcacacctg    200040
taatcccagc tacttgggaa gctgaggtag gagaatcact tgagctcggg aggcagaaat   200100
tgcaatgagc cgagatggtg ccactgcact ccagcctggg cgacagagcc agactccatc   200160
tcaaaataaa ataaaaaaaa tcaggaaaga ctttccaggg atcctctgtt tcagctgcaa   200220
cctgaaaggt aagctgggag tggagcaggt aaggggta ggaataagca ttgcaggcag    200280
aggaagcatc aggcaagagc agggcagtgc cttgaaagga agggccagtg cagcaggcac   200340
```

-continued

```
agagagagct gggtgccag cgggaggcg ggagccctg gaagagcctg cagggccttg   200400
gggtttcctg gggtgttctg tctacatcct gagagcagtg ggagctgctg cagacttttc   200460
gtgttggaaa ggtcatctgg cttttgtctc catggtcatc catggagaat ggatgggagg   200520
tgctgcaggt aaaccactaa gagaccattg cagatgttca gaaaagagat gacaggctag   200580
actcgggacg tggggtggt ggctttacag agaagcggaa atactagagg ggtggagatg   200640
aggtcacagc catctgatga ttgatgggct gtgtgggtga ggaagtgaga gttgtcaaga   200700
atgatttctg ggcttctggc ctgcatcatt ggagggggta gttgaaccat ttactgggac   200760
aggaggaccg gaaaaggcca gagtcacaga ggagagaatg aatttattcc ttgagtaaat   200820
atttattaaa ctcctaccat atacttggct ctaatatagg catgggagca gagtcaaaac   200880
gaaccaaaat cttgaaatta tctagcttat gttccagctt ggagagatca aaaaatgaga   200940
taaatcaata aactatttag tatgagagat ggcctagaac actgcctcct acagtgtagc   201000
tactcagtaa gtatcatgga gaaaggact tagggaaggg gactagagag gcaggtgttg   201060
gggatggagt tacaatttta aatacagtaa acaagaaaga cttcagaaag aaaatggcat   201120
ttttgcaaaa accagaaaaa aagttaaaga ataagctatg cagctatcaa gaggttgagc   201180
aaaggtccca gaccttgaga atagcaggtc caaaagctat gaggctggag tagttgtgta   201240
caagagggtg tataggagaa tggggcaggt ggctgttggt accagatagc agagggcctc   201300
ccagggcttt ctaaagtgtt tgcaaagttt ggttttgcac gtactcaagg ggaggtacat   201360
ttggaacatc caaaaggcac aagtcaacca ttagctgtat agatctggaa ctcaagtgaa   201420
gttacagaca ggagagaaaa gttggtgagt tacttgtatg gagttaaaat aaccgtggtt   201480
ggggatgagg tggaccaggc agaggaaaga ataaagagtg gaaggtctga ggccaagcat   201540
ggtgactcat gcctgtaatc ccagcactgg taggccaagg caggagtctt gcttgagccc   201600
aggagtttga gaccagcagt ttgaggccag cctgggcatc atagcatgac cccgtctcta   201660
taaaaaatt ttttaaaaat tagccaggca tggtagcatg tgctatggtc ctagctactc   201720
agtaggctga ggcaggagga ttgcttgagt attggaatta gaagtgacag tgagctgtga   201780
tcaagccact gcactccagc ctggatgaca gagtgagacc ctgtctcaaa aataaaata   201840
aaaaatagaa agagtgtagg gtctaaatgc atcagggtct agtgttagct cagcttcaat   201900
ccaggtcaac ataaaagaac aaccctgcc atagccgtta catatgcctg catgtcccat   201960
gaaatcagaa atgtgaccac agagacagca gtgattctgt gaaatcaaga acaccagact   202020
ttcaagtcga aagcattctc gtctaaatca cctgctgagc gagtgtgcaa ttttggtgaa   202080
atcacgtaat cactgagtct tggttttctg atccgtaatt tagaaaaata atgcctacat   202140
cgcaggaaag ttttgagaat taagttaata gcatatagga gtgctttata aactgtaaag   202200
tagtttagag atgttaacat acctcaaagg catactgtag aatataaaat cctcaggagt   202260
gatataacct cactgccact ctcttctatg ggatatttcc ctgaattcag aatatttaaa   202320
attacatcat cctctccttc caacccaatg agatctcatt atctcttttg tttctgtcag   202380
gggtaccact gttcttccta ctccaagacc agtgactttt tttttttttt ttaagaggtc   202440
tcgctctgtc atccaggctg aaatgcagtg gtgtaatcac agctccctgc agccttgacc   202500
tcccaggctc aggcaatcct gcctcagcct cctgaggagg tgggattaca ggtgtgcacc   202560
atcacgccca gttaatgttt ttatttttc ttagatatgg ggtctcacta tcttgcccag   202620
gctcaagacc agtgatcttt gaatcagcgt cgactcccct gtctgccctg cccttctccc   202680
```

```
gacaccaaag aagcaaacac tgaatgctgt tacttctgtc tctccttctg ttacttttcc    202740
ttcttctgct cagtccagcc tgtgagcttt cagttgggca tagatgccac tgttggctta    202800
cattgtctac acttcttctt tcatcatgca tctcctgcct tccagaacct ccagtgaaca    202860
ttccaagtct ttgaaacctc tgcctgccat gcgagaccat tcattttctg gctcattctt    202920
ccagtccaag ctcatttctt ctcccagaat tctgtgcttt ccgcccctgg gcctgactct    202980
ttccacatac ccacctggtc cttcgcaccc cttctcttta cgcttcctta tcccattcat    203040
ctgtctatgc ccatctaagg cccatgtctt gcttgaagcc ttctctttcc agtcgagcta    203100
attcttcctg acctgcttct gtgattcctt ttacagttat cgtctgcatc atacaactag    203160
cgttgtatta cactctgatc ctttacccac cattgtttca tctgaatgat ggaatttcaa    203220
caggcttgag tcccatagac ttttcctaac ttggaaaagt tttatcatat attccaaaag    203280
atccagtagt ttttactccc ttcattcagt gtttgcctgg aaagtgtaat tgccctcacg    203340
gtacttacac tatcatgttt actaatatat ttacttgctt gttttttatt ctctcctcta    203400
gaaggtaagt tctgtgagag caagatcacc attgtattcc tgttgtccag ctgatcttct    203460
ctttgtgcaa tacatatttt tatatgaatg acaagtgat tttgaaagac attttacaag    203520
acaacctggg cccaagtgtt gcttaaaaag gaatcatgtg tgggctacca atggaaactg    203580
ctcatttcaa acatggctat gtttgcactt gcccaggcaa ccacacctgt gagacaaatt    203640
actcccatgc ctggggccta ggaaatctct ttggggaaaa aaaatgatt aaagagatta    203700 tatttacagt ctagagtgga gaaaatagta tttaatgcag taattttcta ttagactttc    203760
aggattggct ggggactgtg gtacattgct tctgttctct gtcactctgt ttctgtgcca    203820
gaagacacat tgcttctcct cattctctta tgcagtgctg tttaagtggt ggtccacaaa    203880
ttgttgctgg atggtgatga gatcgattag gagtttatac ctcaatgtaa attaatgcac    203940
ttccttcctt ccttaagaat gtcttgccat gaaaatatca gcatgcctgt ggatgtcatt    204000
gatttaaatg agggcacaag ttccgtattt cctttgcagat gggtccagac tgtttgcaga    204060
ctggccatgg tccttgggcc acactggaag aagaactggg ctaagtattt tttatgcctg    204120
tgatttaact tctccaataa accgcagctc ttgtaggata tgatggtcgc tgtcaggcaa    204180
ggactagatt ttcagtgaga acttgatggt ggggattgaa cgttggctgg ggagtgcagt    204240
ggctacctca gtacccggaa ctccagttgc ctctccactc ttcctatgta atgacttccc    204300
tttctgtgtc tcacctgcag aataaaatct tcatctatcg gggaaaggag tatgagaggc    204360
gagaggactt cagcctgagg ttgttaaccc agttccccaa tgcggagaag atgaccagta    204420
ccacgcctcc tggggaagac atcaagtcgt cccccaagca gtgtatcctt tccgggggga    204480
gtatggcccc gaggctctta tggctgtgca cagccccagc taagccagag aacataggag    204540
ctacagtccc ttctctgcag acacaccatc ttctcaagca ttctgacaca ggttcccatt    204600
ccatgtaaaa tctttgggac cctaatagca ttagctggtg gtgatgacat aacaaaagag    204660
gagagataat agacaaatga tggatatgaa atatacttcg tagccagatg gggagcttaa    204720
gtggaatata tactttctat tgtgaattct ggattctgtt gtagactttg agacagtatc    204780
tctgtcctgg tgggttgggg agctaagact ttctaagact tgatcattaa atcagagcag    204840
gagcgcttac acttgagctg ctttttgaagc ctaactttac catttaccag ttgtgtgatg    204900
ttggatttta acctctctta tcctcagatt ctccatctgt gaaaagagaa taagaatatc    204960
cctcatgtag agttgttgtg tatagtagag ataaacacatt caaataccct agcacagtgc    205020
ccaactatgg cactggataa acagacggga tccaaagata aagtaattc ttgttgcctg    205080
```

```
ggctctgatt ctggtgattt cagagggatg cttgtcccaa gaaattgttt aaatccattt 205140
ctaagtacct atttcctgat attgcattga tgtctatttc cctatggcaa ggattgtttg 205200
ccagatgtct gaccgaaaaa aaaaaaaggg ccctaggatt aattataatc actgaataag 205260
gcattccagt gatacacaaa ggaactccca ttttcagtgt ggtcctggca ttggggtcaa 205320
agggagtgat tggtgctggt ggcatttccg gctgtgaagc aggaggaaca ggggtgtttg 205380
gtgtctgaca ccttcacgac cccagcccct ctcctttcct taacgagctc ttcagacatg 205440
cagtgcttca ctgtaaagcc agtgatgagc ttgccgccca gctacaagga taaacctgtt 205500
ccagagcaga tcttaaagta agtggttttt catttaaaaa aaaaaaaaat ctgtgtctag 205560
gcacagtggc tcacatctat aatctcaaca ttttccgaag ctgagggagg agtattgctc 205620
gaagccagga atttgagacc agcctgggca acaaagtggg atgctgtctc tacaaaaaag 205680
agaaaagttt gtctctccct cacacctgtt tggagtacat caaaaccaaa gccttacatt 205740
tattacagtt tgcaagacct actgtctgtt ctactttgag tgtaagataa aagcttggta 205800
atacaaaggg atgtgggggt tttggttttt ttaggcagag gaaaatcaga aatttcacac 205860
ctagcttaca gatccctgag cttttatttt cacccaaaag catcgcagag gagtggctgg 205920
tccccagtga tggaggggct cattccttgt cttgaaaagc tgaatgctaa cagtattgaa 205980
agaactgtta taaaactaga ctaatgagat cacaaatgta tgtgtaagtg catacaccct 206040
tttttttgtt tttttttgag acggaatctt gctccgtcac ccaggctgga gtacagtgcg 206100
tgatcttggc tcactgcaac ttctgcctcc caagttcaag caattctcct gcctcagcct 206160
cccaagtagc tgggattaca ggtacacgcc gccacacctg gctaattttt tgtatttaa 206220 tagagacggg gtttcaccgt gttgcccagg ctggtctcaa actcctgagc tcaggcaatc 206280
cgcccactaa gagacagggt ctctctgtca actaggctgg catgcagtgg cacgatcata 206340
gcccactgca acttcaaact cctgggctca agagaccctc cctcccacct cagcctccta 206400
agtagctggg acatacacca ccacacctgt gtgtgtgtgt gtgtgtgtgt gtgtgtgtgt 206460
gtgtgtgtgt gtgtgtgtgt aaatgggatc ttgctgtgct gcccaggttg gctggtcttg 206520
agttcaagcg atcctcccac ctctgcctcc cgaagtggta ggattacagg tgtgagccac 206580
cacacctggc cacatatacc ttttaaaatt gtgtgctgtg actttgaggc tgaggcgggt 206640
ggatcacttg aggtcaggag ttcaagacca gcctggccaa catggtgaaa ccccatctgt 206700
actaaaaata caaaaaaatt agccagtcgt gatggtgcgt gcttgtaatc tcggctactc 206760
aggtggctga ggtaggagaa tcacttgaac tcagaaagtg cagcctgcag tgagccaaga 206820
tcgtgtcact gcactccagc ctgggtgaca gagttagact ctgactcaaa gtagataaat 206880
aaataaaaat aaataaataa aattgtgtgc tgtgaaataa attcctaaat aatataaaag 206940
taaggtgtga aataaaatca aattgtacac tttctcaggc cttcatgtgg aggcactatt 207000
gattatgaga tagcttagtg ggtaaaactc agaccaggca gatgtgttat aggttttgtt 207060
gaagtcaagt caagcagtgg ttgttctaag agagaaaaat acagcattgc tttgtccttc 207120
tccagctact acagagccaa tgaagtgcag cagttcagat actcccggcc gttccggaaa 207180
ggagaaaagg atccagacaa tgaatttgct gtgagttcac ccctttttgtc ctttaagagg 207240 taaaattaac gggctgagca cggtggctca cgcctgtaat cccagcattc tgggaggccg 207300
atgcgggcgg atcacgaagt caagagatcg agaccatcct ggctaatacg gtgaaacccc 207360
atcggtacta aaaatacaaa aaattagccg ggcgtggtg gcacgcacct gtagtcccag 207420
```

-continued

```
ctactcggga ggctgaggca cgagaattgc ttaaacccag gaggcggagg ttgcagtgag 207480
ctgaggtcgc accactgcac tccagcatgg gcgacagagc gagacttcgt ctcaaaaaaa 207540
aaaaaaaaaa aggtaaaatt gacatcccaa gtggagatct tccacctacc taaccagctt 207600
ccacaggaga aacgatggca ccctgggaa cagagacttc acctgctaat tacctagaca 207660
gcaagtacta attacctaga cagccagctg tcatctccat ggaaaatgct agactaggag 207720
tccagaatct ggtctcttcc tgggcctgct gcttgtaatg accttgggct agtcatacct 207780
ctctagacct cacatttccc tctgtagggt gagaagtccc aagtagacga tcccttcag 207840 cttaaacat ccagaatcct tgaattttat gagaaaattt ggctcagtct ctacgaggca 207900
tttgagaata gaatctcact taagtgaacc agggagtctt gctgttttcc ctgggaattg 207960
accaacattt catgttttcc tcctgggaat tgaccaacat ttcatgtttt ccttcttgcc 208020
accagacgat gtggattgaa cggaccacgt atacgactgc ataacccttt cctgggattc 208080
tcaagtggtt tgaagtcaaa cagatttcaa cagtgagtca tttgaaattg gcatttagaa 208140 aaaaacttc tgtttccaaa tataataaca gcctttgttg aattccctct gcagttcaca 208200
ccagcttggc cagcctcctc tggccaactt tgttttcaa aagagaaata aaaggcatgc 208260
ttatataata gagctccttt gtaaaactga tgtgacaaca ccagcccttaa aggtcaatca 208320 cagtgaatga ctcttttatg tccagaggag tggtgtctgc tcagcgatcc tgccagcacc 208380
cagaaacatt tttggaatgc tgctttggag tttcttgtca attacatctt ccctcccaaa 208440
gcctgttctc ttcttttatt ctctgctaat catatccaca gttacctag actcctccct 208500 cttcatctcg cccaaaagct gcttatttta cctgtttagt attgattaaa tctgttttat 208560
ttcccacctc ctcattggcc tccctgccat gcatggcctt tcaggtcca gttacctcac 208620 tgcctcagtg ggaattccat taaggaaatc tcaccatttc gtccattctc gtgcttaaag 208680
tccttccatg gctccaagta cctggagtat aaagcctgtc ctccttagca cacacgta 208740 tggcctaact cttctgcccc atctcctagg caatctgttg gaaccatact gttcatccca 208800
tgctaatttc agtcctctgt gacactggat cgttttctct gcctgaaaca cactcttgca 208860
atttctgcac ctaactaact cccatcaagg ttcagtttag gcaccagctt tcaatgaat 208920 ccatctctgg aacacccaag ttgggtgacc tgccctttgt ctgtccctg tggcatcctg 208980 ggcgtgttc taacctacca tgtttacatg tcctgagacc ccgctaacac catcagctcc 209040
tccaagccat gaaatacata catcttaatc acttttgtat ctgtggtgca tagcatggca 209100
cttagcctaa agtaggtgtt caagaaatgt ttccttgacca aagctgaact gaagtttgat 209160
gtgttataag tcatggctag gtacagtggc tcatgcctgt aatccctgaa cttgagaag 209220 ccaaggtggg aggatcactt gagctcagga gttcaagacc accctgggca acatagcaag 209280 accccccacct ctacaaaaag aatagcagta tgtggtggca tgtgcctgtc atcctagcta 209340
cttgggaggc tgaggcaaga agatggcttg agcccaggag ttgaggtta cagtgagctg 209400 tgaataattg cactactgca gtccagcctg gtcaactgag tgcaccctg tctctaaaag 209460 aaaaaaaaat tagacattat tcctcagtta tggatatgaa ttttggatgg agacttttgg 209520
aatcaagtct ggaataggag gtcatgttga ctgataatgg gtaaaatgaa gaggagata 209580 cttttttttt ttttgaaacc tgattttgta gacatttcca taggaagaac tctctgaatc 209640
tgtactgtgt ctcattttct tttcattcaa aattcagcct gtatattcga atacatccta 209700
ttatttctga cttctgatac acatagaatt catactaaga ttatgtatgg tctgaatgca 209760
tggcctccaa gatcacttac ctcttttcat ggaggaagca tcaaacgttt tgccagtgga 209820
```

```
cattcttggt ggttcagaag tgactcagat ctgatatcct gctgttctct tgtcgttgat 209880
cttctcaaaa gtctccaagg aagtgttgcc taggaaatga ttcttactac aggtccagtt 209940
cttttcttct caaattttct gtagacattt tgtccaagga ataatcatta ccatagctcc 210000
aatgtttaag tcatcattct actttgtaag gagattttaa atagcttatt ttgtatctta 210060
ccactattcc aaaaaattgt ggtgtcctta taagctagca gtccccaatc ttttgacac 210120 agggactgct ttcctggaag acaatttttc catggacctg gggtgggaag gtgggggtg 210180 ttggggata ggggatggtt ttggaatgat tcaagcacat tacatttact gtgcactata 210240
tttctatcat tattatattg taacacatat tgaaataatt atcatgtgga atcagtagga 210300
gccctagctt gttttcctgc aactagaagg tcccttctag aggtaatggg agacagtgac 210360
agatcatcag gcattagatt ctcataaggc atgcacaacc tagatccctc gcatgtgcag 210420
ttcacgatag agtttgcact cctatgaaaa tctgatacca ccactgatct gacagcaggc 210480
agagctcagg ttgtaatgcg agcgatggag agtggctata aatacagatg aagcttccct 210540
cacttacctg tcgctcacct ctggctgtgt ggcctgtttc ctaataggcc acggactgat 210600
actggcctgg cattttggga cccctgctat aagtctaacc ttgattagca aatcttccct 210660
tttctatagc ttgtgggcat tttataccct ttcaagggaa gagttaaact tttttcagtc 210720
tttacttgga gctgacaagt gtcctctttc tcccatgtgc tctgtcactc aggaagagat 210780
cagtcctctg gagaatgcca tcgaaaccat ggagctgacc aacgagagga tcagcaactg 210840
tgttcagcag catgcctggg accggtccct ctctgtgcac cctctctcca tgctgctcag 210900
tggcatcgtg gacccggccg tcatgggggg cttctccaac tatgaaaagg ttcgcttggt 210960
cccagaatcc cctagggatt cacagacctg ggtgtctgtg tgcctccctc tgtgccattt 211020
gccactgaca aattcatttc ctacagctgc tctaagaaat gttcactttc ccttctggca 211080
agtgaagtga atgaaacgat tgtccctgac ttcttagaga ctatcagcaa cccagctggt 211140
atagaactta cctagtaaag cgtcacagaa aaaaaaccaa catgcctctg gtcaaagcac 211200
ctgttattct gtctcccctg agggttatac aaactgattg gtggaccccca gaacccaggc 211260 gcactggaaa tgaagcagca tctctgggga tggcagagcc acactctctt tagaattagc 211320
ttctaggggc caggtgtagt ggttcacacc tgtaatccca ggatttaggg aggccaaggc 211380
aggtggatca cttgaggtca ggagcgcgag accatcttgg ccaacatggt gaaaccgcgt 211440
ctctactaaa aatacaaaaa ttggccaggc atgatggtgc atgcctgtag tccgagctac 211500
tcaggaggct gaggcacgag aatcactttt aaccccagag gcaaaggttt cagtaagccg 211560
agattgggcc actgcactcc agcttgggtg gcggaattag cttctaggac ccctgcctga 211620
cttggtgtgc cagaggttgt atggacaact gatggccctg actctacaat taaattagtt 211680
caactaagta ttcttagttg agacatgaaa gcagtacttg gcacaattta atccatggga 211740
tagggttagg atgtaacagc atttaaaata cacatcatgc attcagtgta tgttaggtat 211800
aattaatgga ggcagaattt ttcattgctg tggtatgttt acagtggtta aatatttttt 211860
gaatataaac tttttggata taaatcaaca tttgtcaagg acgcccctgt ggagccgcct 211920
ggagagtggg tagaaattaa aggagccaga ggggaagggt gagcagcatt aattgggtgg 211980
cactcttgtg tccgtgtgtg tgtgtgtgtg tgtgtgtgtg tgtgtgtgtc ccgggaagag 212040
caggagcttt gcactcagtt gctcccagga cccagttctg gcttccaatt ggccactgtg 212100
tgctctgggc aacatgcttc acctctctga gctccatata tctgcaaagt gagaagaatg 212160
```

```
cctgacttgg ccaggcacgg tgactcatgc ctgtaatccc agcactttgg gaagccgagg   212220
cgggagatca cctgaggcca agagatagag accagcctgg cgaacttggc gaaaccctgt   212280
ctctaataaa aacataaaaa aatcagctgg gcgtgatggc gggtgcctgt aatctcaggt   212340
actggagagg ctgaggcatt agaattgctt gaacccggga ggtggaggct gcagtgagcc   212400
aagattgtac cactgaactc cagcctgggt gacagaacaa cactccgtct aaaaaaaaaa   212460
aaagaagaaa aatgcctgac tcacaagata gatcacagga tggtttggaa gattaaggga   212520
gacatcctgt gtagaaggaa catcagacag tgcttgacat agagtcgagg cttcaccagt   212580
gttggttttc ttcctgccta cttggagcag acggtgtaat tggaatgttc ttcatgggtg   212640
gtgacatcta tgctctgtgg ctgccactat gatcgtcttc tttctgtcct ttttctcagg   212700
ctttcagcct tctgtagcct tattatactc agcagctggg aaagactcaa caccagagac   212760
aaattctagt ttctccatgt taggtgccat aataatatcc agtgttacaa tggcagtcaa   212820
tataaaaata ggatctaata tacactactt tttaaatact gtaatacttt cagtgtgtac   212880
tttttcatat atattgtttg atactaatct tcatgtattt tttccaagta ttaattttta   212940
cagaataccc ctaatcacag atttatatat gccaatatct gtgactgaca cataatatca   213000
tatgaagttt ttccagcgtg acagtgttct aattaaaatg aacaaaaagc taggataaat   213060
acatacatac atacatacat acgtacattt cgggaccttt ggcttaagat actaatgtat   213120
tcatttagtt aatatgtatg actgcacatt tctaaacgta agaaaaaggt aaactcatta   213180
atcaccatga tgtattgcaa tcagtggggt agcccgtcat tacatatttg atgtaatatg   213240
taatggtaat aggtagtagg taaactattc taatccagct ctttattcat cgccaaaatg   213300
ataagaacac aggagctgtg tgctgtaatt catctcccct ttctgttctg aggcagaacc   213360
ctactagaaa aatgaatttc agggctctct gctccagtgt tccctgatct aaccaatact   213420
ttgggaattt ccatgtgtcc taccatttac caaaaacaaa attgttacaa ctttcaaaaa   213480
tttcaagtac ttgtatttga aaggtaaaag tcaatgaaaa cttaagtaaa tactccttt    213540 tcatttatac tgacagtccc tctaaatacg atcctggcta gaatgagctg ttttgctaat   213600
gtattatatt gtcatgcttc ttttctgat aattattca tatatattca tattctctgt     213660
tgtattagtt tgctagggct gctgtaacaa agttctccaa actgggtggc ttaaaacaac   213720
aaaaacttct tgtttcactg ttgcacgagc aagaagtctg aaatcaaggt gtcacagtgt   213780
tggttccttc caaggatgtg tgaaagaatg ttccatgtct ctcgtcctgg cttctggtgt   213840
cttcttggtg ctccgtggct tgaggatgct cctccatgtc ttgtcgatgg ccatcttctt   213900
gcatctcttc acataatgtt ctcccagtgt ttgcacttct gtctccaaat ttcccctttt   213960
tataaggaca ccagtcatat gggcttaagg gcccaccta ctccagtatg tatgacctcc    214020
tcttaactaa ttaaatctgc aacagccttg cttccaaata gggtcacatt ctaaggtacc   214080
aggcattagg acttcagcat aggaatttgg gggacataat tcaacccata atgtctgctc   214140
gcaagatagg ctttgcacat actttgtttg ccacgcaaaa tgggccattc acttttataa   214200
gtctgtcctg tagttccagg agctcttggt tttatataat gggggtttg gctctcaagg    214260 cattaaagca gaagaccgaa ggggaatctg aaggctggtc ttcgaaagca ctttcagaaa   214320
tgaatgttaa ggtctgggaa gaaaacatgt cactccaatt ttggagtctg ttggaaacgt   214380
ttgctgcaaa cttctatttc tctttcctga tgaattctgt cttaaaaaca gtaccctata   214440
taaggcctgt gtttggaatt taagtttggg ttttatttac ctgttacagg gacttagctg   214500
gggggtcatg agtgttact gatgagcctg gtgctgatat ataataataa gggcaaccag     214560
```

```
catttaatat atttgaaatg tcttcacatc tacatctcat tttcttttta aaatagcact 214620
tgggataggg gactagtaag aaagtgcaaa tattaacctt cacttaatat aggaaaaaag 214680
cgtgatatag ccaatgtcac gggacgagca gaaaaactgt cacctccatc ttctgttttt 214740 taacttttg ctctttccct tataatatct atgcacttaa tttaatgatt agccttgaga 214800
tattgccatt tcgcctttgc tttgttcttt gggaaagtta ttttaacgaa tgacgttttg 214860
ctttgttgat gatgattatt tgattagtgt gtgtgtgtgg tgggctggtg actgttaaga 214920
atgtagtttt gctaagaatt tgctaattaa ggaaagacca cacaatagca cacactttt 214980 tgcattgtcc aacatagtat aagagctgtc tgaggaaagg gatgcatttt tagttagaca 215040
catctggttc ttccgcacag gacacatgtt tcacccttcc aggctttcct gcacagatag 215100
gaatgtgttc taattaaaac ttgcatatgc ttttttttag gcttttttta cagaaaagta 215160
cttgcaggag catcctgaag accaggagaa ggttgagctg ctaaagcgac taatagcatt 215220
acaggtacag gacggctttc tctacactc ccagggaggc cacagtgtgg gacacccatt 215280
attctccagg gcttaagtct acaagcccac tcagggtgac ttttcttct tttttaacc 215340 cttgtgaaag caccacctat ctatgtattt gtttgctcgg ccggcagtta aactgcccag 215400
ggttgacgga gccttcttaa agctgagatc aaagttcatc ggctggggcc gggcccagtg 215460
gcttatgcct gtaatcccag cactttggga ggctgaagtg ggtggatcac ctgaggtcag 215520
gagttccaga ccagcctggc caacatggtg aaaccccatc tctactaaaa ctacaaaatt 215580
agccaggcat ggtggtgcat gcttgtaatc ccagctactc aggaggccga ggcaggagaa 215640
tcatttgaac tcaggaggca gaggttgcag tgagccgaga tcacgccaca gcactccagc 215700
ctgggcaaca gagtgagact ccatctcaaa aaaaaaaaa agaaaagttc atctgttggt 215760
ttcctggcat gtgtttccag ctgagagatg ctggcctcat ttttttctct caagacttca 215820
gtgggcagtg gtagaaaaca tgactaccaa attcagtcta agacttaaac ctatcagttg 215880
ctcatccacg gaagtgcccc aggactccgt tagatttgcc tcatcccaca gtccttcccc 215940
agtttagggc caacctgtat tcttggtgtg cacattttcc cacatcattg accaaagtcc 216000
atccagtcca caagtcctac actgagaagt ggccttccca ttggccagca ctatgtctag 216060
cagtttacct ttccaccca tccctccctt ccccaaccaa atcaaaacga tccctcttcc 216120
tgaagcacac tgcactcatt ttttgccctt ctttccagat gccctgcta acagaaggga 216180 tccgcatcca tggggagaaa ctcacagagc agctgaagcc gctgcatgag cggttgtctt 216240
cttgcttccg ggaactcaag gagaaagtag aaaagcacta tgggttata acactggtaa 216300 gcatgatcta agtagccttc acaccttttt ctaggctctg tgacctttta tgacactgat 216360 tcgttttca gatgccaagt gagttgtaat aacttagcta tggcatggaa atagtgaggc 216420
tggtgggaga gagtgtgttc ccctcttggt gaccttgagc agtccttgtg ctggtcagag 216480
gttctccaac ttgaacaact atcagaacct cccagcgc ctgtgaaaat acagatggct 216540
gagccatcat aaccctggag tttatgattc catagatctg ggggtggggc ccaagtagtt 216600
gcaattctga gaagttcccg ggtgatattg atgctgctgg tctggggaca acactttgag 216660
aaccactgta ctagaaatca ggccaggtgc agtggctcac agctgtaatc ccagcacttt 216720
gggaggccaa ggagggctga tcacttgtgg tcaggagttc gagaccagcc tggccaacat 216780
ggtgaaacac catctctact aaaaatacaa aaaattagct gggcatggcg tcaggcacct 216840
gtagtcccgg ctattcagga ggctgtggca agagaattgc ttgtacccag gaggcggagg 216900
```

```
tttcattgag ccgagatcac accattgcac tccagcctgg gcgacagagc gagactctat  216960
ctcaaaacaa acaaacaaac aaaccaaaat aactcaaagt tttctgaatc ctagacactg  217020
gttattcttg tgctgtctgg ccaaattctt acattttttc ctaatcttag aaatagtatc  217080
tattttgatg aaaagtatac agttttcacg cctttgaagg gaagaaggaa ttgtgaatta  217140
catttcatat gcatgtagct gctttcataa ttgtttttga cgagctcctc acagctacaa  217200
ttttcttttc tcctcctgag cagttcagtg gatagtgcgt gtatgtacta acctttctc   217260
tccagtgagt gatggtgtaa tacgttctag ctctacttat ctgcatttt ttctttgaat   217320
tcatcctgtt ctctttaatg gtcttattct ttttgttttg ttttgttttt gttttgaga   217380
caggatctct ctttgtcacc caggctgaag tgcagtgcga gatcacagct cactgcagcc  217440
ttgacttccc aggctcaagc catcctccca cctcagcttc ctgagtagct ggaactacag  217500
gtgtgctcca ccacacccag ctaatttttt tttgtttgtt ttttgagaca gagtctcgct  217560
ctgtcgccca ggctggagtg cagtggcacg atctcagctc actgcaagct ctgcctccca  217620
ggttcacacc attctcctgc ctcagcctcc tgagtagctg ggactacatg tgcccgccac  217680
catgcccagc tatttttttg cattttttagt agagacgagg tttcaccatg ttagccggaa  217740
tggtctcaat ctcctgacct tgtgatccgc ctgcctcggc ctcccaaagt gctgggatta  217800
caggtgtgag ccaccgcgcc cggcccacac ccagctaatt tttaaaactt ttttgtagag  217860
atagagtctc cctatgttgc ccaggctggc ctccaactcc tggactcaag caatcctcct  217920
gcctcagcct cccaaaatgc tgggattaca ggtgtgaacc agcatgccca gccctttaat  217980
ggtcttattc ttaaacccct tattttcaca ttatttcctc aaaccaaagc tctgagtttc  218040
ttttcatgct cttttctccc ccattcctgt ctgcccacct tcagtacagt ttcctccagg  218100
gtatcttttt gagcgtgtct ttcagccatt aagtgttcag tcgtgccttc ttcctaagat  218160
tgtgcctcct aacctgctgc tacttaagag ttttttctagg agcatttgtc ttttgcacac  218220
acattcctag acagcaaaga ctgtcttcga tttaatgagc ttagtcatta ttagaacttg  218280
gccggtatta gtgagtcatt ttcatatggt ggcatctggg ggtaatccta ctggtgacat  218340
ttctagagaa cataggattc accaggttaa gctgcatgtc tacagtgtca atctaacaat  218400
tttctctaac cccaatattc catatttaa aagactgaaa gcagctgagc tggggaagca   218460
gacggaaggt tttgctattt attggagagt gtgaggcaca tcttaatttt ttcctgtctc  218520
atttaggtag cagaaaatta tgacaacttt ttctctagtc ttagcatcag ggaggtttaa  218580
cctaagttgt acctatagct aacagtatca gtacatgcaa tatttaacaa tagaggcagc  218640
acaggcacca accaatcaga atggggtgcc agccacataa ccagtacaga tgggtactgg  218700
ttagccacaa gcaaacaggg cagctgtggc cagttcatag gggctggatt ccaggtccgc  218760
taaccatgtg gagtcatatg ttttcagcca cccaacttga cggagaggaa gcaaagccgc  218820
acggggtcta ttgtgctccc ctacatcatg tcttccactc tgcggaggtt gtccatcacc  218880
tcagtcactt cctctgtggt ttccacctct tcaaactcgt ctgacaatgc tccttccaga  218940
ccgggatctg atgggtaagg gtttcatctt taatctgcag gaagggtggg gtaacgcctt  219000
actaatgttt gcctttagcc acgcatcact cctttgagaa aaatagcctt tgggtcattc  219060
tcattgtctt cctcatgagg aatgtcatga ttagcagaat aataacaaca gttactaaaa  219120
atgaaaaatg acaaagaaat cacccataat cctaccacac tattacatac ctatagtcat  219180
tacctatttt tttcatcatt tccattttaa aaataaatt tttacatcta ttttatgaat   219240
aggttttata atcacatggc atgaaattcc aaaagaacca aacgatatat cacaaaaaat  219300
```

```
ctccctttaa tctgagactt cccactacag tagaagccct gcagtagccc cacccctaga   219360
gccagatgat gctaacattc aggttcttgg tagccccatg gcagctcttt ataggttcac   219420
aagcattgcg taattatgtg ttcttcccca cactttttt atatgaatgg tagaattttc    219480
tttactttgc ttttttcat ttaatattat atcttgaaac tctttccatt tcagaacata    219540
aaaagccccc tctttatgct ttctgtagct atagatatgg ctcattgtat gtatgtggca   219600
tgatacagat tgagtatccc tcatccaaaa tgcttgggc ccgaagtgtt ttgaatttcg    219660
gatgttttag tattttggga tatttgcgtt atacctgttc agcatcccta atccaaaaac   219720
cccaaatctg aaatgttcca gtaagcattt cctttgagcg tcatgtcagc attcaaatat   219780
ttcacatttt ggagcatttt ggattttgga ttttgggatt ggggatattc aacctgtata   219840
ttctaccagt gcttactggt ggttattcag ttgctttcac tctattactg ttacttcagt   219900
gtgacaatga ataaccttaa acacatgtta ttttgtacat atacaactat atcaatatgg   219960
gaaaaatctc gtatgtgaaa ttgctctgtc aaagatgtat atttgcaatt ttgaaaatta   220020
ttcctaaacc gacttccata agattatac cagtttacac tcccaccagc aacacacagg    220080
agtgcctagt tactcaccct agccaccaaa ctgtactctt agtctttta aatttacca     220140 atctgatagg tggaaaatat tttcttgtat acttttgtt tgttttttgg ttttgttta    220200 tttttcttgt tttgcctgaa gttgaacatc ttttcatttg tttgtagttt tattttctgt   220260
gacctgtggt caaatacttt ttctgttga attgttggcc ctttgtctgt gaatgagtt     220320 gaaatgtttt ctcctaattt ctcctttatc ttttgacttc taatttgttg cttctaattt   220380
tttattgagt tgtgctgatt tttttatgta gttatataat caatcttta ttttatgact    220440 tctgggtttt atttcacaat taaaggcctt tcccactcta agataacaaa aaaggtactt   220500
tttttttttc attgactttt agggtttcac tatttacaat tttgtctgta atcctttaga   220560
atttattcta ataagatg ttaagtatgg agccaacatt tttatttcca aatggctact     220620
caattcttct tataacattt agtgaacaag tcatctttt gtttttttg aaatgtcaat     220680 cttataaaaa atcaaatttc cacatactct ttagtctgtg dacattttt ttctatttct    220740 tagatttacc tgtctattca tgtatcagta ctatgcaatc ttaattatta tagatataaa   220800
acatttttta tttcctaata ttccttttca gaatttaatc tggctagtgt cgctattgct   220860
cactgttaga ttaacttgtc tagaatccta ttgctatttt tattaggatc atgttaaatg   220920
tatggactaa ctttaggaag agtgatggct ttttgatgct gaggcttcct tgccagaaac   220980
ataaaatgcc tttccatatg ttcaaattta aaatatttga aaggagttat agttgtgttc   221040
tttctgccta gcaatatatt taaataatat attgctaaaa tacaggaaag gtttaaaaga   221100
aaacaatgct ttattacttc atcactcaaa gataaccacc gttaaagctc aggtatataa   221160
tatcaaaaaa gtatgtttat tttttatttt ttattttat ttctttgaga tggagtctgg    221220
ctctgtcacc caggctggag tgcagtggtg cgatctcggc tcaccgcaag ctccgcctcc   221280
cgggttcacg ccattctcct gcctcagtct cccgagtagc tgagactaca ggcgcccgcc   221340
accatgcccg actaattttt tgtactttta gtagagatgg gtttcacca tgttagccag    221400 gatggtgtcg atcctctgac ctcgtgattc gcccgcctca gcttcccaaa gtgctggat    221460 tacaggcgtg agccaccaca cctggccctg tttattttt atacaagtgg aaaagcattg   221520
catctatcat gttgtgacct actgcttaat ttaatatagg tgatgagcat ttatgcatca   221580
ttaagtattt aaaatagtct tgaatataag ttatcagttg actcaccatt ttttcacaaa   221640
```

```
tgtttaattc cataatacaa taattacatc ataaaaataa cctacctgaa tgccaccctg    221700
cctggaaatc aaatatgtag tgtttcttaa attatgcatt cttttccgtt gatataggta    221760
tatttacata gctccaatta tagcatatag tttggtactt tgctgttctt tcttaccttt    221820
ttattataag catttgtcat gttgctgtgt aattttatt tatgtatttt tttttgagac    221880
agagtctcgt tgtgtcgccc aggctggagt gcagtggtgc aatctcggct cgctgcaacc    221940
tctgcctcct gggttcaagc tattctcctg ccttagcctc ttgagtagct gggactacag    222000
gcgcccacca ccacgcctgg tgaagtttta tattcttagt agagacgagg tttcaccgta    222060
ttggccaggc tggtctctaa ctcctgacct catgatccgc ccacctcggc ctctcaaagt    222120
gctgggatta caggcgtgag ccaccgtgcc tggctgtgta atctttatta ctatcagctt    222180
ttaccatcat ttttgatggc agttgacatt gcatcataca aatatgccat gattaattat    222240
tcttctacta tagaatattt aagctgtatc cttctttcta aacaattaac cataaaactt    222300
cattatagat tttaatacaa aaatatgtat gtaacttgta tcagtataaa atatatttt    222360 attaaaaact atagcaaaca tatttggaca tgtagctttc ttattaggat gcattcttag    222420
aagtggtggg attatttcta gaatgtagta atctagattc tagattactt ctagaatcta    222480
gattacattc tagtagtata tagtaatcta gattactaca ttctagtagt atgtagtttg    222540
tgggtaggat ttgaacacag gctatctggc tccagagttg tgctcttacc cactacataa    222600
aactgtctat tgaatctctt actttaaaga ttctgtcttt gcctgtacat tgaattaagc    222660
ccttcacttc ctgggataag atactcccta atattttcgt ccagtcgtct gatggtcttg    222720
tttctgtaca ttaacacctt gagatgtttg ttcagttgta attgaaaatt tagatttaga    222780
atctgagagt gaagtcatag gtcaagagta ggttgaggag gccgggcatg gtggctcacg    222840
cctctagcct tagcactttg ggagggctga ggtaggagca tcacttgagc ccaggagttt    222900
gagacagcct gggcaacagt ttgagaccag cctgggcaac atggtgaaac cccatccta    222960 ctaaaacaat acaaacttta gctgggcatg gtggtacaca cctgtagtcc cagccactca    223020
gaagtcaagg ttatagtgag atgtgatcgc accactgcac tccagcctga atgatgggag    223080
aaagaccctg tctcaaaaaa aaaaaaaaa aaaaaatagc ctaaagagtc ataactgctg    223140
gtactttcat agtgaatttt gattgcaagg tgatcagtat ttgtgatgtt tgtccttgtt    223200
cctggccaat agctcaatct ggagccact tttggagcgc agggcctcgt caggtgccag    223260
agttgaagat ctgtccctta gagaggagaa cagcgagaac cggatcagca gtttaagag    223320 aaaagactgg agtctgagca agtcccaggt cattgcagag aaagcaccag aacccgatt    223380 gatggtaaaa aacagaaaag aaaaaaagaa atctctggag gcttgccccc ctctcccctg    223440
tacccaggca tatcaccatc ccctcccaga ttgaagctgg gctatggctt gtttcaggac    223500
tcagcagcct gggttagtgt caggtcgcag attgtggtaa ggaaagcaca tacctcatga    223560
gaagttcgag tctataaatc aacattggtg aagatcttgt acccacaatg taaacatgtg    223620
ggttgatgct tagagctgtc gttcttgcca ctctgtcccc tgagtcaatc caaacattgt    223680
catttctctt cttttaatttt tttaaaaggt acttttcctt ccatatcaag ttgttaaatg    223740
tggcaagacc accttttcct gagaatcagg gtggcttatt tccaacataa atgacacagc    223800
ccaactgtga tcagaagaat caagtctgtg gccattcaga aaataatctg tggttcagtg    223860
gttctagtca gtgcctgttc ggtgttgccc atcatatgac aatgcttaaa aatcgctcct    223920
tcagttaagt ccttttccaa gtgtcttctc agaagacaag gctgttgaga gcattgttga    223980
gctcagcctt cctcaccgtg aaaatgtttt gcttttctc tctggtccta gagcccaacc    224040
```

```
agaaaagcac aaaggccaaa gagtctccag ttgatggata atcggctatc accatttcac  224100
ggttcttcac ctcctcagtc aacacccttg agcccacctc cactcactcc caaagccacc  224160
aggaccctaa gtaagttttc ctgtattcct tatagtcttt ttactaggga atggagtatg  224220
tttatgcatc tgggcagttt gtaactaaac cagccagaat gtatgtaaga ccattgtaaa  224280
actggttcaa tttcgtgttc gtgtattata cagttagact ggagtttggc aaggaggcca  224340
ctaggactca ttaaacttt ctggatagtg atccaaaggg cattagtgtc agttttataa   224400
ttgtgaaggt ataaatgagg cagatctgca ctaggactag acagataaca agtaacttac  224460
aagctaacca ttagttaggt agacctgaac agggacaaga aatagaccca ttccatctac  224520
tgcttatagt ctggcttggg gaaccagcag tgcacaacac ttgagaagaa ttgcaaagta  224580
cccatagtcc agaggcatgg tagagggata aatctatcga gccagatggg agacaattgt  224640
caaccaagag ttagagataa tcagttacag tttcctggag gaagtggata ttttcctaag  224700
cacttgggct atatcagaga acagaataat accatacatt ccagaaaatg ttgtcatctt  224760
cagcttaata ctaaaaccct gaacaaaaaa agttttggcc aggcacggta gctcacgcct  224820
gtaatcccag cactttggga ggccgaggca ggtgaatcac gaggtcagga gatcgagatc  224880
atcctggcta cagtgaaacc ccatctgtac taaaaaatac aaaaaattag ctgggcgtga  224940
tggtgggtgc ctgtagtccc agctacctgg gaggctgagg caggagaatg gcgtgaaccc  225000
gggaggcgga gcttgcagtg agctgagatc gcgccactgc actccagcct gggcaacaga  225060
gcgagactcc atctcaaaaa aacaaaaata aaaaaaataa agttttttgct tcagaacacc  225120
ttgtggagct cttgaaactt ctggcgaggg cgtcacctgt gtgatgtggg gtaagaagtc  225180
ttcttcgttc tatccgcaga aaccatagaa tgtggctttc atcagttggt tgaccaggtt  225240
ggcttaggtg ttacagtgcc agcaacattt ccatgagctt ccttgctcag tgcctctctc  225300
tgccgcctgc actttctgtc atttctaggc tccccatcgt tgcagacaga tggaatcgcg  225360
gccactcctg tcccacctcc acctcccccc aaaagcaagc cctatgaagg cagccagagg  225420
aactccactg aggtagggaa atcacagctg gcaactgtgg ccaggagcg ccactcctgg   225480
gaaggcagca tcaggttttc caggctcttt agtgggcagg tttgctcata gacctgtcac  225540
tgcagtcgat tcttggctca ttcctgaaac cacaggagat agagaagttt tcaatgggaa  225600
ggacagacat gcaagcagat gatgaaggta gaggcaggtg ttctctgtac ctcgtcctgg  225660
gtacctgtga aataagccgt gagttctagt tcaccttttt aggggggcgg gggcagggtc  225720
tggctctgtc acccaggctg gagtgcaata gtgcgatcat agctcactgc agcctcaaac  225780
tcctgggctc aagtgattct cctaccttgg cctctcaatt agctgggact acaggcatgt  225840
gccaccatgc ccagctaatt ttttaatctt ttgttgaaat ggggtctctc catattgccc  225900
aggctgatct caaactcctg gcctcaagtg atccccccca cccacctcag ccttccaaag  225960
tgctgagatt acagatgtga gccactgcct gcccccagcc ctctatttca catttgaaga  226020
gtttacttct tctgaataaa ggacagtcat tctggagtga cctcagatgg gtttccttca  226080
gtcatttaac aaatgacttt taagtgcctc ctgtctatac gccaggaacc caagtgttgg  226140
ggatatggca gcgagagaga gagagaaaat gtgtgtgtgt gtgtgtgtgt gtgtgtgtgt  226200
gtgcgcgcgc gcgcacgcac gcacgcacgc acgcgtgtgt ctgattagct catgggaaac  226260
aaggaggata agtcagtgta gttttccatt tcactttgca aagcctgtgt agataaactc  226320
agatcaatta gaagctaaag cagaatatga gaaataggag gagaaggcag aattgggaag  226380
```

```
aaagctaaga cctgcttcta attttgtgtt tctgcttctg cagctcgctc ccccactgcc    226440
tgtccgaaga gaagccaaag caccaccccc tccacctcca aaggctcgga agtctggcat    226500
ccctacttcc gagcctggat cccagtaagg atcttgccct ccctgcaaca ccgagtgcct    226560
tagacagctg ctgcctgaga actggcctcc agccggtgtc ctcattccat ggggctccct    226620
gctgactgca tttcctgatc tgggatgatg tttaccagcc caaaaccagt catgttcttc    226680
caaaagcttc tctttgatag aattttgagg ccatgccacc tcccttccag tccacatgga    226740
attccagaat cagtcacagc ctctgatttt ttccaagaag agattgcctt caccattgtt    226800
aaatgtcagc ctgtacggca gagacatggt ggtctgcaca agcctggaca agttcttcca    226860
tattgatggt ggagcaaccc ctgtaatcta ctccttggaa ggattttttg ctttgcttat    226920
gaaaagctgt gcttgagact taggtacttt tctcacgtgg acacactgat cccatcccat    226980
attgcatctt ggaagagatg gatatcaagt acactttggt agctgaaata atcatatctt    227040
tctgatgtct attgtatctc ctttgaggaa aagaacacac attttaatg gagattggct    227100
gctttcaggt atgtgtgtct atcattgaaa gagcatggac tcaaacatca gccctgagtt    227160
cttgagtcca cccaactccc atcttcttgt ggcacaggaa agctgccctc tccctctccc    227220
accacactcc tgactaatgg ccttcactgc gtcgcagtca ctccttccct acggacttct    227280
ttgaagctct tccttttgca catacggctt tttttttttt ttttttttt tgtcctatta    227340
cctcctctga gcgcaaatca ctggctacaa gggacttacc agtctggatt cagcagtttc    227400
tttctaaaa cccatttggg tgactcagca gccgcatctg ctacctgatt ttatcctgga    227460
gaatacagtg caatatttct ctttgattat ttattcctct tgattgtgga attaatttga    227520
ttgcttgcta atggtactag tagtactcct ttcagaagaa aaaatggagc gatttaggtg    227580
accaaatatt acatacataa atagccacat gaagttttag acgtttggac ttgaagcctc    227640
aaagatcaac caaccagtcc ccttatttag taaataagga aattgaggct acacacagaa    227700
aattgtgcta cagattatta ctaataaccc agcttgctaa attaggctat acctaggtaa    227760
tctctagaag acaactctga cagactcttt aatatttacc cctggttgga acaatatttg    227820
aaatgtccca gatatttcta tgctacttag atatttgtgg caaagcagaa agcttttga    227880
ctgtgaaggc agaggtcagc actgggggaa acttgctggt ggtctctccc acaaccttgc    227940
ccagagtcct ttccactaag gaggtgaaga gaacagagaa agagatttcc atttctgctg    228000
ccagagctgg tatttgcctg cctgattctc tgtgtttcct gtttcaccgc caccctttca    228060
ggagagaact acaccagttc atcatgaggg tcagggaagc aaaagctctc agatgtgtcc    228120
agggcgttac ttaagaaatg agtatgcaga ttctggaagg ggtgtggaaa aggtgatcct    228180
ttaccccac ccaggaaaac ctgcattgtg ctagcatgga agaatcatgg gctttggaat    228240
taaacccatt tggtggaatt aaacccattt ggtttcaaat cccagttatg acatctgtta    228300
actttgcaaa ctcacaaaaa ttatttgaaa tta                                 228333
```

METHOD FOR IDENTIFYING COMPOUNDS USEFUL FOR TREATING AND/OR PREVENTING DISEASE-ASSOCIATED BONE LOSS

FIELD OF THE INVENTION

The invention relates to the field of diseases associated with bone loss, and more specifically to a new method for identifying compounds useful for treating and/or preventing diseases associated with bone loss.

BACKGROUND OF THE INVENTION

Bone is a dynamic tissue that is continually remodeled throughout life depending on factors such as nutrition and the load the bone must carry. Normal bone formation depends on the delicate balance between new bone addition and old bone resorption. Bone formation is based on the deposition of bone matrix by osteoblasts and bone resorption and more specifically mineralized tissue, chiefly calcium carbonate and calcium phosphate resorption in vertebrates is achieved by osteoclasts. Typically, in a normal adult, about 5-10% of bone is replaced by these processes annually.

These osteoclasts are multinucleated cells of up to 400 μm related to macrophage and other cells that develop from monocyte cells, which are actively motile cells that migrate along the surface of bone. Like macrophage, osteoclasts are derived from haematopoietic progenitor cells. The bone resorption is initiated when an osteoclast attaches to the surface of mineralized bone, forms a tight "sealing zone" and secretes necessary acids and proteases that initiate the resorption of mineralized tissue from the bone. After a period of several hours to days, the osteoclast detaches from the bone, leaving a pit on the bone surface. Under normal conditions, the pit is a target for osteoblasts, which deposit a material that ultimately becomes new bone.

Bone loss can result when the bone resorptive process is dominant over the bone formative process. Diseases associated with bone loss are usually accompanied by increased osteoclast activation. Such diseases include any bone loss resulting notably from an estrogen deficiency after the menopause but not only and comprise osteoporosis, osteopenia due to bone metastases, periarticular erosions in rheumatoid arthritis, primary hyperparathyroidism, hypercalcemia of malignancy, Paget's disease of bone, periodontal disease, immobilization induced osteopenia, and glucocorticoid treatment.

As an example, there are currently 20 million people with detectable fractures of the vertebrae due to osteoporosis in the United States. In addition, there are 250,000 hip fractures per year attributed to osteoporosis. This clinical situation is associated with a 12% mortality rate within the first two years, while 30% of the patients require nursing home care after the fracture.

Since diseases of bone loss are associated with increased activity of osteoclast, it is important to understand the mechanisms by which osteoclasts are activated in these disease states, and to devise rational and therapeutic means to inhibit or reduce this activation.

Thus, the aim of the present invention is to elaborate new screening methods which can be useful for treating and/or preventing bone loss diseases, and to use such compounds to prepare a drug for treating and/or preventing bone loss diseases.

BRIEF DESCRIPTION OF THE DRAWINGS

FIG. 8A shows that the expression of osteoclast differentiation markers is normal in osteoclasts differentiated from Dock5$^{-/-}$ BMMs.

FIG. 8B shows the ability of Dock5$^{-/-}$ preosteoclasts to respond to M-CSF and RANKL was not the result of a compensatory increase in Dock1 or Dock2 expression.

FIG. 8C shows M-CSF-driven phosphorylation ERK and p38MAP kinase.

DESCRIPTION OF THE INVENTION

Figure 1:
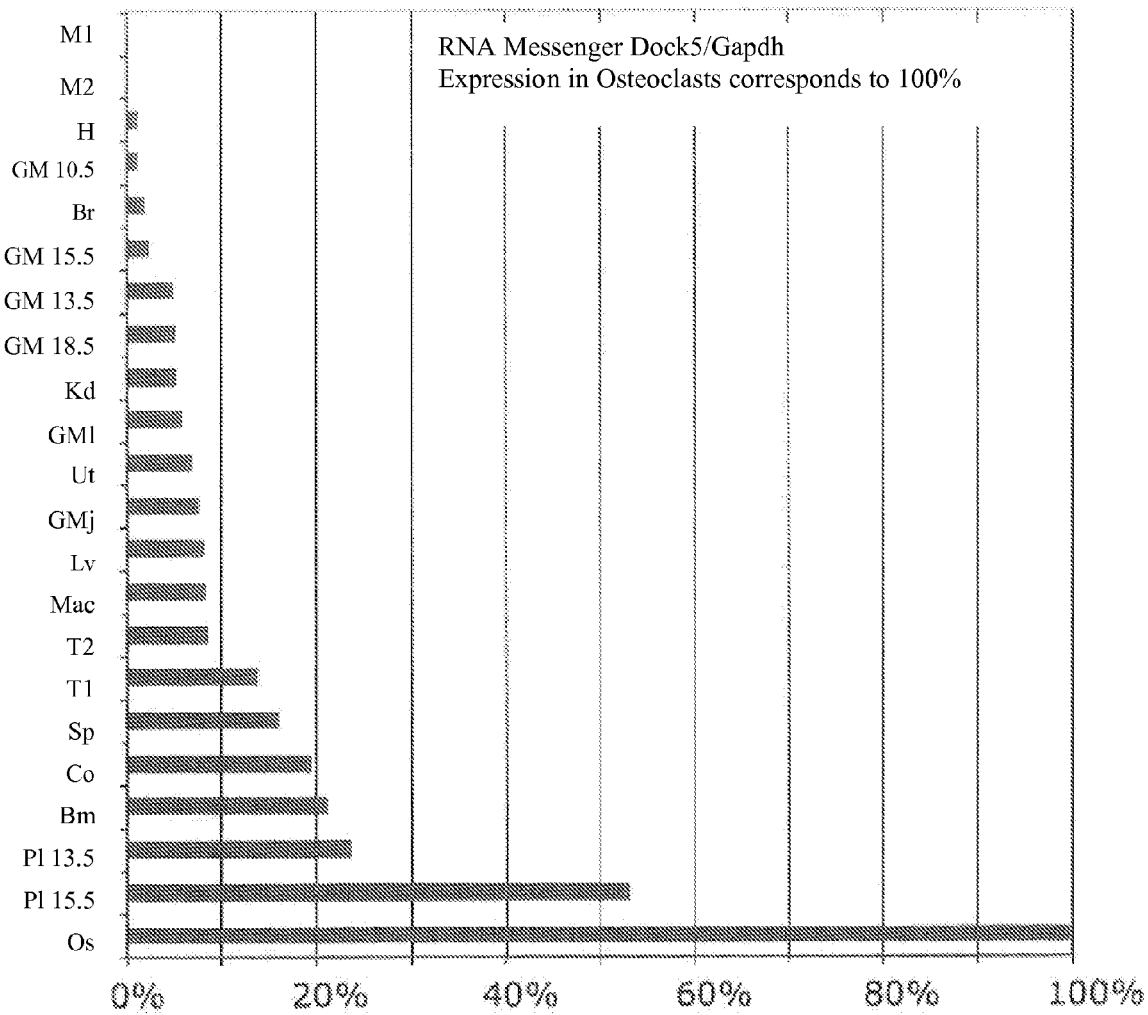
Figures 1A and 1B show the expression of Dock5 in different mouse tissues.
Figure 1:
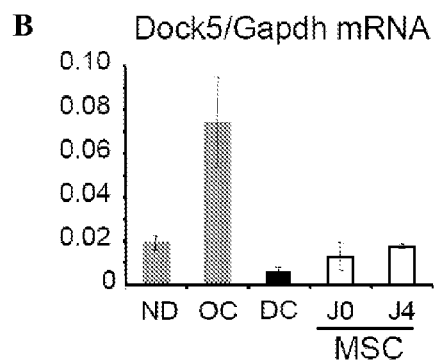

The inventors have presently identified the DOCK5 protein is implicated in sealing zone formation and consequently in bone resorption. Thus, DOCK5 corresponds to a new therapeutic target for treating and/or preventing bone loss diseases. Finally, the inventors have used yeast exchange assay (YEA) for identifying inhibitors of DOCK5, which inhibitors can be useful for treating and/or preventing bone loss diseases.

Thus, in a first object, the present invention is directed to a method for identifying a compound which inhibits the activation of RAC GTPase, more specifically RAC1/2 GTPase, by DOCK5 protein comprising the steps of:

coexpressing the DOCK5 and the RAC proteins in a cell, wherein said DOCK5 protein induces the conversion of inactive RAC, which inactive RAC is bound to GDP, to active RAC, which active RAC is bound to GTP, contacting or not said cell with said compound, determining the conversion of inactive RAC to active RAC, more specifically the conversion of inactive RAC1/2 to active RAC1/2, in the presence or absence of said compound, and selecting the compound inhibiting the conversion of inactive RAC to active RAC, more specifically the conversion of inactive RAC1/2 to active RAC1/2.

The selected compound is useful for treating disease associated with bone loss. In fact, the inventors have established that the conversion of inactive RAC to active RAC by DOCK5 is associated with the sealing zone formation.

According to the present invention "RAC1/2" means "RAC1 and/or RAC2". In fact, the inhibition of the activation of RAC1 GTPase and/or of RAC2 GTPase give rise to the same kind of results, while both RAC1 and RAC2 are involved in (and thus necessary for) the osteoclast differenciation and resorption functions.

Advantageously, the present invention is directed to a method for identifying a compound which inhibits the activation of RAC1/2 GTPase and which is useful for treating disease associated with bone loss by DOCK5 protein comprising the steps of:

coexpressing the DOCK5 and the RAC proteins in a cell, wherein said DOCK5 protein induces the conversion of inactive RAC, which inactive RAC is bound to GDP, to active RAC, which active RAC is bound to GTP.

contacting or not said cell with said compound, determining the conversion of inactive RAC to active RAC in the presence or absence of said compound, selecting the compound inhibiting the conversion of inactive RAC to active RAC since this conversion is associated with the sealing zone formation, and testing the inhibition of bone resorption, corresponding to the testing of mineralised matrix resorption by osteoclasts, by the selected compounds.

As an example of disease associated with bone loss, one can cites menopause, osteoporosis, osteopenia due to bone metastases, periarticular erosions in rheumatoid arthritis, primary hyperparathyroidism, hypercalcemia of malignancy, Paget's disease of bone, periodontal disease, immobilization induced osteopenia, or in glucocorticoid treatment. Preferably, said disease associated with bone loss is osteoporosis.

Results from the cellular and bone resorption assay systems used herein are widely accepted in the art as predictive of in vivo effects. As the bone resorption assay uses material that includes bone marrow isolated cells, it is an ex vivo assay. Thus, the showing that the inhibition of RAC activation by DOCK5 inhibits bone resorption in these assays is evidence of the clinical utility of inhibitors of this specific activation for treating osteoporosis. Various scientific publications, such as Carano et al. (1990); Blair & Schlesinger (1992); Schlesinger & Blair (1992); Vaananen et al., 1990; all support the fact that such assays are accepted as being predictive of in vivo activity.

Methods for determining the conversion of inactive RAC to active RAC are well known from the skilled person. As an example of such methods, one can cites the methods disclosed in the examples and in COTE & VUORI (*J. Cell. Sci.*, vol. 115, p: 4901-4913, 2002).

In a preferred embodiment, the method of the invention further comprises the step of testing the inhibition of bone resorption by the selected compound.

In another preferred embodiment, the method of the invention includes a further step of comparing the conversion of inactive RAC to active RAC in presence of the tested compound and in the absence of said compound. Said inhibition of bone resorption can be simply tested by method well known from the skilled person, such as the one disclosed in the examples, wherein mineralised matrix resorption by osteoclasts is tested by culturing said osteoclasts on calcium phosphate substrates and mineralised matrix resorption is determined by VON KOSSA staining.

As used herein, the term "compound" refers to a natural or synthetic compound, such as chemical or peptidic compound.

Preferably, the compounds are chosen in the group consisting in:

4-[5-(4-bromophenyl)-3-(4-nitrophenyl)-4,5-dihydro-1H-pyrazol-1-yl]-4-oxobutanoic acid;

2,2,2-trichloro-N-(1,1-dioxido-2,3-dihydro-3-thienyl)-N-(4-methylphenyl)acetamide;

3-(3-chlorophenyl)-7-methyl-4-methylene-3,4-dihydro-2 (1H)-quinazolinone;

3-[4-(3-bromobenzylidene)-3-methyl-5-oxo-4,5-dihydro-1H-pyrazol-1-yl]benzoic acid;

N-2,1,3-benzothiadiazol-4-yl-5-bromo-2-furamide;

1-acetyl-4-(2-chloro-4-nitrophenyl)-2-methylpiperazine;

3-(3-methoxybenzylidene)-5-(4-methylphenyl)-2(3H)-furanone;

3-[5-(3,4-dichlorophenyl)-2-furyl]acrylic acid;

(2-chloro-4-{[5-(2-chlorophenyl)-6-(ethoxycarbonyl)-7-methyl-3-oxo-5H-[1,3]thiazolo[3,2-a]pyrimidin-2 (3H)-ylidene]methyl}-6-methoxyphenoxy)acetic acid;

4-{[4-(diphenylmethyl)-1-piperazinyl]sulfonyl}-2,1,3-benzothiadiazole;

4-[4-phenyl-5-(2-thienyl)-1H-imidazol-2-yl]-1,2-benzenediol;

N-(3,4-dimethoxyphenyl)-4-[methyl(phenylsulfonyl) amino]benzamide;

1-[(2-hydroxyphenyl)carbonothioyl]-3-phenyl-5-(trifluoromethyl)-4,5-dihydro-1H-pyrazol-5-ol;

2-methoxyethyl 4-[(4-tert-butylbenzoyl)amino]benzoate;

N-(2,3-dichlorophenyl)-3-(5-methyl-2-furyl)acrylamide;

N-(4-fluorophenyl)-3-[3-(trifluoromethyl)phenyl]acrylamide;

3-(2-furylmethyl)-2-(2-hydroxyphenyl)-2,3-dihydro-4 (1H)-quinazolinone;

N-(4-ethoxyphenyl)-2-{[5-(4-methoxyphenyl)-1,3,4-oxadiazol-2-yl]thio}acetamide;

5-(4-nitrobenzylidene)-2-thioxo-3-[3-(trifluoromethyl) phenyl]-1,3-thiazolidin-4-one;

(3,5-dichlorophenyl)[(phenylsulfonyl)carbonyl]amine;

N-(2-bromophenyl)-3-(5-methyl-2-furyl)acrylamide;

2-(2-chlorophenoxy)-N-[2-chloro-5-(trifluoromethyl) phenyl]acetamide;

N-[4-(4-acetyl-1-piperazinyl)phenyl]propanamide;

8-[(dimethylamino)methyl]-9-hydroxy-2-methyl-4H-pyrido[1,2-a]pyrimidin-4-one;

4-tert-butyl-N-[1-{[(2-methoxyphenyl)amino]carbonyl}-2-(2-thienyl)vinyl]benzamide;

2-chloro-N-(3-chloro-4-methoxyphenyl)benzamide;

2,6-di-tert-butyl-4-(2,3-dihydro-1H-perimidin-2-yl)phenol;

3-benzyl-2-(2,6-dichlorophenyl)-2,3-dihydro-4(1H)-quinazolinone;

1-(3,4-dichlorobenzyl)-1H-indole-3-carbaldehyde;

N-[5-(1-adamantyl)-1,3,4-thiadiazol-2-yl]-N'-phenylurea;

N-(3,4-dichlorophenyl)-N'-{5-[(4-methylphenoxy)methyl]-1,3,4-thiadiazol-2-yl}urea;

N-(2,3-dihydro-1,4-benzodioxin-6-yl)-2-(1-naphthyloxy)acetamide;
N-[4-(4-acetyl-1-piperazinyl)phenyl]-4-ethoxy-3-nitrobenzamide;
N-(2-chlorophenyl)-3-(4-fluorophenyl)acrylamide;
1-[(dimethyl-lambda~4~-sulfanylidene)amino]-2-methoxy-4-nitrobenzene;
5-benzylidene-1-(2-chlorophenyl)-2,4,6(1H,3H,5H)-pyrimidinetrione;
4-ethyl-5,6-dimethyl-2-phenylpyrimidine;
2-(3-chlorobenzylidene)-1H-indene-1,3(2H)-dione;
5-{5-[(3-methyl-5-oxo-1-phenyl-1,5-dihydro-4H-pyrazol-4-ylidene)methyl]-2-furyl}-1H-isoindole-1,3(2H)-dione;
N-(2,5-dimethylphenyl)-3-(4-methoxyphenyl)acrylamide;
2-({2-[(4-nitrophenyl)amino]ethyl}amino)ethanol;
N-(3-methoxyphenyl)-4-propoxybenzamide;
2-(4-hydroxyphenyl)-3-phenyl-2,3-dihydro-4(1H)-quinazolinone;
4-methyl-1-(2-nitrobenzoyl)piperidine;
2-hydroxy-N'-[(2-methylphenyl)sulfonyl]benzohydrazide;
4-(1,3-benzothiazol-2-yl)butanoic acid;
4-(3-methylbenzylidene)-1-phenyl-3,5-pyrazolidinedione;
4-(2,4-dichlorophenoxy)-N-(2-ethoxyphenyl)butanamide;
N-(2-methoxyphenyl)-N'-(phenylsulfonyl)benzenecarboximidamide;
N-[2-(2-chloro-5-iodophenyl)-1,3-benzoxazol-5-yl]-2-methylpropanamide;
5-(4-butoxyphenyl)-3-cyclohexyl-1,2,4-oxadiazole;
N-(3,4-dichlorophenyl)-N'-4H-1,2,4-triazol-4-yl urea;
6-chloro-4-phenyl-3-[3-(3,4,5-trimethoxyphenyl)acryloyl]-2(1H)-quinolinone;
6-bromo-4-phenyl-3-[3-(3,4,5-trimethoxyphenyl)acryloyl]-2(1H)-quinolinone; and
N-(1H-1,2,3-benzotriazol-1-ylmethyl)-4-nitro-1,2,5-oxadiazol-3-amine.

More preferably, the compounds are chosen in the group consisting in:
4-[5-(4-bromophenyl)-3-(4-nitrophenyl)-4,5-dihydro-1H-pyrazol-1-yl]-4-oxobutanoic acid
2,2,2-trichloro-N-(1,1-dioxido-2,3-dihydro-3-thienyl)-N-(4-methylphenyl)acetamide
3-(3-chlorophenyl)-7-methyl-4-methylene-3,4-dihydro-2(1H)-quinazolinone
3-[4-(3-bromobenzylidene)-3-methyl-5-oxo-4,5-dihydro-1H-pyrazol-1-yl]benzoic acid
N-2,1,3-benzothiadiazol-4-yl-5-bromo-2-furamide
1-acetyl-4-(2-chloro-4-nitrophenyl)-2-methylpiperazine
3-(3-methoxybenzylidene)-5-(4-methylphenyl)-2(3H)-furanone
3-[5-(3,4-dichlorophenyl)-2-furyl]acrylic acid
(2-chloro-4-{[5-(2-chlorophenyl)-6-(ethoxycarbonyl)-7-methyl-3-oxo-5H-[1,3]thiazolo[3,2-a]pyrimidin-2(3H)-ylidene]methyl}-6-methoxyphenoxy)acetic acid
4-{[4-(diphenylmethyl)-1-piperazinyl]sulfonyl}-2,1,3-benzothiadiazole
4-[4-phenyl-5-(2-thienyl)-1H-imidazol-2-yl]-1,2-benzenediol
N-(3,4-dimethoxyphenyl)-4-[methyl(phenylsulfonyl)amino]benzamide
1-[(2-hydroxyphenyl)carbonothioyl]-3-phenyl-5-(trifluoromethyl)-4,5-dihydro-1H-pyrazol-5-ol
2-methoxyethyl 4-[(4-tert-butylbenzoyl)amino]benzoate
N-(2,3-dichlorophenyl)-3-(5-methyl-2-furyl)acrylamide
N-(4-fluorophenyl)-3-[3-(trifluoromethyl)phenyl]acrylamide
3-(2-furylmethyl)-2-(2-hydroxyphenyl)-2,3-dihydro-4(1H)-quinazolinone
2,6-di-tert-butyl-4-(2,3-dihydro-1H-perimidin-2-yl)phenol
3-benzyl-2-(2,6-dichlorophenyl)-2,3-dihydro-4(1H)-quinazolinone
1-(3,4-dichlorobenzyl)-1H-indole-3-carbaldehyde
N-(4-ethoxyphenyl)-2-{[5-(4-methoxyphenyl)-1,3,4-oxadiazol-2-yl]thio}acetamide
5-(4-nitrobenzylidene)-2-thioxo-3-[3-(trifluoromethyl)phenyl]-1,3-thiazolidin-4-one
(3,5-dichlorophenyl)[(phenylsulfonyl)carbonyl]amine
N-(2-bromophenyl)-3-(5-methyl-2-furyl)acrylamide
2-(2-chlorophenoxy)-N-[2-chloro-5-(trifluoromethyl)phenyl]acetamide
N-[4-(4-acetyl-1-piperazinyl)phenyl]propanamide
8-[(dimethylamino)methyl]-9-hydroxy-2-methyl-4H-pyrido[1,2-a]pyrimidin-4-one
4-tert-butyl-N-[1-{[(2-methoxyphenyl)amino]carbonyl}-2-(2-thienyl)vinyl]benzamide
2-chloro-N-(3-chloro-4-methoxyphenyl)benzamide
N-[5-(1-adamantyl)-1,3,4-thiadiazol-2-yl]-N'-phenylurea
N-(3,4-dichlorophenyl)-N'-{5-[(4-methylphenoxy)methyl]-1,3,4-thiadiazol-2-yl}urea
N-(2,3-dihydro-1,4-benzodioxin-6-yl)-2-(1-naphthyloxy)acetamide
N-[4-(4-acetyl-1-piperazinyl)phenyl]-4-ethoxy-3-nitrobenzamide
N-(2-chlorophenyl)-3-(4-fluorophenyl)acrylamide
1-[(dimethyl-lambda~4~-sulfanylidene)amino]-2-methoxy-4-nitrobenzene
5-benzylidene-1-(2-chlorophenyl)-2,4,6(1H,3H,5H)-pyrimidinetrione; and
4-ethyl-5,6-dimethyl-2-phenylpyrimidine.

As used herein, the expression "DOCK5 protein" refers to a polypeptide comprising at least the DHR2 domain of the protein DOCK5 corresponding to the amino acid 1132 to 1661 of the DOCK5 protein from *Mus musculus* SEQ ID NO:1 and derivatives thereof.

Therefore, the present invention is directed to a method for identifying a compound which inhibits the activation of RAC GTPase, more specifically RAC1/2 GTPase, by DOCK5 protein comprising the steps of:
coexpressing a polypeptide comprising at least the DHR2 domain of the protein DOCK5 and the RAC proteins in a cell, wherein said polypeptide induces the conversion of inactive RAC, which inactive RAC is bound to GDP, to active RAC, which active RAC is bound to GTP,
contacting or not said cell with said compound,
determining the conversion of inactive RAC to active RAC, more specifically the conversion of inactive RAC1/2 to active RAC1/2, in the presence or absence of said compound, and
selecting the compound inhibiting the conversion of inactive RAC to active RAC, more specifically the conversion of inactive RAC1/2 to active RAC1/2.

The full length Dock5 protein has an aminoterminal SH3 domain, between aminoacids K11 and E68, followed by the DHR1 domain, between aminoacids G440 and E682, and the DHR2 domain between aminoacids M1132 and Y1661 (FIG. 3E).

Preferably, said DOCK5 protein corresponds to SEQ ID NO:1.

Again preferably, said DOCK5 protein corresponds to SEQ ID NO:4 corresponding to *Homo sapiens* DOCK5 protein.

As used herein, the expression "RAC protein" refers to SEQ ID NO:2 and derivatives thereof.

According to a preferred embodiment, said cell is an eukaryotic cell, preferably a yeast cell.

Advantageously, said method comprises the expression of any protein, capable to interact with the active RAC protein and not with inactive RAC protein. One skilled in the art knows such protein known as a GTPase effector. According to a preferred embodiment, the protein capable to interact with the active RAC protein is chosen in the group comprising PAK1 protein.

As used herein, the expression "PAK1 protein" refers to the SEQ ID NO:3 and derivatives thereof.

As used herein, the term "derivatives'" refer to a polypeptide having a percentage of identity of at least 80% with amino acid 1132 to 1661 of SEQ ID NO: 1, SEQ ID NO: 2, SEQ ID NO:3, SEQ ID NO:4 or SEQ ID NO:9, or orthologs thereof, preferably of at least 90%, as an example of at least 95%, and more preferably of at least 99%.

As used herein, "percentage of identity" between two amino acids sequences or two nucleic sequences, means the percentage of identical amino-acids or nucleotides, between the two sequences to be compared, obtained with the best alignment of said sequences, this percentage being purely statistical and the differences between these two sequences being randomly spread over the amino acids sequences. As used herein, "best alignment" or "optimal alignment", means the alignment for which the determined percentage of identity (see below) is the highest. Sequences comparison between two sequences are usually realized by comparing these sequences that have been previously align according to the best alignment; this comparison is realized on segments of comparison in order to identify and compared the local regions of similarity. The best sequences alignment to perform comparison can be realized, beside by a manual way, by using the global homology algorithm developed by SMITH and WATERMAN (*Ad. App. Math.*, vol. 2, p: 482, 1981), by using the local homology algorithm developed by NEDDLEMAN and WUNSCH (*J. Mol. Biol.*, vol. 48, p: 443, 1970), by using the method of similarities developed by PEARSON and LIPMAN (*Proc. Natl. Acd. Sci. USA*, vol. 85, p: 2444, 1988), by using computer softwares using such algorithms (GAP, BESTFIT, BLAST P, BLAST N, FASTA, TFASTA in the Wisconsin Genetics software Package, Genetics Computer Group, 575 Science Dr., Madison, Wis. USA), by using the MUSCLE multiple alignment algorithms (Edgar, Robert C., *Nucleic Acids Research*, vol. 32, p: 1792, 2004). To get the best local alignment, one can preferably used BLAST software, with the BLOSUM 62 matrix, or the PAM 30 matrix. The identity percentage between two sequences of amino acids two nucleic sequence is determined by comparing these two sequences optimally aligned, the amino acids sequences being able to comprise additions or deletions in respect to the reference sequence in order to get the optimal alignment between these two sequences. The percentage of identity is calculated by determining the number of identical position between these two sequences, and dividing this number by the total number of compared positions, and by multiplying the result obtained by 100 to get the percentage of identity between these two sequences.

Advantageously, said cell further comprises a reporter gene under the control of a promoter sequence, and said RAC and PAK1 proteins are each fused either with a transactivation domain or with a DNA binding domain specific of said promoter sequence, wherein the interaction of RAC with PAK1 results in the induction of expression of the reporter gene.

The method corresponds to the Yeast Exchange Assay (YEA) as disclosed in DE TOLEDO et al. (*FEBS*, vol. 480, p: 287-292, 200) and International Patent application PCT WO 2005/064007 using the DOCK5 and the RAC protein.

Thus, the disclosure of YEA in Patent application PCT WO 2005/064007 (page 6, "description de l'invention" paragraph, to page 23) are incorporated herein by reference.

The term "reporter gene" is well known from the skilled person and can correspond to an auxotrophic marker or to a gene coding for a protein which can be simply detected such as GFP, luciferase or β-Gal.

In this embodiment, the determination of the conversion of inactive RAC to active RAC is done by determining the expression of the reporter gene. The inhibition of the expression of the reporter gene corresponding to an inhibition of the conversion of inactive RAC to active RAC.

In another embodiment, the present invention provides a method for the selection of compounds, which permit to decrease the level of expression of a DOCK5 gene (SEQ ID No 10) in diseases associated with bone loss comprising the step of:
  a) contacting a test compound with an host cell expressing a reporter nucleic acid comprising a nucleic acid sequence coding for a reporter placed under the control of a promoter, which promoter comprises all or part of the promoter sequence of DOCK5 gene or a derivative thereof, and
  b) measuring the level of expression of the reporter.

As used herein, the term "derivatives'" refer to a nucleic sequence having a percentage of identity of at least 80% with the sequence of DOCK5 promoter, preferably of at least 90%, as an example of at least 95%, and more preferably of at least 99%. The percentage of identity is as defined above.

By "compound" or "test compound", one should understand compounds of different nature, structure and origin, particularly biological compounds, nuclear factors, cofactors, and the like, chemical, synthetic compounds and the like, which are tested for their capacity of enhancing the level of expression of said gene implicated in antimicrobial defence.

The concentration of said test compound can be adjusted by the skilled person according to the characteristics of said compound (its toxicity, ability to penetrate cells, etc.), the number of cells, the length of the incubation period, etc. Generally, the cells are exposed to concentrations of test compounds ranging from 1 nM to 1 mM. Of course it is possible to test other concentrations without deviating from the invention, and also to test simultaneously different test compound concentrations.

Different adjuvants and/or vectors and/or products facilitating the penetration of the test compounds into the host cell such as liposomes, cationic lipids or polymers can also be used, when necessary.

By "decreasing the level of expression of a DOCK5 gene", one should understand that the expression level of DOCK5 gene is diminished or inhibited compared to a control level.

It should be noticed that said expression level of the DOCK5 gene is correlated to the expression level of the reporter gene in the method of the invention. In fact, one of skilled in the art can deduce that a test compound can decrease the expression level of the DOCK5 gene from the capacity of said compound to obtain an diminished expression level of the reporter gene in the method of the invention.

In the present invention, the control level can be determined, by example, by measuring the expression level of the reporter gene in the absence of the test compound.

Thus, in a preferred embodiment, the method according to the invention further comprises a step c) of comparing the level of expression of the reporter gene as measured in step b) with the level of expression of the reporter gene in the absence of said test compound.

In another embodiment, the present invention provides a method for identifying a compound which inhibits the activation of RAC1/2 GTPase by inhibiting the binding of ELMO1 protein (SEQ ID No 9) to the SH3 domain of DOCK5 comprising the steps of:

a) contacting a test compound with the ELMO1 protein or a derivative thereof;

b) determining the possible binding of said test compound to the ELMO1 protein or the derivative thereof; and optionally c) selecting the compound inhibiting the conversion of inactive RAC1/2 to active RAC1/2.

As used herein, the expression "ELMO1 protein" refers to SEQ ID No 9 and derivatives thereof.

The binding between said ELMO1 protein and the tested compound can be measured by methods well known from one skilled in the art.

If the binding between said ELMO1 protein and said test compound is observed, it can thus be conclude that the compound is an inhibitor of the binding of ELMO1 and the SH3 domain of DOCK5, and that this compound is useful to inhibit the conversion of inactive RAC1/2 to active RAC1/2. Optionally, said method can include a further step after step b) of contacting a polypeptide comprising at least the SH3 domain of DOCK5 or the derivative thereof with said test compound and ELMO1 protein, and comparing the binding between said ELMO1 protein and said polypeptide in the presence or in the absence of said compound.

Alternatively, the present invention provides a method for identifying a compound which inhibits the activation of RAC1/2 GTPase by inhibiting the binding of ELMO1 to the SH3 domain of DOCK5 comprising the steps of:

a) contacting a test compound with the ELMO1 protein or the derivative thereof and a polypeptide comprising at least the SH3 domain of DOCK5 or the derivative thereof;

b) measuring the binding between said ELMO1 protein and said polypeptide in the presence or in the absence of said compound; and optionally c) selecting the compound inhibiting the conversion of inactive RAC1/2 to active RAC1/2.

The binding between said ELMO1 protein and said polypeptide can be measured by methods well known from one skilled in the art. If the binding between said ELMO1 protein and said polypeptide in the presence of the tested compound is lower than the one measured in absence of said compound, it can thus be conclude that the compound is an inhibitor of the binding of ELMO1 to the SH3 domain of DOCK5, and that this compound is useful to inhibit the conversion of inactive RAC1/2 to active RAC1/2.

Optionally, the compounds as described above are coupled with a bisphosphonate radical. The bisphosphonate radical permits a fast incorporation of the compound after its administration.

Another object of the present invention is a compound as described above for treating and/or preventing bone loss diseases in a subject in need thereof.

Therefore, the present invention relates to the use of at least one compound as described above in preparing a drug for treating and/or preventing bone loss disease in a subject in need thereof.

Another object of the present invention is a pharmaceutical composition comprising at least one compound as described above and, optionally, a pharmaceutically acceptable support for treating and/or preventing bone loss diseases in a subject in need thereof.

Therefore, the present invention relates to the use of a pharmaceutical composition comprising at least one compound as described above in preparing a drug for treating and/or preventing bone loss diseases in a subject in need thereof.

As examples of pharmaceutically acceptable supports, the composition can include emulsions, microemulsions, oil in water emulsions, anhydrous lipids and water in oil emulsions or other types of emulsions.

The inventive composition can further include one or more additives such as diluents, excipients, stabilizers and preservatives. Such additives are well known to those skilled in the art and are described notably in "*Ullmann's Encyclopedia of Industrial Chemistry, 6$^{th}$ Ed.*" (various editors, 1989-1998, Marcel Dekker) and in "*Pharmaceutical Dosage Forms and Drug Delivery Systems*" (ANSEL et al., 1994, WILLIAMS & WILKINS).

As used in the present application, the term "subject" refers to a mammal such as a rodent, cat, dog, primate or human, preferably said subject is a human.

Another object of the invention relates to a therapeutic method for treating a subject and/or preventing bone loss diseases, comprising the administration of a therapeutically effective quantity of a pharmaceutical composition as described above.

A "therapeutically effective quantity" means a quantity that inhibits or reduces the osteoclats activation. Those skilled in the art will be able to determine said therapeutically effective quantity based on their general knowledge and on the methods described in the examples.

The compounds can be administered by any mode of administration such as, for example, by intramuscular, intravenous or oral route, etc.

The inventive compounds preferably will be administered at a concentration chosen by those skilled in the art according to the state of advancement of the disease and the targeting mode used, the age and the weight of the subject. Preferably, the compound will be administered at a concentration of between 5 and 200 µM, preferably at a concentration comprised between 10 and 100 µM.

In the following, the invention is described in more detail with reference to amino acid sequences, nucleic acid sequences and the examples. Yet, no limitation of the invention is intended by the details of the examples. Rather, the invention pertains to any embodiment which comprises details which are not explicitly mentioned in the examples herein, but which the skilled person finds without undue effort.

EXAMPLES

1) Dock 5 mRNA Expression

The expression of Dock5 was established in different mouse tissue. For this, DNaseI-treated total RNA was extracted using the High pure RNA isolation kit (ROCHE DIAGNOSTICS). To generate cDNA, RNA was primed with 10-mer random primers and reverse transcription catalysed using SUPERSCRIPT II reverse transcriptase (INVITROGEN). Quantitative PCR was performed with a Light Cycler (ROCHE DIAGNOSTICS) or a Mx3000p PCR system (STRATAGENE) using the PLATINIUM Taq DNA polymerase (INVITROGEN) and SYBR GREEN I (BIOWITAKKER) as in described in COELHO et al. (*Proc. Natl. Acad. Sci. U.S.A.*, vol. 102, p: 11917-11922, 2005) with the primers Dock5-Up (TGGTGACACAGGGACAGTGG, SEQ ID NO:5) and Dock5-Do (CACCCCAACTAGCACGTGG, SEQ ID NO: 6) for Dock5, and Gapdh-Up (ACAGTCCAT-GCCATCACTGCC, SEQ ID NO: 7) and Gapdh-Do (GCCT-GCTTCACCACCTTCTT, SEQ ID NO: 8) for Gapdh as a control.

The specificity was assessed by purification and sequencing of the PCR product. All real-time PCR measures to quantify cDNA were done in triplicate, and the 95% confidence limits of the ratios to Gapdh were determined by Student's t-test. The FIGS. 1A and B show the expression of Dock5 in different mouse tissues In FIG. 1A, said expression has been normalised according to Dock5 osteoclasts' expression (i.e., Dock5 osteoclasts' expression corresponding to 100% level).

The analysed tissues of FIG. 1A are as follow: Muscle 1 (M1), Muscle 2 (M2), heart (H), mammary gland at 10.5 days of embryo's development (GM 10.5), mammary gland at 13.5 days of embryo's development (GM 13.5), mammary gland at 15.5 days of embryo's development (GM 15.5), mammary gland at 18.5 days of embryo's development (GM 18.5), mammary gland of juvenile mouse (GM j), mammary gland at lactation (GM 1), brain (Br), kidney (Kd), uterus (Ut), liver (Lv), macrophage (Mac), Testis 1 (T1), Testis 2 (T2), spleen (Sp), colon (Co), bone marrow (Bm), placenta at 13.5 days of embryo's development (Pl 13.5), placenta at 15.5 days of embryo's development (GM 15.5), and osteoclasts (Os).

Furthermore, total RNA of bone marrow macrophages (ND), induced for osteoclastic differentitation (OC) or dendritic cell differentiation (DC) and from mensenchymal stem cells (MSC J0) induced for osteoblastic differentiation (MSC J4) were extracted and level of Dock5 mRNA relative to Gapdh mRNA was determined by RT-PCR.

The results of FIG. 1B show that Dock5 mRNA is not expressed in dendritic cells and osteoblasts.

The results show that Dock5 is predominantly expressed in osteoclats, but an important expression of Dock5 is also found in placenta (i.e., nearly 50%) and testis. The expression of Dock5 is reduced in bone marrow, colon, spleen and testis compared to osteoclasts (i.e., nearly 20%), whereas its expression in the other tested tissues is fewer (i.e., nearly 10%). Thus, the results established that the expression of Dock5 is very specific from the osteoclats.

2) Obtaining of DOCK5 Polyclonal Antibody

A rabbit polyclonal antibody was raised to a mouse DOCK5 C-terminus peptide corresponding to amino acids 1658-1869 from mouse DOCK5 and purified by immunoaffinity. In fact, the amino acids sequences significantly differ between the differents members of the subgroup DOCK-A.

Osteoclastogenesis was induced by RANKL-stimulation in purified mouse bone marrow macrophages were purified and in RAW264.7 cell line as described in BRAZIER et al. (abovementioned, 2006), which cells were maintained in culture. At 0, 3 or 5 days of stimulation, the cells were subjected to SDS-PAGE and blotted on polyvinyl difluoride membrane (MILLIPORE IMMOBILON-P pore size 0.45 µm). After transfer, the membrane was incubated in TBS-T (Tris buffered saline containing 0.1% TWEEN) with 2% skim milk at room temperature for 30 min and then with rabbit antisera diluted 1:1000 in TBS-T overnight at 4° C. The bound antibodies were detected by peroxidase labelled anti-rabbit immunoglobulin chemoluminescence system (AMERSHAM) and LAS-1000 image analyser (FUJI FILM). As a control, the membrane was further incubated with GAPDH antibodies, the bound antibodies being detected as previously.

Figure 2:
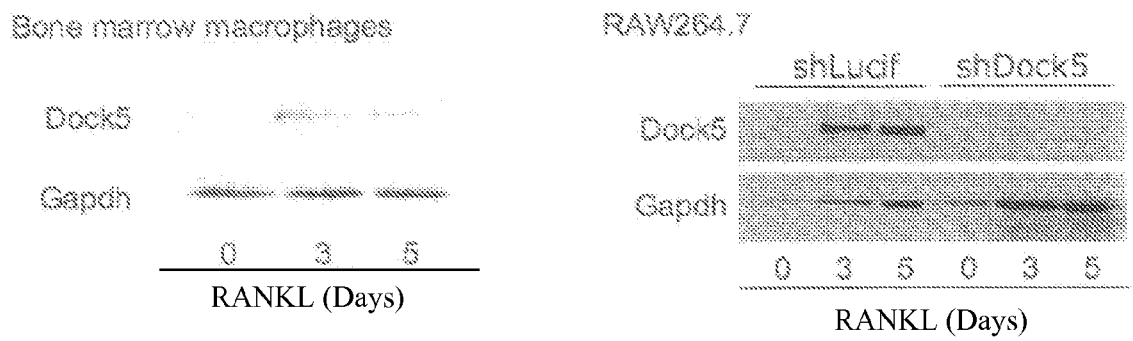
FIGS. 2A-2B show the expression of DOCK5 and GAPDH proteins in purified mouse bone marrow macrophages at 0, 3 and 5 days from the RANKL-stimulated osteoclastogenesis.
FIG. 2C shows specific analysed tissues.
Figure 2:
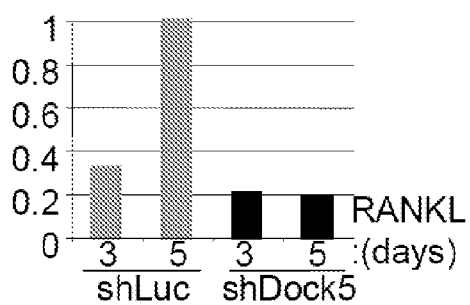
Figure 2:
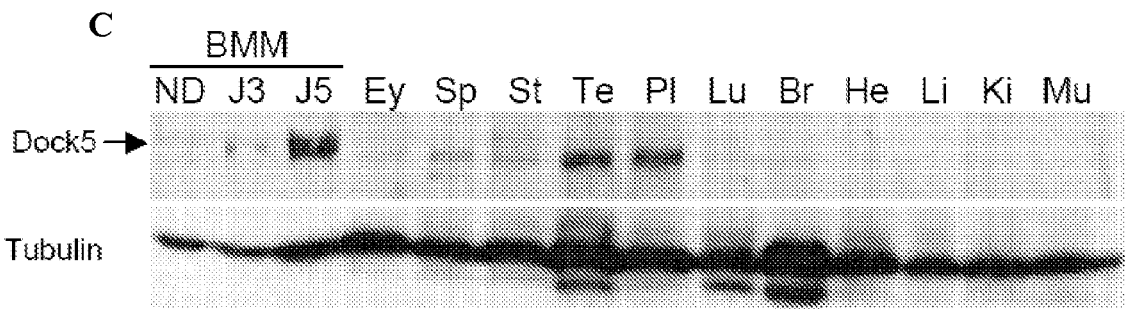

The FIGS. 2 A and B show the expression of DOCK5 and GAPDH proteins in purified mouse bone marrow macrophages at 0, 3 and 5 days from the RANKL-stimulated osteoclastogenesis.

The results established that a protein of 215 kDa was induced during RANKL-stimulated osteoclastogenesis of purified mouse bone marrow macrophages (FIG. 2) and of RAW264.7 cell line (data not shown). This size is compatible with the size of the DOCK5 protein deduced from its mRNA.

Furthermore, total proteins were extracted from mouse tissues and subjected to western blot with antibodies against Dock5 and against tubulin for normalization.

The analysed tissues of FIG. 2C are as follow Ey: Eye, Sp: Spleen, St: Stomac, Te: Testis, Pl: Placenta, Lu: Lung, Br: Brain, He: Heart, Li: Liver, Ki: Kidney; Mu: Muscle.

The results of FIG. 2A confirm that Dock 5 is predominantly expressed in osteoclasts, testis and placenta.

3) DOCK5 Polyclonal Antibody Specificity

ShRNA target sequences were selected in mouse Dock5 open reading frames, and the 65-mer sense and antisense strands of DNA oligonucleotides were designed according to the CLONTECH BIOINFORMATICS DATA server and are described in BRAZIER et al. (abovementioned, 2006). The oligonucleotide was then synthesized by INVITROGEN annealed and cloned in pSINREN-RETROQ vector containing a puromycin resistance selection marker according to the manufacturer's instructions (CLONTECH). The pSIREN-RETROQ-Luc vector (CLONTECH) targeting firefly luciferase was used as a control. Retrovirus packaging was done by co-transfection of pSIREN-RETROQ vectors, the Friend MLV-based Gag-Pol expression vector pC57GP (LASSAUX et al., *J. Virol.*, vol. 79, p: 6560-6564, 2005), and the VSV-G envelope glycoprotein expression vector pCSIG (BATTINI et al., *Proc. Natl. Acad. Sci.*, vol. 96, p: 1385-1390, 1999) into 293T cells using Jet PI (QBIOGEN) according to manufacturer's instructions. Viral supernatants were harvested 3 days after transfection and filtered through a 0.45 µm pore size filter.

For infections, RAW264.7 cells were plated at $2·10^5$ cells per 6-cm dish. The next day, the medium was replaced for 4 h with 1.5 ml of viral supernatant and 0.5 ml of growth medium containing 8 µg/ml polybrene. Cells were left to recover in growth medium for 24 h, and infected cells were selected by addition of puromycin (3 µg/ml) for another 24 h. Infected RAW264.7 were scrapped and reseeded in growth medium at $5·10^4$ cells/well of a 6-well plate for RANKL-stimulated osteoclastogenesis as described in BRAZIER et al. (abovementioned, 2006).

Then, the detection of the DOCK5 protein was realized with the rabbit polyclonal anti-DOCK5 as described previously.

The FIG. 2 A shows the expression of DOCK5 and GAPDH proteins in RAW264.7 cell lines infected with retrovirus coding for either small hairpin RNA directed against firefly luciferase (shLuc) or dock5 (shDock5) at 0, 3 and 5 days from the RANKL-stimulated osteoclastogenesis.

As described previously, the results established that a protein of 215 kDa was induced during RANKL-stimulated osteoclastogenesis of RAW264.7 cell line infected with a retrovirus coding for a small hairpin RNA directed against firefly luciferase. For RAW264.7 cell line infected with a retrovirus coding for a small hairpin RNA directed against Dock5, no protein of 215 kDa was detected during RANKL-stimulated osteoclastogenesis. Finally, the results confirmed that the protein DOCK5, such as its corresponding RNA, is induced during osteoclastogenesis, and that the obtained rabbit polyclonal anti-DOCK5 antibody is specific of the DOCK5 protein.

4) Dock5 Mediates Rac Activation In Vivo

We therefore examined whether the DOCK5 protein, and more specifically its DHR2 domain, could activate small GTPases of the Rho-family—i.e., RAC1/2 and cdc42—.

To this end a GFP protein fused to the DHR2 domain of DOCK5 (see FIG. 3A) was generated.

In vivo GTP loading of Rac and cdc42 was analysed as previously described in COTE & VUORI (*J. Cell. Sci.*, vol. 115, p: 4901-4913, 2002).

Briefly, 293-T cells were transfected in six-wells plates with a vector coding for the GFP fusion protein comprising the DHR2 domain of DOCK5 (DHR2) or with a vector coding for GFP (GFP). 48 hours after transfection, cells were lysed in MLB buffer (25 mM HEPES, pH 7.5, 150 mM NaCl, 1% NP-40, 10 mM MgCl2, 1 mM EDTA and 10% glycerol). The clarified lysates were incubated for 30 minutes with the GST-PAK-PBD fusion protein bound to Glutathione sepharose. The beads were washed extensively with MLB buffer and the bound GTP-loaded Rac and cdc-42 were detected by immunoblotting. Equal amount of input lysate were analysed by immunoblotting to verify the expression levels of Rac, cdc42, GFP-DHR2 and GFP proteins. GST-PAK-PBD was expressed and purified for these experiments as described previously in ABASSI & VUORI (*EMBO J.*, vol. 21, p: 4571-4582, 2002).

The FIG. 3B shows the expression levels of Rac, cdc42, GFP-DHR2 and GFP proteins in total cell lysates (total) and the protein detected after GTP-trapping.

The results show that the expression of the DHR2 domain in 293-T cells induces the activation of endogeneous Rac but has no effect on cdc42 (FIG. 3B). Finally, the results established that the DHR2 domain of DOCK5 is able to activate the Rac GTPase, whereas it has no effect on cdc42.

5) ELMO1 Binds to the SH3 Domain of DOCK5

Figure 3:
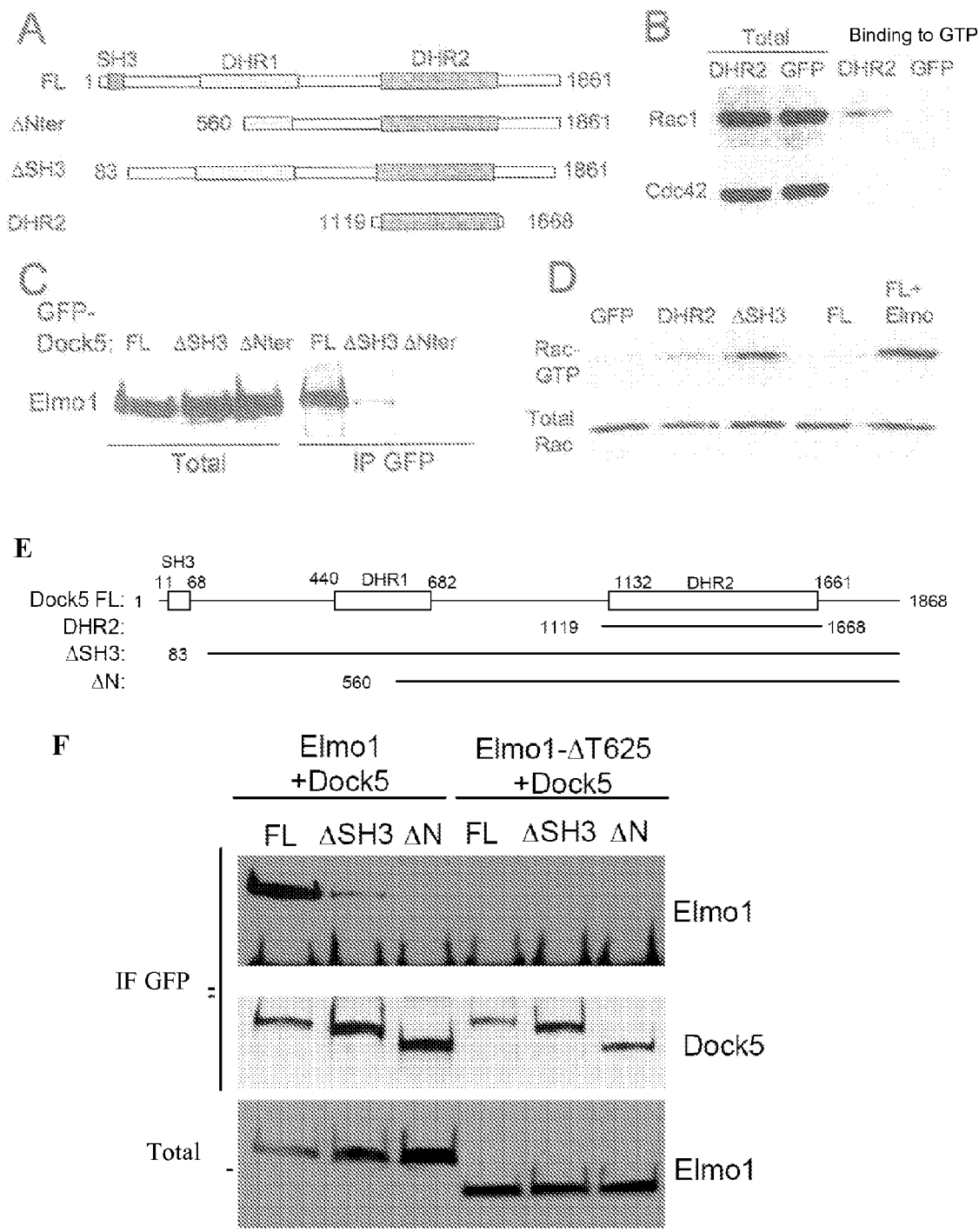
FIG. 3A shows a GFP protein fused to the DHR2 domain of DOCK5.
FIG. 3B shows the expression levels of Rac, cdc42, GFP-DHR2 and GFP proteins in total cell lysates (total) and the protein detected after GTP-trapping.
FIGS. 3C and 3F show the expression levels of ELMO1 protein in total cell lysates (total) and after immunoprecipation with anti-GFOP antibody (IP GFP), in cells cotransfeted with a vector coding for ELMO1 protein and full length DOCK5 (FL), the DHR2 domain (DHR2), DOCK5 deleted from its SH3 domain (ΔSH3) or from its N-term domain (ΔNter).
FIG. 3D shows shows the expression levels of Rac in total cell lysates (total) and the RAC-GTP protein detected after GTP trapping in the cells transfected with a vector coding for the GFP protein (GFP), for the DHR2 domain of DOCK5 (DHR2), for the DOCK5 protein deleted from its SH3 domain (ΔSH3), for the DOCK protein (FL), eventually cotransfected with a vector coding for the ELMO1 protein (FL+Elmo1).
FIG. 3E shows the full length DOCK5 protein (FL), the DHR2 domain, the DOCK5 protein sequence deleted from (i) the amino acids 1 to 559 of its N-terminus extremity (ΔNter), including the SH3 domain and half of the DHR1 domain, or the DOCK5 protein sequence deleted from (ii) the amino acids 1 to 82 comprising the SH3 domain (ΔSH3 ).

293-T cells were cotransfected as described previously with a vector coding for the ELMO1 protein or deleted from the C-terminus (ΔT625)—(GUMIENNY et al., *Cell*, vol. 107, p: 27-41, 2001) and a vector coding GFP fusion proteins comprising the Full length DOCK5 protein (FL), the DHR2 domain, the DOCK5 protein sequence deleted from (i) the amino acids 1 to 559 of its N-terminus extremity (ΔNter), including the SH3 domain and half of the DHR1 domain, or the DOCK5 protein sequence deleted from (ii) the amino acids 1 to 82 comprising the SH3 domain (ΔSH3) (see FIG. 3 E).

48 hours after transfection, cells were lysed in MLB buffer (25 mM HEPES, pH 7.5, 150 mM NaCl, 1% NP-40, 10 mM MgCl2, 1 mM EDTA and 10% glycerol). The clarified lysates were immunoprecipitated with anti-GFP antibody and the bound ELMO1 protein was detected by immunoblotting. Equal amount of input lysate were analysed by immunoblotting to verify the expression levels of ELMO1 protein.

The FIGS. 3C and 3F show the expression levels of ELMO1 protein in total cell lysates (total) and after immunopreciptation with anti-GFOP antibody (IP GFP), in cells cotransfected with a vector coding for ELMO1 protein and full length DOCK5 (FL), the DHR2 domain (DHR2), DOCK5 deleted from its SH3 domain (ΔSH3) or from its N-term domain (ΔNter).

The results show that deletion if Dock5 SH3 domain or coexpression of full length ELMO1 with full length Dock5 greatly increased its exchange activity on Rac thus establishing that the N-term domain of DOCK5, and more specifically its SH3 domain, is necessary for the binding of ELMO1 to DOCK5 (FIG. 3C). FIG. 3F shows that Dock5 N-terminal domain binds Elmo1 C-terminus.

6) The SH3 Domain of DOCK5 Inhibits Rac Activation In Vivo

In vivo GTP loading of Rac was determined as previously in the presence of different domains of the DOCK5 protein and, eventually, the simultaneous presence of the ELMO1 protein.

The FIG. 3D shows the expression levels of Rac in total cell lysates (total) and the RAC-GTP protein detected after GTP trapping in the cells transfected with a vector coding for the GFP protein (GFP), for the DHR2 domain of DOCK5 (DHR2), for the DOCK5 protein deleted from its SH3 domain (ΔSH3), for the DOCK protein (FL), eventually cotransfected with a vector coding for the ELMO1 protein (FL+Elmo1).

The results show as previously that the expression of the DHR2 domain is able to activate the Rac GTPase and that the SH3 domain inhibits this activation (FIG. 3D). In fact, the deletion of the SH3 domain results in the activation of the Rac GTPase by the deleted DOCK5 protein. Finally, the binding of ELMO1 to the SH3 domain results in the activation of the Rac GTPase.

7) DOCK5 is a Major Activator of Rac in Osteoclats.

RAW264.7 cell lines stimulated with RANKL were infected as described previously with a retrovirus coding for either small hairpin RNA directed against firefly luciferase (shLuc) or dock5 (shDock5).

Furthermore, the levels of active Rac in TCL from Dock5$^{+/+}$ and Dock5$^{+/+}$ osteoclasts were determined Dock5$^{-/-}$ mice were obtained by gene trap (Laurin et al. 2008) to generate Dock5 deficient osteoclasts.

The in vivo GTP loading of Rac was determined as disclosed previously.

Figure 4:
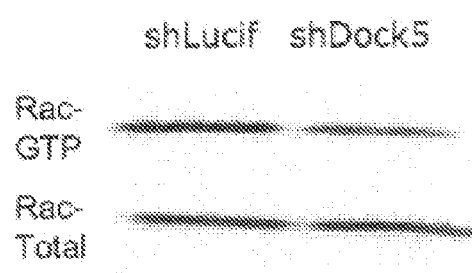
FIGS. 4A-4B show the average of three independent experiments with active Rac levels set to 1 in control shLuc and Dock5 $^{+/+}$ osteoclasts.
Figure 4:
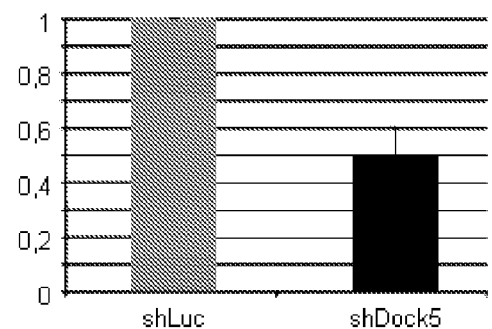
Figure 4:
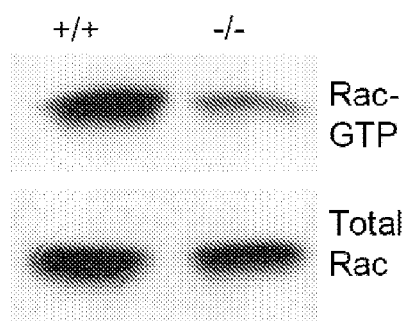
Figure 4:
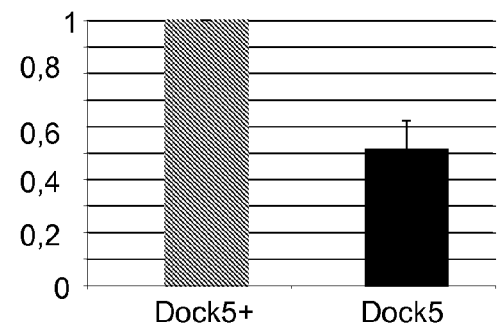

The FIG. 4 shows the average of three independent experiments with active Rac levels set to 1 in control shLuc and Dock5$^{+/+}$ osteoclasts. Error bars: SD.

The FIG. 4A show the expression levels of Rac in total cell lysates (total Rac) and the RAC-GTP protein detected after GTP trapping in the cells infected with a retrovirus coding for either small hairpin RNA directed against firefly luciferase (shLuc) or dock5 (shDock5).

The FIG. 4B shows that Dock5$^{-/-}$ osteoclasts have reduced active Rac levels compared to the control level of Dock5$^{+/+}$ osteoclasts.

The results established that the inhibition of DOCK5 expression results in a decrease of the levels of active RAC (i.e., 40%) in osteoclasts expressing Dock5 shRNAs and osteoclasts derived from Dock5 KO BMMs as compared to controls. Thus, DOCK5 is an essential exchange factor of RAC in osteoclasts.

8) DOCK5 is Necessary for Mineralised Matrix Resorption

Figure 5:
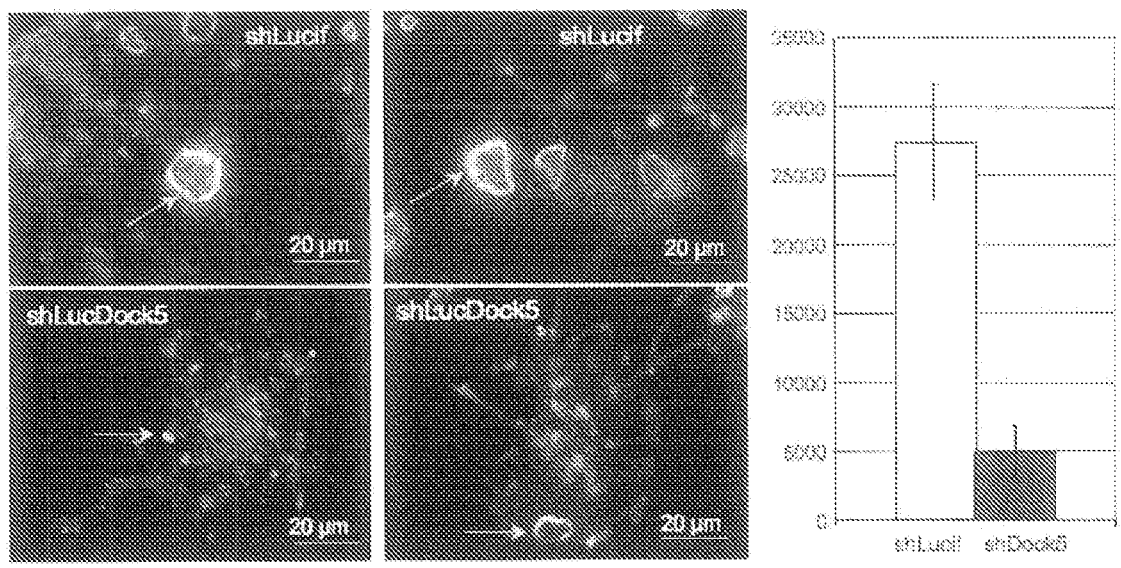
FIG. 5 shows the results of fixing and staining cells for actin using rhodamine-labeled Phalloidin.

RAW264.7 cell lines were infected as described previously with a retrovirus coding for either small hairpin RNA directed against firefly luciferase (shLuc) or dock5 (shDock5), and then osteoclastogenesis was stimulated with RANKL. The obtained cells were then cultured on calcium phosphate substrates to induce the formation of the actin ring. After 48 hours, cells were fixed and stained for actin using rhodamine-labeled Phalloidin to reveal the sealing zone (FIG. 5).

Figure 6:
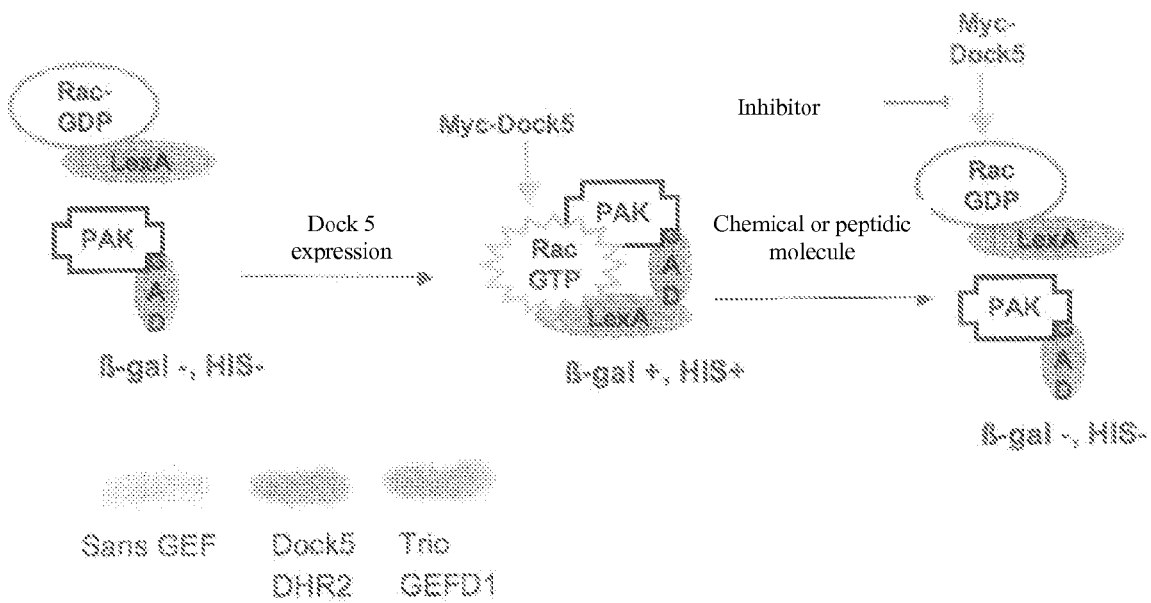
FIG. 6 shows the polymerisation of actin in RAW264.7 cell lines stimulated with RANKL.

The FIG. 6 shows the polymerisation of actin in RAW264.7 cell lines stimulated with RANKL which have been infected with a retrovirus coding for either small hairpin RNA directed against firefly luciferase (shLuc) or dock5 (shDock5) and the mineralised matrix resorption in the presence of said osteoclasts.

The results show that in the osteoclasts, the DOCK5 protein is associated with the podosome and with the sealing zone (data not shown). The osteoclasts wherein DOCK5 expression was inhibited show a default of contraction and of sealing zone formation. The measure of mineralised matrix resorption surface by VON KOSSA staining shows a strong decrease of the resorption by osteoclasts wherein DOCK5 expression was decreased.

9) Confirmation by Osteoclasts from Dock5$^{-/-}$ Mice

BMMs (bone marrow macrophages) isolated from Dock5$^{+/+}$ and Dock5$^{-/-}$ mice were differentiated into osteoclasts in the presence of 100 ng/ml RANKL and 10 ng/ml M-CSF. TCL (total cell extracts) were prepared at days 0, 3 and 4 and subjected to western blot with antibodies against Dock5 and β-gal and against tubulin for normalization.

Figure 7:
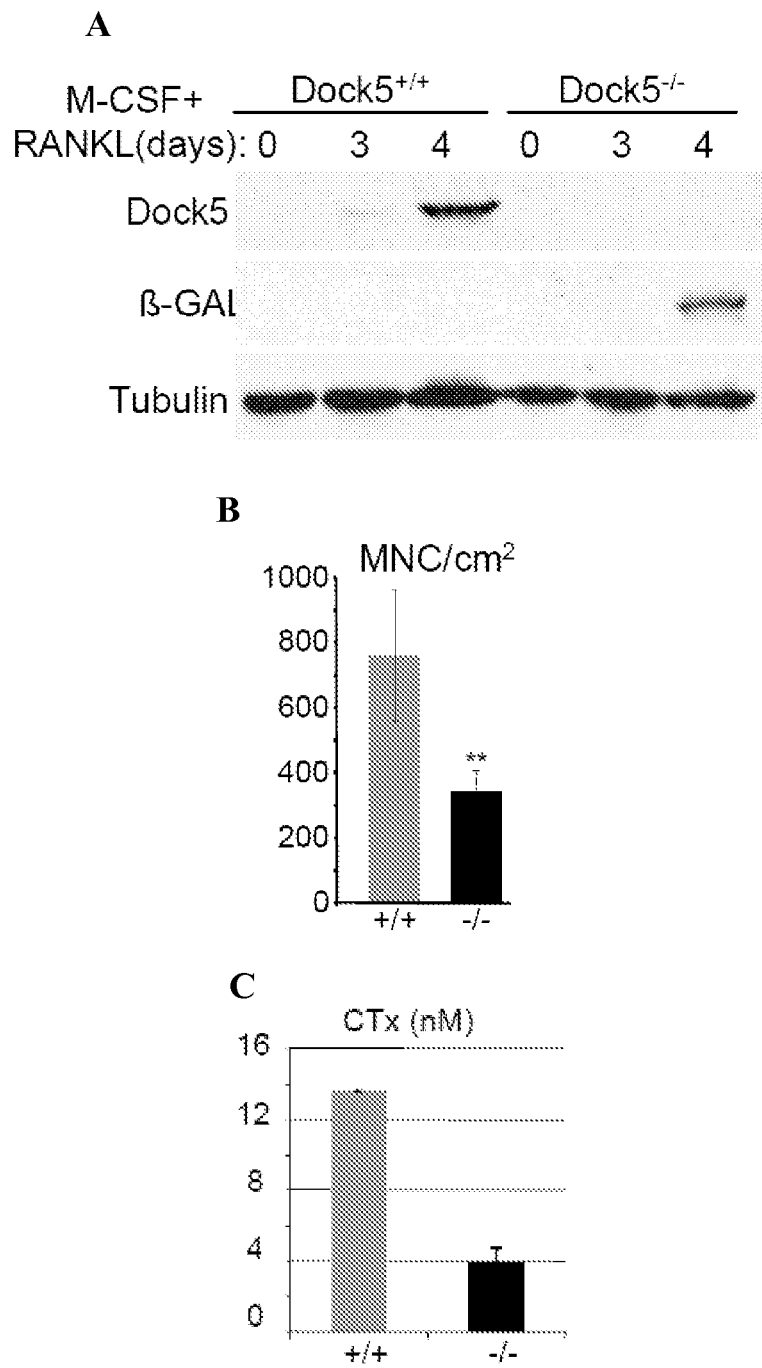
FIG. 7A shows osteoclasts derived from Dock5$^{-/-}$ BMMs express Dock5 truncated after aminoacid 1115, between DHR1 and DHR2 domains, and fused to a β-geo cassette.
FIG. 7B shows that the efficiency of TRAP positive MNCs formation was reduced in Dock5$^{-/-}$ BMMs as compared to Dock5$^{+/+}$ and osteoclasts were smaller.
FIG. 7C shows average and SD of three osteoclast-seeded wells from one experiment.

Osteoclasts derived from Dock5$^{-/-}$ BMMs express Dock5 truncated after aminoacid 1115, between DHR1 and DHR2 domains, and fused to a β-geo cassette (FIG. 7A).

Furthermore, the differentiated osteoclasts were fixed and stained with TRAP and Hoeschst at day 5 to determine the number of MNCs (multinucleated cells). FIG. 7B (average and SD from four independent experiments **: significant difference, $p<0.01$, Mann & Whitney test) shows that the efficiency of TRAP positive MNCs formation was reduced in Dock5$^{-/-}$ BMMs as compared to Dock5$^{+/+}$ and osteoclasts were smaller.

Furthermore, in order to show that osteoclasts differentiated from Dock5$^{-/-}$ BMMs can't assemble a sealing zone, they were seeded on calcium-phosphate substrate to induce the formation of the actin ring. After 48 hours, cells were fixed and stained for actin using rhodamine-labeled Phalloidin (green) to reveal the sealing zone and with Hoeschst dye to stain nuclei (blue) (data not shown). It was observed that on calcium-phosphate substrates, sealing zone assembly and resorption was defective in Dock5$^{-/-}$ osteoclasts.

Finally, to demonstrate that Dock5$^{-/-}$ osteoclasts can't form resorption pit, derived from Dock5$^{-/-}$ BMMs were differentiated on bone sliced for 5 days, fixed and observed by scanning electron microscopy.

The results show that when seeded on bone slices, Dock5$^{-/-}$ osteoclasts did not form resorption pits.

Moreover, in order to show that Dock5$^{-/-}$ osteoclasts are defective for bone resorption, the levels of collagen degradation peptide (CTx) were determined in the medium of Dock5$^{+/+}$ and Dock5$^{-/-}$ osteoclasts after 5 days of differentiation and bone slices were stained. FIG. 7C shows average and SD of three osteoclast-seeded wells from one experiment, representative of three independent experiments.

The measurement of collagen telopeptide (CTx) confirmed that the resorbing activity of Dock5$^{-/-}$ osteoclasts was defective (FIG. 7C).

10) Suppression of Dock5 Impairs RAC Activation in Osteoclasts.

The levels of osteoclastic markers in wild type and Dock5 deficient osteoclasts derived from BMM of Dock5$^{+/+}$ or Dock5$^{-/-}$ animals or from control and Dock5 shRNA expressing RAW264.7 cells. Total RNA was prepared from Dock5$^{+/+}$ and Dock5$^{-/-}$ BMMs grown for 5 days in the presence of M-CSF only (black bars) or in the presence of RANKL and M-CSF to obtain osteoclasts (white bars). The levels of indicated gene mRNAs relative to Gapdh mRNA were determined by RT-PCR.

Figure 8D:
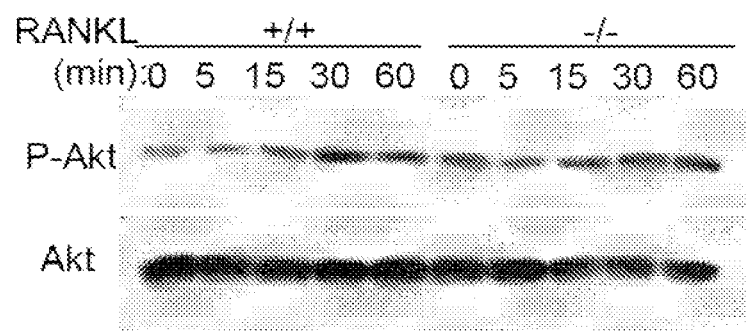
FIGS. 8D shows RANKL-driven phosphorylation of Akt.

The results of FIG. 8A show that the expression of osteoclast differentiation markers is normal in osteoclasts differentiated from Dock5$^{-/-}$ BMMs. This indicated osteoclast maturation was not affected and suggested Dock5 deficiency did not impair the capacity of osteoclasts to respond to M-CSF and RANKL in vitro.

Moreover, the ability of Dock5$^{-/-}$ preosteoclasts to respond to M-CSF and RANKL was not the result of a compensatory increase in Dock1 or Dock2 expression as their mRNA levels were identical as in Dock5$^{+/+}$ (FIG. 8B).

Preosteoclasts prepared from Dock5$^{+/+}$ and Dock5$^{-/-}$ BMMs were stimulated with M-CSF or RANKL for the indicated amount of time. The levels of ERK, p38 and Akt phosphorylation in TCL were determined by western blot.

The results show that M-CSF-driven phosphorylation ERK and p38MAP kinase (FIG. 8C) and RANKL-driven phosphorylation of Akt (FIG. 8D) were unaffected in Dock5$^{-/-}$ preosteoclasts as compared to controls.

Finally, these results established that DOCK5 is a new therapeutic target for limiting bone loss in menopause, osteoporosis, osteopenia due to bone metastases, periarticular erosions in rheumatoid arthritis, primary hyperparathyroidism, hypercalcemia of malignancy, Paget's disease of bone, periodontal disease, immobilization induced osteopenia, or in glucocorticoid treatment. Because of the specific osteoclasts DOCK5 expression, the targeting of DOCK5 may limit side effects such as the ones observed with drugs for treating bone loss.

11) Identification of DOCK5 Inhibitor

In order to identify DOCK5 inhibitors, which inhibitors can be useful for treating bone loss associated disease, we use the Yeast Exchange Assay (YEA) as disclosed in DE TOLEDO et al. (*FEBS*, vol. 480, p: 287-292, 200) and International Patent application PCT WO 2005/064007.

Briefly, we transform a yeast strain TAT7 (Mata, trp1, his3, leu2, ura3, ade2, LYS:: (LexAop)4-HIS3, URA3:: (LexAop)-8-lacZ) provided by J. CAMONIS) with vectors expressing the DHR2 domain of DOCK5 fused to a myc-tag (SEQ ID NO: . . . ), the wild type Rac GTPase fused to LexA and its effector PAK fused to the transactivation domain of GAL4.

In the obtained transformed yeast, the expression of the DHR2 domain of DOCK5 induces the activation of Rac, which activated Rac interacts with its effector PAK resulting in the expression of reporter genes β-Gal and His3 (see FIG. 6).

In order to modify yeast cell membrane permeability, a mutation in the Erg6 gene has been introduced as disclosed in BLANGY et al. (*Biol. Cell.*, vol. 98(9), p: 511-22, 2006). This mutation of the Erg6 gene increases the entry of the screened compounds in the yeast cells, and thus enables to limit the concentration of the screened compounds.

For screening DOCK5 inhibitors, which can be useful for treating bone loss diseases, the transformed yeast is contacted with several chemical or peptidic molecules, and the chemical or peptidic molecules inhibiting the expression of reporter genes β-Gal and His3 are selected for further testing in the bone loss model disclosed in 8 and then in bone loss diseases models.

The yeast strain TAT7 was used to identify DOCK5 inhibitors. The strain was seeded, in a 96-well culture plate in a selective medium devoid of histidine or in a non selective medium where histidine is added. 2560 compounds were screened to select the ones which inhibit the growth of the strains in a selective medium without having effect on the growth in a non selective medium. DMSO was used as a control.

The compounds were tested at a concentration of 200 μM in presence of 1% DMSO. The growth of the yeasts was measured by optical density at 600 nm at t=2 hours, 15 hours, 20 hours and 24 hours after seeding. The inhibiting compounds were defined as follows:

At time n, the growth derivative Cr (medium)=(OD600Tn−OD600T2)/Tn−T2 in test medium (−HIS) and in toxic medium (+HIS).

At each time and for each plate, the Cr (−HIS) and Cr (+HIS) medium control was calculated on the control.

the ratio R(compound)=Cr (−HIS) and Cr (+HIS) and R was calculated for each plate the inhibition rate was determined by dividing by the control ratio I(compound)=R(compound)/R(control)* the selected compounds are those showing a ratio I(compound)<0.9 at each time.

Results are shown in table 2.

55 compounds were thus selected as inhibiting the activation of RAC1/2 by Dock5.

12) Toxicity Test on Osteoclast Precursors.

The selected compounds were then tested for their toxicity on osteoclast precursors. Since these cells do not express Dock5, a Dock5 inhibitor should not affect their growth. RAW264.7 cells used as osteoclasts inhibitors were allowed to grow for 72 hours with 10 to 100 μM of compound. The growth of the cells was compared to control cells which were grown with 0.5% DMSO.

The results are presented in table 2. The optimal concentration was the determined for the compounds which were not toxic (the concentration which does not affect the growth of the cells).

13) Toxicity Test on Differentiated Osteoclasts.

The compounds were tested for their toxicity on differentiated osteoclasts at the concentration determined above. RAW264.7 cells differentiated in osteoclasts were allowed to grow for 72 hours in presence of the tested compounds. The tartrate-resistant acid phosphatase (TRAP) was then revealed in osteoclasts by coloration (SUDA et al., 1997). This osteoclasts specific labeling permits to visualize the cell morphology. The cell morphology was then compared to control cells which were allowed to grow in presence of 0.5% DMSO. The compounds were then classified in 3 categories:

compounds which induce the death of all the osteoclasts after 72 hours (−)

compounds which induce morphological anomalies and/or death of part of the osteoclasts (+/−)

Compounds which do not induce visible modifications of the osteoclasts.

The results are shown in table 2.

14) Resorption Inhibition Test

The identified compounds were used at the same concentration as defined above on osteoclats seeded on mineralised matrix resorption surface of calcium phosphate (Osteologic Biocoat Clontech Reference 354609) during 72 hours. Then the mineralised matrix was coloured with silver nitrate in order to show the resorbed areas. The compounds were classified in 3 categories:

Compounds that totally prevent resorption in 72 hours (−)

Compounds that induce an attenuated resorption compared to the control (+/−)

Compounds that do not visibly modify the osteoclats resorption activity compared to the control. (+)

The compounds of the resorption categories (+/−) and (−) represent new inhibitors of the bone resorption. They were used at a concentration of 10 to 100 μM.

To confirm the results, the compounds were then tested in vivo in a mouse which presents osteoporose.

TABLE 1

| compound identified by the screening method of the present invention | | | | |
|---|---|---|---|---|
| Structure | Mol Weight | Mol Formula | Mol Name | compound n° |
|  | 446.3 | C19 H16 Br N3 O5 | 4-[5-(4-bromophenyl)-3-(4-nitrophenyl)-4,5-dihydro-1H-pyrazol-1-yl]-4-oxobutanoic acid | 4 |
|  | 368.7 | C13 H12 Cl3 N O3 S | 2,2,2-trichloro-N-(1,1-dioxido-2,3-dihydro-3-thienyl)-N-(4-methylphenyl)acetamide | 5 |

TABLE 1-continued compound identified by the screening method of the present invention

| Structure | Mol Weight | Mol Formula | Mol Name | compound n° |
|---|---|---|---|---|
| 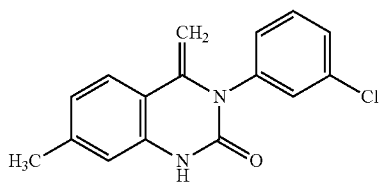 [SMILES: C=C1c2ccc(C)cc2NC(=O)N1c1cccc(Cl)c1] | 284.7 | C16 H13 Cl N2 O | 3-(3-chlorophenyl)-7-methyl-4-methylene-3,4-dihydro-2(1H)-quinazolinone | 11 |
| 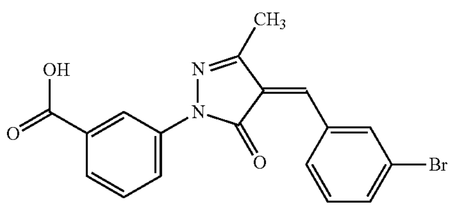 [SMILES: CC1=NN(c2cccc(C(=O)O)c2)C(=O)/C1=C\c1cccc(Br)c1] | 385.2 | C18 H13 Br N2 O3 | 3-[4-(3-bromobenzylidene)-3-methyl-5-oxo-4,5-dihydro-1H-pyrazol-1-yl] benzoic acid | 18 |
| 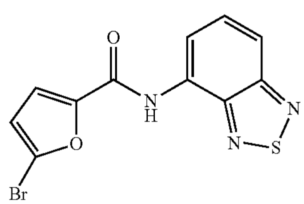 [SMILES: O=C(Nc1cccc2nsnc12)c1ccc(Br)o1] | 324.2 | C11 H6 Br N3 O2 S | N-2,1,3-benzothiadiazol-4-yl-5-bromo-2-furamide | 20 |
| 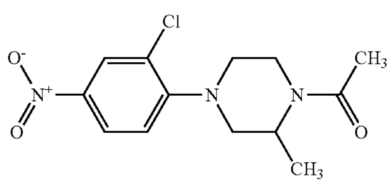 [SMILES: CC(=O)N1CCN(c2ccc([N+](=O)[O-])cc2Cl)CC1C] | 297.7 | C13 H16 Cl N3 O3 | 1-acetyl-4-(2-chloro-4-nitrophenyl)-2-methylpiperazine | 22 |
| 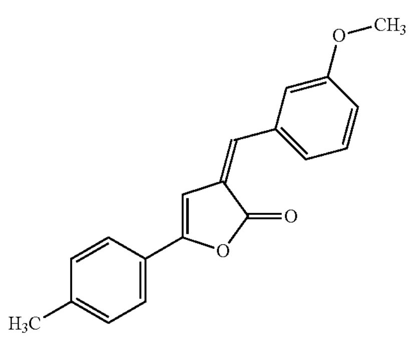 | 292.3 | C19 H16 O3 | 3-(3-methoxybenzylidene)-5-(4-methylphenyl)-2(3H)-furanone | 23 |
| 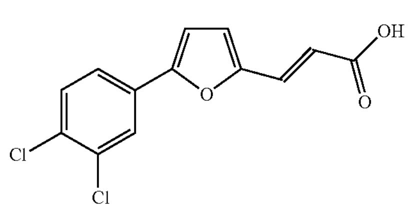 [SMILES: O=C(O)/C=C/c1ccc(-c2ccc(Cl)c(Cl)c2)o1] | 283.1 | C13 H8 Cl2 O3 | 3-[5-(3,4-dichlorophenyl)-2-furyl]acrylic acid | 24 |

TABLE 1-continued compound identified by the screening method of the present invention

| Structure | Mol Weight | Mol Formula | Mol Name | compound n° |
|---|---|---|---|---|
| 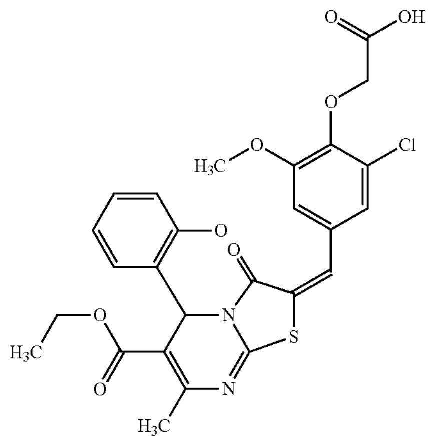 [SMILES: CCOC(=O)C1=C(C)N=c2s/c(=C/c3cc(Cl)c(OCC(=O)O)c(OC)c3)c(=O)n2C1c1ccccc1O] | 577.4 | C26 H22 Cl2 N2 O7 S | (2-chloro-4-{[5-(2-chlorophenyl)-6-(ethoxycarbonyl)-7-methyl-3-oxo-5H-[1,3]thiazolo[3,2-a]pyrimidin-2(3H)-ylidene]methyl}-6-methoxyphenoxy) acetic acid | 25 |
| 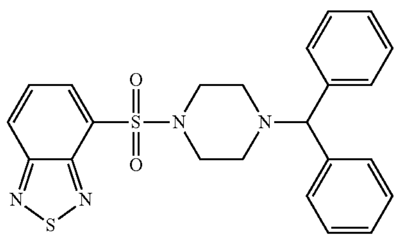 [SMILES: O=S(=O)(c1cccc2nsnc12)N1CCN(C(c2ccccc2)c2ccccc2)CC1] | 450.6 | C23 H22 N4 O2 S2 | 4-{[4-(diphenylmethyl)-1-piperazinyl] sulfonyl}-2,1,3-benzothiadiazole | 26 |
| 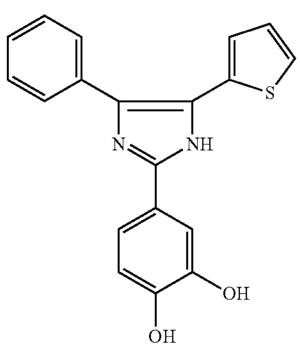 [SMILES: Oc1ccc(-c2nc(-c3ccccc3)c(-c3cccs3)[nH]2)cc1O] | 334.4 | C19 H14 N2 O2 S | 4-[4-phenyl-5-(2-thienyl)-1H-imidazol-2-yl]-1,2-benzenediol | 34 |
| 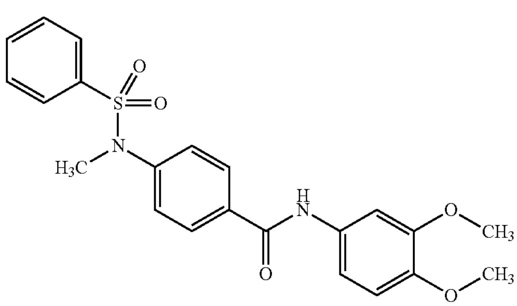 [SMILES: COc1ccc(NC(=O)c2ccc(N(C)S(=O)(=O)c3ccccc3)cc2)cc1OC] | 426.5 | C22 H22 N2 O5 S | N-(3,4-dimethoxyphenyl)-4-[methyl(phenyl-sulfonyl) amino]benzamide | 37 |

TABLE 1-continued compound identified by the screening method of the present invention

| Structure | Mol Weight | Mol Formula | Mol Name | compound n° |
|---|---|---|---|---|
| 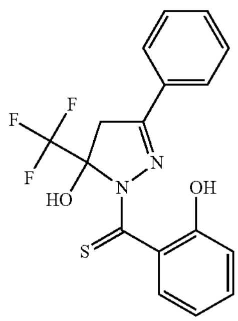 [SMILES: Oc1ccccc1C(=S)N1N=C(c2ccccc2)CC1(O)C(F)(F)F] | 366.4 | C17 H13 F3 N2 O2 S | 1-[(2-hydroxyphenyl)carbonothioyl]-3-phenyl-5-(trifluoromethyl)-4,5-dihydro-1H-pyrazol-5-ol | 42 |
| 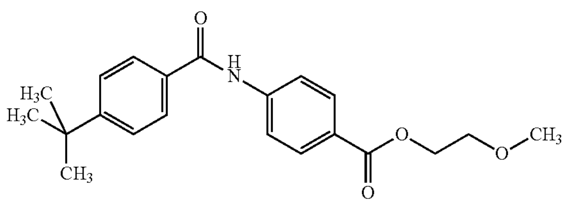 [SMILES: COCCOC(=O)c1ccc(NC(=O)c2ccc(C(C)(C)C)cc2)cc1] | 355.4 | C21 H25 N O4 | 2-methoxyethyl 4-[(4-tert-butylbenzoyl)amino]benzoate | 44 |
| 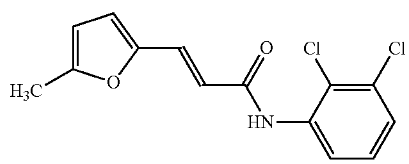 [SMILES: Cc1ccc(/C=C/C(=O)Nc2cccc(Cl)c2Cl)o1] | 296.2 | C14 H11 Cl2 N O2 | N-(2,3-dichlorophenyl)-3-(5-methyl-2-furyl)acrylamide | 47 |
| 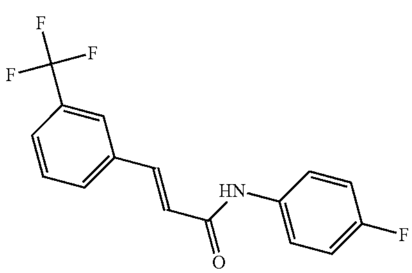 [SMILES: O=C(/C=C/c1cccc(C(F)(F)F)c1)Nc1ccc(F)cc1] | 309.3 | C16 H11 F4 N O | N-(4-fluorophenyl)-3-[3-(trifluoromethyl)phenyl]acrylamide | 54 |
| 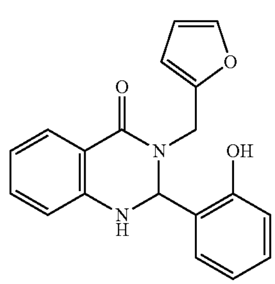 [SMILES: O=C1c2ccccc2NC(c2ccccc2O)N1Cc1ccco1] | 320.3 | C19 H16 N2 O3 | 3-(2-furylmethyl)-2-(2-hydroxyphenyl)-2,3-dihydro-4(1H)-quinazolinone | 55 |
| 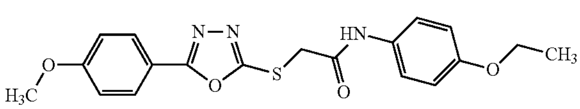 | 385.4 | C19 H19 N3 O4 S | N-(4-ethoxyphenyl)-2-{[5-(4-methoxyphenyl)-1,3,4-oxadiazol-2-yl]thio}acetamide | 3 |

TABLE 1-continued compound identified by the screening method of the present invention

| Structure | Mol Weight | Mol Formula | Mol Name | compound n° |
|---|---|---|---|---|
| 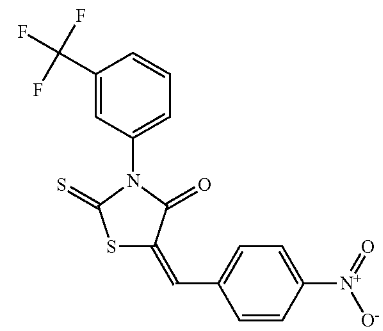 [SMILES: O=C1/C(=C\c2ccc([N+](=O)[O-])cc2)SC(=S)N1c1cccc(C(F)(F)F)c1] | 410.4 | C17 H9 F3 N2 O3 S2 | 5-(4-nitrobenzylidene)-2-thioxo-3-[3-(trifluoromethyl)phenyl]-1,3-thiazolidin-4-one | 16 |
| 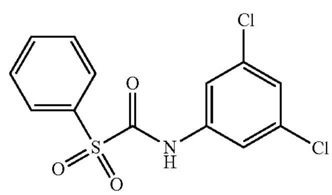 [SMILES: O=C(Nc1cc(Cl)cc(Cl)c1)S(=O)(=O)c1ccccc1] | 330.2 | C13 H9 Cl2 N O3 S | (3,5-dichlorophenyl)[(phenylsulfonyl)carbonyl]amine | 21 |
| 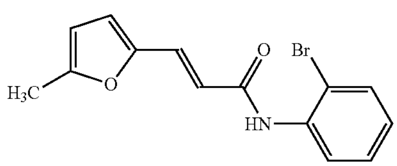 [SMILES: Cc1ccc(/C=C/C(=O)Nc2ccccc2Br)o1] | 306.2 | C14 H12 Br N O2 | N-(2-bromophenyl)-3-(5-methyl-2-furyl)acrylamide | 6 |
| 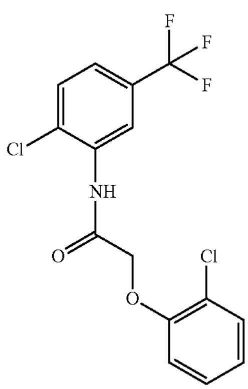 [SMILES: O=C(COc1ccccc1Cl)Nc1cc(C(F)(F)F)ccc1Cl] | 364.1 | C15 H10 Cl2 F3 N O2 | 2-(2-chlorophenoxy)-N-[2-chloro-5-(trifluoromethyl)phenyl]acetamide | 12 |
| 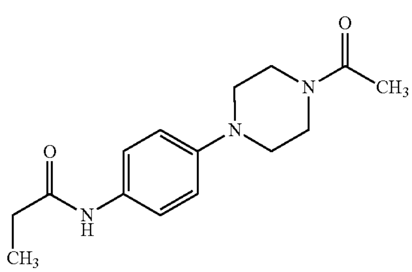 [SMILES: CCC(=O)Nc1ccc(N2CCN(C(C)=O)CC2)cc1] | 275.3 | C15 H21 N3 O2 | N-[4-(4-acetyl-1-piperazinyl)phenyl]propanamide | 13 |

TABLE 1-continued compound identified by the screening method of the present invention

| Structure | Mol Weight | Mol Formula | Mol Name | compound n° |
|---|---|---|---|---|
| 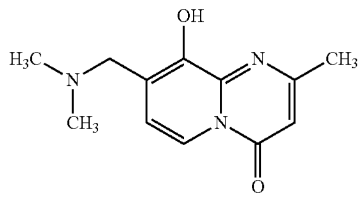 | 233.3 | C12 H15 N3 O2 | 8-[(dimethylamino)methyl]-9-hydroxy-2-methyl-4H-pyrido[1,2-a]pyrimidin-4-one | 14 |
| 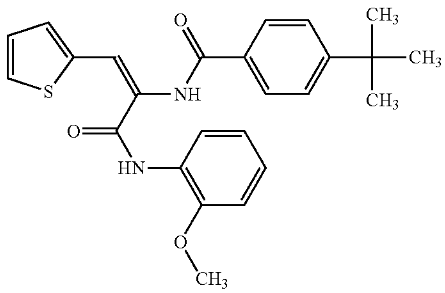 [SMILES: COc1ccccc1NC(=O)/C(=C\c1cccs1)NC(=O)c1ccc(C(C)(C)C)cc1] | 434.6 | C25 H26 N2 O3 S | 4-tert-butyl-N-[1-{[2-methoxyphenyl)amino]carbonyl}-2-(2-thienyl)vinyl]benzamide | 46 |
| 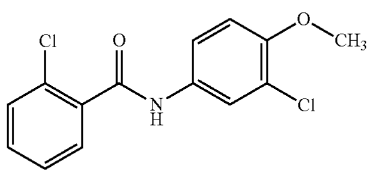 [SMILES: COc1ccc(NC(=O)c2ccccc2Cl)cc1Cl] | 296.2 | C14 H11 Cl2 N O2 | 2-chloro-N-(3-chloro-4-methoxyphenyl)benzamide | 51 |
| 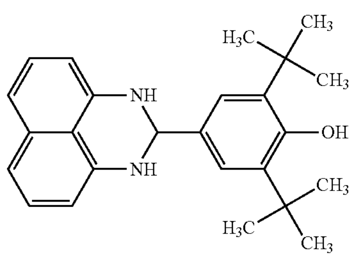 [SMILES: CC(C)(C)c1cc(C2Nc3cccc4cccc(c34)N2)cc(C(C)(C)C)c1O] | 374.5 | C25 H30 N2 O | 2,6-di-tert-butyl-4-(2,3-dihydro-1H-perimidin-2-yl)phenol | 30 |
| 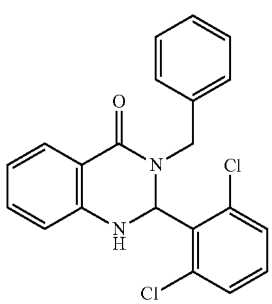 [SMILES: O=C1c2ccccc2NC(c2c(Cl)cccc2Cl)N1Cc1ccccc1] | 383.3 | C21 H16 Cl2 N2 O | 3-benzyl-2-(2,6-dichlorophenyl)-2,3-dihydro-4(1H)-quinazolinone | 33 |
| 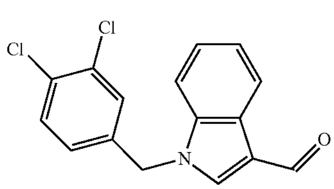 [SMILES: O=Cc1cn(Cc2ccc(Cl)c(Cl)c2)c2ccccc12] | 304.2 | C16 H11 Cl2 N O | 1-(3,4-dichlorobenzyl)-1H-indole-3-carbaldehyde | 35 |

TABLE 1-continued compound identified by the screening method of the present invention

| Structure | Mol Weight | Mol Formula | Mol Name | compound n° |
|---|---|---|---|---|
| 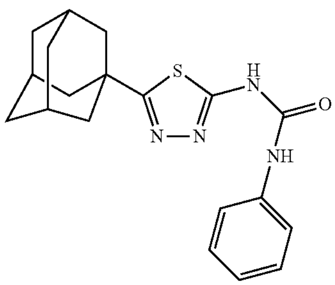 [SMILES: O=C(Nc1ccccc1)Nc1nnc(C23CC4CC(CC(C4)C2)C3)s1] | 354.5 | C19 H22 N4 O S | N-[5-(1-adamantyl)-1,3,4-thiadiazol-2-yl]-N'-phenylurea | 49 |
| 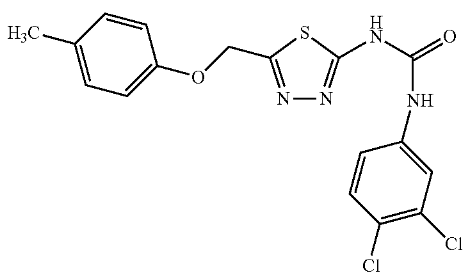 [SMILES: Cc1ccc(OCc2nnc(NC(=O)Nc3ccc(Cl)c(Cl)c3)s2)cc1] | 409.3 | C17 H14 Cl2 N4 O2 S | N-(3,4-dichlorophenyl)-N'-{5-[(4-methylphenoxy)methyl]-1,3,4-thiadiazol-2-yl}urea | 53 |
| 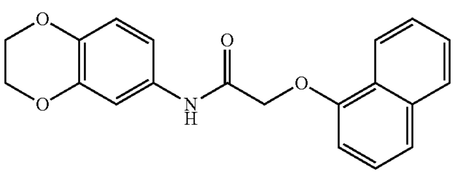 [SMILES: O=C(COc1cccc2ccccc12)Nc1ccc2c(c1)OCCO2] | 335.4 | C20 H17 N O4 | N-(2,3-dihydro-1,4-benzodioxin-6-yl)-2-(1-naphthyloxy)acetamide | 10 |
| 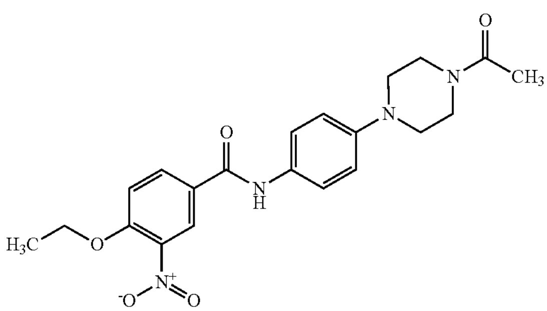 | 412.4 | C21 H24 N4 O5 | N-[4-(4-acetyl-1-piperazinyl)phenyl]-4-ethoxy-3-nitrobenzamide | 27 |
| 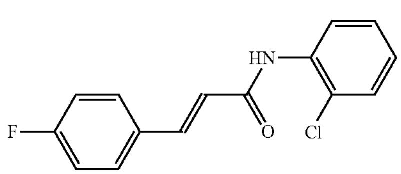 [SMILES: O=C(/C=C/c1ccc(F)cc1)Nc1ccccc1Cl] | 275.7 | C15 H11 Cl F N O | N-(2-chlorophenyl)-3-(4-fluorophenyl)acrylamide | 40 |
| 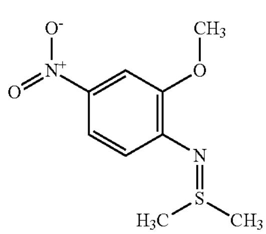 | 228.3 | C9 H12 N2 O3 S | 1-[(dimethyl-lambda~4~-sulfanylidene)amino]-2-methoxy-4-nitrobenzene | 43 |

TABLE 1-continued compound identified by the screening method of the present invention

| Structure | Mol Weight | Mol Formula | Mol Name | compound n° |
|---|---|---|---|---|
| 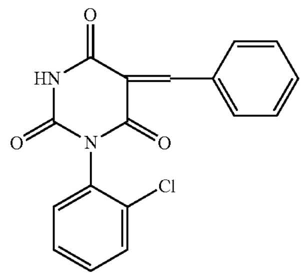 [SMILES: O=C1NC(=O)N(c2ccccc2Cl)C(=O)C1=Cc1ccccc1] | 326.7 | C17 H11 Cl N2 O3 | 5-benzylidene-1-(2-chlorophenyl)-2,4,6(1H,3H,5H)-pyrimidinetrione | 48 |
| 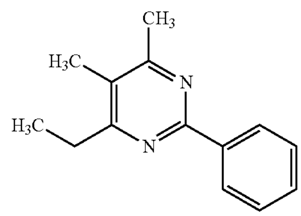 [SMILES: CCc1nc(-c2ccccc2)nc(C)c1C] | 212.3 | C14 H16 N2 | 4-ethyl-5,6-dimethyl-2-phenylpyrimidine | 50 |
| 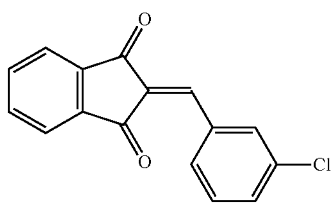 [SMILES: O=C1C(=Cc2cccc(Cl)c2)C(=O)c2ccccc21] | 268.7 | C16 H9 Cl O2 | 2-(3-chlorobenzylidene)-1H-indene-1,3(2H)-dione | 1 |
| 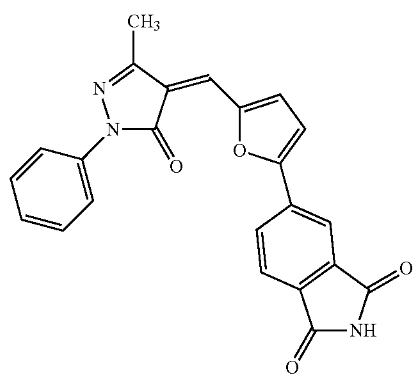 [SMILES: CC1=NN(c2ccccc2)C(=O)/C1=C\c1ccc(-c2ccc3c(c2)C(=O)NC3=O)o1] | 397.4 | C23 H15 N3 O4 | 5-{5-[(3-methyl-5-oxo-1-phenyl-1,5-dihydro-4H-pyrazol-4-ylidene)methyl]-2-furyl}-1H-isoindole-1,3(2H)-dione | 7 |
| 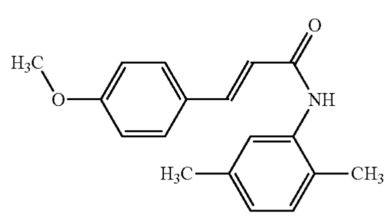 | 281.4 | C18 H19 N O2 | N-(2,5-dimethylphenyl)-3-(4-methoxyphenyl)acrylamide | 8 |
| 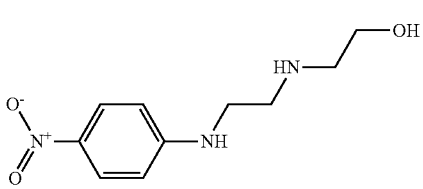 [SMILES: O=[N+]([O-])c1ccc(NCCNCCO)cc1] | 225.2 | C10 H15 N3 O3 | 2-({2-[(4-nitrophenyl)amino]ethyl}amino)ethanol | 15 |

TABLE 1-continued compound identified by the screening method of the present invention

| Structure | Mol Weight | Mol Formula | Mol Name | compound n° |
|---|---|---|---|---|
| (structure) | 285.3 | C17 H19 N O3 | N-(3-methoxyphenyl)-4-propoxybenzamide | 17 |
| (structure) | 316.4 | C20 H16 N2 O2 | 2-(4-hydroxyphenyl)-3-phenyl-2,3-dihydro-4(1H)-quinazolinone | 19 |
| (structure) | 248.3 | C13 H16 N2 O3 | 4-methyl-1-(2-nitrobenzoyl)piperidine | 28 |
| (structure) | 306.3 | C14 H14 N2 O4 S | 2-hydroxy-N'-[(2-methylphenyl)sulfonyl]benzohydrazide | 31 |
| (structure) | 221.3 | C11 H11 N O2 S | 4-(1,3-benzothiazol-2-yl)butanoic acid | 39 |
| (structure) | 278.3 | C17 H14 N2 O2 | 4-(3-methylbenzylidene)-1-phenyl-3,5-pyrazolidinedione | 41 |

TABLE 1-continued compound identified by the screening method of the present invention

| Structure | Mol Weight | Mol Formula | Mol Name | compound n° |
|---|---|---|---|---|
| (2,4-dichlorophenoxybutanamide with 2-ethoxyphenyl) | 368.3 | C18 H19 Cl2 N O3 | 4-(2,4-dichlorophenoxy)-N-(2-ethoxyphenyl) butanamide | 2 |
| (N-(2-methoxyphenyl)-N'-(phenylsulfonyl)benzenecarboximidamide) | 366.4 | C20 H18 N2 O3 S | N-(2-methoxyphenyl)-N'-(phenylsulfonyl) benzenecarboximidamide | 9 |
| (benzoxazole derivative) | 440.7 | C17 H14 Cl I N2 O2 | N-[2-(2-chloro-5-iodophenyl)-1,3-benzoxazol-5-yl]-2-methylpropanamide | 32 |
| (5-(4-butoxyphenyl)-3-cyclohexyl-1,2,4-oxadiazole) | 300.4 | C18 H24 N2 O2 | 5-(4-butoxyphenyl)-3-cyclohexyl-1,2,4-oxadiazole | 38 |
| (N-(3,4-dichlorophenyl)-N'-4H-1,2,4-triazol-4-ylurea) | 272.1 | C9 H7 Cl2 N5 O | N-(3,4-dichlorophenyl)-N'-4H-1,2,4-triazol-4-ylurea | 52 |
| (6-chloro-4-phenyl quinolinone derivative) | 475.9 | C27 H22 Cl N O5 | 6-chloro-4-phenyl-3-[3-(3,4,5-trimethoxyphenyl) acryloyl]-2(1H)-quinolinone | 29 |

TABLE 1-continued compound identified by the screening method of the present invention

| Structure | Mol Weight | Mol Formula | Mol Name | compound n° |
|---|---|---|---|---|
| 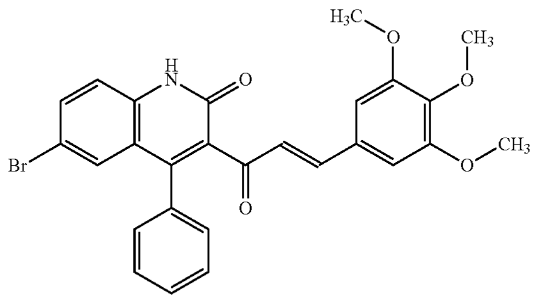 [SMILES: COc1cc(/C=C/C(=O)c2c(-c3ccccc3)c3cc(Br)ccc3[nH]c2=O)cc(OC)c1OC] | 520.4 | C27 H22 Br N O5 | 6-bromo-4-phenyl-3-[3-(3,4,5-trimethoxyphenyl)acryloyl]-2(1H)-quinolinone | 36 |
| 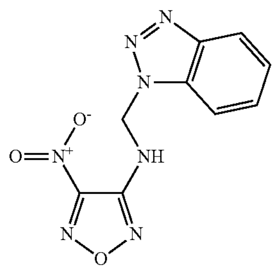 [SMILES: O=[N+]([O-])c1nonc1NCn1nnc2ccccc21] | 261.2 | C9 H7 N7 O3 | N-(1H-1,2,3-benzotriazol-1-ylmethyl)-4-nitro-1,2,5-oxadiazol-3-amine | 45 |

TABLE 2

| Mol Name | Compound N° | Concentration µM | Survival at 72 hours | Resorption |
|---|---|---|---|---|
| 4-[5-(4-bromophenyl)-3-(4-nitrophenyl)-4,5-dihydro-1H-pyrazol-1-yl]-4-oxobutanoic acid | 4 | 100 µM | – | – |
| 2,2,2-trichloro-N-(1,1-dioxido-2,3-dihydro-3-thienyl)-N-(4-methylphenyl)acetamide | 5 | 100 µM | – | – |
| 3-(3-chlorophenyl)-7-methyl-4-methylene-3,4-dihydro-2(1H)-quinazolinone | 11 | 100 µM | – | – |
| 3-[4-(3-bromobenzylidene)-3-methyl-5-oxo-4,5-dihydro-1H-pyrazol-1-yl]benzoic acid | 18 | 100 µM | – | – |
| N-2,1,3-benzothiadiazol-4-yl-5-bromo-2-furamide | 20 | 100 µM | – | – |
| 1-acetyl-4-(2-chloro-4-nitrophenyl)-2-methylpiperazine | 22 | 100 µM | – | – |
| 3-(3-methoxybenzylidene)-5-(4-methylphenyl)-2(3H)-furanone | 23 | 100 µM | – | – |
| 3-[5-(3,4-dichlorophenyl)-2-furyl]acrylic acid | 24 | 100 µM | – | – |
| (2-chloro-4-{[5-(2-chlorophenyl)-6-(ethoxycarbonyl)-7-methyl-3-oxo-5H-[1,3]thiazolo[3,2-a]pyrimidin-2(3H)-ylidene]methyl}-6-methoxyphenoxy)acetic acid | 25 | 25 µM | – | – |
| 4-{[4-(diphenylmethyl)-1-piperazinyl]sulfonyl}-2,1,3-benzothiadiazole | 26 | 100 µM | – | – |
| 4-[4-phenyl-5-(2-thienyl)-1H-imidazol-2-yl]-1,2-benzenediol | 34 | 10 µM | – | – |
| N-(3,4-dimethoxyphenyl)-4-[methyl(phenylsulfonyl)amino]benzamide | 37 | 50 µM | – | – |
| 1-[(hydroxyphenyl)carbonothioyl]-3-phenyl-5-(trifluoromethyl)-4,5-dihydro-1H-pyrazol-5-ol | 42 | 25 µM | – | – |
| 2-methoxyethyl 4-[(4-tert-butylbenzoyl)amino]benzoate | 44 | 10 µM | – | – |
| N-(2,3-dichlorophenyl)-3-(5-methyl-2-furyl)acrylamide | 47 | 100 µM | – | – |
| N-(4-fluorophenyl)-3-[3-(trifluoromethyl)phenyl]acrylamide | 54 | 50 µM | – | – |
| 3-(2-furylmethyl)-2-(2-hydroxyphenyl)-2,3-dihydro-4(1H)-quinazolinone | 55 | 100 µM | – | – |
| 2,6-di-tert-butyl-4-(2,3-dihydro-1H-perimidin-2-yl)phenol | 30 | 100 µM | – | +/– |
| 3-benzyl-2-(2,6-dichlorophenyl)-2,3-dihydro-4(1H)-quinazolinone | 33 | 100 µM | – | +/– |
| 1-(3,4-dichlorobenzyl)-1H-indole-3-carbaldehyde | 35 | 50 µM | – | +/– |

TABLE 2-continued

| Mol Name | Compound N° | Concentration μM | Survival at 72 hours | Resorption |
|---|---|---|---|---|
| N-(4-ethoxyphenyl)-2-{[5-(4-methoxyphenyl)-1,3,4-oxadiazol-2-yl]thio}acetamide | 3 | 100 μM | +/− | − |
| 5-(4-nitrobenzylidene)-2-thioxo-3-[3-(trifluoromethyl)phenyl]-1,3-thiazolidin-4-one | 16 | 100 μM | +/− | − |
| (3,5-dichlorophenyl)[(phenylsulfonyl)carbonyl]amine | 21 | 50 μM | +/− | − |
| N-(2-bromophenyl)-3-(5-methyl-2-furyl)acrylamide | 6 | 25 μM | + | − |
| 2-(2-chlorophenoxy)-N-[2-chloro-5-(trifluoromethyl)phenyl]acetamide | 12 | 100 μM | + | − |
| N-[4-(4-acetyl-1-piperazinyl)phenyl]propanamide | 13 | 50 μM | + | − |
| 8-[(dimethylamino)methyl]-9-hydroxy-2-methyl-4H-pyrido[1,2-a]pyrimidin-4-one | 14 | 100 μM | + | − |
| 4-tert-butyl-N-[1-{[(2-methoxyphenyl)amino]carbonyl}-2-(2-thienyl)vinyl]benzamide | 46 | 100 μM | + | − |
| 2-chloro-N-(3-chloro-4-methoxyphenyl)benzamide | 51 | 50 μM | + | − |
| N-[5-(1-adamantyl)-1,3,4-thiadiazol-2-yl]-N'-phenylurea | 49 | 50 μM | +/− | +/− |
| N-(3,4-dichlorophenyl)-N'-{5-[(4-methylphenoxy)methyl]-1,3,4-thiadiazol-2-yl}urea | 53 | 100 μM | +/− | +/− |
| N-(2,3-dihydro-1,4-benzodioxin-6-yl)-2-(1-naphthyloxy)acetamide | 10 | 50 μM | + | +/− |
| N-[4-(4-acetyl-1-piperazinyl)phenyl]-4-ethoxy-3-nitrobenzamide | 27 | 100 μM | + | +/− |
| N-(2-chlorophenyl)-3-(4-fluorophenyl)acrylamide | 40 | 100 μM | + | +/− |
| 1-[(dimethyl-lambda~4~-sulfanylidene)amino]-2-methoxy-4-nitrobenzene | 43 | 100 μM | + | +/− |
| 5-benzylidene-1-(2-chlorophenyl)-2,4,6(1H,3H,5H)-pyrimidinetrione | 48 | 100 μM | + | +/− |
| 4-ethyl-5,6-dimethyl-2-phenylpyrimidine | 50 | 100 μM | + | +/− |

The invention claimed is:

1. A method for identifying a compound which inhibits the activation of RAC GTPase by DOCK5 protein, comprising the steps of:

coexpressing at least the DHR2 domain of DOCK5 and the RAC proteins in a cell, wherein said at least the DHR2 domain of DOCK5 protein induces the conversion of inactive RAC, which inactive RAC is bound to GDP, to active RAC, which active RAC is bound to GTP.

determining and comparing conversion of inactive RAC to active RAC in the presence and in the absence of said compound, and selecting the compound inhibiting the conversion of inactive RAC to active RAC, wherein said compound is useful for treating diseases associated with bone loss.

2. The method of claim 1, wherein said disease associated with bone loss is osteoporosis, osteopenia due to bone metastases, periarticular erosions in rheumatoid arthritis, primary hyperparathyroidism, hypercalcemia of malignancy, Paget's disease of bone, periodontal disease, immobilization induced osteopenia, or glucocorticoid treatment.

3. The method according to claim 1, wherein said method further comprises the step of testing the inhibition of bone resorption by the selected compound.

4. The method according to claim 1, wherein said DOCK5 protein refers to a polypeptide comprising the DHR2 domain of the protein DOCK5 corresponding to the amino acid 1132 to 1661 of the DOCK5 protein from *Mus musculus* SEQ ID NO:1 and derivatives thereof.

5. The method according to claim 1, wherein said DOCK5 protein corresponds to SEQ ID NO:4 corresponding to *Homo sapiens* DOCK5 protein.

6. The method according to claim 1, wherein the RAC protein corresponds to SEQ ID NO:2 and derivatives thereof.

7. The method according to claim 1, wherein said method further comprises the expression of any protein capable to interact with the active RAC protein and not with the inactive RAC protein.

8. The method according to 7, wherein said cell further comprises a reporter gene under the control of a promoter sequence, and said active RAC and protein interacting with are each fused either with a transactivation domain or with a DNA binding domain specific of said promoter sequence, wherein the interaction of active RAC with the interacting protein results in the induction of expression of the reporter gene.

9. The method according to claim 7, wherein the protein interacting with active RAC protein is selected from the group consisting of PAK1 protein which corresponds to the SEQ ID NO:3 and derivatives thereof.

\* \* \* \* \*